United States Patent
Konda

(10) Patent No.: US 8,642,045 B2
(45) Date of Patent: Feb. 4, 2014

(54) RECOMBINANT VIRUS VECTOR ORIGINATING IN HHV-6 OR HHV-7, METHOD OF PRODUCING THE SAME, METHOD OF TRANSFORMING HOST CELL USING THE SAME, HOST CELL TRANSFORMED THEREBY AND GENE THERAPY METHOD USING THE SAME

(75) Inventor: Kazuhiro Konda, Tokyo (JP)

(73) Assignee: Virus Ikagaku Kenkyusho Inc., Osaka (JP)

( * ) Notice: Subject to any disclaimer, the term of this patent is extended or adjusted under 35 U.S.C. 154(b) by 1691 days.

(21) Appl. No.: 10/570,589

(22) PCT Filed: Aug. 30, 2004

(86) PCT No.: PCT/JP2004/012487
§ 371 (c)(1),
(2), (4) Date: Jun. 12, 2007

(87) PCT Pub. No.: WO2005/021746
PCT Pub. Date: Mar. 10, 2005

(65) Prior Publication Data
US 2010/0247486 A1    Sep. 30, 2010

(30) Foreign Application Priority Data
Aug. 29, 2003 (JP) .................. 2003-307335

(51) Int. Cl.
| C12N 15/00 | (2006.01) |
| C12N 15/09 | (2006.01) |
| C12N 15/11 | (2006.01) |
| C12N 15/33 | (2006.01) |
| C12N 15/36 | (2006.01) |
| C12N 15/63 | (2006.01) |

(52) U.S. Cl.
USPC ............ 424/199.1; 435/320.1; 435/456; 435/325; 514/44; 424/93.2; 424/93.6; 424/229.1

(58) Field of Classification Search
None
See application file for complete search history.

(56) References Cited

U.S. PATENT DOCUMENTS 5,972,666 A * 10/1999 Hippenmeyer et al. .... 424/205.1
2008/0226677 A1 * 9/2008 Mori et al. ................. 424/229.1

OTHER PUBLICATIONS

Romi H. et al, "Tamplicon-7, a novel T-lymphotropic vector derived from human herpesvirus 7", Journal of Virology, The American Society for Microbiology, US, vol. 73, No. 8, Aug. 1999, pp. 7001-7007.
Isegawa Y et al., "Comparison of the complete DNA sequences of human herpesvirus 6 variants A and B", J Virol, 1999, vol. 73, No. 10, pp. 8053-8063.
Turner S. et al., "Characterisation of a human herpesvirus 6 variant A 'amplicon' and replication modulation by U94-Rep 'latency gene'", J Virol Methods, 2002, vol. 105, No. 2, pp. 331-341.
Megaw A.G. et al., "The DNA sequence of the RK strain of human herpesvirus 7", Virology, 1998, vol. 244; No. 1, pp. 119-132.
Kondo et al., "Detection of a gene cluster that is dispensable for human herpevirus 6 replication and latency", J Virol, 2003, col. 77, No. 19, pp. 10719-10724.

* cited by examiner

Primary Examiner — Maria Marvich
(74) Attorney, Agent, or Firm — Edwards Wildman Palmer LLP; David G. Conlin

(57) ABSTRACT

It is intended to provide a virus vector by which an exogenous nucleotide sequence can be inserted and easily transferred into a mammalian host cell and a gene encoded by the exogenous nucleotide sequence can be expressed in the host cell, and which has a low risk of pathogenicity and is appropriately usable in gene therapy of mammals. Namely, a recombinant vector originating in HHV-6 which has an exogenous nucleotide sequence in a portion corresponding to at least one region selected from the group consisting of U2, U3, U4, U5, U6, U7, U8, U24, and U25 regions of HHV-6; or a recombinant vector originating in HHV-7 which has an exogenous nucleotide sequence in a portion corresponding to at least one region selected from the group consisting of U2, U3, U4, U7, U8, U24, U24a, and U25 regions of HHV-7.

8 Claims, 21 Drawing Sheets

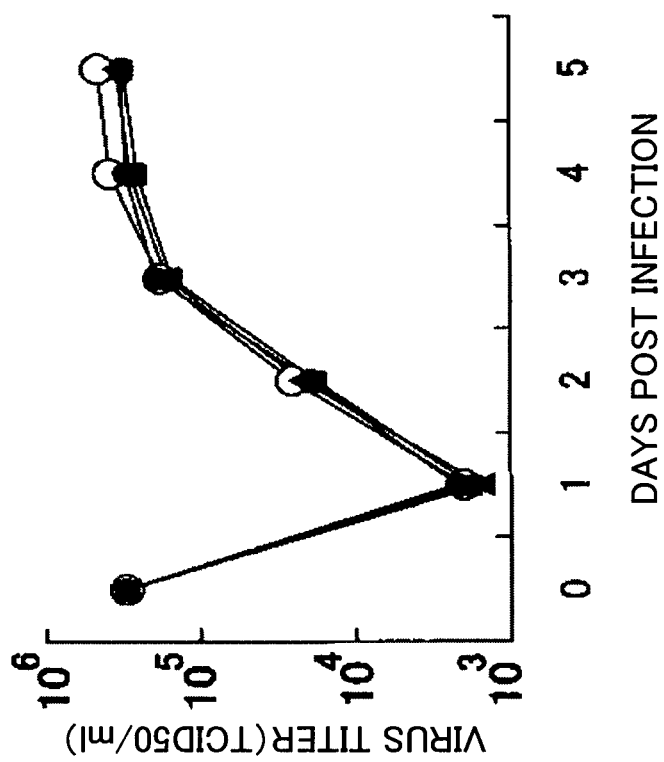
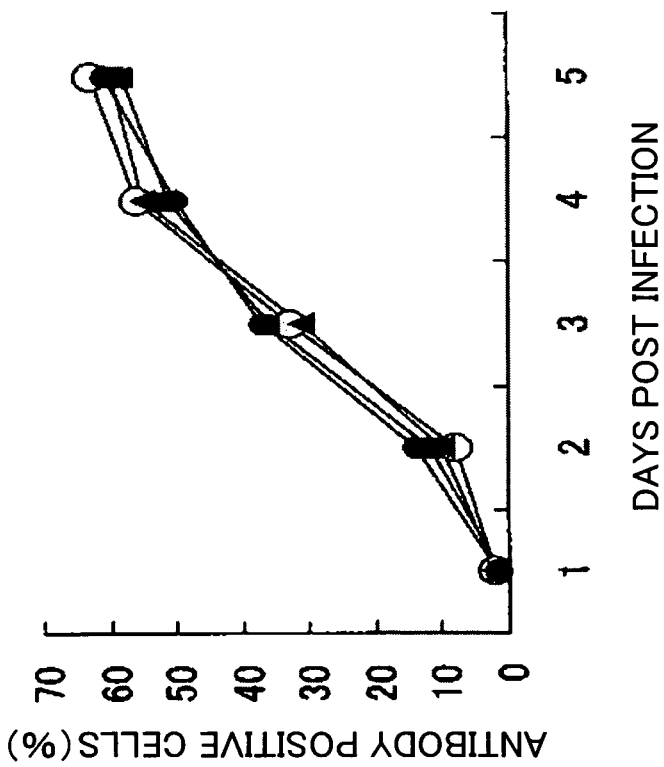
FIG. 3 (A)
FIG. 3 (B)

control

H6R28

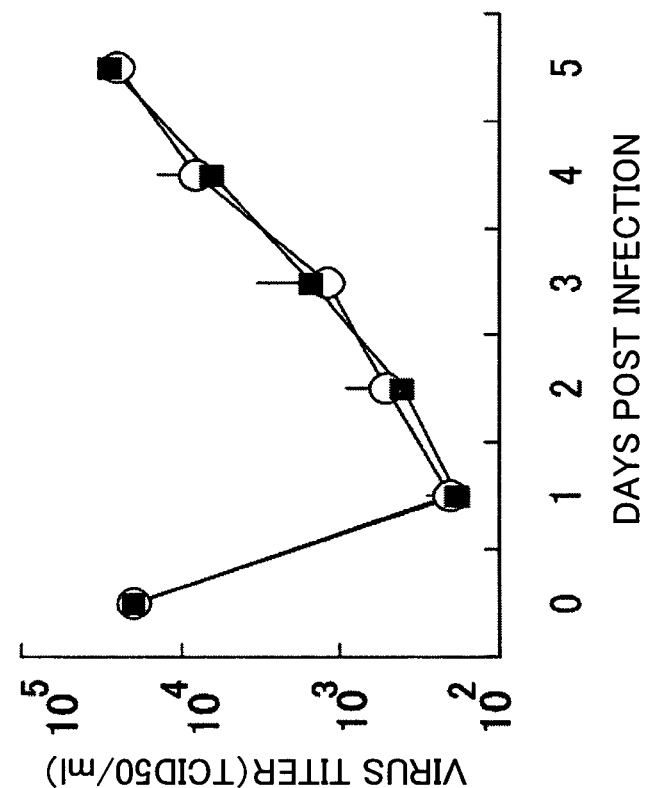
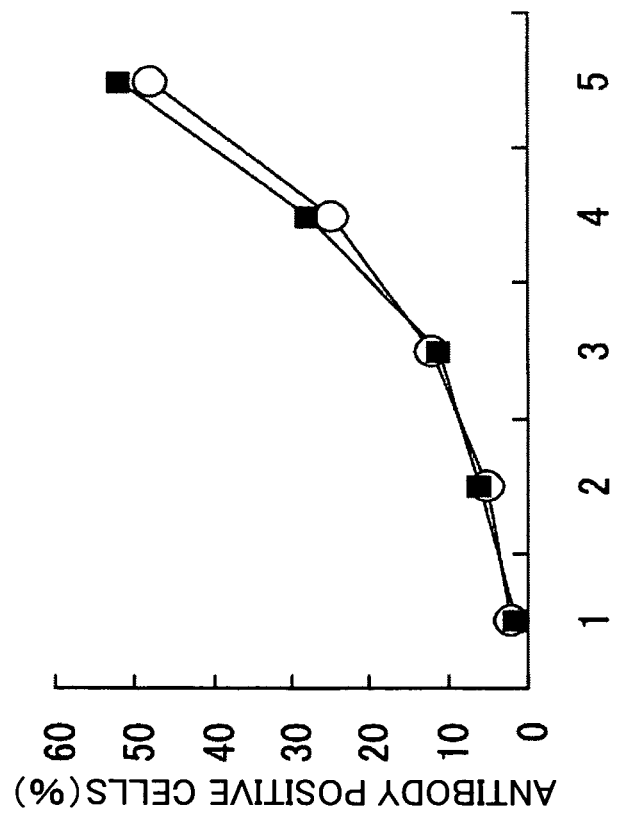
FIG. 15 (A)
FIG. 15 (B)

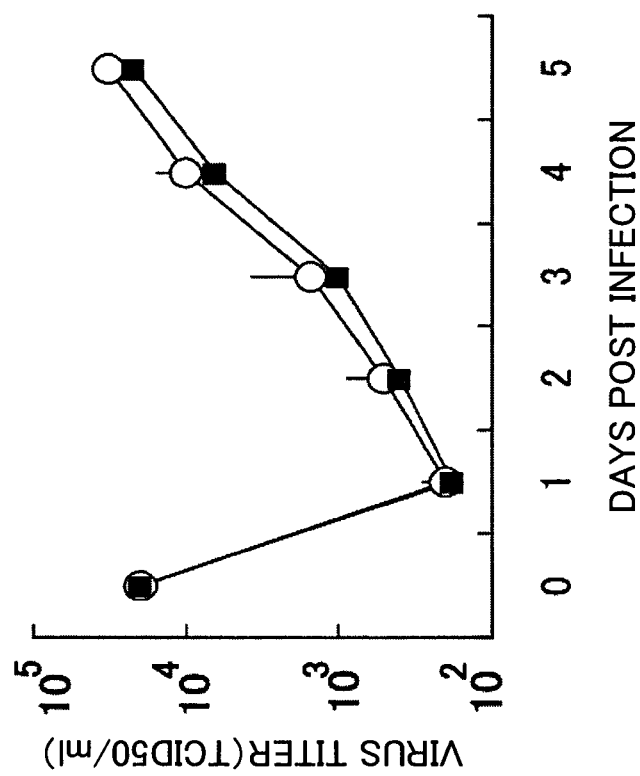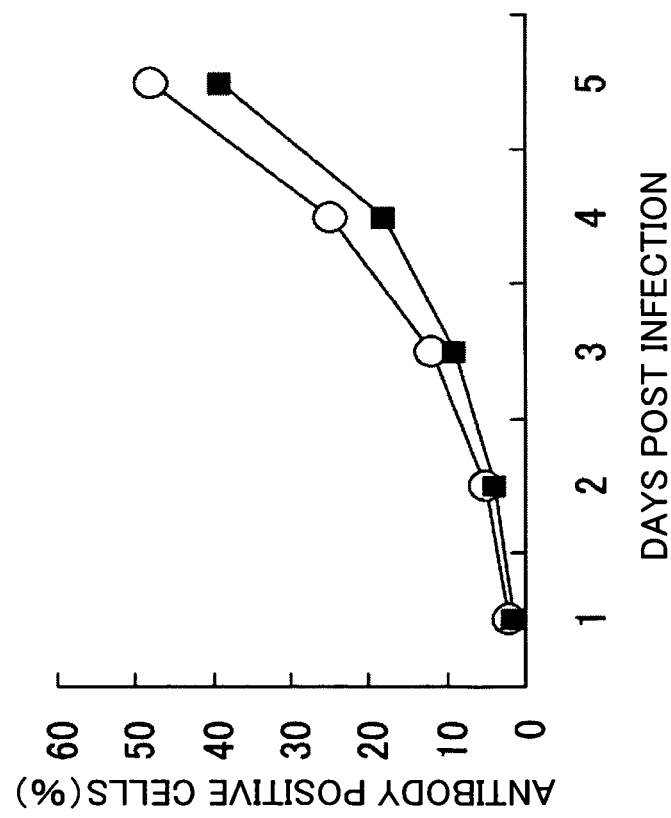
FIG. 17 (A)
FIG. 17 (B)

SEQUENCE LISTING

```
<160> NUMBER OF SEQ ID NOS: 46

<210> SEQ ID NO 1
<211> LENGTH: 161573
<212> TYPE: DNA
<213> ORGANISM: Human herpesvirus 6

<400> SEQUENCE: 1
tcctcgcgtt tcaaaaatta ctttaaactc cccggggggg ttaaaaaaag gggggtatta      60
accctaaccc taaccctagg cctaacccta accctaaccc taggtctaac cctaacccta     120
accctaaccc taggtctaac cctaacccta accctaaccc taggtctaac cctaacccta     180
accctaaccc taggcctaac cctaacccta accctaaccc taggtctaac cgtaacccta     240
accctaggtc taaccatagc cctaaccata gccctaacca tagccctaac cataacccta     300
accatagccc taaccatagc cctaaccata gcactaacca tagccctaac cctagcccta     360
accatagccc taacactaat cctcgcatct ggccctaaca ctacccctct ttcaaccact     420
caccatcacc ccacccgctg ccccccccca cacacacaca cacacacaca caccgccacc     480
gctaccacca cctctgaact tcaccttttc cctccatctc gccccacttc tctctacact     540
tctccgcccc tctattctta ctcctgtttt ctaggatgcc gctgccggcg cgtgtcagcc     600
acgccctgca tcgtcttccg ctgtcccact attggtggct actgttgggt cgacactccc     660
ttcgtcatgt ccattcctac cttcgcctgc acaaaggtct acgccttcct ttaccttggc     720
ccgagcaaga atgcctgcat ttacatccta agccttacaa gtttctcctg cgttacccta     780
gtctaacaag acaaccgcat cttcttcagg gctggcccgc ggattcttct ctatgtgagt     840
gacatttaca cttccacttg ttcacatgat ttattgtgtt ttgtctgcta caccaagcac     900
atttcggttt ctcttttata catttgtctc tattctctcg gtctcagggt tcgaccctaa     960
accctaccat cttcggccga cagcaagttg ctaccgctgg gcctgatcac gctgtccgcc    1020
ttttccatgc gcgtttctga gccgacacac tgcagcggct tccacgcggc acatccgtct    1080
ctcagttggt taacgggatc gtcccttgg ctcgtgctcc tacaagcgcc aggagggtct    1140
ctgttctgcc acgacgtgtt ccaaggccga ctctatctct gtcgcactc cgtgtcgctc    1200 tttctaaaga cgggccttcg ccagtgtgag gccatctatc gcgcaccgct gtggcgcgta    1260
```

-continued

```
cggcccctgc cgagcctatg gacgtgtcga gatcccgaca cggccttctt gccgaaatta    1320
ctggcgagaa ccgcccgacg cggcctggcc gctttctatg ccctgtggag actgcatctg    1380
ggatcccgct cggagctctc tcaccccgtg ttggagtggg agagaacaga gctggtcctg    1440
acggatcgga gacgcaggtg gccgtgtacg cacctcctgt ccggctcgga gttccagcgc    1500
gtttcctcga gtgacgccgg agacacatgg aacgcagcga cagagaaggc ggcgggggga    1560
aaagaggagg cggagagagg cgggcgacag caagccactg acagactcgc aagtccgcac    1620
ctgacgcggg gcctccgcga ctccggtcgg tcccttcagg gtgaggagcc cagcgccgcg    1680
gaagactttg cgaggtgcag accgctgctg acgaactgt gcggggaggg cggctggctt     1740
cccttttgcgt ttctcacggc atctccgcac gtctgtctga tcctaacgga gggaggcccc   1800
gtcctggcgc ttgacctgaa cgacacctcc ctgtggcgca tcgcggacga cttggagctg    1860
ctgctgcgcc tggggagcct gctcctgctc tcagggctcc ggcttcctct ccgtcccccg    1920
agcgggagcg gcgaggcggc gagaaagccg gggtacgaga aggaagaggg aagagggaga    1980
gcggcgacgg cgagcgcgac ggccgcgacg tcgccgcgca gaccgacccg tccgaggggg    2040
gtgacggaga agggacgtgt gacaaccggg gacgtcccct tctccgcaca tcccgaatct    2100
gaggaacaga cagacggcca ccacgggcgc caggaaagcg gccacggcga ccagcgcggc    2160
ggggacggac gaggacaccg cgatgacggc gcgcgccgcc acgcgaatga cgaaacagag    2220
ccccagcagc gcggagagca cgaggacggg gaacagaccg actccgggcg cgaggaggac    2280
gcacaggaga gcgaggtcgc aagaagagac gagaagggaa cggagcaggg cggtagcgga    2340
aggagctgcg ggagggcaaa gcagacgtac ggcgggagag gcgaacatgg tgcctggtcg    2400
tcgatccccc tgtctgtccc caggcccgat cccgcgtgt gggtccctcc tcctcatctg     2460
ttattcccctt cccgctgcc gtcgataacg cccgtcgaag acgagccgtc cgcccgccct    2520
cggtgccccgc caggtcccgc ggaggaaccc tctaagtgtt ctccgtgccc gccctgcccg    2580
tcgcccgacg ccccgcagtc cgctgtcccg cgcctcccg ctctgtccgt cccctcgccg     2640
tccaccgcgc gtgtccgttt ctccctctcc tccctctcct cctcctctc ctcctcctct     2700
tcctcctcct ccccgtccta ctctccctcc ccgttgtctc cgccctctcc cgtctctccc    2760
tcgtctccca gatctccgtt catctccccc attagatctc cgggactccg agcaaagccg    2820
cgggtgtcct ccgggcatcc cgtggcgttc ccgccggcgc cctcgtccgc gccgcccttt    2880
tccaaaagag tcccgtccgt tccctcatcg gcatctccgt ccgcgccgtg catcggcagg    2940
tcgcggccgc cctccgcaca gacggcgtga gacgccgcgt gaggtgacgg aggcggcgaa    3000
gggacacgag aagaacatgc agaagaacat gaagacgaag aagacgaaga acgaggacg     3060
aaaggagggg aatacaccgg agaccgagcg cggatggag cccgctcggt tttgcacgtc     3120
cgcgataccg agcggactcc gtcgccgctc cggaccctcc acgcccctcc gtccaggacc    3180
cgaggtccga cacgccccca cctcgcgcac ctcctccgcc accaccgctg acagtcaccg    3240
catatcacccc ccatacacac ccagcagcag aggccggcgc acacacacgc gcggagcacg   3300
cacgagaaca cgcgagacat cggccgccga aattaacgga gtctatgcgc gcgccgtgac    3360
acggaaaacc aagcggagcg agacgatcga ccgactcctg ctatccttcc tccctgggta    3420
cggtccacac gccagtctgc ggagtcacct gagggccgga tccgctccgc gccccccgcc    3480
cgatccgccc cgataaaaaa aaatcatctg actcgtgcca gttcacacag atgcaaccga    3540
tgacaaaaaa aaacacacca ccacaagcaa acgctcgccg gcccgttcac cgtccctctc    3600
acccccactc gaatcgcgca ggcgcgtcgg cgggcagtcc cccgaacgcc tccacggcaa    3660
```

-continued

```
cgctcctccc acgcccctc ggtccccccc cccctccct ccatccccct ccccggagca    3720
tacacgccga ctctctccgc agaggcggcg accacagcgg cagcgaaaac tgtaacggcc    3780
acgttctttg aacagtgaca gtaacggcgg cggcggctgt cgccgtcacg gtagtcgtgg    3840
cggagcaccc ggggaggcga cgacgggac taccgatgct ctcagatcat cgccatagtg    3900
aaagagtacc gaataaaaca agttaaattt tgttgtaaat aaaaaaaaaa tactatgtgg    3960
aaattaaaaa taaaaaaaaa atgaaaataa aggctaaaca ctgactaaac gtgcatcctt    4020
ctccgtacgt ccccttttcaa taaatggcgg acccgacctc tccataaacg gagacacgcc    4080
gggagactcc ggccctccca atccacaggt agcccgagac ctaatcacaa aactgtacct    4140
gaaaccgaaa gtatagaggg cggcctcgaa tgccccacct atgaggcggg acttcgcgac    4200
gcgccaccct tcctatacgc ccggccttcc gcgtgcgcgc ctataggacg catcccctcg    4260
ccccgaaacc gcaacgcggc agagtcggcg ccacaccccc gtccccgag ttcgcgatgg    4320
gctggcgccg accctgccgc ggcaacgaag gcgaaacgag accccgacgc atgcgggcat    4380
aaagagcgag aagtaaacgc ggggtcccga attatcgcga gactatttgc ccgggcccgc    4440
cctcgtcctc atgcccttcc ccgcccctc atccccgac acaccggtg ggaaaaacga    4500
aagacacata aatttaaacga attttgttgt taaaaatgtt tccacgtgac gtccccggtg    4560
attcccggag atgcggcacg cggcggattc gcccgtttac atcggggtcc gcagacgcgg    4620
ttctgccagg gcgttgcggt gtcggttccg cacagaacac cgcggtccgt cgtcaccgtt    4680
caaccgcgcg gtagttccgc gattctatgg ttcatctccg ctcacagcgt tctctttctt    4740
ttatttttca ctgagccgct ccaccaccaa gagtgttact gactacaccg tatacatgtt    4800
tttttatctc tccaccccctc cccatcacag accatcaaac accttgccgt atcgacactg    4860
actatactcg accgcggatg acaacggtcg ttggtcacaa caagagctac agcggacagc    4920
aaaaataaga taaatacagt aagagagagg ccccggtcca cataggaagc caagggcgga    4980
cgaaaataaa aacccgtccg tgattcacac acgaatcggg ggttatgaca acgcgacaca    5040
cgcagatgag ggacggacgc atcgcgatcc ggcgcgacgg ggcgcgattg gcccacgcgc    5100
gagcccgtgc ccgcttcgag tggctgctcc tggctcgcgg caggccgtcc aaactgtacg    5160
gctatacgag tcggcaccgg ggagaacgga tccacctacc gtggccgcgg tactggtgcc    5220
tagaactcca tccggatccg tacagggacg ccaggagcgc caccgtgtgg ggtcaccgct    5280
ggggttggcc gccaacgcac gtgagaccca gatccgttca agactgcggt gagtgagcgc    5340
cgccgcgacc gacgacgcta tgcgcacacg ggcgagcggc gggagggac gtcggccgca    5400
gggcgagcgg gtggagggcg agcgggtgga gggcgagcgg gtggagggcg agcgggtgga    5460
gggcgagcgg gtggagggcg agcgggtgga gggtgagtgg gtgagggtt cgtcgaaaac    5520
caccgaagac attggctggc ggagagtggg gacaaaacaa cgtcacgtca ggggcggaga    5580
aatatagggt gcgcagaccg tcaaagcgcg agttacggaa aacgagtacg gatacacggg    5640
ggggggggg gggaaggaaa catggtgaag tctgtgacac gcgtgaccgt cagccggcaa    5700
cgcctgccac ggcctccggc ctcacagacg actcacggag tttcctccag acattgtttt    5760
tttttttgt attcatcggt aatgcggtat acgtaaattc cccgcaaagg tactttccgt    5820
taaggacggt acaggcggta tgacttccgg aacacgatga ttacggatat cctgcatagt    5880
gtacaggaga ccgcttttt ttaggttccg tataaaacgt acgtcggcga cgtacacaca    5940
acggttaaaa aaataaaaaa aaaagaggaa acagtaaagc cctcctttc ctctgtgtta    6000
tcgcgttgag ttagtagtcg ccattgctgt tgcgtatgct tttcgcgtta acggtacgcg    6060
```

```
acaggatacg aatgcgttac acgccgcaaa ggcatcccta cgatgactct atgcggcatc   6120
tcccgttcgc gcagaaacgc gagttcccgg gacgccagtc gtgacgtccg gccgatggga   6180
tgcctttgcg tgtgcggatg ttttctgctg ttttatagga acagagacaa gagacgaaaa   6240
tagcggaacg cccactataa cgtgcatttt tctctgtgtt ttgcgttttc atgttttatg   6300
attcttctac ggtatcggcc ggaacggtca tcctcgatcc ttctcgtacg cgtgtcccgc   6360
cccagccctg gactcgagtc tgtacgtatg ttgcggatac ggagaaaaac ttcaacccgt   6420
gggcttcgta agctcgtatc tgacccactc cccgctcgac acgcttcgcg tgctcctggt   6480
cggtagagac ggagccgtgt acgtccacca catgagggcg ccagactct gccgactggc    6540 gtcgaacgta acggagtttg caaggcgagg gctgcagcgg gaccccgtgg cgtatgagga   6600
ggacctagag ctgccggacc ggcgtatgtg cggaacgaac gtcagacatc tgttcgacgt   6660
gatcgccgcg gccgccgacg aacacgacct gctgaccgtc ggcggcctgt gtcaaacgca   6720
cgccggagtg agctgtgaat tactagagac cgtgcgagat ccgtggacgg cggttccggg   6780
cgtacgcatg actctgaccg tggcgcgggc tcagtatcgc ttgtggcccg atgcccggag   6840
acagctccgc ctgcacctgt acgcgggaca ccccctggga ccgtggatag tgtgcgccgt   6900
tctgtctcga gagagggaga cgcagacgcc gtcgcctccg ataggcagcg gaggcgtgac   6960
tctgggaaac gtgcccacgc cggggccacg cgaagtggag acggcttggg tgatcgtcac   7020
ctggcgggac cgctgttatc gttctggccc gataacggca agatctgccg tctggcgaac   7080
tcgttcgccg ccctgtggag gatgggccgc gggccatgag aggacattgg acgtattcgg   7140
ccccgggtag acatctcccc gggaacgctt ggccactcct gtgaacacgt gagaccgccg   7200
gtcggaaaac ttccccggca aagagcgtac ctggattaga cgccacgcg gagacgtaag    7260 gatgcgatat acgccagag acatgaccgg aggaagatca tgacaaggat ctcgaaatat    7320
aaaacaaaaa aaaaaagtg aggagtcgc aaacgcaaga aaagaaaag cagaaccgcg      7380 gtggagatgt ctatccgcct gcgtgtatgt gtggggtgtg tatatgtgcg cgtgaccgta   7440
tccctccctg cctttaaccc gatgagaaat aaaatcggcg aatgtacaca atcacacaca   7500
atgtgcttac gttccgtgtt actgacacca cataacaaaa aaaaaacata cttcctgtcc   7560
gtgagacacc gccgccctct agcggagttg ctatagcagc gcccgatgcc aacgcgacac   7620
ggtgagtcgc atagatcggg actgcttgaa agcgcgccac attcgccttt tatatagacg   7680
ccccggggag tgggaggagc caacatacac acgaggtcgg tctggggttg gagacgaacg   7740
cggaaaatca acgcgtaaa aaaataaaa aaggcggaga cacatagcct tggcgggaag    7800
acgataacag gttcaaagat agacagtgaa aaaaaaaaaa agaggagacc atgacattga   7860
atacacgtgc ggcggcaatc caatcaacgg gacgtgccgg ggcgcaaaaa aaagtatacg   7920
gaagtgcatg cgacagacag tcacgcggac cgacgacaaa ggccgactcc tagcatggca   7980
actaggaaaa aaaataagc aacgctgcaa aatactaaca aaggaaacat cccttcaccc    8040
cctccctacc ccgtctacca caatacccccc ccccctccgt aatcacttct gtccgcgttt   8100
ctcccacagg cgcgtgcaca cgcagacacg cagacacgca cacaccacct ctatggcagt   8160
cgcgggcggg caggcgggga gcatacgggg ggcagatgta aagtcaatga ggaacggcat   8220
agcgcgcgac gtgccgtcgt ctcggaccct tgctattctg gcacgacgcc aagggaagcc   8280
tctggcgcaa tctataaccc taaccctaac cctaaccta accctaaccc taaccctaac    8340 cctaaccta accctaaccc taaccctaac cctaaccta accctaaccc taaccctaac    8400 cctaaccta accctaaccc taaccctaac cctaaccta accctaaccc atccccaac    8460
```

```
gcgcgcgcgc gcgcctctat gggaggcgcc gtgttttca ccaaaacgcg cgccactgcg    8520
agaggcgcgt gaaaaaacct ccctccgg acgggcccga gtcgtccgcg cgtgtcgccg    8580
gtgcgccccg cgcccgggat ccccccacct ccccccccca agaacgggc gagggtatgg    8640
gggtggatgg cgtgtagttt aaaggcgaag gtgcagccgg cgccggagc ccggtgagag    8700
cgaaaaaacg atggcgcgcg cgagagagaa agagaggcag aaggcagagc cgcagaggga    8760
cagacgagga gacgccggag gaaagagaga acggccgcga gggccatgag ctccacctag    8820
cgtcagacta cgccaccgcg gccgcgtgc gctcgttccc gaggagggcc cgcatgtggc    8880
gcgagagagg gagaagagcg gacgcgtgta gaaacggcca acgggcggat gcgcagagcg    8940
ccccgccggg cgattgacct ttccacagac ccccgaccca tttcggtgat gcagatacgc    9000
acgcgaacac gcacagacat gcctacgcgg cctcaccgag cagactgcca cgtgagcgaa    9060
agcatacaca cacacgaaaa aatacacaca agaaaataca cacaagaaaa tacacacaca    9120
caaaaataca cacacaaaaa aatacacaca caaaaaaaaa tacacacaca caaaaaaata    9180
cacacacaaa aaatacacaca cacaaaaaa aatacacaca cacaaaaaaa tacacacaca    9240
aaaaaataca cacacaaa aaatacacaca cacaaaaaaa aatacacaca caaaaaaata    9300
cacacacaca aaaaaataca cacataaa aaatacacaca caaaaaaaaa ccattttatt    9360
tatgcgctgt tctcacaatg ttaacatagg acaaagacaa ccacgaaaac gaccacaaca    9420
acaacagcag caacagcatc aactacagca acagacgagg gcaggatcac gaggtgtcaa    9480
ctcccgcatc tccgtcgcgc aacgtgtcct cgcagtccct acggactacg gtagaagccc    9540
cgcaagagac tgcggacatt tccgctcta ccatgtgcgg agaaagttga tagacggcag    9600
gtagatttat cacaggcgcg tgcacgcacg tcacgggcag ctgcatggtc cacagatgtc    9660
ccggagggaa tcgatggttc ttgaagagtt ttctgacacc catggcgaga aacgccctga    9720
agctatcgga caggcgcacc acggctcccc cgtcgagact ggccgcatac accctgccga    9780
cctgatccat gagcacccgc tgtcgtctga gcagaggtaa agtaacgccg cgtccgaaga    9840
atctgccgat caccaccgcg acgcctccgc cgggtatgag ccgccacctc ttctccgccc    9900
tcctgggtac ggcaaactca agaaagctc cgcgcggcca aggcaacggc acgagagcct    9960
tatcgaaaga cacggcgaaa gccagggcgt cgtcaactcc actcatgccg ccgaagaaag   10020
aggcgccggt ttcatgaga cacttggaac cgtagacggg ctcgaagcga cgcaagccgt   10080
gcttccagag accgaacgcg tcctccgcga gacggtacag cgcgtcatcg aacacgccgt   10140
taaacgcgta tatctccccg cactctccga ccagcaccag cgcggaaact ctgcgaagaa   10200
tagtgaccccc gatgaccgtg agatccatac cgggacagca cccgtatccg cgagacagct   10260
tggccaactc ggcctgcgtg atcccgagca tgtcggaagt ggcgaatctc agttctgccc   10320
ccacgggcca cgagagcgcc aacctgcaat gggcaaaagt agagacgaag tccctcacgt   10380
cgtccgccga tagcggccgg gcgacgagag tccgaacgaa cgccgtccat ttaacctccg   10440
gtactgccgc atcgcaccgc aggtcacgtc ccgcagagaa agagcacgaa gaagggcaga   10500
gagcagcaga ggccagactc caagaagata tgccgagaaa cggagagcga caaaacattt   10560
tttttctgtg cggaatccga gataaaatta aaaggataaa aaaaaaaaa aacgataacg   10620
gcagcgttac cggcagtctc acataaacgt ctacgatcac gttaaggacg ctacaactgt   10680
tagaaacaaa caacgttgaa tcgacatatt cccgacgtct tccacgaaaa tggaagtgaa   10740
ccgaccgccc acaaaactgt gaacacatcc catcccgggg taaatatac aatgatccca   10800
gacgtcaaaa gcgcccgtaa gaactcgatc taccacgctt ccattctttt ttttaaaaa   10860
```

```
aaaaaaccta accttcaacg ttagggcgaa ctatcgaact acgtcgtgca cggcactcct    10920
agtgccggcg tccggaaatt cctgacgctc atcgtttcta gcctttacaa acagcagatc    10980
atcgtcggcc tgcctccaag ttttctgata aacattcgc gagagatgac aagtcggaag    11040
aagcgcccat tcgggctgct ccctacgaaa acgtagctc ttataatact gaatgactcc    11100
tatccgtcta aactgctgaa aattttccgc cacaaagcgc ggccgtccgt cttcgtcgtt    11160
gtcgttgaat ccgaaaatcc gtccgtcgtc ggccacgtag agagaaatcc gaccggcgtc    11220
cgcaaagtac ttgtagccga agctgccgaa gaaacacatt tccgcgagcc tgcgccgtgc    11280
ctcgtcgcac ctgacgaata caaaagaatc ccgccgccga tgaaagagca gagtctcgtt    11340
cttgggccac ctcagggcga aagaacgacc tatgtgccgg tctcgaaagc acagcacgtc    11400
ccgacaactg cagacgccgt ccacctcggt gtcctccacc acaaactgca gcgatgatac    11460
cagctgatgt gcgtaataga acctcttcag acctttacga agaaaatcgt caatggtgtc    11520
accgacgcgg cacagttgct gcggcaataa ccacgtatgc gcataaacgc gaccggcacc    11580
gccgagcaga acgactatgt caccttcag aaaccagtaa gccggctccg atccgatctc    11640
cccccttttc ttcacgtgcc ccagtacgac gaggcgctcc cggaaacaca ctagatcggc    11700
cagtccgccc aacttttcat cggcatattc attctcgtct ctacagttgt taataaccag    11760
ctcgtatcct tcaggccaag ccaagggaat tcgcctgccg aaattgacga acgtaaacat    11820
tcggacgcta ttcaggcacg tatagacgcg caagagatcg acgagatctc tcttggactt    11880
gttatagaga cgtggacgtt tcttcatcct ctcctgagac tgcagctcgt catcccaca    11940
catcatagaa tcttgagccg gctcatgaag gccttcgata aatcgcaccg tagccgtagc    12000
caaaatctgc cgttgcgccg aagaaacacg ccggctgttt gtcgtttcca ttacgggctc    12060
acagcgacag agaaatagca ctcaaaactt agtaagcaaa agttgcaact cgcaaaaaaa    12120
aatgaaagat aatatagtca caaagaaac ttgtcacaat gtacacccaa aaagaacgat    12180
atggatgatc acacgacaac ggcaacaata atatcgtttt tttttaaagc taaacaaagt    12240
gaaagaagcg taccggtttt ccggattcgt ctgtatcaga taaggtcac acaagccagc    12300
ttaggaacgc ggcgcgcttc gcgaatgtct aaccctcgct gttgcacgcg tcttataagc    12360
ctacgtctga ggactattcg cttttgacgt ctccggtgct cctgcaacct gatgtcaaac    12420
gagccgccgc cggccacagc gtaaggaacg acgttcggat acaccccact ccacatatgg    12480
gtcccgtaaa gattgcagtc gtgaaaacga aaaaacctca ccggattcga catgtaagat    12540
aactccagag tattgaggaa gccctccaga acatcgtgcc ttatctcgcg agcgagtcgc    12600
atggatgcac acaggtcgcc tagacagatc ttttttaggc acagatgctc caagagcgca    12660
cgaacgcgat gccgttcctt gtcataaccc gatacgagaa tcgtcacgat ctcaagaaag    12720
aaaaaacaca accgagggac gcgcatggga tctttaatct cgaactgaga actgacaact    12780
aacagtttga tcctgacacc gtggaggcca gaaacggtat cgatgcaacg ctccatttct    12840
gagatcgctt ttacgaagaa acgagcaatg gccgtgagat cacttacgat gcgctgtttg    12900
acgcgtctca gcagaaacag acacagaacg atgttgcagt acaccttcaa gatgttacgt    12960
tcgaaatgcc ctctccccaa ctgcttatcg tgaagaatgg gcaaatgccg cctttccata    13020
gagttaagaa taagaagaaga accaagatct cggtcaatct ccgcccggag agcgaccgct    13080
tcacgcgcgt cgaggtgcag ctggcctaaa attagatcag ctggatcgaa ttcggaaata    13140
tcagatatgt tcaggccccg ggaatctttt ttacccagat agatccgaaa gagagacgcc    13200
cggcactgat cgcaactaca gagcacagaa gacacaaagc gataagaaga agcgtacgcg    13260
```

```
acaaagatgt aatcggacaa aaagtgtttc aagagcacac tcgtcggaga cgccgcgtcg   13320
ccatagatct ccttgggatt gggcaaaata tcgaacaagg tcaacagagt attggactca   13380
ctcctgttcc tcagcataag gaactgcagg aagagggagt ccaacaactc caaaagacgg   13440
ttgaaatgcg ccgagatagt atccctcttc tccccatcga cgatgtactc cagaatcgag   13500
aagtgcgcca gagcggtgca cttggtcagg agtcgataaa aagctgacgt ttcgtcctca   13560
aaagttaacc gttctaagag agacatgaaa gccgagagat ccatggtcgt cttttccacgc  13620 ctttggaatt ccacagaaac tttctccgcc agagccgccc agagaacact atcgtcacaa   13680
aatcgtaagc cgcgggtcat gaacagatcc tctgcggtca acgtgccgct atctataatc   13740
atctcctccg ttatgtcttt cagatcaaca tcaagttccc tggaatggtg aacggtcagc   13800
gagagatagg gatggttggg aatggtatac gtgacccgtt ctcgaacggg tcccttataa   13860
atgtcgtggt ccaataactc catcactcaa gtaagtatat atctgagaca gcgtttattt   13920
ttttgtcgca gaaaaaaaca aacgagcaga attcaaattg caggagacgg ccacgtacat   13980
cacaatcgag aaaacacaca atcactcatc cccatcatgt ccattcagtt cgccggcaca   14040
gtccggtgca tattcataat acttgtaatc atccctgagg acgtccaacg accccaattt   14100
atacccgata gctctgacgt ctttctcggg acttatttga acaccccgat gattaccact   14160
cccaaaatat ttcaagccac tgaaaaaaaa agccatagtc ccgtttatgc acctggtgtt   14220
agttaaataa tcttcggcga cgggcaacac tacccgttgt agccgctgta agaaattctc   14280
ttcatgggta ttaacgataa aaaaacccgg aatgagatta tcagaagaca ccaggtcacg   14340
atcattgtgc tcgtggaagc gttttatatg aagatgatgc agaaaaaaca tttccatgaa   14400
ccgagtctcg tcgtagtctt tgtaagcagg aacggaaaaa ccgattctca gagcttccca   14460
acactttaag ataaactgac tcttttcccc gggacaccta acaatttctt tcatttgttt   14520
catcgaagaa aagtagcaca ggtctccgag gcacccgttc cgccccagct tcatttcttc   14580
ctccatggtc acacacaatt ttcccacttc ttccgtgaag aggtcgtaat atatgtccaa   14640
ctcagcattt atgacacggt agagggtgtt cacgacgaac acaatgaaaa caatgttagt   14700
taagaaggtt agcaatgcct tcttatccgg ggtgacagag atctgtagcg aaataggcag   14760
cctactgtgc tctatctgac cttcaatcat gctcaaccct aaatccttcg ctatgagact   14820
cgacagactc acactgtagg gttcacccaa atgcagaaaa gccggaagac gaattgaacc   14880
tatcatagga aaacactgaa ttcggacaca gtggccaaaa tcacacttcc tgcctctctt   14940
gttatacatg ataaacatgc gcctacactc gacacaacca cacaggagca taaagtgctc   15000
gatgagacag gattcgatac gctcaaagaa atcgtatctg aagaagacat cggatttgtt   15060
ctccaagcag tccttcaatt cttgaccccca gtgacaaaga ttataacctc ccagctgccg   15120
agtagattcc tttgtcaact cttttaactt gctttcaaac tgaaataata acatggaggc   15180
gtactcacat agatagcgac accagtagcc cagcgtaggt ttggacgcga agttaaacag   15240
agacgctcca gcatagagac cgataaaagc cagtttagtg atgcactgcc acttctcatc   15300
aaaattgtcc ataaatttca gtttttcac catgtcagca atctgatcgg ctctgacgta   15360
ggtggaagga tacttgtaag tttcatactc ataatctatc agtctgttcc acactacgca   15420
gtccgaagag ggatgtagtc ctttaatgcc aaatctagct gctgaggttc cctgcagacc   15480
gttcgtcaac ctagcgcagg agacgggaac gacaaacctg ctggtagcgg gcagtcgacc   15540
gacgaatacc ggcgtgagaa attttgtgat aaatttaacc gtcggcgaat cctcttcgtc   15600
cagacgcacc gcaaacagaa ttttgctgcg gtctttcacg agcctgttgt aagaaaaaac   15660
```

```
aagttaacgg agagtcttca tcctcgaaga attgtctttt cgggaaaaac gacacacaac   15720
acatctaccc acctgtcctt tcgcacgcac atatgccgag gcttactgcg gagaacgggc   15780
aactccccat tcaacatcct attaagattc tccgtctcag tgtcacttat ataaaataag   15840
gtatcgtcat tccagtccaa tgaatacttc tctttataga gcaattcatc aaatcctcta   15900
cgtataaaag tcctcaaact tttagagact tgctgattc tgttttctac gtagatatag    15960
atgtgacagt tcgagcccat aacgatagca gctctgcaat ttggttcagc ttgagagcgg   16020
gcacacgtcc ctatgatagc ataatccttt tctgtgattt tctctagaat gccaggtcca   16080
gtcagataat aaatatccga caaggaacaa aaggaaaagt caaagtcctg aaagcatcc    16140
accctgattc tcttgccaca atgttttgct acgtaatcct tcatagccgg gagattcctc   16200
tgtaaaagga taaattcctc tcggccgcat ttagtctctc cgaaccacat cttttcctgc   16260
tctggatcta actccgcttc ggcaaagggt ggaaattgtc taagtccgat attgaagaac   16320
tggaccagtg attctgctat gatgtacact ttctccgtca ccgtgtccac ggcaatggtc   16380
tttccagttg aactatgcat cacgtatgga tcgtagtcag gattcggatc acgatatatc   16440
gggtgagcgt acccaatggc ggacaaaaat tcatcagtat ccagaagact gctccagtca   16500
taggcactta cccatctatg cgtgtgaaag tgataaaact cacccagagt taatgcatac   16560
atgggaggcc aggcgataca acatcgcaag cccggagaac tgatctccaa cccgtctccg   16620
taagctgcag acagcacgtc tacatcaaaa tccaaagtag gcacacatga tgacaaggtg   16680
aactcatcgt tgcagaccgg tacgatttct gtttgaaaca taaacgcaaa atgaagtaca   16740
atactttcac acaagactcg ctttccgccc tccgtttcaa gtatcagacg aaaattcgac   16800
atgaactact tactgaggct catgcacgat tgataagtct ccgacatgcc caacgtcgac   16860
atccgtccga agcgcatgga tatttttcca atcttctcat aaccgcagtc cgcaaaaagt   16920
ctggcaaatc ccacacgcaa aaagtcagt agacaatcgc ccagcttcac cagcacgttg    16980
tctatccaat cgtaataata tattttttcca gatttcccta tacatagaat aggtcttgta   17040
catttagact cataatcatg gtcattcagg taacctaaca ctactacttt ttctactaag   17100
tcttcctgtt cttctagatt tgccaagcga catgtcccta tccagacact gtcacgagtc   17160
cctagagtca aactcttaaa aaccggcata tccaatctca gatcccggcc gacgttgaga   17220
gacacgaaac gttccacatc gtccaaactg gcacaacggg ccagctcatc aaactctcgc   17280
aacatggcaa tgtaatgttt cctcatagcc ttgatgccca aaacgccttt cctattcaac   17340
ttcagatgga cattcaaagt acagggactc cttaacacat cattattcct taaattttcc   17400
agcgattcga atctggggcc gtcatacaag ccatgacggt acacaggctc cgcgcatgtg   17460
atgatgttag tacccaggac gccgtatctt acaaattgct caaaattatc acacacgaag   17520
tggagagtat ccgtctctag atcgtgcaag aaaattcttt tagatcggcc gatcaaaatt   17580
ggaacatctc tgtaaggaat ctgaatagtc cccagtagac acagttttttc cacaaaaccc   17640
tgatagtgat cattcatatc ttcaaacatc ttttctgtat atccagctac atctttacgt   17700
agagtgaatc tcagccagca gttccgaggc cagataatag acagacacca gttcttatac   17760
gtgccgacaa aattctcgat tcgagaaaga tcagcagatt cacagaaacg acacaattcg   17820
gcaagagcgt tctcgttcgg aatctcacct gagacctcct tcgcctcgag gtccatcttg   17880
aaaactccga ataacactag aagtgaaaca atgaaatatc tgaaatataa gacctcgatg   17940
cgagacgccg tcacatgaca ggaaattgga aaaagagag tggtgtgaca aactttatta    18000
aatttcaacc cccgttttga ctcacacgct ttcctccgca tgtacagaaa aatccgttcc   18060
```

```
accaacgatt tcctgcgaat gttggacaac aaacaccttc atttcctcgg aattatgaaa    18120
atcttcctta catacatcag aagcaaaagt atataaacac tcgcattccg aaagtttttat   18180
gcattgcgat ttgacatagc tgcaatccgc attcaaacct tgcaccccgt actttaagca    18240
ggagacctcc atcgttccgg cttctgtatt gcactcctcg gatttcgatt tagaaaacag    18300
ctgtacgact gtcttccata actttctaac agccatcggc agatccactt cagaaaaaac    18360
gaactcgaag cgccactaaa aacagatgga aatagtcaca tacaagacgg cttcagcgag    18420
atctccgacc gtcacctggt catcgggatt cggacgagct atagcctcaa ttcaaaaaag    18480
gcatcaagaa aatatcagga aaccctacg cttctacagc ggtctcctac actgccttat     18540
aaaacagtat gagcattgcc tcgtcccgcc aaataaatca atacgtttcg acaaagggaa    18600
gattgaagtc gcggccctaa ttctagatct cggacaccag gtacttggtc gtcagataca    18660
cgtccgacaa cgtatctaca gctggactag catcacactc cctaaactct ttactcccag    18720
agaactttac tttttagttg cctctccaga agacgaagac atcgtattta atccaactat    18780
aacaaaggga gggtggatct cgggaagttt ttcgtatccc gttaataca gatcaaactt     18840
ttcgctaacc ggaatgtcgg ctaacgtatt aatggtgccg ttcgttccgt atagataccc    18900
actaaactat gctcgcttca tatcgtcaat agatctgatg atactaaacg aacaatttcc    18960
ggaacacgaa tgcggagaca tacagatttt aaagcagcga aactacctct acctgggagt    19020
catcaaaaat cttacatgga aaaaagcgt caccggcaca ggtcagacag ctccacatag     19080
aatcctaaaa gcttcgttca taggaagttg gccggacacc tccctgcctg acagagtagc    19140
actgcgtttc tttaataaca ctaggtttac gatacactgc cacgagttcg caattaatat    19200
tgaaaatctc ggtctcgtca aaaataaaga gaaagtcttt gggacactag ccaccgtatg    19260
ctgcgagcaa atcccttctc tactaacgac tgaaaatcta ccgagatatt taatagttca    19320
gtttgaagta gtaacgcaaa tcgaagatcc cgaacccctg ttattttcca gtaacccgaa    19380
actatatttt acaggagacg tactaaacgc aacgatgcaa ctacagcaca acccaaatta    19440
ttacgatcta ctcgtacacg cgccatacga catccatttc tatccaagcc gatgtcacat    19500
agtaattcta cctatccgat atttcacgag gggtgacaag caaatcctca tatccggcta    19560
tcagaacgaa ggtttcttcg aaacccaggt gatgctgtgg gctcctggaa caccgttgca    19620
tattacgctg cgttcattct ctccaaatct gatcctgccc caaagcacac ctatcgcaac    19680
cctgttttat gtagaaagaa tgacaagcca gaacactgaa caaaagacg taatcgcaaa    19740
gctgtctgag aatggacatt ttattggcaa cctgaagctc cccagagaaa attttttaca    19800
tcacgacgcg atcactgact tgtctttggc agctataccc aaggactcag cgactcccgg    19860
cccagggacg gtttcttcat cagtttcccc gtcttgacgt atcctcagaa ccatcttttc    19920
aattacatcg tctttttctt caggtgtctc aaccttcatt aattgcgtgg gaataagagt    19980
ttcatcctga ccgactttga aatctgaggt ttctctctca cctgccttca cttttgaag    20040
agcgagatct atttcccgtt ctccgttacc cgggagcttc acgtccagcg catccttaaa    20100
tgacacagaa tctaaatcgc gagacagatc agcatttggc agcctaaacg gggactgcac    20160
agaatcgaga tcgttttgca acttaaaatt tttaaacaga ttttgaggat cactaacttc    20220
aagaattctt tctacgttag cttcctccga ttcgcgtccc aacttgtttt ctgtaggcaa    20280
cttaagctcg gtcccagact gattgtgcaa aatgtcttga atgcccttct cgcctaaact    20340
aatcagattt gtaaattcgg ctagaatctt gttaactcgc tgcccaagac ccgcttgaac    20400
atactgttcc tctccggcat ttctagcagc ttccattaaa ttaggtaatg gctcttgctc    20460
```

```
gttttgcgtc atttctttat cgacattaaa ctttcctgag gtttccttttt tttctgcatt    20520 gccgccagaa tacaagtccc tgctatttcc tttccccct cttgatacgt cacgagcata    20580
tttcttattt aacccggcaa aaatatcatt cgcgtgctta gtttttctca acactgggga    20640
atcccgagca gtcacagttt cagtcgcatc gccagagtct ccggtcactt cgcgtgagtg    20700
tactatagcc ttatcatttt tttccttagt ccagcttcca agcagatcta acttcttctg    20760
tttcctaaaa ccgtctttgt ccctcaaatc tttaatgaga gaaacgttat ggggcgacac    20820
tccggtctca gtactgtgcg tcgtaagttt cgcctctgat ccagccacat cggaattatt    20880
caacacgaag ggtgtccctg tctgctcaga aaccaaacga tgcaccggat cgaaaacatc    20940
tgcattcgcc gctgtgtttt tactccacgg ccgtgaaaca tccgatttat tctgacgcag    21000
attgagatta gcgagaccat ttaccacatc agtaataccg ctactgggac ttctgatcga    21060
agttttatcc tgtagtaaat ccacgtctcc cgtattagat tgcgcctcag ctggaagttt    21120
aacaccaaaa tctaaaatcc ccgaagggcc aattctataa ttaccgtgcg acttatctcg    21180
cagatccaga ttggtagaag tcaaagacga caacggctca actccggaca ttaaagagac    21240
agacgaaaca ggcgttgtcg ctctaacgtc tctaccccg agtgtttctt tcttatcaa     21300 aattttcccc ccggcattat cgacgctatc cgactctgga aatttatgtc gcctctgcgt    21360
ttttaagggc gcgtccaaac ttttgggttg acttattttc agacgagcca atccgcaga    21420 tggtctcttt gtatctatag atatactagg taaactcaaa tctgaaggca tgcggccgtc    21480
taaagaggcg aaatccatta aagagtgagg cccattctca ggcaccgaaa atgctttcga    21540
cgcgctgtat gattccagac tacttttgat aatctcataa tcactggtga ttattttcaa    21600
aaaactctct actctctgac cagttagagg ggtctgcaaa accctctgag aatacacagc    21660
attaaaattc tcgttcttcc tcaaatgacc cgagagatga ttttgcgtgg ttacaatttg    21720
agacatagca acctttctta gctttgacca ggactggttt aacgttacaa ataacttacc    21780
aagataaact aatttattaa tactcgtcac taagtaaccg ttttcgtccc agggggtcatt    21840 tatgttatag acggtgtacc agagcatgtt ttttcagcg tcttgcaaat tattttctat    21900
ctcgctgctg tcttctgcag taagatttac ataaggagta tcgatcggaa cattgctacc    21960
ccacctaata gaatttccta aacgcagtaa agcgcgatga atatcactga attgcgattc    22020
aaacttttct ttgttcgtga acatattttc aaaatttcct ttattcagac ctttggattt    22080
taagtactcg tttacgacat tctggagttt cgtgatgtct tgccatatag cattataatc    22140
cggcttccgt ttagataaca cgtagtgata cataagccat aaaataaatg tgttatacag    22200 tgttttaac tcgtctacat cttctccctc tctcacgaca caagaattag tcacataggg    22260
atgttctcgt aaatctacat tctccagatt ttccaaattg ctaagaaaat ttgtaagacg    22320
ctgaactttg tctcgatcta gccacgcaaa cgggatcgac tgcgctttca aatccatctt    22380
ttagaaaaca aactcaaaaa caaaactgct cgtcttcgcc aagactcaat gtttaatagt    22440 cctttttta cccacacaga aagctgacaa gcgacgagat ggacactgtc attgagctgt    22500
ccaaactcct ggtaagtctc cagagatcat tgttaccgaa tatttattg tagcgtacca    22560 tgacaataac attcaatatc tttaatagca cgatgaagag ttcaaagaca acgcttcctg    22620
tacctcgacc cccacgctaa agacagcacg aatcattgag agcgcagtta ccggaatcac    22680
gctcactgca tccgtaccca tgatcattat agtgattacc accatgattc tctatcacag    22740
agtcgcaaaa cataacgcta cttcattta cgtcatcaca ctctttgcta gcgattttgt    22800
gctcatgtgg tgtgtctttt ttatgacagt gaacagagag cagctgttct catttaaccg    22860
```

```
tttcttctgc cagttagttt acttcatcta tcatgcagtc tgttcatata gcataagcat   22920
gctagctata atcgcaacaa ttaggtacaa aactttgcac cggcgtaagc agaccgaaag   22980
taaaacatat agcacggggc gaaacatagg aattctccta ctagcttcct caatgtgcgc   23040
gattcccacc gctctctttg tgcagattaa cggagcaaaa aaaacgacgg gaaaatgcgt   23100
cgtttatcta tcctctccga aagcttacga actgtttcta gcggtgaaaa ttgttttcag   23160
cttcatttgg ggagtcctcc caaccatggt gttcagcttc ttctacttta tcttttgcaa   23220
agctttgcac ggcgtcacca agaaaaaaca caaaaagact ctattttta ttagtatcct   23280 tctcctgtca tttttactca tacagatccc ctatatagct atccttatat ctgaaatcgc   23340
atttctctac atgccacaga acacctgctt ttggttagcc cgtgcagaga tattgcagtt   23400
aatcattcga ttaatgccac aggtacattg tttctctaat ccgttagtct acgcattcac   23460
tggaggcgaa ctaagaaacc gatttaccac ctgtttccaa tgtccatttt ttcccaaaag   23520
actatgtagt acacagaatc gcaaacagtc agacgtctcc gaacatgatc agaactcgcc   23580
atcagaatcg tcagtggatg aaaacgaacc cccttaaaca cgttttccaa cttaataaat   23640
gctacccaca taaaatcacg tgctagctct gttttctttg ttttgtcttc catagagcat   23700
ggcgcacgct aaaaagcggg cacgacgaaa acttttaact tcgacggacg atcccatatt   23760
gtccagcact tttaccatgc gcccgacaag taagattgca gacgctgaaa tcatttcaag   23820
agaacatgat tatatcgcaa gcaaaacaca ggcggattca aaaaaaaaat tatcgtccct   23880
gtctgtgatt tttgacaaaa ctgtcctgtt tgaattttac ggtataggag acaacaacga   23940
aaaagctatc gtctacccta tcgatccaga tttcttatta tgtgattcgg aaaataattg   24000
caccctatca cctttcttat aaaattttt tctcctgatc tcacgtcaca gttttttttt   24060
tcatatgtct cgcgttgata catcccgtat gaaatattta aggtggttga aatcacacca   24120
atgatcacac acgcgatgga agggtcgaag acattcaaca ttcccacttt cgtcttagac   24180
gaaaattgta acttcatacc cgatgttctc tcacgcgcca acgctaaatt tatcaaagag   24240
gtactcatcc gagactccta caatgcggtt tgtcttgcaa acagctttat tcccatggcg   24300
actcaaaccg tagagcaaat tctgattatt atcacaaagt ttaagttctc acgttcacga   24360
gatctgctca tgtcagtatt tcgcctcggc gtacatataa acagatttta tgccggaaaa   24420
aatcaagtca aacatatgat cacaatgatg aaaagtcttt tcgataccga agaagccatg   24480
cgacaactcg acagagctct tatggggctg tttgtcgatg ctcgtgataa ttcatatatg   24540 cctctctag cattgtccct gcacgaaaac ggcttaccgg attctaaatt cataaaagcc   24600
gtcagattaa tacaaacaac cgtaaactcc tttcataatc gaccggacgc agatatcgaa   24660
cagtatgcag aaaaattacg agcatacaat tacctctata aaatacccaa gtatactctg   24720
aaagaagctg tcgacattta ttccgataat cttaaagatc tcactattgg agttaataaa   24780
aagcccacct tactgtttac gtcttcagat gacgcatatt tatctcacat ttacaacgac   24840
ttactatttt taacttctac ttggaatatg atttataatt gcaaaaaaga gataaggcgt   24900
ttgaatactt ggatcaaata cgaaatcaac tccataatgg aaactgctgt attggtagga   24960
ttccaacttc cagatctgaa ggaaacaatt ctagacctag cggcactcat atcaaatatg   25020
aatctcgtca gccccgataa agaacttttc cctcactaca aactcatatt agcaaaattg   25080
tttgaaatct gtattttgc aactaaggca aacatttgca ttttaccatc cttcataaag   25140
ggtcacctaa tagagttcga ggatgtctta aaaagaagca atgatgacga agacctcaac   25200
tatctgcttc tgaaatctcg agattctgat gacgaatacg atgaagacaa accccccaata   25260
```

```
caagtcgatc caggcagagt agacaacgtg cttacagatt ctgactttt  taacgtaacc  25320
ccggaaaatg ctttctcttc tatagcgatc atgccaattt cttatgataa gacgatagat  25380
gtggaagaca atgaaattca agtcctagag gttgagatgc agagcctctc agcagttgtc  25440
tacgagccg  ttgcaagcaa atacggctta agcctggagc aagttatcag aaagttaaat  25500
caaaatgaag gacggacctc ttctcgtgca tcccccagcc acagtacttc taccgtccca  25560
tactccccc  cgcaaaggca tcgctccact ccaacttcta ttctaagaca aagagtacca  25620
atacgttcca acagcagatc atcatcggtt tctttctcac aggaagacag caatcgtagt  25680
cattactctg acgaaacaaa tattagtgat tattcatatc ccatggcaga tctagaatta  25740
gaagacgaag aacccatgga ggaccatccg cactcccctc aatcaacatc atctaacaac  25800
tccatgtctc gtcaaagccg agctctacaa aacggacaaa aagacgtgc  tcccacaatg  25860
gtcccatcat ctcagacacg aagacaaaat aatgcccgcc ccagacgcgt agccaggcgc  25920
ctaacgaaa  tgatgaacga cgcaaggtta aatcacaaa  taattttatt gactgtgaaa  25980
agtgctttat ctggccaatt cattgtacga aataaaagt  tccattgttt gattgatttc  26040
cgtattcttg agcttgtaga taatttccaa tagaacatcc cgcgttagat gtaactcatc  26100
aacgtaagaa aaaaaacgaa tagcattctg ttcttcatca tcaccaagtc taaggtgact  26160
cttctctaaa aactaaaaaa aaaacacacc atcaattta  ttcaaccaat ctaagatagt  26220
tttgcattaa acaataaatt actgccagaa aaactatagc ctagcaagct agtgaatcaa  26280
atacctaatt ccaatttaat atatcttgaa atctaccata acacgtacaa aatcaaactc  26340
accgcatata tcatattaag gaaaagctgt ttctcttgtc tactggttaa catgtacaac  26400
aacacaatta tcttcctgta aaagaaaaac acatcaatcg gcatacagta gcttgtcatt  26460
ctctcttcct gtaacaaaat aaacaattta tacaatccaa ttaaagtccc ttgtctttgt  26520
atcgaaagaa aactattaaa gcccgcttcc acgtatactt aaatcaatac ccacctttt   26580
acaggaatat tggtgaactg agctacgacg aaacagtcgt ttacttccg  gatgttcaat  26640
ctaaaaaatt gattaatctc ttcccatctt tttaaaataa ataacatttc aataactacg  26700
gatttagtaa ccgtcatact caacgtcaga gccggcaaaa taaatctata catagtagaa  26760
aagtccattt taaatagata tttaacgtat ataatttcgg tatttgacaa gatattcgac  26820
agtgacatta atacaggcaa aggacacagt tcacggcatt cttgaagccg ttgacgcttc  26880
cacacatcca tcctcgtcac agccaaagct ctgttccgct cagctcggca gctctccgta  26940
ttataaaaac agatactgaa tcacacgctt taagaattaa gaatcattgg ctgcttgccc  27000
atccgttagg acatctcatt cttaacacat atccaataca atggtaaaaa aacaggatta  27060
aaaaacaaac aacgacaaat cttatcatca gctgaaattt ttattctgta tactaacatc  27120
caacatctcc atacatcaag ttaaatacaa ctcaaagtat gacgtatcta tctactcttc  27180
atcctcagat gataaatcat aaatgtaatc attcgagaat gtgggcccta gaaaagtatg  27240
aggacacaac ggcagaattt cttggacggt gctaatgttc tgatggaaaa acttatagcg  27300
acgatatccc ctaacaatcc cctgtcttaa aaaagattca aattcgtctg ctatttttaac 27360
acatgatcca attcctgttc cgatcgtatc aataccataa attgccccg  ataaatccat  27420
catcacaaac atcgtcttcg gatacagtaa tgttttttcca atgctcccaa taacatgccc  27480
gtgatacggc atgctctcgt agacatccga aaagaaattc cattccatcc tactaggaaa  27540
atcttctttc ctagtaagaa ataaaacaaa aactccgtcg ttatttttcca aacaagactt  27600
cataatgtaa tgcctcccac tatttttata aacgatcgta gcaaatttcc ataaattatc  27660
```

```
ctgcacatca atcaacgatt gaagaacatc atcaattttt gttaaaaagc gaatgtcctt      27720
ttctcgatat accggatcat aacgacgcaa tccgagaact gcaaatcgtt ccgtcgtttc      27780
cgccaacaaa tacagtgtct cattcacgaa gtcgagacca tagaatcgtt cgtcttctcc      27840
cacaaacacc aacgttttag ttaggcacac atcacgagtc tcctttcccc aggcagaaac      27900
atatccaagt agttgcaatc tctctgggca gcaaagcaat aacgaacctt gtttaaagg       27960 aaaaataact ttattttcac aacaaaaaac gagaaagaca cattacaaaa ctgacacgaa      28020
acactgatac ttacacattt cttgcaactc tgcggcagac tttgtgggaa atggaattt       28080 acacagtgtc gaaatcacca agcaccgact tttcggccaa ttaaactgta tagttaagcc      28140
ggtcttctgt tcaacgtatg tcgataaaga atcacgaaaa actgcaattt ttatatcgtt      28200
taaattcatt agtgcaatgt cataacgagt tttaacatag tcgccgattc gttcgtctgc      28260
catctctacg ttatgaaacc gtcaactacc cctttggacc caaaactaca aataaaccag      28320
ctcgcatttc ttatccatct tttatagcac acagagataa aaaactcaac ttaatcaact      28380
accatccaaa aacaaggaac gtcatagtgt tggactaaaa ttaccatttc gttcgcccat      28440
agaaaatcaa cagagactac cggacaattc cctacgttaa taatatccat ccttgtgtat      28500
gtaaaataat acaatgtaaa caataatgat tcaacaatga ccttggtttc ttctcataca      28560
actgatttcc cgtaaaggaa acgaatgata aaaaatcaca gtcgcggaaa attcaaatac      28620
tcgtcatatg agaaattccc taaatcttta tatataagaa agccacaaac cctcacaacc      28680
tcatagacac caaactttct gaagagcaaa aagagtagca aatcacggcc accattacaa      28740
ctatgttcgc cttcaacatc aacattttct tcatctattc taccggaaga aacaatccag      28800
agattatctc tcaagataaa cagatccata agcggcagcc atcgaatgat actgacattg      28860
aagtggtaag aaatatcaaa aaacgcggat acaaattttt accgatagaa acgcgatatt      28920
tatttaagca ctgttcaatc cttttccacag gcagacttct tacccgaaaa ctacagtagt      28980
cgaatccgta attcccaccg acaaaacaaa acggtaaaca ctttttatcgt tttgttatac      29040 actaatacccc aggagagctc agattttgac tgatctgcac attacgaata ccccagaata      29100
tttacacctg tttgcgattt ttttataggt ctcactgctc cacattctaa cgacactggg      29160
aatgaacgtt atccgtgctt ctctatcaaa tacgcattga cgcagatgag taagttttt       29220 cactaatcca ttttaaatcc gacagaaaaa cacaccattg actatatgta attaatattt      29280
ttttatttcc gcagatatga tttaatccga cgaccactac atgtttract gtccacgatc      29340 acctttctcct taatgcaaat agcactcacg gcactttata gaaaatgtct cacgatagtc      29400
cacaccaatt ttctgaatgt tttcatgtaa tttaataaac atttatttgt atcctaaatc      29460
tttcacaaca tgtttccgcg taatcattga taaacagcat agcaataaca gcatcgtaaa      29520 tgcacccca gccaaaaaga acaacccagc agccgacatt gaatgcgtaa tttcagacac        29580
attctcgtaa tcccttgaaa aatccaacaa cgcttcaatc tccttgtatt tataccaatt      29640
agtccatgca gacttccatg tatttcttaa gaatttttc ggcatcgtat cattttaat        29700 taatgaaaaa tatttcgaat gcacaacctt tttcttgtaa atttcatccg acaattgagg      29760
acagatcatg ctcaggaaat agctatccag agacactctc tcatttaaaa tgttcaaagt      29820
gccattggca tctggcccgt cacttgtcca ttgactcgca ttcatttcag tgctggactt      29880
gagaacaatc cgttccgttc cataaaatag agtcatcaca cctcctgcgc tatgaccttc      29940
tagccagcaa tttacagtac tcgatagctg agcggcattt ggaagccttt tagcgatcaa      30000
agctctgagc atcactcctc taaaataata attaataatc acacgtagaa aagccgtttt      30060
```

```
ttcagagata gatgtgatat ttccaacttt catggcttta aagccatctg ttagcatcgc    30120
aaggttgatc agatatgaag ttctgacaga aacacagctg gaattcccag ctaacactcc    30180
attcacataa caagtagaga tgcatatagc tccaagtttc tgttcctgaa ttaaaactat    30240
tttttgctcg catgtgagat tcgatgtaaa gcagactccc attacaaagg tataaactaa    30300
caaggactcc atagttaact tcttcatgat atttagaatt cacagatcgt ttgcaatttc    30360
ttccaaaaaa tctgccgcat ctctgtggaa tacaatagaa acaaatttga aactttataa    30420
aagaacaaac ccatttaaga cgcggcaaca caattcagtc atctataatc cacatcactt    30480
tcgtgcactc ttgtaccagc acttgccaca tgcatcaagt aaaaacatcc accatcccta    30540
aaactaccct tgcgcgcac gctctcccca tccgtgaaat aattaaaaaa cctacctcag      30600
cacagctgcc gattcatgaa cagcattttc tgggctctta agccaatgaa tgttcggttt    30660
gcattccgat ggagtagcaa tgatacaata accttttaaa ggttttctt gcgccaaaga     30720 cgcaccaccc tgaacatgtt tacaacctac atcatcggtt gccatagcac cgaccactgt    30780
tgtatcgtac accgagtcga ttcgaggatc agagacatca aaggtatttt ttgcggtcgc    30840
ttggacttcc gtttccaaaa ttgactgatg aaccaaattt ccaccgagaa acagagtttc    30900
tgaagaatta ccaccacgt cttcagtttg agtggcagcg tcacacatcg cctcagaccg      30960
atctgtctgt gtatgcctcg ataacataat ttttatacca ggagttttgg taagtccata    31020
gattgtgcaa tggcgagcgg agttgtcttc ttgacacgat aaagccatac acaccgtccc    31080
cccaacatct ttttcgcag atggctgcaa caattcttcc gtcggccaac aaaatggacc      31140
cttagcaccg aaagagtcag actgaattgg tctcatggaa gcacgagcat cttcttccac    31200
gcaagcacca ctctctacct tctgaaaccg tctaggtaat acacctgtca aagaaattgg    31260
ggtatgtctc attctcgtaa aatattttg aaattgatca ctgtattcat cgcgggactt      31320
ctgtgcaata aaattactca agatcgcgtt ctgacacgag aactccatgg cagttgtcca    31380
gaaatctgaa aacgtaggtg acaaataaaa tatcacacca tcttcatatc caagcacttg    31440
accagttgac gataacaaaa aaacaacttg tctctccgga gccgcagatg caccttccca    31500
ttcctccgtt acaccaaaca tactcatcct accctcaaaa ggatacaacc cgtttattaa    31560
taaacatctc aactgacggt cagatagaat atcggaattg tcacagatcc gaactttgat    31620
acaagtgata tgttgaagaa caattccgga agccatagct tcctgtacaa ctttctcaaa    31680
tctcagagcg gaccccgccg aagaaatcat cttatcctta aactgcaaca tgcgcgccag    31740
ttcatcaccg gtgaatgcca ttacgatgtt ttttctcgtt aatgattaag ataatcggcc    31800
atccaaatat gtaagaactg cacaatctta gttaaattta tacgaaaaaa tactgcaact    31860
ccggaaatgg gtgtggcata atctctaaaa gcaccttaag aaaaaaaaca gacactgtta    31920
acaaaaaaaa ccaatttatt taaaaaatct ctgttcaaat caccctcacag tcatggaaac    31980 attttacaaa ggcaacattt ctaacttgac attgctaaaa ctttcgtgag attttattga    32040
ctgtcgttct atatcaaacg aattatttcc gcagacaact gctattgaat catcacggac    32100
gttttgaacg ctatgaagtt ccatgtcgtg attttcagct tcgtagttgc agtattctac    32160
ttccataatc accataggca cttcatcatt ccctctacgc cttttagca ccctatttgg     32220 attcgatgaa gatcccccag aaacaaaaaa ctgaatatac cgcgttaaaa tatatagaaa    32280
catacaccca gcagcaattg gaattacaat gaaaatccac aacagctgca atttattaaa    32340 ttttttttctg tgcggcgctg gaaaattatg acgaggaaac gtgtcctcgg attccttcac    32400
gggattcaca aaacctttga aactaaaagc atcctctctt gttaagagag ctggggtaac    32460
```

```
taataatttta tgcgtaattt cacatgaaaa ctcatgatgt gtcatgctca aagctctact   32520
caatgctctt tcataagagt atagaagttg accggaaatt tcggttctaa tgaaatcgtc   32580
agtcgtatga tcatctgaaa ctgtttgatt gtgaagactc cattgaatgt tcgttccaat   32640
gggccgatat cgtcgagctg tacagacgag caaacctgta tctctcttgc tgaaaacttg   32700
cggaggacga tatttagagt ctccgaaaac aaccttacca tagaaattta agatgtcttc   32760
tacacaaaaa cgtcttgcat aaaacgacaa tacgtgcaaa gaacgatttt gtaaaaaact   32820
gctcacattt ataagatcgt gaacaaaact acgattctca ttaaacagat ctatctgtac   32880
ataggttgta tttctcgcta aaaaacgta gctgccagac aactgcgtat tattgttgac   32940
gaagcaaacc aattcgctta cagaaaaatt ttgaactgag acatactgaa gcccagcgtg   33000
caatctatga aattcacgta ttaccacatg tcctaaaaaa cggtctacgg tagaatttt    33060 tccttcttcc aggcttcccg cgaggtcaaa caacgtctct ccaacagccg tatggttccg   33120
caaagtcaaa tctccataaa gcctctcgta agcaaaaacg atatcgttat caatgccgat   33180
aacggtctga gtttaccga ttccttcagc cagagtagtc ttgatgtaaa gtttagccgg    33240
caacgaagaa acgcattgaa ataaacatgc gacaaaaaca gttatcattt ttaaatcttt   33300
aattcacgtc gaagaaaggt acggcccttg aagaaacagt taaccgccgt agtcaataac   33360
ttattacaaa aaggccacat ggaattaaca ctaacaaata taagtatat tatctccttc    33420 agtcctacaa acaggaaat acccagaata cccacacaaa ccgccaccgc acccatgaac     33480
ataaggttca ccatgataga tgttatctct gcgaatgcta acatagtcga accttcgtta   33540
taaatctgaa tagactttc gacattcttc tccggaagcg taacgataac attatcgcca    33600
ctctccttat tcgtgcacat gcagaaatat ttatccccta cccacttatc caatgaaata   33660
agtccccacg tcacatcatc gcgaaacaaa gacgtatatg caccggacga tctcatcttt   33720
accgttttcc ataccatatc aaacgtcagc ggctcctccg caaagatctc gatctttccc   33780
agcttgctaa caccccaacc tgaatattca caaactgcaa attctccttc tgcgcccagc   33840
cacctagaga acgaacattt caaatcatca gctctgaaca atctttctga agaagatcta   33900
ataaccggca taaaatttag ttttaactcc tcgtcgtaag acagagccat tcgtctaaat   33960
tcgccgtaca actcagatag gactttaacg tcgttattgc acgaagatat caagtactgt   34020
cgatatgtcg agagttcagt ccaaagacgt aacatcgttc tgtcttcacc ctggaaattc   34080
ttatctgcaa tccaagagtt attgctacca tcgaggaaaa aagcaacacg tagtacttgt   34140
ttcttgagat ttgtttcatt cattctactg agtcgtatcg atttttatt aacagagcat    34200 tggacttgaa tgctaataaa tgtcattttt ccatgaccac attttgaac acgctttctt    34260 gcaagatgca tggttgcact actcacggta ttaaacaata gttatgtac gttatgaaaa    34320 acctggaaac atcgaaaaac caaaaacttt ccaaagtcgt attcaatttg actgtcttcc   34380
attcctccgt aaaacacttg gttgtttacc gccgcactac cccataactc cattttaccg   34440
cttctccaat ttctgtatgc agatatctct aagagcatct ccccagatct aaccgcttca   34500
ccgttccctg cgccaagggc cggacaagtg gaaggataga tttcaccccg gacgaacgtt   34560
aagacgcata agaaaacaaa gcagatcatc atgctgcgtt ttccttctct tttgcgatca   34620
ctagcgccca ctaactccag cgatgcaatc tttaatataa gatcgccgtc ataccacagc   34680
gtcgaggggt tacgcccaca tattaaacaa aggatccaaa gcaaaccagc aagaacaaaa   34740
aaccacaaca gcaaaaggt aaaccgagat gcagtaataa acaaagcgct catagcgggg    34800
taaaaagcgt cttctttctt ttcggcagaa tgctacagaa atgaagcaat cacctctctc   34860
```

```
tgtagttttc ctagcgtaat ccactacata cgttttagtt ctaattgact ccatcaccga   34920
ttgatttagt aattgtaact gcacaccgct cggaaaggaa acattacacg tagtatcatt   34980
gtccacaaac acaacaccaa tatttttatt gtatcgacat aatatcttag accccatggc   35040
agtctcgata acgcatcgag ggttaaataa aaaggctata tctctttcga ataagcatt    35100 aataggcaca ctagccatcc gccaccaagc agttccactt ctctgagcca ttttacaaa    35160 aatcaaccaa tgtcttaact ccgtttcact atgtgttccg ataaaaactg aattttcatt   35220
gttaataata tgcaaagacg ctatcaccga cacgtataat acactcaccc atgctaaact   35280
ccaaccctga ggcaccataa tcactagtaa caatctatgg gagcctcatc tgcaagtctt   35340
tgcatccctc ctgatttgca catccggttt attctcttca tcccaaagca aagacctctg   35400
cttgtctttc ttataccaat tatacaaaat aactatcaca attatgaatg ccccgacaaa   35460
actaatcccg caaatccaaa ttactaacga gcttagaaaa tctttaaaat actcttcatc   35520
tccctcattt gtatctgtta actcaggac ttgaacagta tcagtttccc aaagagcatg    35580
aaccgtcttt tttggtgtgg atttcgtcgg caaaccctga ggcgtctttt cagacacatc   35640
ggaaagtgtc gacgctaaga ttactgtgaa aaacgtctca atatcctgcg cctcatcacc    35700
cttgaccgtt ggaaacgaac ttgttgtaac atttacatta ttgccactgg atcgatttgt   35760
ggttcccacg gctagcgtag aggtcaccat agaagactgg tttaaatatg ccacagaagc   35820
tattgatatt tcggtaacat ttttacccca cgtttcggga ttcgccgaaa acgtagtttc   35880
agatttccca gttaaatagt cgctggatgt cgatacattc gtttccatat ttttagacgc   35940
aattgaggca aattcagttg ccgaaacttc tgtagtcgtt aggttgagca tttgcacctc   36000
ttcacagaga cacgcgagta aaaaagacaa gaacaacatg tttttgcgat tacccaagtg   36060
caacggtttt ttaatcacac ccacaccaag atagcagaat gaaaacaatc ttttagaaca   36120
atgttccgca ttagtttta taatacaact cgacgaattc aaattaaaaa cacaaatgcc    36180
gatcataaga aaacacgatt ttgcattaaa ttcagacttc ctcatacatt cagatttgtc   36240
atgttagttt aatagtcgat gcctgctatt ccttttaaac aatagagatt tttcaacgtt   36300 catgttttccg ttcacatcg ggtcagcaaa tgcttctaag acaggtaatt cattttttc    36360 gacgattcac attgaaaacg taaataacaa aagcaataaa caaaatcatt gcgatacgca   36420
agcccgtcaa aactaaaaaa gcaaacgtct ttcgtctctt gttccacaaa ttccacgctg   36480
agcgagatga ctgcggaggc ggtaagcatt caacaaacga tgtatcattg ctagcgtgcg   36540
gagaaacctg tccgtacatg acgtccatca tcagcacctc tgaataggac ggcggcggcg   36600
tccgagggcg atccatcctc ttcccgacga agattcacgt tgaaatacac ggcgaggaca   36660
aaatttctcc aaacggactt aaattactaa gataatcgga gtagacgaga atgcgagca    36720 caaatgcgac tacgagagtg tatgttcctt cccagagttc ctcggcactt ctaggaatgg   36780
ggaatagagt tttgcttata agcaacatgg taaaacaata caacctaccc tctttcaata   36840
caattaattc ccctgactag agacgtacat atctttaata atcctcgatc ccggcgcgac   36900
ctctgacagt gctcacggag aggacagagg acgtctctag aaaacatctc atccacctgc   36960
ttaatatagt ccgtatcttg cgtaaaccat tgcgtatgca accgacgatt ctcattataa   37020
cgcagacatc caatttttaa aaaatctgac atattgcgag ctataaagag aaggctctcc   37080
tcgcggtcga cgcaaaaaag cataccgtgg ccgtcaaaca ctactacgag ctccctccag   37140
tcaccgaaaa aattatgctg tacaataaac actacatcta gtagactcgt ctgcagtttc   37200
ctccgccact gaatcaaatg tttactagaa aacccagtca tgctcagatt gcaaaagcga   37260
```

```
acaaaggtct tgtacggata cgttttcaag gtaaaaaaag cattctttct ttcatttcgg    37320
taatgtaaga gctcagaaaa cgatttactg tgagcaatca tatccagtgc cacagtactg    37380
tccagtgcat aatcacacgt ctcataaatc ggataaaaaa accgcaaacc attagaaaac    37440
aaatcgtgaa aagaagaagc cacgtgataa agacttctgt caaaaaaacc attatacaca    37500
tagatgtgtc cccgcgcccc ctgaaggaca atcggtcccc tgcaggttct ggttttttgcc   37560 ttatgtataa ccccgaccac aaccaattcg ccttcgcaac acatataggt cttcgcccag    37620
ttttgaacat cttcacgtga atatccgga atgttttcta cactatgtag agtcaaccga     37680
taatcctcgg gccagggcaa agctaaagtg gcgccctggc gattttcgat aaaatttacc    37740
aacaaatcga tgtctttgct tgaagacaaa cccataacga tgaactgccc ggctcagagc    37800
aaataaacac aaatttgaaa aacattaata ctgcaaaaaa ttttattggt gtccaccaaa    37860
acaagcacga taaattgtct aatcacacac caaaatacat gcaacacacg actaaacaaa    37920
aaaagccgtt caataaatca cccgcataaa aagatctgtc tttcagatcg ctgctcaaag    37980
tcaacataat cgaactaaac ccgagaccta aaaggcttc aaagataatt cgatataggc     38040
agacgttcat catcagtccc gacaagatcg ccaccattgc gcacgcagca gctttgaaaa    38100
catttagttt aaaaaacacg ttgttgacca ccgtcagaaa aaaagatga ttagattttg     38160 gcatactcaa aagatttttt ccgatccaga gtatcgtaaa taataacaaa aattcgaccg    38220
taaactttac aaggtatttc aaatcaactt cacgaaacga cgttgacttc aaaatcggac    38280 gatattttg caaactaata agaaatccag atgatcgtat catccatcca tatctcagag     38340
taaacggcag gagaaacgca gtcgtcgtca agacagaata atcatcgaac atttgactct    38400
taaaaaataa agacaccatc atccccgtaa acacagcggg ggaataagac ggcataatca    38460
ggacacaacg acttaaaatc attctcaacc tcatctcgga aaaatcaag cagatcatga     38520 ccactgcaga caagaatgat ggcagttttcg ccgccattaa agacagaaac acaatcttga   38580
aatcacctat gggtttataa aagcgtggat caaattttttt aaaagtcaac aaaaaggaaa   38640
tcgcaacggt tatcacaacg cctatctgtt cgagggagga cctcccctct gtcattctaa    38700
acggatacag ccctggaata acggcaccct tagcaagacc gagaataaaa ctatctgtca    38760
gacgacgcat ctctgtctct taggattgga gctgtattca aaatgcatgg aatcgtcgct    38820
ctcgctatct tctttctcat taaataagct agagcccgca gtcccgtttt tagtgggaac    38880
catgtagttg gttatttttat attgcgtttc ctgttttgat gccaacgcac ttccgtcttc    38940
gttcttatga ttcctatccc cttttccgtc atcttgttta cccattcgtt caaagcgaga    39000 ttcctctttta agctgctcct gagttaaaaa tgcttccacc gtcaacaacg tgcttttgga   39060
agttaagatc aatttacagt ctttagcggc taccgtacgt aaactacacg acgtcttgat    39120
tacagcacac atacttaaag cctgctgtaa attttttggca gataaattaa atcgcatgtt   39180
cttaacatcg taaatataa ccttattgct gtttgaaaac tccagttcat tcatctctgt     39240
cacgaatttt atagtcgggg ggttaacctg tactataatg tgcgccatga aagtgtcaga    39300
tttaccagag cgtttagttt tagttacggg cgaaagccat tttaacaccct cggaaacggt   39360 cgaatgatca aggtcaatcc tcaacggcga tttcccgctg tctcgcacca cttcttgtcc    39420
atgcacacag ggaaccgacg cctgtgtaca tgtatcggaa gccgtcacca aaaccctcgt    39480
atacaaatca ctatcatgct gaatgtacat cttcgtaacc tcaggattcg agatgatgtt    39540
cataaaactt tcaaagagtg gaatatgatt attaatggtt ttcgttaaaa agtgctccgt    39600
atctgataaa aacaaacatt ccgcctgaat ggtcagcttg tgcacgagat gatttttagc    39660
```

```
agactgaatt attatcgaag gctgcggagt gaaagtcact gtagtattct cttttaacag   39720
ttttgtaaac gctttaagcg gtttattaat agttttccag cttttcatat gaaaagctag   39780
ggtcggcggt tctctcagtt ctctatgttc ccgatgatca cggtgatcac gatgatgatc   39840
tcgactaccg cgctccatct ctgtcaagaa cgaagtccta gcaccaactc gcgccttctg   39900
tgctttaaaa aacaaatgaa atgaccaaca cattatatac tgtatttttt tggcgccaac   39960
attttattac atcattataa aatgttcttt acgtgcataa ccacaccatc cgagcatttc   40020
ccgatcaacg gtaacggatt tgataaatca aggtgtttat acatctcaga actacacaaa   40080
acctatacat tagcgacttt gaatccagtt ttatacagca acggtagcaa gtgtttcaaa   40140
ctcacagtat cgttgaaata aaatacattt gcctgcccct gatccaaaaa aggcaaccca   40200
ctcttataca tctcaatcaa atcattcaaa ggataactaa aaccatcttt gaaaacagct   40260
aaatcatcca actccttgtc cgtaaataga ttcgtgtcca cgtttaaaac cctatatccc   40320
acagtcttca aatattgctg atgcttatta aatctgttga gcaacagatt gttatacacg   40380
ggaatatata acgattttaa ttctgacgaa taaaccgaag tgacatcatt taaaccgtct   40440
tttccaatta cgactttgat gtttgaccgc ctgagaattt tattgtcttc catcggccag   40500
aacgattcag aagagttgat gatatcgaat tctttctgca tggcagtacc ggcagtgaaa   40560
tgaatattgc gaactccgtg catcagcaca tcttttcctta gcgttgtcca caattcctcc   40620
ggaagcgtgc attcgacatt atcgaattga tcaaagtata acatcccag tgcgtatttt   40680 gacctgtcaa ataaattgca tggctctgct cctttcatgc aacaatccac actcgttcga   40740
acacaagtat aataaatgtg ttcacacatc attcgatata atcgacaagc atctggatgt   40800
gcataggata acccgacggt catgaaaacg gaatgaagac ccgtaataca gatacctaga   40860
cttcgtccat ctacaattcc ctcacgcaga aaatctttat tctctacagc ataatcaatt   40920
acagcattag cgaccaacac catttttcga accaccgcc ttaattcatt aaacataaaa   40980
aatttacact gcaaacgcac aaaatcaatc tcctcggtta gctcatcgct tacttcgtca   41040
cccaagaaat gcaccacatt aagcaacatt ctcaaacaag tgttaatacc gtctctgaca   41100
ggtaaaacat ccaaaaaatc accccgcaa tacaaaggca catgaggaat catagaatac   41160
tgatatacgt tttttcggaa aataagtccc attctgcccc ttttaaaca acggcaaatt   41220 ttttccacaa aactagccat agtaatttt gcatgatctg ttgtccgctc aaactccaaa   41280
tattttgtcg agaaagtaac ttcgtcacac tttcccagtt caaaagctat atttttatga   41340
aaaagagacc actgcgctct ttttagctcg tacctatcca tgaaaatccc aggaatgatc   41400
aagcaaaatg tgacccgaga agtctcaggt agaacttgat acaagtccag ccacgttagt   41460
gcggacacat gccagacttc cacatagact gtcaactgaa ccgtcttatc agtatcacgt   41520
tccaccacct gaatttgaga cagtaatatc tcaaaaatat tcttggcttc ctgttgataa   41580
cgagtcacat tcatgcttat atttgaaccg tttaacaaag ccggaaaaag atgctcgccg   41640
tttactgtta taaaatccgc aagcgaatat aaacatgtat tgtaaatcgc cacgtcgaaa   41700
accgtactat tagcctttc cacgaggccc aaatttgtca tacaagaaaa cggtaaaacc   41760 cattttttgag taaaaaggga aaacgccaat tcttcgaata tcacgtaagg attctcctga   41820
tatatctccc gcagataacc atttcttaac acgatctctg tcaaagtagc acacatacga   41880
agatagatgc atggaatact ctcttcgaca ccgtttaaag aattggaaat ctcctctaaa   41940
aagcgagatg cacccaaaac tcccggcata tattggtttt tccaactcac acttacttta   42000
tagaggacgc tacgaataaa atctcgatac ttctttacaa agttcaatac atttggcata   42060
```

```
atcacattag ggcatgataa aattaaatcg tccggacaaa agtcgtaaaa aatactcgtc   42120
tttagatacc atcttcctag cattcgatcc actcgtggaa cgcaatgtgt agctctcaaa   42180
acagagatta tggcatcccg caaacaccaa gcatctaaac ctgagtcgag ccgatccatt   42240
atcttagcga tgtcacgaac ccgttcatac aaaacagaag cgcatgaata ttgagaataa   42300
caaaaacgtt tttgcgacgc ttcgtaatga caaacgcatt ttctgttgta gccaaaatct   42360
ttattaatac gacgctcctt tctcttcatc ttcagacaga aggctcagaa gctatacgaa   42420 cactttttc tcagaaaggt caacgaatat gttctctagc tttatcaccg gcagggtaat    42480
tccacgatac tgcagaaaac ccgatttaat gtcctccgtt gcgcaacgac caatgcgctg   42540
aacgcttcca aagtaactca gcgtggtatt gctattaatg agatagttca aaaacagaaa   42600
ccgctccttt tcgaaatact gtcgcaagat atcaactacc aggtcctcgt tctgaaaact   42660
ggtcagaact acgtagatcc catactggag ctttgataaa acctctttgt aaacatgaac   42720
cacgtaaacg tactgggtgg aatgctgccg cggttcccag tctggctcta ggaaaatctc   42780
ttttaatacc gtaagcccgt gaatgttttc tttgttagcg tcatagacat ttccttgcat   42840
gacgcatgac aacagacaac tgctgccgca agaaactaag ctcgtcacac caaacaaaga   42900
cactttgtct tccaggtact tacacgtgtt gatcatcgat aacacgttat caaccattga   42960
gtttgtatac atggtagtta aagcggttct cacgcaagca gacacattga aagcgttcga   43020 acaaggaaa aacagaccca caaacagaat tttagggttg tccacatcag tctcaaaacg    43080
atacatcaac attcccaaat tttcgagctc cggagccaat aattcgcaag gcgtgaaaac   43140
ccttgccgct atacgtaaat tctccctgcc ggacaaaaac tgtttcagaa atttcctttc   43200
tttttctaca acattattta aggttcccgc ctcgatagat atatattttc tcttcttcac   43260
agcttccaca gtatccacaa tggcagctcg tgcactcgat ttagagttca ttcttagttc   43320
actcaaaaac agcacgtccc cagaatcatt actagccgct acggcaaaaa tcgagatttt   43380
atccctggca gccgatagcg taacacacaa cagagtaata gctttatta atcgactgcc    43440 cccgaaaaaa tatcactttg accttatcag ggaatataca gttttctact ttttaaactc   43500 tacgaccta acatcagaaa ataaattgct ctccgcagaa cttttacacg aagaactcag    43560
tcaaattcgc tcttcgagtt cgccgggcac agaacttgaa aacttaaata atgcagaggt   43620
cctttacgtg ttcgatcgaa tactcaattc cattaaaatg ctaaaaaatg agttatcgtc   43680
tccaatcggc aaacttcgag tacaacccgc cgccaacgac ccaggtaccg ataaaacgat   43740
aaaatactcc aagattcaat ccatcataca aaaggtacac agctttacac gagaaaattc   43800
acttcttgcc aactgccgcg ccgtcgtaga actgatagac gatctatatc ggaaactta    43860 ctcatggttt ctacatattc tcactttcga ggacattcag tttccaggcg acacatttct   43920
agacaggctg ttgaaaatgg actactgttt tacatattac ccttcttcaa atcgccatct   43980
aatagatctt ttcgaaaaga cgttggacaa tcaaacatcc acagacatcg ataaatttt    44040 tgacacttca ggaaacagtc cagaactact ttatcaaaaa acgtttagct tgaaaatatt   44100
ttcaaaaaat ctcacagccc aggacaatgg attatatatc tatccactac ttaaaaccga   44160
cctgtccatc ctcgacttcc tcggaaccga aaatattctc ttccatcgag gtctcatcta   44220
tcacatactt catcaaaaaa caatccctca agaacgggag aatgatctca ataaaatcaa   44280 tcaattttc gctactgtca tccagcaggt tatcgaaacg agaagctcat gcttacccgc    44340
gtcgttatcc cgactcttag atacgatttt tcacttcaac agaatcggtt taaacataga   44400
aacgtgcaga atctacgtcg agatcctctc aaaccacatg gcgacaccag acacccaacc   44460
```

```
cataatcaat acattcacca tcaacttaat ccatattgtt ttcaccgcgc acgtgttttt   44520
catctgcatg gaaaatttca gcccgacatt cttattctat aataggaaaa aactcatatt   44580
agaacaacag agagccattt tgatcatcga acgaaatgaa tattccacac tctggaaaca   44640
aatatctgat cacatcgact gtctcttcaa catctctctc tccgaatcct tttttaaaga   44700
atataccaaa ggaggaaacg aagaacataa acagtttcta tacaaaaacc tattcgaaaa   44760
atggggtgac gtctttttcc ctttcacgta ctcggtaacc acctcaaaaa actccacggc   44820
acaccatatt acaacccttg agctaagggc catctgcaaa gaggtctatc agagcgattc   44880
cccggaggca tacgaatcgt tacttcccta cagcactcat ccagctttta aaacattatt   44940
cattaaaatc tacgttatac ctatggtcac atacattacc aatcttacct ttgataaatt   45000
acaatctgat tacagactca taactctgat ccacgcctgt aaactcttac tcccctcgca   45060
acatctacta ctacactaca tggtgtggct atacgctttt tccataaacg tagaccacat   45120
agatctaggc actttcaccg taataaagtc cgtaatcttg aaaatcgctg accacataaa   45180
cgtgatgaag catacgatct actcccctga gacaaacctt ctcgtaagca ttctactaaa   45240
ggcgtatacc gactacctta aaaaatacgt aaacccctgg atcaaacaga ccataacggc   45300
aaacttctcc ctgttacaga cgtacataac cttcacgaaa caatgcgcca gcatcttagc   45360
gaccaaatgc aacataaact tagacaatct atttatctcc atgactatcg gaacagaaaa   45420
aattgatacc acttcgtttt actccttcat cgctacatgc agaaatttag tacgtcaaca   45480
cgaagaattc aaaaaatcac taaaaacgat cgaaacttcc aaaaccgcac tcacgaatat   45540
gctactaaac ataataacaa gcgtctcctc ctccaaggag ctgctgacca acgaagcact   45600
acaaaaattc atcgacactg tccaacgcat ctcccaacac gtaaacgaaa cataccagtt   45660
aatttccgtg aacctcgaaa aatgtaaaat ctcaaacgac atcctaatcg aatccctaaa   45720
gaagaccatc tccatagttg atgtactcag ctccgatgca atcctaaaca cgtcgttaac   45780
ttctagatgt ctggaggccg ccacgctcgc ggtttcaaac aattctttca caatactcga   45840
aattaaaaag gacgcagttg ccgttttcaa gccttttata acacaactat ttgaaagcat   45900
gaaacccacc acgagtctat ataagaaatt gatggctacc caaaaattga ccaccgaccg   45960
cattccattt ctcgatatct tcgacgatag gtacaaccta gtcagacacg tcgaacgaca   46020
attaaactgg tacgccgcat atgccgaagc agcgcagcaa gatcttattg cttctcttac   46080
gttttaacgg tcgcgttcta acccatgaaa atcattacca gtagcacgaa ccaaaatgac   46140
tctaaatacg gaccgagagc cggaaaacaa tgcatgtcga acagcttttc atttctccac   46200
actgttcact aaacggaat taacaattct ctcaatgcgg gtactataga cgccataatg   46260
gaagaaggct atcacttaga cacggccagc accttagctc taatgctaga taactcagat   46320
tcgcaagact acagactcct caccgaaatc cccagaagga tccattctag gtacggcgtc   46380
acacagcatg aactctcacg gccatttaac ggaaccctag acacacagaa aattgacaat   46440
gaggtatatt ttggcctcat agatttcata ctgtatggca aaaccaagaa ttgtccagct   46500
tttgcagtca tcacgatcgg cgtcgtatcg cgagcaattt ttttttcttaa caatactctc   46560 tacttattcg actctcaccc gactgaacga gaagccacag cagccatcta catctgtcaa   46620
gacattgaag aagcttatga actgctcacc gcccacggca ctgaaggctt ctactacgac   46680
gccagcttca tttttttcat agaaacctcc aatttgtcgc tctctagtca cgacgccgag   46740
cttcttatcc taaaaactta taagacccc gacatagcga ttacgctaga taaattttct   46800
tccacggaaa tccatgatat aaaaaaaaca gatgatatcg aatcgcaaca agacctcgtt   46860
```

```
gcggctaaaa cgacagatct agaacgcgcg ccccagaaaa gaaagaaaaa ctctcatagt   46920
ctagaactag aactaaatga caagaagaaa aaagataccg catccttgac atattacgca   46980
acggaagtcg acctaattcc gagcttttat gaactacgat cacaatttca atctttattt   47040
cacgatctca aatcttttcc tataatgaaa tctcaattca actggaccat atacttacaa   47100
gattctccca tgaatcctaa tcagcccttc gcaacaccct ttctctggaa cagagttttt   47160
cacttattgt gtcaaatcgt cgacgtgttt gtaggcgtcg gatccacaaa tgacgattct   47220
agcaaacaaa agcagcaaac gattttcata aattatttat tgcctttcaa ggacttttcc   47280
gaagtattca acgaggcgtt gacagcttgt caagaaaaca atctggacat cctcttgatt   47340
tacaataatt acctgtgcaa aaccacgacc tttcgaacac tcgagagaat cttactaagc   47400
aaatttctgg caatagctga taatgagcac gaaaaacatt atgaatgggt caaatcgtgg   47460
accacacaaa tgctccaaga gatgccaaag aaactagatg acatagagaa ttatctaaaa   47520
gcctatgtga gccagaaccc tgtgaaacac ttccatgaat tcgtttgtct gaataaggca   47580
gaaaaacaca acatagctgt tctgctcaac gaaaaacgaa aagagattca agaagatatt   47640
gaacgagaca agaatatttt cgcacaaatc tctaatttta ttgacaaaact cggcgaaact   47700 cccgcacttc ctatcgaatc agaaaacgtg cacaaagttc acgagcga catcactgaa   47760 gccatcgttc cgcgtttcat gactgaatcg attgaattac caaacatctc cacactgaac   47820
aacacccaac aattatccct agaaaaacaa atcagtgaaa aactcaccaa caccatccac   47880
acactcagaa acaaattcac aaaaatcgta caagataact ataacaatct cgctgccggt   47940
ttcatgccag ttaccgaact gaattgccta tttgcctacc tggtaaacct ttattttaac   48000
attgaagttt taaaacacag cggcctaaac attaacactg agttgcttca agaagtggaa   48060
aaactgtatg acaacacgca atttctacgc ttcggaactt ctcacttcaa tataaacaac   48120
ctttcgaact ttaccctatc tatcagaaaa atgttcgtcg atttctataa cagtcaaaaa   48180
ccctcggaca gagcttccga aatcctagcc gcaatcgaat ccatcttagc ggaccccagc   48240
aaaaacaaga caatcgtaaa tatagaaatg atcaaatcac aactggaaga actggggaaa   48300
atggaaatct ccaccaccga aaacaagcaa acagctgaaa tcacaaaaca aatccttggg   48360
gaccaagagt taacccctat ttacgatttc ctgcaccatc tctctgctta taacctacct   48420
aatactacga ccgtaaaaaa tttacacctc catttcatct tagaaaaacg accagatatc   48480
gctgcgattc tccacgataa aatacaatcc atacttgaca tatgtataga cgacatgctc   48540
aatgacataa cagtccctga gcagacgttt tcaaccgttc tatttcttgt agatctcttc   48600
ccaaacagca ccgaaaaaac agcactgttc gaatccgttc tcacactacg gcaattagca   48660
aagaaatgcg ctaacttaaa aactctagaa gaattcgacg atctggccca gttcatcacg   48720
acgaacagcg aacaactcca aaacatgatg aaacagcatt ttggaaaaaa aataccaacg   48780
ctgatggatc atatcaaatt tctctactct caaaaaataa tcaccgctga agagaaaaat   48840
tggatacaga gagcaaaaac agccgtcatt acatctcccg aagaactgac agccttctta   48900
gccactgcac ccactaaaca cgccttacaa acttgcaagc ctgagctcga taagcacta   48960 caacgacata tggaagagca aatgaaacaa actgctgaaa acgacaaaaa acacatcctt   49020
acaatcagaa acaccctcga aaaaagactg aacgacatct tactcattct aaaaaacggt   49080
caattctcgt ctttggaaac agtgcatttg aatctttag aaaccttct aaaacaactg   49140 caggataacg atctcatcat tcacttcact catgcactac tgccagtgtt aaaggacata   49200
gaaacgacca tcagcaagac catctccgac attctcgaaa agatattaat caaaactcct   49260
```

```
ctaaaccccg aacagatgtc caaggaagaa caaaaatata cccctttact cagtttctta   49320
tccaagttca aaaaaacaac attctgcaca gaagatgtaa aaacagagat cgaccaaatg   49380
caaaaaagta tcacgttcct cacgaaaatt gctacctcca ctaataaata tactagaatc   49440
agccactccg tctacggaca agaattaaac ctctacgaag aacgcatcac agagctgaaa   49500
aaagagacga acaaaataaa agaaccgctc tccaaagaat acgcagtagc tgagaaaaaa   49560
attcttctct cgtcacaaga tgcaaaaacc aataaaattt atctagtcct aaatacgcac   49620
acgctgaaag aaataaaaaa cacccaattc agagaaacgg catctgctaa agctctcacg   49680
gtcgaagtca acaacaaaga aaatcaactc caggagctgt taaaccactt taacgcacac   49740
ctaaaggcga aaatggatca gaaccatata acaaaacttt cattcgatac aaaatggaca   49800
gcctttgttt cggattccag gctctacttc ccagacttcg ttgacatcaa actgcaggac   49860
tttatttctg atcccttaa agttataagt cagctgatga acaaagcagc caacgagatg    49920
ccttacattc aagcagagat aactctcaaa tggttaacac aattagtaca cgacatcaac   49980
aaattctgcc tgtcagctat aagcgaattc gggaaagaag caatcccgtt caattacgcg   50040
gccctacgag atttggagta ccagattaac accaagtacg tagaaattga aaacaaagtc   50100
atctgcaacg aaaccgtcga gaacacgaaa acattccga  aactgactaa gctcttgaag   50160
gagttagatc ctaaacgcgt tgccggtggc cagaaacagt atcaaactct catgaacaag   50220
attctcactt ccgaaacttc tatgcaacag acctacgaaa agaacaact  caaaaaagaa   50280
tacttcgaga ccgtcaataa tgtcgccagc ttcaagttag cattcaactt tcctaagcaa   50340
cgacaaaatg tggaacgact aatggagaag ttcaagtcgc tgcccaaaag ccagccattt   50400
gaaaaatttc cagaggaaaa tgacctattt tctgactcac tcatcacaga aaattatatt   50460
aacggtctgc gcgcactcct caacttcata acgcgtgcgc aaaactacat ccagaacaca   50520
cttctgaaaac aatgggcggt atttcagcaa caaaatttca tcccgatcga tgactcagta   50580
gcgaatgtca agcctatttc ggatttatat gcccgcctca ggattgaacg ggaccgtcaa   50640
gtgttctacc aagtaaactc tgtctttgga actcaactaa ttgttgacga aacaggagtt   50700
ccgctgcaat tccacaacat cttttacaac gccgtagtga agttttttctc cctgaactac   50760
aagcagattc atgtaccaga agacaccccc cgcctggtat ctagccaata taaactcctg   50820
tccgtgtgta aatctttcat aattatacta cagcagttct gggagaatat aatcactctg   50880
gacctaggct ccgacctcag agacggtaca caaaatttta aaagagaact tataccgaac   50940
gtgaacttga aattatttat atacatcata acacaagcct ggacagcatc tgaagacagt   51000
actgttttcca cagcgttcga attgcccatc aagcaattca cactttttgat actatgctca   51060
catcctgaat atctctacgg ctgtctcagt catccaacag atctggttat aaattcatta   51120
gccaaaagca tagacaaaga cagtctctat gacacattcg tcgttagcca caaccctccc   51180
gagaagccca tgcatttgat gagaagtata tgtatcgaca cccagctatg gcaatccgcc   51240
aaacttatga aagatacctt ccaacaaaca tttttttacac aactgtgccc ccaaaacgaa   51300
aagtttttta tctatctcac tgccttctta attctcccct ataaatttct gaactatatt   51360
tggattcaat acaaaccgat cacttttacc caaagatctt atcaaaactt aattaaggac   51420
ctatgctccg aatacgtaca ccaaaataag atcaccatgt cctcggtaac tcccacgaa   51480
ccggacacaa taaaatccgg agaaaagatt acctcaaaaa tcaccgtaca caaagcacaa   51540
aacacaccga cactcactcg cctgcaggct caggaatatg tcttcgacta cattctttac   51600
tctttcttga cgggtacga  aatgacattc gctatgtaca tcgacaccat cgaaaaaaca   51660
```

```
tacctgctttt gcatgagaca cctggaaaac gtactccacg ataaagactt ccaatccgtc   51720
ctcagagcac gcacattcga catcaactac atcctgaaac agtcatggac taagaacata   51780
gtcgaacatt caatctttc agtacagctc aataaaatcg tctcctacct caaccacaca    51840
aacagagcga cacccaatat tccctgata ctatttaatt atgacaacga agttgtcaac    51900
gtttatctac cgccgatgtc caccaatcca aaaaagtcg ctttctacat aaaaaatcct    51960
ttccactttc ccgtgcaaga atacgaagcg acagatttaa tttcctttca tctctaccca   52020
aaaacaacag atattttaaa ccaacttccg cccaataaaa ctgtgtctac tcgcccatac   52080
aaccttagct ctgaaacttt aaccaccaaa aacctctccg aaccaaagtt taaacagcct   52140
accgttactg gacttatgcc caagagccaa tcaatcatcc tatccactga taccaacgta   52200
ctggaaacca gtccagacat aaaagctaac acggccagcg cagcgataaa agatgtcact   52260
ctagctcgag aacaaatcag cgagttctcc gaatcgataa atacaactct ttcaaaatta   52320
aaatctttgt atctgtaaca ttcgacacac aaagtcatgc tccttttata aattttatt   52380 agttaaacat acgaaataaa tgaagctttc atcaatcact ccctgttttt gtgttcagtc   52440
tatgcagcgc cagcattctt atcaaatcga gtcggaacgc cgttttatcc acgttaccgc   52500
cgttctgctt agcgtatttt ggcaaaaaga ccccaaggac gggatgattg gccatggtag   52560
gctgcagccc taaaacaccg gtaagcatct gctgcttctt cttttcctcc tcttttttg    52620 aagaacttcc tgaaatctga gtgatctgat tcgacaaatc atcaccacgt atggtcgtca   52680
tttcaaatac acctcacgtt ttgggaaatc tgacaacctt gacagatatt aacacagtct   52740
tccagatcta agcaagtctc tctaaacgaa tgctgacaat gctgacactg aaaatcagaa   52800
ccgtgtgaaa caagccgtaa caacttcttg acggtcacgt tgtagagatg cacagtagaa   52860
taacaggatc tacacgaaca aggaacaata acatcgaact tcacattgtc atttaaaata   52920
gtgcaagcag aatttgttcc gatcaccgcc ttccatgaaa cagttttcac cttcatcccc   52980
aatacacaat gctcagacat ttcatatatc cgctcgaaca ccaactgctg actcccacac   53040
agcgaacaat acattacatc cgtatgcatg ctgtatatca aatttttctc ctgcttgtct   53100
ctaaaataga acatggagct caacgaaaag ccctgcggcg aacacaactt ttcttttccg   53160
gagtttaaac agtgaccaca ttttgcacaa ataacgcaaa tgtaactctc ttcaagtata   53220
aaccgagaac atttagtctt acaatagcac atgacgggta acgaaataac actggtagct   53280
aagccatcct ttaaggacgt tgccagggca aaggttagaa tctttggaaa atcaccccgt   53340
tcaggtttgc tcggcaccat aggtactaga ttattatgct ccactggaat aagatatctg   53400
tctgcgctaa aacagaagtt ttccaccaaa gccttcgcca tagtaaacat gaaattcccc   53460
gccggagatt tcaaagcata cttttgcaac atggagggaa atgacaaaac gtgctctctc   53520
tgcctatatc gcaacatcac cgtctcggtc tgctcatagt cacgtaaaca gaatagcctc   53580
atacacggta agttgacgtg cgtcggaatc ggaagcaaca actgttgctc gaacagaaac   53640
atgtgcaact cattgatttc ggaaaacgag ggcatctcca gcaacttatt aagcttgtac   53700
gagggataaa ccctaaatct agtctcgacg tccatccatt tgattctttt aagtttataa   53760
agagacaaca attcgagaac tttgcactgc cgatacacga aatacagata ggcgagcaaa   53820
acaaaaagac cctttgtcat aaccattttg ttaaaaagtc gcttagtgat aaatcgcgtc   53880
tccggcctgc aacgcagcca aattgcaaaa aactcattat aaaattttc cgttacttcc    53940 ttattcagga atttttttatt tgtcaagaac attgtaagaa cacattttcc tggcacacag   54000
gcgtcaccca tcacaaacaa ttgcaaatga gtgtacggcc catgtttaca caaccgggcc   54060
```

```
agaagctggc gtaggagttt ttttaagtag aacataacaa aaatacaagg ctaaaagaaa    54120
gcagatgctg acaatcgcaa cccgacaatg cctttcactt agtctcgaaa acttcacacc    54180
ggacaggaat gacttttctt tttcatagaa ctggtttata ctctcctgtg atgtcacaac    54240
cgcagaagct ttatttgcaa tttctccgct acttccgagt tgcccctttt ccaaaacatg    54300
tgaagacctt cttcgcaaac cttgacaaaa cctattcgat tcgagatgct gtttccccat    54360
agaacacttc tttaagaaaa ttgccttcaa aagcgaaatg tattcagatt cgttttcagg    54420
cccaaacgcc acaaactcca caacgtaagt ttcgtctcga ttacgcctaa ttatacattt    54480
cgtgaacact gcaaaagttg aaggcttcat agccactatg tcgctcatgc gaacagtcaa    54540
acattcatta acacgcagaa tgttgcattc tctcacagca tgatggcctt ctgctttaac    54600
cggggcatgc aaataacaag acatcgacac acgtccgcct gtgttttga acacaaatct    54660 cggttcctgc ttagttacat gttcccagag actcaacaga tattctagat tataagcgta    54720
gtctaacttg agaataatat cacacaaagg aaatttcgga ttttcgaca ataaattccg    54780 ctcagtcatc ctatagtcat gagaccccaa ctttaagata cgacaggtcg cactcagtag    54840
ttcatcgtac atcttttctt tgagtacgtt agccatttca cctatttaaa agctattccg    54900
tatttaaata ttcttgatgt tctaatattc catttacatt taacagcttt gacaatatcg    54960
aagtgagaag tatgattttc tgagccatga cctctcgatg cacgcaatcg acatcccgt     55020 gaacgtatct agaaaaagca acgtgtctat atccaacact aagaaaattc agtcgcgcct    55080
ccaaagaagg aagcatcatt tcatataatc gtggcagcat tggataaaac acgacctcaa    55140
actcccttcc ctgctcacag acttgctcat acaaaagttc aagattcgtc ttttcaggtg    55200
aggagtccat catgtacaaa ggatgggact cagaagcgtt gtctatacaa tctgagatag    55260
taaacgagat tctgttatat tgctacctca ctccccaacc accaattcct tccgaaacga    55320
caacagccac cagccccacg aacatagaaa acgaaatctc caatttagaa agctctgaaa    55380
acctagagga attaaagcga ttatccgtcg cattaaaatat agacagacga tgcaatatct   55440
gctccatcgt aaatctgtgc ctcaaacaaa acaaatcatg gatctacgac tacagtctac    55500
tgtgctacaa atgcaactac gcgccaaaga ctccattgtc tcttctgatc gtctccgcgg    55560
aatttataat gttaatacga gaacgatttc caaacatcaa ttttgacggc ctttttcaga    55620
acaacattgt ctccatcttt gacttccacg ttcatttttt tattcacaga tgcttcgcaa    55680
atacggtcaa cgatcacatc caaagcgaaa acataaccct gatcacatgc atatcgatcg    55740
accctactaa aagagacagt ataccgcaca tcaaaataaa aaaatttcta accaaaaaaa    55800
tgaacccgaa aaaaacacaa aaccccgaac tgaataaaaa actcacagtg cccatgaaga    55860
ctcgcttcac gacactctta ttctatatgt ggtctggcac aaacgtcttc gaccgagttc    55920
ccttcacgga cctaactatc cgcaaacatc gcttcatcaa aaacctgtat tccaacaaaa    55980
ccgacatcga actcacagct ggtcccattc tattggcaca gattccattt tccatcacca    56040
aaaacaaaac aaccagcgtc tgtctgctat gtgaactgat ggcagcttcc aaacaagatt    56100
acctattttt aaaatatcta catcaaagca tcatggacta ctgtcaaaac aacctaaaga    56160
tgatagatag agttcagttc gtcattgccg atatcttcga aagacaaaa atacacatgc     56220 acgtcaagaa tctttccgac tacagcaagg cgatattcga taacgaattc tcattctccg    56280
atgataactt cactctcgat acccacgttt acctgatact ccgccagact ggaacagtgg    56340
gagtctataa gcacttcttc tgtgatcctc tgtgtctggc aaactgtaaa accattaacc    56400
cggaggttct cttcaacact acagacgccg gagaaatcca agacttgaaa gtcaccatat    56460
```

```
gctaccgtaa cgaatattta agcatcgtcg aaaaacatgt ttggctagcg atacatcttt    56520
tcaaagcttt tcagattatt aaaccaaacc ataaaaataa aactcaaatt gcagagtttc    56580
tcaaagactt cactaactta ttagcgcttc accacttcga tatcgtcgat cccattttca    56640
ccgtcaacta ctacgtttaa agaatgactg tacacaaaaa ccgttttcga cgatcgcgaa    56700
gcctgtccgt gacacacaga atacaaaaac gacctgatca cagagaaaaa acaaagcttt    56760
acttacaact gaaactccac gatctacacg ccgtcttcaa cctgtttcca gaatacgaac    56820
agaaatttct agcgatcata aaactgccaa ttaccggtaa agaacccatc gacgtcccat    56880
tcagtctcag caatcaccat caacacacct gcctagaatt ctctccctac gctaacgaac    56940
aaatctccaa aagcgcctgc ctacactgcg aatccgtctc cgttccaacc tcctcagatg    57000
caatggtcgc ccacttgaac caagtcacca acgtcatgca aaacagattt tacttctacg    57060
gctttcgaaa ggacatggag ctgatacgca tgtccgccaa acaacccact atctttcaaa    57120
tcttttatat tgtccacaac acgatcaaca acatattccc tatcatgttc gaaaaaaaac    57180
aaaagctcgg aatgcacata gttttccagt ctcgcactct gcacattcct tgtgaatgca    57240
ttaaacaaat aatagcggta tcttcgggct acaacgttta tctagatata ctacaagaca    57300
gtgtaatcct aactgtcctc tgcgaaacac tagatactaa tactaatatt cacattgaca    57360
tagggatgct tcaaaaaaag ctcgaagaaa tggacatccc aaacgaaatc agcgatagac    57420
tcgaaaaata caaaggacat ctaataggtt tccattaaac cactttattg ttaacatgta    57480
caaacgacaa aaccgaaata cgttcacatt acctctgcaa tagcagaaaa cgtttcatcc    57540
aaatacactt tcataggaag taaatacaat agtaacttct ctttttttat atcggtcttc    57600
ggaaaaatgg gtgaaatcgc attagtcaca gccttgataa tctgatcgaa atacttctcc    57660
gcatgtatag gaatcttgtg ttctaacaca tagtttggat cttctgctaa ttcatagtta    57720
tgcgtctgtt tattaccagt agatggtgct attaacacat acataattcg gtcaccaaca    57780
ttcggaattt cttcctttct ctgcgccaac cttctaatga cgctaaggtg agccagattc    57840
ggctgcttat atgcagccac ctccttggaa agcacagaag acaacatcaa atgtctcacg    57900
tctgcccgat tttgaaaaag ctcctcccgc gctttgcaca gacgacgcaa aattttatga    57960
atacccacag gcactccttc gtcacgcaac tgtgtttgcg tcatgtgaga aaactccaca    58020
gcagcagtct gaacctcttc atcaaagaac aacaagtcca cgatgtcttt caccacacct    58080
ttcacaaaat cgcaagaagt ctttctcacc agatctaccc ccttaaaaat taaaagcgag    58140
tcatcctgtc taccaatata tcttttttta caaatcaaaa tgagcggaca taaaatcttc    58200
tcgaactcga gcttgatagg cgatttgaac aagcgatctg tgatatgttt ggcgatcatc    58260
ggcgcaatcc tccgcagaga ctcattagcc atatttctga cagacataaa gatgctatcc    58320
gtatcaccat agattacctc cacttttaaa tcaccagtaa aatctgatgc cgttagaccc    58380
agttcttcgc aaaagaattg ctcggactgc atcttggaat taacataatc caccgtggaa    58440
caaagcatct ctcttccaag acaggttaca gaagcagcaa tcgcaacaca cggcaataac    58500
ccgtgcgccg ctcccgtgac accgtacacc gagttacatg ttgttttgag agcgagctgc    58560
tttttatcca gaaggagttt catcattgga tccgaacagt tttgcatctc cgccttcact    58620
tctcgtctct tggccagcca gtcctttagt agacttccaa gcacagactc gcgaacacaa    58680
ggcttcacaa accgatgggt ctcatccccc aacttcacgg ttaagatgtc actctctgat    58740
aatccagcta tttgccgttc atccaaaact aaggtactat aacacagatt atgcgccatc    58800
ataatgctcg gatacaaact ctgaaaatca aacaccacag tgggcacagc ataataaccc    58860
```

```
gtcttaggct ccaagacggt agcccctttg taacctatcc cttgtctatt atgcgaagac   58920
accatactcg gaagaatcat gttacgacgt tttgcttccg taagaatgca gggaaatatc   58980
ttcttctgct gaccctcgaa caccacacat ctagccgtga cgtgtgccaa tctggcgacc   59040
tcggcaacct cataatgata attaatctgt ttaaagagac gcacaactaa gacagagtcc   59100
tgcagacaat atttaccgac aacagccctg ccactgggtc cgctaataaa tttctttggt   59160
atttccttgt acgataactg ctcttttttct tgctggagac agatcttagc aatagtatcc   59220
agtttgtaat tctgcgccgt tatcttacta gaatagactg gatacatatc cagatataac   59280
actccggaag taaacacctt ggtttgcgcc tgaaggaacc ccttcttgta ctgttcatgt   59340
ggaacagaga ttccaatctt tccattcttc agtttagaaa aacaaccaat ctcatagtgg   59400
taaatcttat ccatccttat acacaaatat tttaaatcaa aattgttaat attataaccg   59460
gtaataaact ccggagattc aatccttaaa aatatgaaaa atcccaaaag taattcaaac   59520
tctgacgcaa attcatatat atgcacgccg tcaatttgtt cacaggttcc cagagtaaac   59580
agatgtctct catcacggtc gccctcagta tcgaaactaa ctacagaaat ctgaataact   59640
atatcaccca aattttcggc atccgggaaa ttcccatttt ggcccaaaca ctctatgtcg   59700
aaggaccagc atccatataa gggccaattg acgttttcca aagaaactaa atccgagaca   59760
tgacagttaa tttccacctc aagattactc ccttttccca tatcttgagg aatatatttt   59820
tttacattat accatccgaa actcaaaaaa ccattatcga cgaagaaacg agtcaaaaca   59880
tctacatcga tttcataaac tacgaatccc tcattctgca gaatcttccc aatacgttga   59940
gatacataaa aatttccaaa actcacttta aacagattaa caacagtgtt ggcattgtac   60000
ccatacaatg acaacttatc agccggctca atgacaaaag aacacgacat cttaacctcg   60060
ccggttaaca tcaaattgtt tatagtagcc ttcaggcttt ttccgtcgac acattcgcag   60120 taaaatatt gctcctgtcc aaacacgttc acacaaatct tctcaccgtc ctcagatctc   60180
ccaaacatcc taatcactgt ccccgaagga atcacaaaat gtctatactg aaaaggaaga   60240
ttctcgatcg aatccgtaaa cattaacgtt tctacagcat catagatgtg gaacttcatc   60300
ctcgtatgat cataatcctt ggaccgaact ctgtccaaac tcggccaagt catttctttg   60360
ctcagtaaat actgtcggtc tcgataaaac atacgcggtt cagagtcaca acatcctttt   60420
attaagcccg cagcaccatc atgcattata ccgcgaggaa gtatacgaat gtaactcgat   60480
ctgctttttt tctttaagcg attcgcttcc aaatatggat taaaaaatga caccgaatcc   60540
atcacgcttc ttctacattt acactcttat aacctctata cctgatcctg tctatcaaac   60600
taggttttga ggcatgagac tcagaagacg aaggttttct tctgtaggac tcgtctaaag   60660
actttatggc cttgagcatt tttaaagcat cttcttgtga atattcatca ccacttattt   60720
gtccactgac gtcagccata ccctcctctt tttccgaaac cgcaacagat gtgccccgt   60780 cagcatcttt aacactaggc gtcttgacgg cagtggtccc cgtaacactg acacagtag   60840 tcaccggatt ggtggcataa ggaaacatca tgtcaatagg cttactaagc acatgttttt   60900
gtctaacgaa aaccacaatt attataacaa caactactat cgctaaaatc aacatgagac   60960 caccccgaa tggatttttt aaaaaagaca ccactccacc cacaatatcc ccaagtgctc   61020
ctgccgtaac acttataacc gagcccaatc cagtgcctat agcccaagc ccttgtaaaa   61080 aagaattaat cccattgaca tacgacggcg tattagtagc aattttagct tctatagtat   61140
atagtgcgct cttatatgag ttatattcac gaagaatatt ctctaaatcg aaaacgtttg   61200
ctctactcaa ttcgtccggc gaatataaat caagtagttt aaaatcagca ttttcgagag   61260
```

```
ggtcaatctt tagtctaata aaagcatcca atacctcaat gtcttctatg ggcgtcgaat   61320
tcgtatgcgt ataatcggta tacacgtgtg catgatttcc agatagaaat atctttgtac   61380
taggtatctc acattcctct gtcctatgat cacccaacag aatctcatta tctaaccta    61440 gctgaccagg gacaacctca ggcgtggagt tcacaaagct aaacgtcacc aagggccgat   61500
tataacacac cgtttcactc cttaatccct tcgcatcgac gacccgcata ctcttatgaa   61560
gctgaacgga tgactgatta acttctatgc atttcgagat agctaacaca tcaccatgca   61620
actgtgcaga tatcggacga ccgtaaacct cagacacgat actcgatgga ctgatcttac   61680
taagttcgtg caacatcgtt atcgttcgtt tttgatcgag gcaccaagat tctgccaaat   61740
tccccaaggc atcgttgata taatctttca agtatcata gaggtactgt aattgcacat     61800
aaagaatatc atgtctagac ttgacatcca ccaaatctcg cctcctacgt aagtttactg   61860
aaccctgctc aagaaccata agagattttt gcacaagagg ctgccaaatc aaaatcagat   61920
ctcccgtagt cttaaaaatt tgataactac cgttcatgct gtatgtatca ttataatctg   61980
acatatagac ttcttaatt atattctcaa attcattctt aatacacgtt tgtttgggt     62040 cggtaagatt taaagaatcc ttgggggtga cgaaagcggc tgtcaactcc ttagaaataa   62100
agtgataagt ctcatccgtc tccgctcgaa gcccgtgagt caccgtagtc caatgcttta   62160
gcatacacac cgattcattc tcttccttga tttcccaaga aaacagagta tcccctttct   62220
cgagaaaagc gatcttcctt actaacgtag tagccccatt cataccattc attagatctt   62280
ctatcatagt atagttttcc aagattgtca attttctaa cggctctgca aaatgtttac     62340
cgtttgaacc gtcgaagaac ggagacccttc cacgatttc accagtcgtc aaagcaaagt   62400
aactaaacgg atatttcgcc ttagccgtag cctccgtcac aatacaattg agagacgtcg   62460
atgtagaata gagccacaaa ggaccccttg caaagtaggg ttctttcgta gtgataaatc   62520
ttttattagt aacagacttg aaattcagag gaaataattc tagagtttcg ttttattat   62580 tatcctcatg ataggcacta acaccgtac catcgggtcg ttttatcgct acggctgaat    62640
aacactgcgc acgagaatta actaaatttg cttcgtacat cggcatagcc aaacccatca   62700
ccgtccgatc cagaaaataa accacaccca catcacggta actggtttgg aacgtcagct   62760 cgttttata cgttctcact ggaaaagtgt aggtctcgat atttgttttg taaatgatga    62820
aaaaaccctc cgacatcttt gcattagact tatatggcga gcacgaaata tctctgtcga   62880
accgcatcaa atccgtacct ttggcaatcg aacaaatccg aaaaggatat ttgtgattat   62940
agcccgctct gatataatta tccgaatcgc aatatatcat taaaacacta ttcatcaaaa   63000
agacagccag gaataatact gtcatcttgc tcattctccc taacgagatc tagtagatta   63060
ggcgttcgaa cagagtaact tactccttcc ggcacgtcta tagtctccct cgacaactga   63120
gcttgcaaat cacaatataa cagcgaatac acgtctttaa actttgtcat gccaccaccg   63180
gtgtgaaata atagaggaga ctcgtgatta aatgtcaaaa cgacatttcc attcaaatcc   63240
tcctcctcat ctatacgtac aattttaat cgctttccga aaacatcatt atatagtgca    63300
acagaaagtg ttaactctct gatgaaattc cacatttttt tctgcatgtc atttacatca   63360
gttacaccgg aaaagttaaa aaactcatta tattcgcaca ccatccacac cctgggatga   63420
atagtgccct ctatgcattt cgctaaatct tccttcatat gcggtaacat ttctgcgtgg   63480
tcgcaaccat acgccattga gatattcgcc ggaagtggat aggcagattt atgaaaatcc   63540
gataacggac ccgttaacaa tgtgtacata atctcactta aatccggcaa aagctccaaa   63600
gggagcttct tcggcatcag attatttta atataaagat gttcatcgta tgtacagcta   63660
```

```
tctacacgaa gagagccatc caagtacatt tttctgagaa cgaaaccgtt cataatcttc   63720
gataaagcct caaaaataaa attcccatac acgttcacac tcactacctt attgatgagt   63780
gattcctgct ctcgaataca tgccatcacc ctattataac cagattcaga aacctttga   63840 aaatacgcct ttttccgagc caagacttcc tgctgaagat tatgagtttg aagcatgcaa   63900
ttgatcgtgt tcagccttcc cggtgtttct gtcgtctgtg gatcccgaat gtcatgcaac   63960
agactcttaa ttttatgttg aacctcatct tcctcagcca atcttttaaa tattggactt   64020
tcctcgagat ttttaatgct cagaccagtg acaagatcta tcaacctcga aggagacaca   64080
taaatagagc caacgtacaa gcgctcgtca tgcgtgagca aattttcact caaagccaag   64140
aagtcttcag agacttcacc gtaaagataa agactaacat cattctgtaa ttgcttatac   64200
aacgtatgac aactatttaa ctgctgaagc gtaatagcaa catttcttac tatcgtttct   64260
gatattttag accaatacgt aaactcactt aaagaatata tcacgtcagg taccttgcta   64320
aaaatattat acttttcag agttttctca gcatcactaa catgcaacga ttcggctgaa   64380
cgctgctgct taaaaatctt cttgatttca gtcacaacag actgaatagt cccatagttc   64440
aaaatggcct ctcctaagtc ttttttctatc gtctcaatat ttttttcaat attaaaaaaa   64500 gcttttttgct cggtcaaatg attacagaac tttccatgta atcttttccg aagtgatttt   64560
ccttggtttg gagtcaaagt caattcttca taacacttca tgcaagtctt ggtttcgaga   64620
taactctccg gtttcgcaac catacatgcg ccacacatga tagttagcaa gtctataatt   64680
tttccgcaaa tctgcaaccc ttcttggggc agaagtaaag catatacgga gttgatctta   64740
ctgattaatt gttctatatc atttagcgta gataattgca cgataaactc aacaccgtta   64800
tttaatgaaa tgtttattga caagtgctca gcacaacgtt tcaaacacaa caccttttca   64860 aaatatttt ttctatcctg gtctaccata aagctttcca acgctgcatc caaaagaagc   64920
acctgttcat acatagcttt tagcagcacc tgcatataaa ccgtcaaagc tgacgcacaa   64980
agaagattct gttctttgat accttcaaaa aaagtttgat ataaatgcag aatgacaatc   65040
ccattctttt tgaaatttgc catatcagac aatactatta caggatcaca aaactttaaa   65100
cattcaaggt ccaaagcaca ttcattaagc ctagcgcaca acacacacag agattgtaac   65160
gaattcatac tctgattata atcggttttt cttagtcatc ggctcatccg tttcggtttc   65220
cgtttcatca cattttaata caccgcttgc ttgatcgtcc tcctccgcta gaatttcaga   65280
aaagtcatag accggagcat cgtttgaaga caccgcctca ataccgact gcaaattagc   65340 tattgaaaaa tctctcacat tcatatcaac taagtgattc agtttaagca ttatggatgc   65400
cgctaaagct tccctaccat ccacaaaaaa aagcatatca tccatagtcg cttgtcctc   65460 cctatccctc atcacctcag ctattattaa taattctgga tcaatatcgt tagttaaatt   65520
ctcaacaatg ctgagaacct tgcccttgac cacttccgta tcaaacataa ttgtctcacg   65580
ccgaaccttt ttcactataa cttctgagaa ctttgtagca ataatcgttt tctgcctcat   65640
aaatctaaaa tcttgcaatg cagaagaggt agggtttaag ttcctatcca cgccacttcc   65700
acctatccaa cctaactggc caaactgaaa atattccccta ttagccaagc tcacaaattt   65760
ctctaatgtc aaaccaaatg taaccaaaga tcgacttgta aaaattgtac caaaattggg   65820 ttcttttggac agtgacgcaa tcacaggatt cggaacgcca tccaaaacta acttttaac   65880 ataaactaaa tattcctgaa tagaagaaaa tttaggctgc ttgtctaaca ccacaggaaa   65940
caacacagga ttctgcgtaa ccagcttaga tgtaagacca tgtaagctag tcaagtagtc   66000
atgaaaacct aaagccgaca aaaacttgtt atgaaagtaa caatctataa aagttgagag   66060
```

```
acactctggc tgtatgtcga taatgtctat ctcatcatag gtattcgtaa tactgaatgc   66120
aaatttgata aaagtcttaa cttcttcggg gttaccaata tctaaagttt tcggaacatt   66180
gttgagcaga aaacgttgcc ataactctaa gcacgaaatt ttgacattcg gaaacaattt   66240
atcatgatat ttaaataaaa gaaaggagat acagccagac aagggattct tcttgtgttt   66300
cacgttcttt ttaaaataag gattgttgtg tgctgtctta ctggacttgt tgaacggtct   66360 gtttttatt ctaaaatctc gaagacattg catagacaaa cggcaaagtt tcgcctgaat    66420
cgtagttttc acatatttac ccgatttata tagatcgcaa tctaagatct gctccatatc   66480
aacattcgaa gcgactttaa ccgttctcgt attcagaaaa ccctttttga gataactgct   66540
gtgaaacgtt ccgtacagtg attgatactg ctgaacgagc catttagaaa ttgaattacc   66600
agtacaaggt ctgtcgacaa catgacctga agccactatc aatgcgaggt tctgcaaaac   66660
cgttaaaatg accttataat atgcaaacgt caaaaaagga gaaaatgcag ttgcataagg   66720
ggtcgtatct acattaaatg attgtagaca atttttctatc tgttctctag gcgtttgtgt   66780
ccttctcatt tcaacaatgc atctagaaac acattcctcg atacattgtg tcaatccgtg   66840
gattatagaa acaaaatctt ttttacttcg gacattgaaa gtatcttcgc ctgttacagg   66900
atcaatcaaa gaattttttt tacagtaatc gaagatctga gatacaaatt taccoctgtc   66960 cagtgagagc gtgttttgtt gatcttttcc aatctctttg agctcgctga caggcttcct   67020
gccaaaagaa cctaatatat caacctcggc ataataccga gaaacatgc tcataacaag    67080 tggttccttt ttaacatttt ttggtattgc cggcaaacga gtaccaaccc gcaccatggc   67140
agttccaata cacgattgac aacatttccc atcacagaat tcacataaat tcgccgaaca   67200
atttaccaga tgattgtaaa tttcagtgta cgcattaccc gcgttataaa cgctcatacg   67260
atttaaattc cacactacat aagaaagcag ctgtgggcaa gtcgcacagg cataagccaa   67320
gtgattagct gaaaatttgt catctttgcc tgatgtcgaa tcacatttga tgattttct    67380 attatcgtta tacacatcct cagtcaaaga cgacaacgca ttacaaaaag acaaagatcg   67440
cagcagtaat tcttgagtca tcaccgaatt aaacgcttgt ttcacgtttg gtataaatgc   67500
caattttgag caatataaga tagaatttgg cgcaaagatc aaaacggcaa gatgactaga   67560
cagatgtaac tttaaattcg tgagctgcgc catgcgttca gcgtgtgtct ctgagtttct   67620
tatgattggc cagtcattga aattcattat ctgactgggg tcatacaccg aatccaggta   67680
ttcggctaca tgactaaacg ataattctgt cacaacggaa tcaaccaaca tcaaaaaatc   67740
tttctcgacc gctgaaattt tctgtccgga gatacccaga taagttttgt ggggtgctaa   67800
tttgacagtt tgctccccat cctgtgtaaa ttgtttcagg ccagcatcga ttaattcctt   67860
agtattagaa aatcgtaacg ttgtacccca tgatgtaaaa acataataaa aaagcgtttc   67920
acttaacgca ggcagaaaaa atcctcgttc ctgaataaat tctgtacagg aagataaaga   67980
aatcgtttct tcagtttcaa ataaagttgc agagtataga ggaattttca cacacgaata   68040
ctccccaact tgtacttgaa tttgttcttc aacacaagga attaacagac cagcgaacaa   68100
caactctttg aaaccgtttc cacacgcaac atggcaaata acagaatctg catctttgcc   68160
gacagcagaa caaagagctt tgatatcgat tactttgcgt gctgtaggca cctcaaacga   68220
ctgcaagtga aatttctgtc tggttttgctc acataatcga ataagatcac catgatcttc   68280
ggccatacca actaactgct cagttccatg gaaaaaaaaa cacacgggca taaaagacgt   68340 aatttttagtt agaattgtgc ctccaaagtt agtgataggt gttttaaccg tggtcgagaa   68400
atcgttttct acagtcaaat tcattaacaa cggcgaaata actacaggag aatttctctc   68460
```

```
cattaacgat aaaacagata aaacatccaa aagttctttc tcttttggaa aaacatagat   68520
ccaagcagca gtagaaacag gagcagaaac caccgtttcg ttttcatcag ccatctttgt   68580
ggattcgatc acaaaaacaa agataatggg ttttgtggt gaaatcctta tatattatgt   68640
ttgacgtaac ataacgcgcg tcatcaaaca taaaagtaaa ccacaagttg aaatataccg   68700
ttttctatat gagttttacg gacaaaagaa aaacgatttt cttatgcaaa tattttccac   68760
gcagatgaca tgacacgccc cttaatttaa atttatgtaa atcgtcgtcc acctcaggta   68820
caatagtata ttatatatat agtttttaa taaacttatt gaggacggga gaacgaaggc   68880
gtggcgttta cgtcatagcc taattataca ttctcagaac aggatttaaa aaggctgcga   68940
gcggccggct gttcagaggg acgctgggt acgacttgag acgtttgact gaaaatgatc   69000
cttcgtgtac tattttctac aaaaaaatta atttgccggc gacagtaaac ttttcagcgg   69060
aatttcaaaa attaattcca catgtaattt aagcattta aaacgtataa ctcacaaggt   69120
gaaaacatat ttacgaatac agtagtttc gtgatatttt ttaaaaatta ataaatttta   69180
aatcgtgtaa gtaataaagc atactattag attcttcacg ttaacagagc aagctcttcg   69240
aggttttcag tagaatttca atatttaatt ccacatgtaa tttaagcatt ttaaaatgta   69300
gaattcacaa agtgacaaaa cattcacaaa tacagtagtt ttcacggtat ttttgaaatt   69360
aataaatttt aaatcgggta aatggtaaag catgctgtta aattcacgtt aaaagagcaa   69420
gttcttcgag gtttgctatg tgtttatcag tgaatgtatt tagtatttca attttagatc   69480
atggttcggt aaagatataa gtccgtgtaa aattttttgg tttagttttc atatctacta   69540
gactgtgagg tgttgaagt cgatggttta gctcatgtca aaacgcaatg tcaaattgta   69600
ataagtcgtt catttcgtgt ttagaaataa ggaattggta tttagaatag ctttgtcgca   69660
tttttagccg cgacgagaag gttatgacga cgttttcgat tgcattgttt gaacctttt   69720 cggagtttga atttaccgtt taaagaaaaa cagtttcacg aatagaatct aaaacaggct   69780
tccaaatttt agttaatatt tatttcgatt ttcacttggg gtacagaaag ctttggcatc   69840
gagatttttt tgatttaaa aagaaatagt tcagagtgtg acagcaaaaa cctttgtaca   69900
aaacatactt gtaagaattt gtttacagta agatagttat tctgagtcag aagaaatgt   69960 gtttaagtta gtttcacagg tgtcagcttc atagtctaaa tctaagtcca tttcaacact   70020
tgattcactt tcatgtttag agttgacgtt ttcattaatg ttaataatca caatttcgtc   70080 ttgtttgct tgattgaagt ttagttctct aggatctggt attttgttgt cggtttccat   70140
tgattcttct atgagaattt cggtagttgt ttttgtcgtt gttaggttg aggtgtctgg   70200 tttttcgacg caaactttgg atttaacctt aggcgtacct tggtttttat gtgaacgatg   70260
agaggtctga ggtaggtcgc gacttgttga atagctgcat gaaggttcca tgtcgacctt   70320
tggacaagta aaagaaagat ttcggtattc gtgaggaaga tttggaaaca gcttaaactt   70380
tggtgcgtct ttggcgaaat aagtgcagaa aaatagactt ggtttccaag gagccatgat   70440
tcgttcgatt ctattttgac agctgacatc atcgcattta tggttgctga attgctttcc   70500
gatgagcctg cttatcagac cgcattcgta tcgctcggct acacgttctg tgtcgaaatc   70560
gcggatgaat tgcggtttct ttgttcgtat gatatgttct ttaatttgtc gtagtattcg   70620
agcgaacgtc acaacgatgg acatggcttg ttgaattggg tgtctaaatg agtctggagt   70680
ttgttgttgt acttcaaatt cggagttggg catctctcga tctagtacag gtttaccgca   70740
gagttgcctg agttttcggt attcgatgtc gccgtgtccg ttgtcgttga aaacacaggt   70800
taatttcgcc atgttgagtt tgttgaaaaa ttcgaatttc atgacggtga tggtatacat   70860
```

-continued

```
gaataagtct tgtgggttga ccggtaggtt gtgcagatcg tgaaatttaa aataactgca   70920
ggcttcttct actgtagcaa ctgtaaaagc aagacaaggt gagttggtca gggagaatat   70980
ccggtcgccc attagttgct gattttcttc tcgcgtgagc gagtcgagac attgtcgata   71040
gcgaagcagc aggtcggttt ccagtatgtc attagttagg agacagattc gttcatgcgt   71100
ctgtggaaat ctgtctcgga tgcgttgttt tggatcacgg gcgtctccgt tgtaaggtct   71160
caggccaaga gattttatcg aaaagtttgt gtcggcaaag gggactgttg gaaggttagg   71220
cagaaaggtg attgcattgt tttgagcgcg ttttctttgt tgtttctctt cgatgatggt   71280
cttcagctgt tctaactctg tcagacttag tgcgtctagt ctagattcat ccagttgttt   71340
cagaggtgcg agttttcctc gaaaattttt ggcgaaatgg ctgatgaact tgctggttgg   71400
tctatgcgtg atggaacgtt ttatcgttct gaaggcggtt tgtttatgac gatcatgttg   71460
tgagcgtttt actccacgag gatacatgtt tgcttataat aaatgaaatg acataaattg   71520
gcctctttat atgttttttg agatgctttc cgttggcgct ttttttgcggt taagttgtgt   71580
gaaagaacga aggacggtgt tgctaatgct ttaatctccg gaaatgctgt gatatggcgc   71640
gatttagtta gcatgtgcgt tggagtcaaa tggtaaatac taaaagaagg tctgggttta   71700
taggtagtaa gttagttttt taattgctct aaggcgatgg aacaatgtac ttgtttgctg   71760
ttggactggc atttagtagc aaagcatgtg ctccacaaga tgagaattaa ccgatttccg   71820
tcggctttga gttgtatgta aactaggacg ttatctcgat ttcctctatg ttgtctgttc   71880
aggcagctaa aatccgaaac tcttccaaat tgtgttttttt tgatctgaag gttcttttgaa  71940
tctattttga gaaaagttac ttgtgaaaac tgttgcgcta cctagtctc gtaatgagta    72000
attaattgcg ttttaatgat tggccatccg attaatctaa taaacgataa aagggagtca   72060
tccgctgatg ttgcattgtt gttaaaacca tgcgtgttca ggtacttggt gattagagtg   72120
tctgtagcta tgttaacttt gttccacagt tgtctggatt ttaaatccat gaaacttagg   72180
ttttcttttag ggcagccttt atccgttatg ctatagatta attcttcgat gggagccttc   72240
ttagtaccgt gatgtagaag gttgtttaaa tccatttgca tctgaataaa cgtcttgcaa   72300
gaatttcggt aaccttctgg gacgataaat atgggagtta gccgtccatg tagcatttttc  72360
cctttgtcca tgtctgtctt gtacatatag cctattctga tgcagtgacc tgtgtggtaa   72420
atgccgatgt cgaaacattc tccgggaaat gttagggaat tgaggatctg actaagctct   72480
tgatctaaac acataacgtg atttaaaatc ttggataatt gttttaatgg ttctccccccg  72540
gcgatcgctg tgccattagg taatgggatt gatattctaa gaccgatctt tttccgacaa   72600
atacagaatt gtttgatttc ggttggatct tcagtatagt ctagtgcgtc gttagtcgtg   72660
tcgcactggg ttttgaagaa gaagatggga tgtgtgtgtg tgtcgatgct tggaaaaatt   72720
ttttttccagg cgttgatgag ggtaagtctt atgaggcgac acatcgagaa aaatgtttcc   72780
tccgtaatgg ttgctgtatc ttgcagcgga agatccaagt ctcctatgta atttgtgact   72840
ggtatgcgtt cgttgaatat ttcgtgtcgt gtagtataga attgttttttc gaagtcgtcg   72900
cagagaaaat gtgtgtcttg tagccagatg gcgcgagtta gagcttcatc agagatatat   72960
tcgtcgggga gatactgtaa gatgcggtta aatcccatgt tttcgtacca atcttcagag   73020
ttcccgaagc aaaaaatatt tttatgtaaa agctgcactc tgaatacagg aaagggacgg   73080
tgataatctt tgtgtaggtg ttgtcttctg tagatgcgct tatcttgtat ctgaacgtat   73140
ttatcggaag cggagatttc taataatcct tgtaatcctg gttttactgg agaaaaaaga   73200
ccttctccgt ttttattaca tttcgctatg gcacgcgtta tttgttcgga agttaatgct   73260
```

```
tggatggtct tcttttaga  ggccagagca tactcgtatt ctgtaacgtt tagatctgga  73320
tttttcagtc tttttatatc gatgtatgtt ttaaagtaac aatccgcatt gaagtattgc  73380
ttcatgatac acagtaaatt ttcgtgcagg gaatttccaa gaatgtggac atttctctgg  73440
cattgttgtc ctattggtaa attagagtcg taagaagtga tattgcagta attgacgaat  73500
tttgtcgtct ctagggccgt gttgtaagcg atatatatgt aatggacacg gaatgtgttg  73560
gttagatgtg aactcttct  aaatagattg atttgagtgt ctagatattt aaattcttcc  73620
ttatcgcgga gattttttg  tctggcgtac gttgcgaagt ctgcaaatag ttttctaaat  73680
tttgatttca aagtaatgtt tataaattcg gacatggaag aatacgtgaa caccatgctt  73740
cctgtgtttt ccgtaaagca ttgaacataa tttttggtag ttgtgatggt gctcttttgt  73800
tcctcgaaca aatagtaata catcgttaat aaaagcagac cttctgtttg cccgtaggtc  73860
gatagaaacc aaaaggggga agtgggcaat aggaatttac cggtgagata tttgataatg  73920
agcgatttgt ggaaataggc catgtattta aattcgacgt cctctttttc ttttccagtt  73980
tgagataata tcatgtcgac ataaacaat  tcggtttctt tgtcgttgag gctgttggca  74040
acatcttcag cctttatcgg acttgcagtt tgtatgtagt ggctgagatt taatttctcg  74100
gcgtggcaga cgaataccgt gtcgattcgc tttgaatttt tgcatttttg agtttgaagg  74160
cagaagctga cgttatttga tggtttatat ttaacaataa tcggaaagat taaatgttca  74220
ctgggacttc tacataggat actaaaaatg acgtttgcgg catcgtattc agtcgcaaac  74280
actacgatgg tcattgtgta gagctctgtt gattacagat gaatttggct ttaaatgccc  74340
ttagggtatt ggggtgttat gggaaattgt tttcgacgat tatctctgtt tggacagccg  74400
actcaggcaa attatgagat gttgtgctct tccgacgatt tagaaagtga agagctgacg  74460
tattttctgg atatgacgta taagattttt ggagtttatc agaatgatat tataagtcat  74520
caaaaagaca cggaaactat gaaaactctg ttaggtttat taccaatgta caaaaaaact  74580
aagctcaggc ataccattat ggagcgatgt ttatccaatt gtcctaacca cgttaaagat  74640
gcactctgtg tagagcttat gaaagctgaa aaaatattac aaacgatgga tgtcgttttt  74700
atgaaaactt taattggcga gttttctatg tgcaccgata atcttaatca gttgcttaac  74760
aaattcgcta cagatcagtc aacacttagc gatgtcgaga aaataaacag tctcatagag  74820
attgatggcg aaaacagcaa gcgtctttta gtagagttgg atccgattct ccatgaggag  74880
acaggattat atcaagcgct gccaaatgtt gtgacggaag ctccgagtga aaaggttaaa  74940
tcgatacacg tcgagtctga aggtgagagt gtatggtcaa gcgttactga aggcggcata  75000
atgaaacaag aaaaaggaac tggcgtctag tacctgtagc cggtttattg cgcgttcagg  75060
cattaaactg aggcagaaat gtccgcaagt aaaaattatt ctggcgatgc agatgcctgt  75120
agggatgtag atagttttgc gtgtagagtt gaagatcttt atggagggaa ttgtgtcttt  75180
gttccagatg taggtttcaa tcaataagcc gagtttgata atttctttgg agggaatcat  75240
gagagccttt agttcatcgg cgcaaacgta catggcgtcg aagcattgta tcgtatagct  75300
gttcggttta attataaatt ctctgcatgt ctttagatgg aaaactgcag attcgggggg  75360
agacagattg atcatctccc atggttccgg gatgtagcaa gggagaaagt tgattgagaa  75420
ttcgacatct cctgggagaa gcattaggga gtgctcggat aagttcatta gaaaactga   75480
aatgtcggtt tcgtcggtta taatttcagt gatgcattcg cagaatacgt cgttgctatg  75540
gccaataatg actccgaaga aaccatccgg gatgcacagg gaaatatcta gttttacgat  75600
tcgaacttga tcgtgcggca cccatatgag ttctctattt acgagtgtga ttttgttggc  75660
```

```
gtccataaaa acgtccattt tactattcct gtgatggctt actaagatag atggttcttc    75720
cgaaatacaa gtgtccgtat ttgcatttct ttttgcgcgg tgtcttgggt agaaagttac    75780
tgggttgcca tgtttcctta catagttaac acaatcggtt tctctttgct tttctctttt    75840
gcaggtcttc gacactgttc cattttgcgg aatacctaga agcgagattg ggcgttgata    75900
agaggttagt tcgttttcta gaaattttt aaatgatttc tcatttatag ctggccacac     75960
atcgtgcgtt ttgtcttcag atatgtctgt agtccaaagt tcattgatgt ccacgtttcg    76020
aaagacgaaa aattcaatgt atcttgagct cgtttgtctc tgtagggtaa tcgtttcaga    76080
gatcttttct gaaattacgc tgtacatttt tccaggtgac agagggctgt ctgctgttaa    76140
tcacgtcgac gcgaagacta gttcaaaata cacttaaga tgagttgtaa gaaaggcgca     76200
aggcaacgct tatatgtcag tctctggctc ttttacattc ttgttttgc ggccgctacg     76260 gaaatggact tttattcttc agagtgccat tcgcacacct atgagatcgt cttgaattca    76320
ttttcttcga tctggctttt gataaatctt ttttactct tgtgttcttt tgcgattttc     76380
ttgaagtact ggtgttataa gacttttgct tcagagacgg tgaagggcta ttagatcgca    76440
tgagacgcct attctaatta taaatgtagc acacgacaaa taaaagcatt ttttgatgta    76500
attggatcgt gttttattat ctccaataga tttcataacg acaaaagaca aacctgattt    76560
cagaattgag ttttattga agactgagga tgagtagctt tgacaaacgt atgcggttat     76620
gtgctatctg tgttgtttaa atcgtgtcgt tcgttgtatg tgtaatgcgt tgcattttgg    76680
gttgagtatg ctttggtagt gaggttatct ggatggttgt gtgagttttt atcggtgacg    76740
cggtagtcgt ttccaggcag agttttgtta gcttcccgac tttctgtgga acttttttt     76800 ttaacgtccg tagatcgttc cgtgattgtt tgggggtaga tgttagtcgt ttgtgacgag    76860
acgtgagctt ttgttagttt ggctgattga gttctgttgc tagtcgttag ctgtgttgtg    76920
atatgatttg tcgaccttag acttgtattc gttaatggtt cctttggcgt tgttagtaag    76980
tttgaccagg ttagaatggc agactttgaa gatgtcgtta aggacgtttc agcggtgaag    77040
ggccattgag gtgtagtcga ttttcccat gtgtgagcgt taagaattgg tgtcattcgt     77100
ggtatttctg tgtggttgat ctctccgtga gtggacgccg acattctatt ttgctttggt    77160
tcttcggtga ctttagtgat tgagtgtgat gaattactag atggtaaagc attgttagtt    77220
acctgtactt cagttttggc agttacattt gacggtagtt ttttttttgg agtgacagac    77280
aacgtctgaa cggtaggtgg ctcgcttgag gatttcaaag ttgtcctctg gaatctgtcc    77340
tctttgaagg ttttgacggt ctgcacttct gtgctatggg tttcgttttgc gtattctgtt   77400 tggttttta cgttgagaag ttgggtagga tttgtgggtt ctttaggcgt gattcccatc     77460
gtttctccaa gagaaatttt aataaaattt tcggtcatgt tttgtacttc cgtgttgtgg    77520
ctcatgtatg tgcgcgccgc gtcttgccaa gtggtaaact ttaaaatcgg agtggtgtgt    77580
tcggtgtcgg tgaattttgt cgtgctctgc tgtgatttgc tcttaagata aatagagttt    77640
tttggtgaag aatagatatt gtcgctaatt tcctcgattc ctattgttgt tgcgaaggtg    77700
gtgctttcga gcttttgagt cgtgtttgtt gccactgtag tgctctcaaa cgtttcggga    77760
attctgattg tggtattttc aaaatttgtt ggttttggtg gactttttgg gttttcggta    77820
gggttttcgg tgttttgttc ggttttaata gtggcgttac gacggattgt aagagttgga    77880
atgtcagtcg gggtgtacat cggtcgagga aaatctgaac gtttaactac tttttttgatg   77940 cttttccgttg tttgcgttgt tatggtgggt gtgttcggtg taacttttat ggtgtctgtc   78000
tgcagttctg taaagttttt tgttacgggg gaaggttctg gggttggtgt gttggtacta    78060
```

```
gggatatgtg gtgatgtgat agacgctgac gtcgatgatg gcgtcgatga tggcgtcgta    78120
gtcagtatcg aatgaaagtt tacgatggct cgtccaaagg aagtggtaac atttataggt    78180
tttggcgaat gttcgaaata ttgatcattt gaacggatgc atgatgttgt gttatagagc    78240
aagaagtaaa caaagctggt gtaattaaag aagatttcag gagtgaacgg agtcaatgac    78300
cgtgtcagat tcgagttgga aaatttactg attgccatct gcaaggattc gtcggtcagt    78360
tttatgtcaa ataactgtgt tcccagaatt ttaaacggta gtagctctac gcatggtgga    78420
tctgcggtat atgtagatag tgtggcaaac agaagataaa atagagaaaa actgctagcg    78480
acgatagatt tgtttgcagc tgttgaggat agcactattt tggtttctgc ccgcggtaaa    78540
ttctgtaatg gagacaagtt aaccgcagac ttgcattgta aatctcgaat gttccaagag    78600
aaaacgttag ttaaaatttg agtgaagcag tcgaggdata gatttctctg acaaaaagtt    78660
gtatacaagt ttcggaggtc gtaaaaatgt tctctttgtt cgtcgctcca attgtggcgg    78720
ttgacggttt tgaaagcttc taagggatca gatgtgtatt ttattagatt aacggagtgc    78780
atgactatcg cgaaagggc cagaaaaagg ccgagtcgcg agatgtgaag catgtcgggt    78840
gagttgacca cagtgaattt ttacaaggag aatgtgtaac taaatagta tttgcttttt    78900 ttatagggtt ggacgatgac ctccaaatgc atgctgtgct ggactgcgat tgtgaatgcc    78960
ctggctatct taatgttctt actagtaatt tatcgggcgc taatcggatt taatgacgat    79020
attttcacga gcacgttgtc ggcgtttagc tgtatacgga caaatctatc taatgccaaa    79080
tataaataaa acgtttattc aacacaatct gatgagtcta tataagccga ataaagcaat    79140
tattgcgatc agaacataaa tgataaccaa tatgatagat acttggtcta tatcgattcc    79200
gacttcagac atctcaaaaa cagagccgtt tttggctaac aaaaggtagt gcgtcctggt    79260
gttgggaaca agtaaattgt tgtttgggatc ggtcagtgtt tttagttcgt ctatgttttt    79320
tatgtagatg tattgtaagg gaccgtcgat atcatcatat tccatgacta cgctctgaca    79380
aaactcgcat gtttgagatg atatgtttcg tagcacaagc agatcttgtc ctgcatattt    79440
ataatttgtt gaaacgcagg tagaattgag aggtatggct gtgattatta tactcgtagc    79500
cacgattgtc gttgtaattg ttaaactcac tcctttaatc acataagagg gagaaattac    79560
aaatgtcaca ttcggcagag gcagagaagc tgctggctca cttggagaga gacactgaat    79620
ggccgctact ctcgccatat ctggcggtct gtatacggat agcatctcca tcatgtctga    79680
tcgataacgg tcgagggaag cgtacgtgag aactgttttt acaaagaat tgttacatc    79740 tctgcgtacg ggagaggcac aaggcgaata aatattttct agattcggtg ccttgtcagc    79800
tgtaagcatg tgggcccatg aaactatttc tacggggtta cacaggtttc caattagtag    79860
ttgcatgtgc ctctgcatgc gttcatcggc agggatgaaa ttcgctattt cggctagcat    79920
gaatagagtt tccctatcgg aaaatgtcag attcgtaaaa aacatgtgtt tttcatagat    79980
cttttgtaga gtgttggcaa tgtcagacca cttgtacctg gaaatcgtta cattggtttc    80040
gtacgctgtc gctaagtacg tgagcagcgt agatacggga atggatttgt ttttggtgat    80100
gtagctatag tccgagggct cgtatttttaa aaattccttc attttttgggt attgtatcgt    80160 accttccgag acgttcacac atcggttgac aaatgagtcg atggacaaga gattttcgtg    80220
tgtctttaac actcttaaca cgggcatcgg tcctgtgttt tttgtgctat atgagaaatg    80280
tacgataccg taaagaaaca tcatctgcgg tatgccggca tagtcgggtt ttttacagtc    80340 tcccccttaat agggtttgga ttcctaggtt attaaatttg agtagtagag cttctacttc    80400
atctacgtca tccaacgttt cgtctacgaa tgtcgcatct gatatgaaac ggtattcttc    80460
```

```
atcgactacg tcttttttcga ctatcaatag tagatcgtct gtcaatgtct gtttgaatat   80520
gaatgaactt ttcctataag gggctttaaa gtttatgtcg gtggtatttc catacatcat   80580
agtcagatct cctgcgggat tttggatgta cagtatcata aagtccggag taaagaaatg   80640
ggtatagatg ttttcgcccg catagcgtgt aattttagcg catctaactt ggactggaaa   80700
gatcagttcg ttgagagaat taggcagctt acaggaaacg ttgtcgtatt gcatctgtcg   80760
gacttccaca accctgatgt aataaattcc gtgtgaaggg tacaggttta aggaatagac   80820
aatctgcggt tggatagagt gatccaggtt aaattgcttg accgcaggta cggtagaaag   80880
tcttaaaata tcgttcattg gcggctcata gaaacgtgta acgcgttttt cataattggt   80940
taacgattct gtcgtgttga tggcatcaaa cagatggtac gtgatatcgg atccgagtaa   81000
gcatttaggg acttgatata tccgagtgtc gttttttgta taaaagttaa agttataaa    81060 gcccgggcga acaattggat tttcagagtt tccattttta caatgctct cgttcgatat    81120 ggtccacggt ctccaactgt aacagggagt caacagaaca aagacccaga gtcggaagag   81180
catagttgtt cttcatcgat gaagtgtgaa agggttctgc tattctttga agttgaaca    81240 cttttttgatc tttccatatt aaatagatta caaaaatgat gtgttatgga actcggaatt   81300
gtttctaaat tctccgcgtc tttttttctc cgtcaaataa catgtctttg acaggtttgc   81360
ctgatattcg gaaaaaaatt ggacagtttc accatttgag gatctataag cagatcttat   81420
ctttgcaagg aaattttgcg cgactaaatt attttttagg agatgtgttt ccggctaatt   81480
tgcgatcggc atctgtctcg gtgttttttcg aggtgcgtct agggccacgc attccggatt   81540
gtatcgtctt gctaaagagt gtagatgcca aagatgagtt tgcttttcat tgttatttttt  81600 ttgagtttaa gacgactttg gggaagtcga caatgcagtc tgtgcatcac aactgcattc   81660
atcaggcgca atatttgcaa ggtttgagac agttgcatca gtctatttcg ttcttggatc   81720
aatatttaat tgcagacgag gttttgtgga acgttgttcc cgtaatttgt tttttcaggc   81780
agtggggact caagttagat tttttttaaaa agttttcggg gaagaccaag cggttgtcat  81840
tttcgtttat atgtgatttg ttcgctaggt ctcaggatgg cgcagtgcaa tctctttttat  81900 caatacccaa ttcaccaat tttagaaggg catgtcagaa acatactgat ttgtacagaa    81960
gaagatatca gaaggcttca aagtcagtcc tcactaagac ttcgggagaa aatagatcaa   82020
gggcatcgcg acaagttgct aagaatgcgc ctaaaaaccg aattagacgc actgcaaaga   82080
aagatgcaaa aagacagtga cgttttgaat tctcatttaa aagcgataga ggatgctttg   82140
ctgtttacga atgatgggga ggtaaacgtc gaaacgaaag ctgatacgca actgttaccg   82200
aaatctcctg agaggctgga aaaatttaat caagttgcca taaccccact cgaccccttt   82260
ataagattta cagacgattt tagaggagaa atgatcaata cttttttcaa taatgctcag   82320
atgtggaatt ttacgttcgg gtcttggttt tataagctca agagggtttt ttacaatgag   82380
cctggcttaa gaagggcttt aaaaattact aatgtggatt ctttgactat ttcgaaagag   82440
ttattaacag ttaccgtcaa tgcgttggag caagcgacgg tgtatcctat attcggaagt   82500
gagatgtcag acctggaagc agccttgtgt atcctggcag cttttttattc cacttatgag   82560 aattcacaga tcgacgaacg tacaaaccta gtagatatta taacccttct gcccgtgata   82620
tttagattac tcggtagtga aattacagca ttgaaaaatg tctctccttc tggcacctat   82680 tttggatttta atgatccttc ttgtatgaaa ttttttttgttc ccatgagaaa aggcaagcat 82740
tatgcagaaa acacatttgg gaatcatgtg cttgtaaaga tgttgctagg tagaggagtg   82800
atgcaaaaaa ttcccggtga gaaagacagc caaaattttg atgttgaagc tcgcttacac   82860
```

```
ggagccatta agaatgatgt tctggtgtat tggacgtatc agctaatgag accaaaattg   82920
ggaaataatg ttccaatctt tatacacgat caacattatt tacggtctgg cttggttgca   82980
attgaaagtc tcttttatt gtggcggatc ttgaactcag aaagtttgtt taacaagaga    83040
gttgggaagt ttctcctgac ttcgattttt ccacagctgg agaatgttga tttcgccgaa   83100
aataactttg aagctgggaa tattcaaaat tttgaatact taatgcacca ttacgttgtg   83160
cctatgtaca acctgcagaa tgacatatca atttcgactc tttttcccgg tctcgtggcc   83220
gtgtgtgtaa atgagagtgt gagattggga tgggaacata agtgtgcagg ggctccgtcc   83280
gatgccgttc aggttcaatc taaagaaaat ccgttcgtgg agtatatccg cgcacaaatg   83340
gaacaacagg cggatgtggc tatacttgaa aagcatgact gcattctctt tcattttgaa   83400
aacggtttaa acattactct atcttttaca ttaccgagac agagattgtt tgcaatggcc   83460
tcttcattat ttaatgtaaa tgatacttat gatttcatct attttctagt tttaggtttt   83520
ctgccaatac cggccattat ataaggcggg atgttgttgt gttgattacg tcaatacgga   83580
tggggttttg aatataaaga cttacagagc ttttaatgaa tcattgcttc gtttcttcgg   83640
gatggagaaa gaaacaaagt ctttggcttg gccagccacc gcggagtttt atggctgggt   83700
attcattttt tcgtccatcc agttgtgtac ggtggttttc ctgacggtta gatttaatgg   83760
tttcaaagtc ggtcgagaat acgctgtgtt tacatttgcc gggatgagct tcaattgttt   83820
tttacttccg ataaagatgg gattgctgag tggacattgg actttgccgc gagattttg    83880 cgcaattctt ctctacatcg atgattttc tgcctatttc tcttcgtggt cgttggtgtt    83940 tatgcgatt gagcgcatca actacttctg ttacagcaca ccgttgttga acgagaattc    84000
caaggctctg gcaaaggtgt gtttcccgat agtttgggtc gtatcgggag tgcaagctct   84060
tcagatgctg aataattaca aagccacagc tttgcagaac gagactggac agtgttttct   84120
cgcgttttta aggagcggac acgacatgtg gttaatgttg gtttattcgg ttgtgattcc   84180
agtcatgctg gtgttttttt acctatacag caaaaatttc atgcttttga aagatgaact   84240
ttcgtccgtg actacgtatc tctgtattta tttgctgctg ggtacaatag cgcatctgcc   84300
gaaagctgcc ttaagtgaaa ttgagagtga caaaattttt tatggtctgc gcgatatttt   84360
tatggcgctt cctgttctaa aagtttatta tatatccgct atggcctatt gcatggcatg   84420
tgatgatcac accgtgcccg ttcgtttgtg cagtatctgg ctggtcaatt tatgtaagaa   84480 atgttttttcg tgtacgcggc gcgaaaaggg gtcggattta gaggttggaa taaaaatgtt   84540
aaaatgagta aggagtttat cgtttttatt cataagagaa taaatcttcg gcgctgattc   84600
ctgtaaggtc aaatatggca gaactgtcga gaaactgtgg gttttcagac atgccgcaga   84660
agactttaaa gtcgttttgg agaaatgaaa acagtccggc tttgtgctcg gctctttgct   84720
gattgtacgc cagcgtggat atctcaaatt ttccaaacat tataaggtag gcgaaccata   84780
ggtgttttgc agataagccg tactgctggt tctcgttctt gatcccccca aaatcggtta   84840
aagaatctgc agatttttaa aagtcggtga ttatagatag ctccaacgga gaaaactata   84900
ttgccttcgc agattattc ttccggaatt ttgagactta gaccaaactc gtccatgaag    84960
agaaaattaa ttatgtgact gacatttccg ctgtagtgca gcttttttga aatatatgct   85020
gagtgacttt cgttaaacat atgtcggagt agttccgcgt cagaatgctg tttcagaata   85080
gaaaatagtc gaaaccagta gttgttgctg attttgcgat tcaaaatcac tatgtctccg   85140
attccagaat tgtataaact ctcgcgtagt agtaagatct tgattccgtg tgacagcatt   85200
gatgtacaga catgttgaat taaaagtagt tcttcttgtt taaagctagt cagattctcg   85260
```

```
tttctaagca gttttgtggt tatgtgtaat attaaattag ggacggcgtc gttcagtttt   85320
atgtactgtc ctatctgggt catctcaaga tgtctaaagt ttgggtaggt ggattcctct   85380
gtgtctatgg tgaagaaccg tcggaagaat gtttagctct gcccagagac acggttcaaa   85440
aagaattgcg gtccggaaat attcctttgc cgttgaatat taatcacaac gaaaaggcca   85500
ctattggaat ggtacgtggt cttttcgatt tagagcatgg gcttttctgc gttgcgcaga   85560
tacagtctca aacgttcatg gacatcataa gaaatattgc tagtaagtca aagttgatcg   85620
cagcaggttc ggtaattgaa cctttaccac cggacccgga aattgagtgt ttaagttcaa   85680
gttttcctgg tctatcgctt tctagcaaag ttttacagga tgaaaattta gacggtaaac   85740
cgttttttca tcatgtgtct gtatgtggag tcggtcggag accgggaact atagcgattt   85800
tcggacgaga aataagctgg attctagata ggttttcatg catcagcgag agtgaaaaga   85860
gacaagtttt ggagggggtc aatgtttatt ctcagggttt cgatgaaaat ttattttcgg   85920
cggatttata tgacttgctc gcggatagtt tggatacatc ctatattaga aaacggtttc   85980
caaagttgca gttggataaa cagctatgtg gtttgtctaa atgtacgtat attaaagcta   86040
gtgaaccacc ggtggagatt attgtagcaa cgggcaaagt tgccggtgat caagttcagt   86100
taactacgga acctgggtct gaattagcgg ttgaaacgtg tgacgtgtcg gttgtgcacg   86160
ggaattacga cgccgttgaa tctgcgacag ctacaacggc tatgagtaat caaaatctgc   86220
caaatactac ccctttgctg tcaagtccac cgttttcgga ttgtgttttt ttaccgaaag   86280 atgcttttt ttctctttta aatgttacaa ctggacagca gccgaaagta gttccacctg   86340
tttctgttca tccgcccgtg actgaacagt atcaaatgct accgtattcg gagtcggctg   86400
ctaagattgc agaacaggag tcgaatcgat atcacagtcc ttgtcaggca atgtatccct   86460
attggcaata ttcccccgtt ccccagtatc cggccgtgtt acacggttat cgtcaaccga   86520
aaacgtttaa aaagcggcat ttccagagtg attcggaaga tgaattaagt ttcccgggag   86580
atccggaata tacaaaaaaa aggaggcgcc ataaagttga caacgacgac gataaggaga   86640
tggctcgaga aaagaacgat ttaagagaat tggtggatat gataggaatg ttaagacaag   86700
agattaatgc tttgaagcac gttcgcgctc aatcgccgca gagacatgtc gttccgatgg   86760
agactctacc tacgatcgag gagaaaggcg ccgcgtcccc aaagccgtct atttttaaacg   86820 cttctttgac gcctgaaacg gtaaacagga gccttgctgg tcagaacgaa tccatggatc   86880
tgctaaaact caacaagaaa ttgtttgttg acgcgttaaa taaaatggat agctaaaatg   86940
tgttttttta tgttgtgatc aagtggtgtt taggtgcgtg ttatgcggaa gatctatgag   87000
aattatgact gacaaggtat atggcgaatg cccacatttc cttcaaagtg aattcctgga   87060
catggtgaaa cttaacacat aattgtttac cgacgcgtta aataaaacgg atggttaaaa   87120
gttgttgttt tggttttta ttttcgtata aaatggtatt taggagctag ttacggggaa   87180
gatctatggg agtaattatt gtgacaaggt atgaaacgaa tgccgacgtc tccttctaat   87240
atcgttaggc tttgtggggt ttcaggcggc atgaattcca tgcgagtaga ttctccgggt   87300
tttagaaaaa agtgcaaggg taccaaatgt tctttgtcga acgcgatgcg gagtgatttc   87360
aaaaaaatgc ccatgctgat ctctggtgtt acgtgcgcga ccgtggttag acttggtgct   87420
cgcgatactg gctggcttgc gagagctaca atgtcttta cggaccatt tggagattct   87480 atgtttacat aaatgttgct catttctgtc cagctgaatt cgatattatt ccccggtggt   87540
aaaatttgct tggggaagaa gaatactttg cctagttctt gcgagtaatt gatgcgacag   87600
ttctttttct gtgctttcat ggtgatgtag agaggccgcg tctcgtccca aatgcaggtg   87660
```

```
gttatagaga ttccgtgcaa gagtttgggg ataaagaaac ccgtaaagtt tgaatttgat   87720
tcgaagatag tgtggaaaga gcaatggaaa ggcgtaatca ggttagagac gatattttta   87780
gttgcgccga cagttattga accgacgttg cattttagaa gtgtttcttg attctgcgac   87840
attgtgatgt ctgcggtgtg gggggtcagt gaaagttgta tgttaagttt ttcgggaaaa   87900
aaagtatcat caaggagata gtcgttttcg tacactgtct tcaaaattaa tagatttcca   87960
caaagtaaga ttctagagat ggagacgtgt cggtgtgata taaattcaat tttagcagag   88020
ttaaaaattt ggtcgagcgg agtgttttgg agattgatcc atatatctgc gttaaataaa   88080
tatcgtgttg gctcttctgg tgttttttct gtccatcgta tatcagccgc gtaaatttta   88140
atgcgcgtga gagggccata tagaataaac tgcgcctcgc actgtccgtg gggtatggcg   88200
tggcgatcgt aggcttcgat gcgttgcacc ggtaaatttg ataaagtcac gttcgcgtaa   88260
gggagtgcga atatgttaag aacgatgggt aatctgccga gatccagatc tagatctgag   88320
atgttatgca ccgcaaaggg tatgttgccg taatcttttg gatcgatgta agtaaaaggc   88380
gatgctgcaa aactgctttc gtctctacaa gtgcacacca cgctggatga aggggggcag   88440
atacctaatc cgcatttaaa atatctcagt tcgccgggtt ttaatatggc ggcagttgtt   88500
aatcttagct gtagtacgta cgaagaccat tgtagagtgg cgggttgcat gtttgctttt   88560
ctggatgtat gaggggaatc ctgttagtgt attttggatg ttaaatagtt gatgtaaacg   88620
tagagagtca tatgcgcatt tttataatag agtgtttttc cacggacggg aggatctgcg   88680
ggtttccacg cgcaggcttg tcttcgtatt ctaaaggatg tagtgtgagt tccggtagca   88740
agtatgcagg aaaacaattg cccatgaagt gtacttcgaa tggcttgtcg gtattctccg   88800
tgtgtgttaa aagagatttc atgtcgctgt ttgagaggga acgaaacggc tttctaaaca   88860
acttcttcgt cacaaaaaag atacgaccta acatgtcgtg ttcggttacg gaaactgttt   88920
tttcgcacga aatccgcaat tttaacggtt cttgggcaaa ccataaaaat gggtacagct   88980
tgaagacatg cgtctgaaca gggatgaaga tgcctacgat ttttttgtta gtgaacttgc   89040
cgcgtagcgt gatctctttg tttgtattaa ttactaagga catatcgctg ggaaagaaaa   89100
cctctagact cttccgtct gcgcagattt tgaaatacgg catattcata ttcagcgtga   89160
cggtactccg attcggaggg gaaaaggtca agcgaagata acattctttc gtgattggaa   89220
accgtcgctc gttttccggc aacactacgt tacgtaaaaa gattgtgaga aaaggatcgt   89280
taaattctat tttgtagata gaaatgccgg gttcggaaat catgttgact ctgcagagtg   89340
gaatcatact ttcgaatagg tttttccaat aggaacattt tctggtatcg atgctgaacg   89400
cgctaaaaac tattagcagc tttctgccat agcggtctaa ttttgagac tgataaggac   89460 tttctgtcca gcttaggtta agtaagatca aagacgtttc aacgctatca ttcgaaacga   89520
ctttaaattg atttatcacg ttggttgtcg agatcggcat gttggtcagg ccatattgtt   89580
cgtatacgat tggatcgatg ttttcttttt ggcatagcgc attgatgtcg tcaatctcca   89640
gtgcaggtga cggcagataa atgggtatgg agaataaatg aatccgtacg ggaactgtcc   89700
tagaaatagg taaatttttt attttgatag tcattgtatt ttcgagaaac tgtacatcga   89760
acaggacgtc ctcagtttct gattcagtgc catctgttat gaataggatt cctggttttg   89820
tgcttgagat tcgacatttc aacgtgattt cttggtaaga attcggaaca atgtgattgc   89880
aatcaaaaac aagctgtaag acatgattta gttgaggaga atacatgttg gtacaaaaaa   89940
acattttatg tttcacccttg cttttttaaat actgtgttttt tttaagggat gaggtaattt   90000
tacatgacgg atggaggacg cgggtgttca ggcggggtgt gtttttataa tcctgcgtat   90060
```

-continued

```
aagtgataga aaagtcatag taggccagtg tgtttttaaa aagcatttaa ttttttataaa    90120 tacatgtagc cattctatta tctgcggaaa cgtcacagac aacaaaatac gttttctcgt    90180
tggtcaaaga attaatttgg tcgatcatag ttaagactga tttgatttttt tttaattcgt    90240 ctttgatgtc cgtagcgtga agttgtccgc agcgctgtgt gcttaacgtt gttcttttag    90300
ataatagttc ttggcatttg atcaaaagca ttgaatggtc ttccagcgtt agccgatcta    90360
tgtaagttct cacgatgtct ggggccatgg ccgtgatcat ggacagcgag atgcaggctg    90420
ttttcatgga gtacattgat tgtttgtcgt tgactatgtc tggtaattta atgagtacgt    90480
ctctgtattg gatagagcat aactcatcga tgattgtttg catctcattg tattctctgt    90540
gaactgctat aagaccaatg catagcaatc tgatgttgat ctcggccgca atggcggtcg    90600
gaacgactaa aggtacagtg agctcccaat cacccagttt caatagcttt tcttccgagt    90660
gcgtcgataa aggtggaatc aatgtcaagg tgtcacccct ttcccagggg aagggtcctg    90720
tgttctttat ggcatactgc tggccggtca tcggctttct caaaattagt tgattacctt    90780
ccaccttctg cagaatggtt acgaccatgg tccgtaatac gttccggatg tggacgtaat    90840
ctttgttgga ggagacgatg ggataaagac ctaaattgcc gctacctatt agatggtggt    90900
gagctgggat cggtatgacg atgttcatga gcttgcagag ggtgctgata tcggaaagtg    90960
acagtttgtg atcgaaagtg cagtagacgg tttccatttt atatggatga ttcgataata    91020
agttggagag gtatggtttc tcctatggcg tagttacaat aatgggtttc gctgatctgc    91080
gtattgcctg ttttagaccg actctctaat agagcttggt tggatgaaca gtgaagaggc    91140
agagcgtttt gtaagaactg gcatggtctg cttacgaagc tatccgtgcc ctcagagcac    91200
gagtattgta tttcgctatc gctgtttaaa catgaatttg atttcatgca gtattcgttt    91260
atcactttgt acatcatctt gttcgttttt aagatgtcag attcggtaaa aaattgagcg    91320
ttaggactgt atgtcttggg attgtaacat agttgttctc tgtgtgccgt gttgtacagg    91380
atatcgccta aggagcctgg tagagatgcc caaggatttg tggttgcggc aaatgtatcg    91440
ctgtctgttt gggtgtgatc gtacaatgct tttctagccg cctcttcgtt gtgtgggtcc    91500
gttcccatca tacacgattc cctgcctctg gggttatggg gcaatttgaa aaagttaata    91560
tttgtcgtga ccggagtcag tacgacttcg cagatagctt gttgaccatg cagcagtatg    91620
gagggtgggt ttttgttaat tccgccgaat gttatgatgt ttagtgcctc gccctcggag    91680
ggattaggtt tttctatccc gacgtgatgc cgaatccacg tatttatgtc cgtgttggta    91740
aacgcgtgta tcgggaaggc ggagaaaagg ttttgtatct tgcttcccat gtctgattta    91800
attcgcttaa gattggcagt ggcggtggta gaactaaaac ctaagcccat atctacaaaa    91860
cttagatgct gggtgaagtt gtaagtggtt acgatatctt tagcttccgc ggtgaccgtg    91920
ggatcgtcta aaattataga tgtggctgcc ctggagctgt acaacaggca ctcgacgtcg    91980
aaattatccg tccggactag tgtggccgca agcccggat ggattttgct tttgctttgg    92040
atcgctatgg caacgggaga cagttttgag tgcatggcgg caagcgtcat aatgctcaac    92100
agggaattgg ggcagaaggc tgagtacacg gaaaacggtg ttcgttgcca attataaaat    92160
tctaatgcta atgggggcgg gagaggaaaa ccgccgtcgt ttctttgata gtgaggaaat    92220
gtatttagga aaacttggat atcagcattc atggtgccgc agattccggg gtcagagaag    92280
aatcgatgaa atgggattgg ctgatagtac cgtcttaggg tggtgatcgg tgagatcagg    92340
caaagcccat tgtatagaat gtgttgtagt gattgaaaat gaacggaatt gccgtgtcgc    92400
tgccgcaggt ctaaggagac ctccacttcc agtatttcg tattttcatt aatgtagatt    92460
```

```
agcgatttaa acagctgttt cgcgatagat gatgtattgg ctatggtgta gccaggaccc   92520
atagcttctc gtatcagaga cattaggacg tcgctgctga tcggattctc ctggaaacaa   92580
tcatctggac agataaacgg ttccgtgtag aataagtcta gaactagttc ctttacgttg   92640
acgccagcgc cacaggcctt gttatttgat agtgccggga gtacgcagaa gtaaaagatc   92700
ttgctcagga tggtgttttc gttcgatggt ctgtcattgt cggtgaagac gacgcttgaa   92760
tctattagat tcattctttg cacatcggag atttcgtaat ttctaactct tacggtgttc   92820
tgtgtcagtg gtgtatcatc cgctgttatt tttgcattcg tgtcgtttct gggcatggta   92880
tgaacgaacg ggcagaacag acgtccgtcg aacaatgcgt tggcgaaatt caccagaggt   92940
tcgccgcaaa gttgctcgtt gatgttggag atagagattg tcctcttcac taggcgaatt   93000
agcgacacaa gatttctgta gtgagcgaaa gctgctcctg ggatcagttc gtcacccatg   93060
tggttagaga ttagcatgat catctcgaag ctgttgcaaa aaagaagtat atgtttcatg   93120
ttaaaccaat aagaaataca ctggctaatt acttgtttta agatcatgaa agcatgcttg   93180
tttccatgaa ctaagatctc gataacgtaa gccaattctg ggtacgagcc actcgtcaag   93240
ctttcggtga caattttgag ggtgaagtcg tagttgtggg agtttgtctt tgcatgttcc   93300
agcatttgat ttgtacgggc ttcgtggaaa gagattggag ctagaggtaa aggcatgttg   93360
cctatcatta ttcttggcgt gcagagtact tctgtggctc ggttttctg gatatacgtg    93420 agatcaaaga agggggtgtct ttcggtcggc agagttggat tgtccggttt gtaaaagtct  93480
tcaacgttta gttcgttttt taagacgttg gtgttttttgg gtacttcttg tcgactttcg  93540
tataagttgt ataaggtctg taagatcctg gttgggtttt ctcgggtaat tttcagttga   93600
catagttgag aaaagcggtg gccggtaggc aatggttcgt ttttcatgag tcgttcgacg    93660
atggtcgagt cgtggacaat gggatggcaa accgacggca gtatgtcggc aaaatcaatt   93720
cgctgcacga cttggtcttt attgtggaaa aaaacgctgg tgggtaggtt gttttccatg    93780
gtgtcgttta atttcacacg tgtttccatt gtactgaaac cggtttctgt cggtatgtag   93840
atacccaaag ggaaaaagaa tgtcagttgt aagctttgtt ctagcggatc gttgacgtct   93900 gtgttttttgt aaactttgtg taggtggtcg aatgcgacta atttatctcc cagttttaac  93960
gtgttcagtt ttaggtcggc gtacgcgcgg cttttgtcaa agattctga tttgttgtta   94020 gtgtcttgtt gttctgtccc ggcgttcacg gtgaattgag taaaatcggc catgattgca   94080
cggtatgcaa tcgcagtcac tgcgttttct ttgcccataa taaagtgacc atatgagatg   94140
ggggcggaga cgacctgtgt ggagatgtac tgggagagta tgttggtgag ttttttggata  94200 gagccgatcg gtcctaataa aacaccgtct aggggatgt tttctttgga agtgtagttg   94260
ttcgtatcat ttagaatgct ttccgtgacc gattccatca tgtcgttcag aattctatag   94320
atatacgaac tattattatt cctgttcaag aaaaataatg acgttaacaa tctgtttttt   94380
aggctctgaa acatgttgct gcgctgtact cggctcagag cttgtttatt atgtactttg   94440
ttctcattca tggtcaggac gataaattgc gggggagatt ttctcaataa ggtttgcatg   94500
aatgcgtgaa tcgagacctcg ttcgagcgaa tcggctgaat tctttaaaga tcttaaaact  94560
gtatgcaacg cattgatgtt taaaatctga tcgatgactg tgttttttaaa agtgttttcc  94620 agatgctcca gacaggcagc actcaaatcg aacgatatgt ttatggggtg tttttctgag   94680
tgtttggcta ccatgatggt ggtttctttt ggagcagtta cgtcgtttcc tgtggcgact   94740
ctgggtaatt ggataaagaa gagaaccttc ccgagggtca ttcgactcac atcgttgaag   94800
cgaattacgt tcgccgcaac ggcgatcggc gtggtgaaaa agttgatcca ttctattttg   94860
```

-continued

```
ttgcagtaga ttccgagcaa ggcttcaaaa ctgatgttgt aacggctcgg atcgtcaccg    94920
aaataaattc gcaaattgtc aaaaagttgt tcggccgtgt atgttttaat gtcattgaaa    94980
atatttagag gtgcttcgat tttaggtaaa atttcggtcg cctgccaatt ttccatgttt    95040
cggcgttatg cagcacaccg gtaattgtga aactttaata gttaattcat gttttggttc    95100
cacttgtgca cggtcgattc cagttttttat agattcctgt gatctgaccg ctgaagtgtc    95160
tcgcgacgag gaaactcgtt tagcgcgatc tgtgcctgta gttctggaaa agatcgagtc    95220
aatcatagag aaaattttc aaacgtctgg gccaaatatc gttcacgata aagacagggc    95280
taaaattgcc ttgtgtcgtc tgttgttagg accggttgcg gtgccatgtt tctgtgaaga    95340
gtgggacacc aacgactatt tatcgaaatc tggatgtaaa tgtctaggtc cgatcttata    95400
tattcatacc agtcgatgtc gctgtagcga tattccggtt tttaagtttt ccattatgaa    95460
agattactac gcttcacacg tgttcagagg tttattatct ctgaaagagt ggaatacaca    95520
tctaccgaat gtattgtgta cgtgcgagtt gtcgatgagc gatagatatg tggcgaccgt    95580
gtttcctaag cagaattcta tatatctaga atactatccg tattttttgt gttatctgtg    95640
tcgctatctt actgtcattg agattgagca gtgtacaaat gatttaattt cgcttcttgg    95700
tcctaaagta gctcagcgag tcataattca tttttaaactg cttttcggtt ttcgtcacaa    95760
gccgcatatg ggcactgttg attcgtggtt ctgggaaaat ttttttatgc tagaattgca    95820
taagctttgg ttaaccgtag tcaaacataa ccgggtgaca acagatttct ttaatgtagt    95880
ctatgagaaa attcaaaact ataaacaata cgccatcaag actttgagaa tgtcgtctaa    95940
ggcggttcct gcaatacaga ggttttgttt ggcaaaattt aaacagcaac tcttgtatct    96000
aaatattaag gttacggtaa aaaaaaataa gcgagaactg tgtttgaatg gttttgttta    96060
cggtaaaaca ttgtatgtcg ttgaatcttc tcagttaata tttcgaaatt tgcttctgtt    96120
gtattacgat tacagtttgc cgggcgaatg caaaacaaac gaagaaaacg ttttgacgac    96180
tcattacata cgggtaattt cgagattgtc gtttaagcag tctcgaagtg cggtcccgcc    96240
aggcgtgaga ccagatttta ccttcgtggc acaactgcct aaacgtaaag agttgcctaa    96300
tgtccccggt ggtattgatt ttgctgaaat tacctcagtg aggcatggcg cggtaattct    96360
taacgcgttt aatacgaaca aagtcatgaa tttaaaagca accatttcaa aaagggctaa    96420
ttttgtgtat catcgcattc ctaagacaat gactcacagt tttgtcatgt acaagcatac    96480
atttaaagaa cctgcgttta ctgtaagcac gtttgtttca aatgatgatt tagatatgag    96540
ttcattgaat atcaatatac gtggacctta ttgcgacttt ttatatgcct taggcgttta    96600
taagatgcat gtttctatcc aagatctgtt tttgccggcg ttcgtttgca atagcaataa    96660
ttcagtggat ttacagggac tggaagatca agatgttgtg agaaatagaa agaaaaaggt    96720
gtattggatc actaactttc cgtgcatgat ttctaatgcc aacaaagtga atgtgggatg    96780
gtttaaagca ggaacaggta ttattcctcg ggtgtctggc aaagaccttc aaaatgtttt    96840
gcttcaggaa ttaaataacg ttcgagagat tccagggtta gtctttgata tggatttgca    96900
tcaattgctt gttttgctgg aacagcggaa tctacatcag attccgtttc tcgttaaaca    96960
gtttcttatt tttttacgtc ttggcctgtt aatgggttac gggcactctc ggcgtaacaa    97020
ggtgcatgat atcatgttac acttaatttc gaatggcctt tttgatttta ataagaactc    97080
cgtagcaaat acaaaaatca aacacggtgt gctttggtt gggacgcggc tcgccaacaa    97140
tgttccgaaa atcattgcta ggcagaagaa aatgaagcta gatcacatgg gacgaaatgc    97200
taattcgctt gccgtgttgc gttttatcgt taaaagtggg gaacataaaa ataaaactgt    97260
```

```
tttcattaaa ctgttggaat atttagcgga aacctcaact gccataaata cgcggaatga    97320
agtcgccaga ttacttcaga ctctgacgac taatatgaaa acatgaatgt acccatggcc    97380
gacgaatggt tcgattgcgc gattaggtta gattcggaaa ccatagctgt ccatgaaatt    97440
ttcaattcgg atttaagtaa actgcttaac ttgcactcga aaacggtcta tatgtccgat    97500
ctgtgcgcct ttatttctgg ttgtgttaat cggaatgttg gtaaacttac catatattgg    97560
cacgtgtacg gagacataat ctacgcattg acgggtattt tacattgtgt aaaaataacg    97620
atagagtgcg gggagagaat tgccgatggt cgatatagat tatacgaagt tccgaaatta    97680
tttttaatga gaggacagtc aacaccccctg gaactgaagt ggaagcacgc cgtgggtatc    97740
gcgacgacga ataagccttt gctgacgcac gttttaacag atgtgttgga aacctctcct    97800
tttaccttgc cagatacgct tctgtcggtg caggagttgt ctattttcag agagagattg    97860
tcgtatattt actatgtgct cgggttagat gttgatatcg tagcgcggac agagagggag    97920 attttttcaaa aatgtgcaga actagctcgc ctacaacaag tctttcttat tcaaggaaat    97980
attatggaaa actttgtcct cgttcaggcg tgtctatttc agctggggggc tgatggtttg    98040 tgggaagaga tgtctggctc tgtacgtcct aggccggagt tgatgtctag tgcgttcatt    98100
caacacagag taatggtgaa taattgttat tgtctcgctg tcatcttcaa tgccatttat    98160
aaacacaaag tttccctgcc taccgtagaa agaagccacg aaatcgttca tcgtgtagtt    98220
caggaatatt ataagtctta tgtgaatgct cctctctctg tttttgtgtg tgcgactaag    98280
gtgcttacct tgtttacaga agaatataac tttcagtcag ctctcgtatt tgtcagtcag    98340 ttttttccagg tggacgtcga ggcttcgaga gcggatgtga ttcgtctgtt tttagcgtgt    98400
ctgaagggtg attagatctc tcggaaagag gctgaactgt ttccagagca cataaaatc    98460 gccataatta tggcgataat taagtcgtca gaacaggctt gttttttagc gctgtatgtt    98520
atgtaattgt taacggagat ctggtgaatg tttctgattt gttctagtgc gtattctacg    98580
ggatcgtagg tgatttttat tgtaaacgat atcaattcct gtgatgcctt gatgtttcct    98640
gaattaaaat tcgagatgaa aaactcaact gctagttttt tttctttacc gagtaggtaa    98700
aatggctgtg ctatctgatt ctggtctggg gtgtggaaaa aagtcacctg tatagattta    98760
ttagccgtga tgttttcctt tatgatacat gcgattttta cggcagaagc ttgattggaa    98820
ttcccttcta tgatgatttt tacttccgtg aagaaaggat gtaggtctag gattgacaat    98880
atcatatgcg cggcacattc agctattgct gtgtcggaac tcgtcattaa actttctaga    98940
aagtagtgct ccatgccgta gacgatatat tgatctagat aggtgcctat cgctgctatg    99000
ccagtgccag aagcacggcg gttgcctgta taggcaggat ctaggtatac gtacagatct    99060
ttacctaaaa aaggaattag atttttattg atggtgctgt atcggaaaaa ctcgaattcg    99120
gtttggcctt gttccgtaat taaaacgtcg ttgatcacat tgcaagtggc tccgcccatg    99180
atttcatgga tgaaagctcc ttctaggaag aggttggccg ttttttttaac ttcggcgtta    99240 atgctgatga acttgggttt gtggagtcgg tagcaagaac aggctgtggc gttaccgcgt    99300
tcgtttagca tatgggcgtg atcttcgcat acgtaagaaa ctacggagag catttcaaac    99360
ggagagttgt tcagcttcat taaaaaagaa gttgaatggt ttccggaatt ggtcgaagat    99420
ataaatagga tcttggtaga tgcttggggc aggaaaccta aaatcgtgct gaacgcgtct    99480
ttctttataa agtggctctc gtcgacaata agtagattga agctttgtcc gcgtatactc    99540
tgagagggga atgaattcgg cgttaaacga gataaaagac gattttgaga actgtgaaac    99600
gaaaaacgac cttttttaaaa taattgataa aataagcaaa aattgcaatt ttatagtgga    99660
```

```
acaggtcgag tccttgcctc ggagggtgga ttcagcggct atcctatttg ataatctcgc    99720
ggtggagata tttaacgatg taatatatcg acaaaatgga gatggcgttc ccgcgaaaat    99780
acgacagggt aacgggcaga atattgacac ataagaataa ccagatgtgc acaaccgaat    99840
gttctcagat gtataattta cataatccta tcacgtttga gttgggactt ggaaacgtgt    99900
ttgtctgtat gcggtgtttg acggttcacc actgtgatat gcaaactgac tgtaccattg    99960
tcaacacgca tgaggggtat gtctgtgcga aacgggtttt attttatagc ggttggatgc   100020
ctacatatgc cgactgtttc ttagaaccaa tctgtgagcc gaatatcgaa acggttaatg   100080
tcgtggtggt attgttatct tatgtatata gttttctgat ggaaaacaag gaacgatatg   100140
ctgccattat tgatagcatt attaaagatg gaaaatttat aaaaaacgtg gaagacgccg   100200
tgttttatac ttttaatgct gtttttacga actcaacttt caataagatt cctttgacga   100260
cgataagtcg gcttttttgtt cagttgatta taggaggaca cgctaaagga acgatttatg   100320
acagtaatgt aattcgcgtc agtcgtcgga acgagaaga cagtttacta aaaaagatga   100380
gattggagta tggaaacgca cttatactat gacaccctgt accaatatca aggcggagtg   100440
tatccggccc atatttgcct gccgacagat gcgtatcttc cgatgagagt ggattgtatc   100500
gagtctttat attttcggtg tgtattttc aagaatggga tgcattatac tgaatggagt   100560
aaattaaagt ttactgtgat ttcacgtgaa ataaagttta aagatgtgtt aaagaatgct   100620
gactttgacg aacttttttac cggtttggtg gtaatgacta ttccaattcc gatagtagat   100680
tttcattttg atatcgattc tgtaattttg aaattggttt atccgcagtt agtgcaccga   100740
gaaatagtgc tgaggctcta cgatctcata tgcatcagac cttcgtcaga ccggccgtcg   100800
gaagtatcag ctaaaaatat tggtattgat ttctatcaac taacttcaca gggaaataga   100860
caaacacccg atgaggaaaa acgttgtcta tttttttcagc agggacccttt agagccaccc   100920 tctaccgtca gaggcttaaa ggcaaccggc aatgcaaagc cgatgcagat tcccgctcat   100980
gtcaacgaaa aaatgaccga atcttttttta agcgatagtt ggttcgaaca aaaggtcaga   101040
tgcaaaaaaa tattggattt tactcaaacg tatcgagtcg tggtatgttg gtacgagctt   101100
tcgttttccc gcgagatgca gatcgagaat aatttactgt ccgcttccca gctaaagcgg   101160
gttaacgctg cggattttttg ggatagaact gatcggtatt tgcgagatat tgggagcagg   101220
gtattgacac acatcgtgaa aacgcttcag attcataata ggcaatttaa acagaaattt   101280
aattgcaatt tcccagttaa tttcagcttt gaacatctat tatcatttat gcagctcggg   101340
aaagattttt ggatttttaaa cttaacttta gacagctgca ttattaaggc aattatctgt   101400
ttcctaggtt ttcgaaacgg gagaaaatct tttttagctc aagatgaagt ttggggagat   101460
ttaatagact gttctaaagg atcggtgatc tatggggaaa agatccaatg gattttagac   101520
tcgactaaca atttatattc gacgcgtcgt gaaaaacaga ataagtcgtg gaattatat   101580 gttgattgct gtgctttgta tgtatctgaa aagttagagt tggatttttgt gctacccggc   101640 ggttttgcaa tcaccggtaa attcgctctt actgatggcg atatcgactt tttcaattgg   101700
cgatttgggt tatcttagaa attttttgca gaatgaatgt aactggttca ggatttgtaa   101760
aaaaacattc tatcgcgaat atcgcagcgt tgcgacatcg tctcctatat tttcgttgaa   101820
gaataagcct aagaaatatt gcatgcattg cgagatggta gtgctcaagc gaagtcatga   101880 attatgttc agccttgcgg taaacggcat acattttgga cagtttttga ccggaataat   101940
gaaatttaag aagaaacagg ttgcggaagg gctctgttac tatgtattgg aattgggaag   102000
cataagccct gtggatttga gctttatccc aaaatataat tctgactgtg ttacaagcat   102060
```

```
gcattgtgtt acaccggagc ttatttatga aaattgctct attgtgtgtc ccgaagaggc   102120
aagtcgcctc acagtaaaag ggcccgggga caataaattg attcctttag gtgggtgtgg   102180
agtatggtgt ctgaaaaatg gtggcgatct gtatatctat gctttcgtac tcgtttacga   102240
tctttacgta gcttgttatg acaaaaccat ctttccatct ctggcaaaaa ttgttttga    102300 tatgatagct tgcgattccg aagattgcgt cttttgtaaa gatcacaaca acatgtatc    102360 gcaagccgga catattgtag ggtgcgtctc taatcaagaa acctgttttt gctacacacc   102420
gtgtcaaaaa aaatgactg atattaacaa tccggagtta atctctttgc tctgtgatca    102480
ggaaattaat aagatagata ttatgtatcc cgagaaaaaa gcaccgttat cacttgacat   102540
taattcttac gttcatgggt acatcggcga cgagccttgt gcgttaaaat gtgttaattg   102600
gatgccaatc aggatcagct cagctctgag caggctgatt attttgtcat gtcctgtgtg   102660
taagcgtgtg gtaatggact aagtgtgcgt tattttctgt attaattttt gtttctgaa    102720 aataaaattg aattgatagt acttacgtgt gtattgtagc agctggcgaa aagtgctgtg   102780
ctctttatat tttgatggtc gattgtaatt acattatcca ggcatgtgat tgtcttttct   102840
ggaaacattc ggcggcattt aaactcgact tctttcatca caaagtgaga tacatgtttt   102900
tgatgtgcta cgtaaccgat gctgattcct tcaatgtttt tcaataaaaa acttataatt   102960
ggaactatga accacgtttt tccatgtctt cttgggacta ggaatacgtt agttttttgt   103020
ttcagcgtat tcagagtact ttcgtttacg aattcaatgt cgaacacgtg ggtcagatag   103080
ttgataacac gattggctaa agccggaagt ttggtgacgg cgatgaaaaa gattacatgt   103140
atgagaatgt tcttctgaaa tggttccagt tgtattttgc gcgtgtctcc aaactcgttg   103200
aattctcctt tgatccattt tctgaaatct ttgataaaac catctatttg caagaatagc   103260
ggttcacgat atagaatctt aaaggattcg agaaactctg tgtattgtga ttcaaaggat   103320
ttgtcggaag cgggtaagaa cttcatttct tgtagcttgc gcgtaaggct cggtagtata   103380
gtaagaggct tacggttttt aagatgtcgc tgtttttcac agaatgtata tagaggtttt   103440
acctgttggt tatatgaatg ggctaacccg agttctggcg tgagcattat aaaacgcttc   103500
ttatagaaga tggcactgtt ggggtatttg gtagatatcg tagaacagtt tctttcgcct   103560
ttccatatga tcgcttcata gttgtttttt atgtgggtta tgtcgcaggt acgtagcatg   103620
gagcccgacc ttacgctggc ggcggtctat caggcggcgg cgaacctcac agagcaggat   103680
aaggagattt tttccgaagc ggtaaaaact gcgttttcag tgtgtagttc ggcagccccg   103740
agcgctaggt tgagaatgat cgaaacgcct acacagaatt ttatgtttgt gacgagcgtt   103800
attccttcgg gtgtgccgtc tggtgaaaaa aaacaaagt taaatatcga tgccgctctg    103860
gataatttgg ctttgtcgtt tgcgaacaaa aaatcaaaaa agatggctag aacgtatttg   103920
ctgcagaacg tttcgcggac tcaagatcaa caagttgcca tttcggggac gtacatttta   103980
tatacaaaaa acacattga aacgtctttg atgctcgata agacgaagtt agttaaacaa    104040
attcttgagt atgccgagac ccctaatctg ttagggtata ccgatgtgcg tgatcttgaa   104100
tgtttacttt ggttggtgtt ctgtggccct aaaagttttt gccagtcaga cagttgtttc   104160
ggatacagta agacgggata taatgccgca tttccgaatc tattgcctcc gtatctgtac   104220
gaatgcggcc agaataatgg actgtttttt ggcattgtgc aagcttacgt gttttcttgg   104280
tactcagatt ttgattttc agcgctagag atttcagaac gcgctcgtcg tcgaatcagg   104340
tcactcctgt acgacttaaa acagaagttt tcggagcaag aaatttctgt tttaccggta   104400
gcgtcacaga tgtgtatctt ctgtgcatta tataaacaaa acaaacttag tctagaatac   104460
```

```
gtttctggtg acttaaagac ttctgttttt agtccaatta taataaagga ttgtttatgc   104520
gtgcagacga caatttctac aactcagatg ctgccaggta caaagagctc agcgatattt   104580
ccggtatatg accttcgtaa gctgctcagt gcacttgtca tttcggaagg tagcgtcaga   104640
ttcgatatat aatgtctttg aaggactatc tgagacagtc aatttctaaa gatttggagg   104700
tgagacatcg agattcttta aagattagat taggggagag acatccgttg agtgtgcatc   104760
agcatatgat cgccgctagg cagatcatta aatcggacaa tgcggaacac cagcatgtca   104820
tatcttcttt gagtggtttt ttggataagc agaagagttt tttaaaagtg caacaaagag   104880
ctttaaagca gctagagaaa ttggacgtcg atgaaataat tgatacgacg gcggaagtga   104940
aagcggtcag taataatata aaagaaactc ttatggcaag cactgaatta gaataattat   105000
ggacaacggt gtggagacac ctcaaggtca aaaaactcag ccgataaatt tgccaccaga   105060
caggaaaagg ttgagaaaac atgacggact tggaaaaggt gttaaacgaa aacttttttgc  105120
cgaagatagt tctccgttaa agaaacagat ccccgcctgc agcgatatgg aaacactttc   105180
ttcgcctgta aagtttggat gcaagtcgcg aagtgcttct gctctcgatg aaagtttcgg   105240
aaaatgtaaa cacgaaactg cttgcgattg ttctgcgata gaggaattgc tttgtcacga   105300
gtcgctttta gactcgccga tgaaactgtc gaatgcccac accatgttca gctcagacaa   105360
atggaaactg gagctagaga aaattatagc ttcaaagcag atatttctag acatgagcga   105420
gaatgttgaa cttgtggcct acggcgagac tttgtgtaac ctgagaattt tcgaaaagat   105480
cagctcgccg tttttgtttg acgtgcaaag cgaggagcgt tcgtattcag tggtttacgt   105540
ccctcacaac aaagaacttt gtggacagtt ttgtcaacct gaaaagacta tggctcgagt   105600
tctcggagtg ggtgcctacg ggaaggtgtt tgatctagat aaagtggcca taaagacggc   105660
caacgaagac gagagtgtca tttcggcttt catagccggt gtcatccgtg gaaaatcggg   105720
agccgactta ttatctcacg actgtgttat taataaccctt ctgatttcaa attccgtttg   105780
tatgdatcat aaagtgtctt tgtcacgtac ttatgatgtt gatctctata agttcgaaga   105840
ttgggatgtc aggaatgtaa tgaattatta cagtgtgttt tgtaagttag ctgatgctgt   105900
aaggtttcta aatctgaaat gtagaattaa tcatttcgat atctcaccta tgaatatctt   105960
tataaatcat aaaaaagaga taatctttga tgccgtgttg gcggattaca gcttgtccga   106020
aatacatccc gagtataacg gcacgtgtgc tattgctaaa gagtatgaca gaaatcttca   106080
acttgtgcca atcagtcgta acaaattctg tgacatgttt aatcctggat ttcgaccact   106140
tgtcgccaat gcaatgatat tggtcaatgt atgcgaggct tttgatggtg aaaataatcc   106200
tcttagacac tgtaatttgg atctgtgcgc ctttgctcag gtcgtattat tgtgtgtcct   106260
gagaatgaca gataaacgcg gatgccgcga agctcagcta tactacgaga aaaggttgtt   106320
tgcgttggct aacgaggcct gtcgattgaa tcctcttaga tatccatttg cttacaggga   106380
tgcttgctgt aaagtattgg ctgagcatgt agtgttgcta gggttattgt tttaccgaga   106440
cgtggttgat atatatgaaa aaatatacga ttttctagat gaaagagggg aatttgggtt   106500
acgagacctg tttgaggcaa cttttttaaa taatagtaaa cttaccagac gtcagccaat   106560
cagaggaggt cttgcgtctc tacagtcgtc cgagtatgga gaaaaacttt tacatgacct   106620
tagagcgttg ttcttgatca cttccttctgc agatctggat aaagatacat catctctctt   106680
tcagatgtga tatagtaatg gatcttaatc agatatctga aacactaagt gccgtggcag   106740
aagaagagcc tttaaccatg ttttttacttg ataaactgta cgccatacgg gaaaagatca   106800
agcaagttcc attttcgatt gttcgcttgt gtcatgttta ctgcatgcta ataaaatata   106860
```

```
acgcttctaa caataattgc attttgggcc gtaaacttat tgaggaaatg cagcagtttt   106920
tgtgcggcgc gagagtggat ggatcggaag acgtttctat ggatctgagt gaattgtgca   106980
agctgtacga ttactgtccg ttattgtgtt ctgctctgtg tcgtgcgcct tgtgtatttg   107040
tgaacaagtt atttaaaatc gtagagcgtg aaactcgggg gcagtcggaa aatccgctct   107100
ggcatgcgtt acggagatat accgtgacag caactaagct gtatgacatc tacacgacaa   107160 gaaattttt agaacataag ggacagcagt tttttgggga agcggtgatt tacggcgcga    107220
aacatgagcg tgttattaga cacctagtag cgatctttta cgttaaaagg gaagtcaagg   107280
aaacgttggg attgctgctt gatccttcat ctggagtttt cggtgcgtct ctagacgcgt   107340
gttttggaat ttcattcaat gaggatggat tcctgatggt taaggaaaaa gccttgattt   107400
ttgagattaa attcagatat aaatatttac gggataaaga agatcacttt gtttctgaac   107460
tattaaaaaa ccccacggag aaatctttt cggatttat tttatctcat ccggtgcctg     107520
ccatagagtt tcgagaaaga gggaagattc cgtcatctag agaatattta atgacgtatg   107580
attttcaata tcgtcctcag agaaagttgc gcacttgccc cactccagct attttgacac   107640
ctcatatcaa acaactgctg tgtttgaacg agacacagac gtctacggta atcgtttttg   107700
attgtaagag ccacttgagt gagcagaagc tgtctgtgtt tcagaaggct gtgtttaccg   107760
tgaacgtatt cgtaaatccg aaacacaggt attttttca gagtctgtta caacaatatg     107820
taatgactca gttttatatt aatgatcata gtaatccaga atatatcgag agtacggaag   107880
tgccttctgt tcacattgtg acggctctct tcaggagaag aacagaggaa gaaggagtt    107940 tgcatttggt aattgatgag acggaatata tagaagaaga aataccttg gccttgattg     108000 tgactccggt ggcaccgaat ccggaattta cttgtcgtgt tataacagac atatgcaatc   108060
tgtgggaaaa taatatttgc aagcagacca gtttacaagt atgggcacaa agtgctgtaa   108120
accagtatct tgcggcatgt gtaagaaaac cgaaaacacc ctgatggatt acaagggaaa   108180
tcctatatta ctgacgacgg aatttactgt tttgaccgat accgaatcgg aagaggaagg   108240
gatggcagat cttgaaaagc ccctgcttga aagagtacag gccacattag ctgctaaatg   108300
tgatacggaa gttgaaaaaa aactgccgct taaatcaaaa aaatgataga cgacgcgat    108360 ttacgacacg ctcgtatttt attttgtggc tatttgacaa taaacatgat tgtaataaaa   108420
aaaagtgtta ttcgttttca tccattaggc tcgagctttc agcgttaagt agttgcttgt   108480
accgacgctt cttttttaact aggtagcgta cgagtcgaca aattatgaaa ccgatcgaaa   108540
ttatggcgac gaccgataaa ttgataataa gtcctgtgct ccactcggat tcaaagaaag   108600
tttcgtactg gagaataggg aaagataggc ctacggcgcc acaaaacata ccgacgtaat   108660
agccgaacaa gggtttaacg tagcgaacca ggacggcttc tattactata ctatatatgc   108720
aagccatgac aagaaaggta ttgatggaag agaaagcaac ggtgatggaa cgtatgtaga   108780
tactatttcc gacgcccagg caagtagtaa tgccgagaaa catcgtagag taacctagca   108840
tgagttcgct tagattgatg acaacggtct tgaattgtac ggtccccttt aggttaggat   108900
gaattttctg aaaggcgaaa aacgacttgt ccgctgactg aaattgcgtt atcagcgtaa   108960
cgttaaaggt ggtgaaacac acgaagaaga tggaataggc aaatgcacct agggcgacca   109020
gtctgaaaga cagggcggtg acgaataact gaaatgtatc catgattaag atgaattgaa   109080
agcaggatga ggtgtccccc atccaggtaa tatccctcgt tgtttggtta acgttagatg   109140
ttttgttaga ggagaacact tttgcacagc agacaatgta ataaataata atcaggagga   109200
ataagatagc cattatcagt acgtagcata taatctgcac agggtttatg taaagttgat   109260
```

```
gcgtcatctg atatatttca ttattagcgg agagattgac cgctttgagg tcattgattt  109320
caaagtaggc gcacggaaat cctaaatttg gaaagtttat ggctatcaga tggaccgtga  109380
cgtttataaa tgacaaggct gcacagatta tagagaccag ccagatccgt aaattaatgg  109440
tgtctacacg actggaggcc ataccagctc tgtgatggag aacaggtttc agaacgatac  109500
tctgttctca gagtggttcg gccagagttt gtccgatgta agatttccgg acaatgtcac  109560
cgtttattct caagccgact cggcggtgag ttttgaaaac gtcaggcagc cgataaaact  109620
ggttcgcgca gcgatgggtt cagggaaaac aacagctttg attcattttt tgaaacaggt  109680
acccaaggaa ctatcgtcc ttttgatttc ttgcctaaa acgttcgctg cggaaatttt  109740
gcaccgtttt actctcaatg ggttggagga ttttgaatta tattgcgata ttacggagcg  109800
gcagataaac aacagaaaag tcattgtcca gatagaaagc ttgcatcgtc ttacagaaaa  109860
ttacgatgtt ttaatattag atgaaattat gtcgattata aagcagtttt attccaaaac  109920
gatgacaaaa accaaagaag ttgattgcaa gtttttatcg ctgatcaaaa attccagtca  109980
tgtaatagct atggatgcga cgctgactcg gcatgtggtg gagttttttg ccgcgttcaa  110040
gccagatact caaatcgccc tcatcagaaa tacatttgtg tccgcgatgt tttccaatag  110100
ggtcgcttac ttttgtgaca cgttttttgg taaagagttt tctttttttg cgcgcttgga  110160
agacaagcta cgatgggata agaaattgtg tttgttttgc agcaccgtgt tggcagcgga  110220
atacatgcat gatttgatac gttctcggtt ttcactcaaa aaagttcttt tgttgacgtc  110280
taaacaaggg aaatgctctt ccatagaatc ttggatacgg tatgacgtag tgatttatac  110340
gtccgtcgtg actgtcggtc tgagtttcga accggtttat ttcagctctt tgtttgttta  110400
cattcagttg gccaaaggag ggccggacat ggtttcaata tttcaatcca ttggtcgtgt  110460
gaggcgagtt atcgatgaag atatatacat ttacatgaat cccgtactaa ttaaaagcta  110520
tgatcctttg gcgcctattg ccatgcctcc ttgcagtgat tggagtgtcg ctgagcagtc  110580
tatcatctca gagagttgca ttgacttccg cggaaagtgc agcggagcgc ataaatataa  110640
tttctgttcc gtactgaagt gtcttttttcg atacaggcat tatatcgaaa agactactat  110700
tacaagttta tcagatagtc tctttctgct ctgcagtctg ttatgtgaga attctattaa  110760
ggtggacatt gttggaaatg gattcccgat gcgcaaagag gttttttttga gtttcttgca  110820 aattctagtt gaggagtgtc attttatcga aagaagatt actttgccgg gtgacaacat  110880
gacgtttcaa gagatcataa gtagcagaga aactatcatg aacggagatt tttatgaaaa  110940
cggtaatcag ctattacata aggactatat taccgacatg ggaaagttca gagcgacttt  111000
tttatctccg ggcgttgaca ttttcattgc atcggacatt gtatctgatc tgaaaaatga  111060
aagcaaacgc tatgttttttg tgaacgtctg gttacaaaaa tgtgtgtctg ctggtgtaga  111120
aagcacgcga atcgaaagag ttttttactga gcgaattaag tcttatgtgc tgccgaagag  111180
ttttttgtgc gatgagtact ttgttctagg tgacatctct ggggtttacg agtgggaat  111240 gttaatagat ctggccttcc tggcggaaat gatccgaaaa gatttgaaac tgaaatcgtg  111300
cacagatact actactgaca tttctgaaga tgatctcctt ttgtgtgcgg ccaggaggtc  111360
gagtgacatc ttacaaataa tgcaattggt gtttacggtg catgtgcaat tttttcaaag  111420
atacagtctg cagactctgc agctttttaa caagttgaga ggcatgcgga ttgtgacggg  111480 tgtgtttttct atagaaaaat tcagcatttc catcctcagg cttttcttta aatgtgcatt  111540
taatatgact ttgtccgcca gcaaacctcg gtacatcccg gggaaggcgt atcgcaatct  111600
aacaaaaaat gatctggaga acatgctaga caattgggag atttcgcgca ccaatcttaa  111660
```

```
gacttgtaaa gaactacgta aagccctcac cgaggcctcg agagcaaggc ggaaacaaac   111720
aatttataaa cttcaaggct cggatataag cctttccgtt agtgaagttg gagtttttgg   111780
gcaacatgca tctccggggg tgtgcgtgtc atcttagcct ttattgtgtg tacaacgact   111840
gggagaataa gatctacaga gtaccgattt ttcagtgttt gttttagaa gcggagactc    111900 gttcgttaaa aacgttttg attagggggac agagcctaga ccaagaatcg ttaaatgaga   111960
tagaagttac aagaaaagaa acaatgcttt gggaccttca ggaacaaagt aatatgatgg   112020
acaaaaaaat agcagcaatc agcagcctca ttatgaataa cggagagctt cttaggaaac   112080
tttcaaaatt tttcgtgcct ctaactgttg ttcttggaga cgacgggtta gagattttgg   112140
aagcatacgt ctgtggcgag gaacccatgc tgcctttgga cacggtacct gttatattac   112200
gatgtgtcgg agactacgca gccttggaca ccaagcatct cttgagtaac gaatgtacac   112260
aggcgtctaa aaaacttcgc tttggataca gtgtaatgga cttttcacttt tcgctaactg   112320 tgtctgatgt aaaaatttgc ttttcacaca cggacaccgg tgaggctgta tgtgaaaaaa   112380
tgaaacaaat tttttatttt tctgtgtgtg cttttggtgg tgagcaagtt ctcttagtga   112440
cgccaaaaaa tgcttatgcc ttattgttcg acgatgattt tgtgtttgctt ttactgcaga   112500 gcgtgtttgc tttcctgcac gagaagatat tcggagttta taaacaggtg ttagttcagc   112560
tttgcgaata catcggtccc gacttatggc cctttgggaa tgaaagatcg gtttctttta   112620
taggatatcc gaatctgtgg cttttgtctg tatcggactt agaaaggcgg gttccggata   112680
caacttatat ctgccgtgaa attctctcat tttgcggttt ggcgcctatc ctgggacctc   112740
gtggtagaca cgcgatcccc gtaattaggg agctaagtgt tgaaatgcct ggaagtgaaa   112800
cctctttgca acgtttcagg ttcaatagtc agtatgtttc aagtgagtct ctgtgttttc   112860
agacaggtcc cgaggacaca catctattct ttagtgacag tgatatgtat gtagtgactt   112920
tgccagattg tctgaggcta ttattgaagt ccacggttcc tagggccttt ctgccatgtt   112980
ttgatgaaaa cgccacggaa atcgaactgc ttttaaaatt tatgtcgagg ctgcaacaca   113040
gatcgtacgc tttattcgat gcggtgatct ttatgttaga tgcttttgtt tccgcttttc   113100
agcgagcatg tactctaatg gaaatgcgat ggctgttagt gagggactta cacgtgtttt   113160
atttaacctg tgacggtaaa gattcacatg ttgtcatgcc tttactgcaa acggccgttg   113220
aaaactgttg ggaaaaaatt acggaaatca agcaaagacc tgcatttcag tgtatggaaa   113280
tttcgcgctg tggatttgtc ttctacgcta gatttttttt aagcagtggg ttgtcacaat   113340
ctaaagaagc gcactggaca gtaacggcaa gtaaatattt atctgcatgt attcgggcca   113400
ataagacagg tctttgctttt gccagtataa ctgtttatttt tcaggatatg atgtgtgttt   113460
ttatagctaa taggtataat gtttcttatt ggatcgaaga gttcgatcct aatgattatt   113520
gcctggaata tcatgaagga cttctggact gcagtagata tacggccgtg atgtctgaag   113580
atggacagct tgtcagacaa gcacgtggaa ttgcattgac tgacaaaata aacttttctt   113640
attacattct cgttacattg agagtgttga ggagatgggt ggagagtaaa tttgaagacg   113700
ttgaacagac agagtttatt aggtgggaaa acaggatgct ctatgaacac attcatttgc   113760
tacatttgaa ttaattttgt ttctttacat aacatagaaa aataagactt agctagacgt   113820
gtcttcattc ttcgaataaa aaatttgtgc gaattgtgtt gctagttgta tgacttggag   113880
agaactgtct tgcagctgtc tagattctaa ggataaattg atgaaattgt gactacgttt   113940
tgtgttaaaa taaagttcca aaacttctat atgcgtgttt ttcatttcat tgtatagtct   114000
aatcatcgga ggcaccttgt ggaggatttc tgaggcgtgt tcgttaaaaa aaatgtgtct   114060
```

```
tagtgtacaa accaatttgt cgcacgtgtt gaataatatt ttcgttaccg gagataggac    114120
ggggaaaaga acgagcctag cgattagttt gtgcagggtg ctttgcttca gtggaagatt    114180
ctctaatgcg aacactagtc cgcaaagcat aaattcttct ggcgtatcca ctttcatatg    114240
gattagtctg cgtttgaact gaaaaggatt gagtcgcagt tcttgcagtg tatcttccga    114300
gtctagtatt atgatgccaa tgaagccttg gaatcccaac tctttttcgc agatggtctt    114360
gtattccagg ccgttgatca tggttccgtc ttccaagtgg aaccatattc cgtcgtctcc    114420
tactgttata tttactaacg aatgtcgtgc gagggatacg cacttatcaa tcttgatcac    114480
ctttaggata gttcggacgt gtaaggtgtt gaatacgtct gaggtttcta attcttttaa    114540
ttttttcaag gatttcattc tccgggtttg gggagaaaat gttcgaatcg aaaatcggct    114600
cgttgttttc ggggtgcgtt tgggttaaat tatacacttc tgagatctga tttagctctc    114660
ggacgtatac gagtcttaaa taatgcttga ttttgctgct ttcgtagatg gctaataaga    114720
tttcaccgag ggatagaaag agaaattcct cgggaattga ttcgaggttg taaatattta    114780
agagtcgcct taggaaaggc acgatgagca gctcgatgct atagttagag tatgtgatac    114840
tttcttcctg tccttgatta ttaacgtttt ttcttaaccg aaaggttcgc atgtattcca    114900
tttcccatag ttggtctatt cgtttgtcgg catattgtgt gtctgggata tactgtgaaa    114960
aaaaactgtt tgcgactgat ctggtgtcat ctatggaaac gctagtgaat gggagccttt    115020
gaactatgtt tagcgctcgc gataaagaga gattctcgag gtcatggtcc agatccgggt    115080
tatagcgatc acaatcgtta ttcgtctcga gcaaagagtg tagatctttg attttccttt    115140
cgaacatttg gtttgttgtt ttgagtgttt cgatttcatc catctgtgtt tgtatctgct    115200
cctccatgca cttgatgatt tgttttttga acagatctcg aacgtctctc tctcctgtgt    115260
cgatcgcaga gcgttttcgg aactgtcctc ggttcagcat gagtttattt tggtctatta    115320 tagaggggt gatttcttga ataaatcctt caacgctgtc cctaatgcct attttagatt    115380
tgctgtccga caagttgagt aaaaatttga ttaaactttt tttcgcgtcg ctgttttttt    115440
cttctttttc tatcatgtcc attatctttt tgttggttac atctgtcttt gctgtggtta    115500
gcacctttat gggaaatgta ttcaataatt ggcacatttt ttgatgacgc cgcagactat    115560
tgtgtttttt tagttctgga gaaggtggg cgaggggtgt agtcagcatt aggcgatttc    115620
taataacata tgggggtgctg tacgtgaaaa acgctatagc cttcttgttt ttaaagcaag    115680
aaatttgctc cgaattccga tctcggaaaa tcttaatatt atgaaaatcc ggaatgatca    115740
cggaagatag acccaataaa atgggagtga caatgttttg tttatgccgc actatgtcgt    115800
ggattagttt agatgacact tgttgtagaa gattgtataa gttcggggcc gtaggggtgg    115860
ttctcatgaa cggaacgatt cctacggtac agatccagtc tacatatctg ttatagtgac    115920
tgttgtctat gctctgaagg ataaaattaa ttatattaga tatatctccc aagatcacct    115980
gtttaatcgc gtgagcccag acactaaaat aatcttgaaa tgacaatttt tgttgtgga    116040 acggaaatga cctcacatga cgtttccatt catcgtggat ttgttgaata gaaacgctgt    116100
ttaaaagggc ttgagctact ccataggcta tttgtttttt cagtacggca gaatctcgga    116160
gagcgttgtg gattgtttga cctttgaaaa aattttttgtg tccgtgtagc atttcaataa    116220
aagtcattat ctgctcagag ggataaatca tgtctatctc ttcgttgttc ggaggtagat    116280
acgataataa gttttttgctt aacatgtctt cggctcccaa aatagagttg attgtagata    116340
aggtggcttc gttatcagaa agacgcttgg aggggcgtct gccagaagat tggtttcgcc    116400
acatcatgga tcctgaaacc gagttcaaca gcgaatttgc tgatgctctg tgcatcggta    116460
```

```
ttgatgaatt cgctcaacct ctgccttttt tgccgtttaa ggccttgtta gtaaccggta    116520
cggccggggc agggaaaacg aacagcattc agacccttagc ggccaactta gattgtatcg    116580
ttactgcaac gacatctatc gccgctcaga atttgagcgt tgttttaaac agaagtaaat    116640
ccgcgcaagt taaaacaatt tttaagactt ttgggtttaa tagttcacat gtatctatga    116700
gcgaacgtca aagttatatt gcaaatgacg agaggtcgat tcaaattcaa caaaagcaag    116760
acctgtctat ctattggaat gttatctccg acatagcgga gagggcgttg ggtgctgtcg    116820
cgtgcaaaac taaagagtta cctgatttgt gtgagagtag tgttatagtt atcgacgagg    116880
caggcgtaat attcgacat attctgcaca ctgttgtttt tttctattgg ttttataacg    116940
cgttgtataa aaccccttg tatgagaacg gaattgttcc gtgcatcgtg tgtgtgggt    117000 cgcccacgca gagtaacgct ttggtgactt catttaatcc gctgactcaa acaaggacg    117060 tgaagagagg aatagatgta ctttcagcct tgatctgcga cgacgtgctc tctaaatatt    117120
gcgaagtcga taataactgg ataatctttg taaacaacaa aagatgtgcg gatcatgcgt    117180
tcggagattt tttaaagcac atagaatttg gcttgccgtt aaagccggag cttatagagt    117240
atgtcgatca gtttgtgaag cccgcttcgt acataagaaa tcccatgaac gaaatagaaa    117300
cgacccgctt gttttatcg cataacgagg taaagaacta tttccgttca ttgcatgagc    117360
aggttgaagt taccaacaga aataacttgt ttgtgtttcc ggtttatttt ctcataaaaa    117420
acaagacttt cgaagactac aaaagtgaaa ttggtaattt ctccttagaa attgaaccgt    117480
ggtttaaatc taatattcat cggctgaata cttattctca gttcgcggat caggatttat    117540
cgaaaactgt tcaattggag gagattgttt tggaagatgg gtcggtggaa gagactttga    117600
taacctgtca tctgaaacat atcagaaaca gttcaatagg tgtgacgtcc aagatcaagg    117660
cttcgaccgt gggtttcc ggaacttatg aaaaatttgt agaactgtta cagagcgatt    117720
tgtttatcga aaaacgtca tgtgagcaga ctattcacgc atattctttt ttatccggtc    117780
ttatgttcgg agggatgtat tctttctgct gttcggaatt caccaccct gaagtgttaa    117840 tggaaatcaa aaacataaag atgcccagta ttgaattctt agaaagtgaa atgtcgagga    117900
tgtctcgaga cgtgcaaacc gtagagacag atgaaaggta tgatttcgga ttagtcgatg    117960
atgggttatc agatatggac ctattagaaa ttgatccttg cggagatcca ttttttacta    118020
ggtatagtaa gttgccttta actaattctc tgtcgttcga ggaaattagt ttgctttata    118080
cgacgtttaa ggatatcttt atatctaggt ttgccattct gcagatgcat acaaaaggga    118140
agttcggaaa gactctccta gtgacttata acagaaacaa cgtttctaga aaacagtgcg    118200
gtgagatata ttcccattta aagagttttt atggtatgct cacctacgct atccctgcca    118260
ataattatac tctggagggt tatacaaatg ataatgtagt tcatttagga acggataaac    118320
aattaccgca gatcttatat aaaaaaggat tacctagatt agttataaaa gatgaaatgg    118380
ggttcatttc tgttttagat aataacgtgt cgaaatttgt cgatgtcgta aatggtcaga    118440
gttttcatct atgtacaacg gtcgattacg ccactgtttc taaagtttct atgaccatca    118500
cgaaaagtca agggctttcc atacaaaagg tcgcaataga tttcgggagt gatccaaaaa    118560
atttaaaatt gagttctatt tatgttggga tgtcacgagt aaccgacccg ataatttaa    118620 taatgaatgt taatccttg agactgaatt atgagaatga aattttatt gctccgcata    118680 ttgtaaaagc gttaaagaac gaaaatacca tgttaatatt ttagggaggt ttttatgag    118740 aatatataaa aaaaactaaa acatcagatg aattgtgcgt gtaattgttg aaattccata    118800
cggtcgaatg agcttatttc cgtcggtccg ttttttctgc aaaacaaaag tagtacaggg    118860
```

```
atttagtaca gtatgtctcg aaaaagacaa gggtgtgaaa ctttatgagg aactgatgag   118920
aaatgactta cggccatgat tttgtttcgt cgctaaattg aatacagctg cagggatgtg   118980
gtatgagatg acatctgcaa aaacaaatga aagtctcccc cggagtacac gtatgtactc   119040
cgggggaaac ctcaaaaatg cacaatttag cctattaagc agccgcgaac tcgttaatag   119100
ttactttgat gttaactcag gtggtggctt ggatggtgtc ctaagtatca atcgaagctc   119160
ctttattttt tgcactactg aagttattct aggtatcggg gtaagaataa gatgacgaaa   119220
aaaatatgct agatccgtcc attaaatcct agagttgttt ttagtaataa taggttattt   119280
acaaaagcct gcatatgatc caatgtttct gtatgaatcc agataaacaa aaatccagga   119340
gtaatgattg aatcacaaa atgattagtt agatgcttaa cttacttaat aactacactt    119400
atagactaaa cttaacttat caactatact taacttttag gtccttataa tgtgaactaa   119460
ataatcaact gttttgtgcc caatccccca ctactaaagc aatcgtcttt gatttatgaa   119520
acaacgaggc ccacttcacg ttattacata gatcaaggtc tatctcttgg cggttttga   119580 attcttccga gagcgtagcg gtttctaggt ttcagacacg tttatccatt cgccgggtat   119640
tgatcgggtc atatcattag ccgtgaataa tctctggctt catttcgata caacgtgtga   119700
aaactagtaa aaaggacaaa agcagccgcc tttgccgtct tcatgagcgt caaacactca   119760
tgaggtccgt atcttacaac acaatatatg aaatactgtg agcgaggtta ccggtgtccg   119820
agtcgcaatc cgaaaatcat atattgaaat ttgtaacaat gttatgcagt tgtactcaaa   119880
gtatatggtg atgaattgaa catgttttg atgttttcaa tggtattcga aaaatatttt    119940
agatatcctg tagttttttt ctgatgactt ttctgatgac ttttctgatg acaatataga   120000
agatggcaaa acaacaagtt actggtagtt cttgatgtta gataaaatga atcggagata   120060
tgacaagtag agagaggtag gtgatacgag taaaattgaa gggtgtttcc acacagacgg   120120
gggaaattct atgagaacca cagccagaag caattgacga caatagagaa aataagcaag   120180
catactcatc tcgtatagaa agaaccagtg acctacgatt ttccattcag gctagcatgg   120240
tgtgaacgag ggtttttcc gaaaactaga tgactatttc tttaagcaag tgtaattttt    120300
agcagtccaa gttttatgc aacgcagatt ttaatgatgt gtccctcgat aactatacgc    120360
tggaaactaa actaacttac atcttggttg ataaacgatt ttctattaaa aagactaaag   120420
gggttttttt ggcatataca aaattgtatt gagctcttgg aagtgcgtag atgcaaaata   120480
ggttaaatct taccttgaag ctacaacagg tcaacgttcg agtagacgta agttccatat   120540
gtcgaatgcg ctgtaaactt tttcacggaa catcaaaaac accgaattta ttcacgttta   120600
cataagcatg aatctgcaat tttaatagtc ccataaagct ttcatttcga tctaactaca   120660
ttttagtatt tatgctccat aatgtatcaa agtgtataca ttcaatctgt ataagagtct   120720
gcatcaagct tcacgtgatt tgtagttcgc ggtttagcat tcgctgtttt gccgtgtatg   120780
agacttacag tttgatccct aatacttctg acgggcgaca agccttttta tatgcatttt   120840
acggtaaagt ccacgcccctt gtcgctgacg caatacgtaa aggttttcgg tttggatgag   120900
gatgtggtta accgttagta aaagtcgtt acagtaaaaa agccgaacgg tattttaga    120960 tgtcggacca catatcggtt taatagattt ttatatcgtg ttcgttgtct gacttagata   121020
tgtcgtttca tgggagaaat aaatcgtttt agttgtgtgc tgtagttttt ggatcgcaaa   121080
cgctcgagcc cggaagtgtg attcgtgcgc ataaaagggc gctggtgtct gtgctcgcta   121140
gctcatttgt gctggatgag cggcaaagaa ctcatctttc tgagattttt ctgggattct   121200
tttggtaaaa atgtatgtct cgtttgtagt cgtttctgga tttctgtaat gttacgattt   121260
```

```
gctatgtgta ttttgatggt gtcgagcatg tttattttgt tcttattttc acacagataa   121320
gatgtatgct gaagaacgtg gatatgggtc atttgacaat gttatacagg cttatgaaca   121380
aattattagt cagtctcttc atttgaaaag gtttgaattc gacaatggct gtttcattga   121440
gttcttagct gactctggaa cgtgtgaaac gttttctaaa ggatggatat caatgattta   121500
ttggacatcg gagacagatt caatgggttc tctaacggtg gatattggga tggatgaagg   121560
aaaatgcaga acgtacagag ctcggggcct tttactgtgt tcaaaatcaa tcacgtcgat   121620
ttctcagaat actgagggca gagagaggat tttgactgtt tcccatgaaa acggaaaact   121680
tcaaataacg tttgttacta ttgctaaagt ttcctcggag cccgagctac gaaatctggg   121740
cgatttgaaa tttatggaaa agtttgaaaa agaatgtcga gctctagaca ggaaaaaaca   121800
cgacgatgaa cacagaaaac gctcggggaa gcagaaagaa aaagaaaaag tggaggacat   121860
tgacaaaaaa aagaagatg agaaactaaa acaagaagaa aaaaacgaa acgacgaaga   121920 caagcggccg gacaaaaagg atgaatttga tggtaaatat gaatgtgtag ctgttgtaaa   121980
tttttttatt attggtgtgt cacggtcgtg gactttttta aatagtatct gttttgttgt   122040
gatttcagaa cccccctaagg agaagagaca gaaatctcac cacgaaacga aacgtaattt   122100
ggaagaacaa agtcacgaag atggcatagc accgacttct acgacattcg tgaatggagc   122160
ggttgagggt gcgttatcgc cctgtgtttc tattgataat cacgaagatc aacaacatga   122220
tgaattagac aagcgcgttt atgcgcaggt gggtggagtt ttgggttcac caaaacctag   122280
gtctttggag tctttgttgt gcgtatctaa agctgatctt tttcttttag gggacgaacc   122340
gagaaggtct atccaatgaa gataattatg gaaattttca gcttaataag tctttagaac   122400
agcttagggc cagacttgtt gcaagcagcg gcgaggttgt agaaagatcg ctttcgaaat   122460
tgaaagagcg tttggattat gtaaaggata atttaataaa aaatgtactt gaatgtgctg   122520
atgttactgt tccaagtaaa tgtttaagta aaacaaaaca tatcgagcaa aagaaacaga   122580
tagtgttttc tgattgtgtc aggtcggtac ctgtgtgtga gattaaaccg tttatcgaca   122640
tgcgagtatt tgaaactgaa acaacgcaga acgcaagaag agttcgacaa cggaccagaa   122700
caaccgtcgg atcaacagat ggtgcaatcg ggcagcagcg tgttatttca ggacaaaacc   122760
ggggcagagc acgaggacgt ggccgaggga gagttcccag gagacggaat tccaatctaa   122820
ataatttaag gacacaaaat tctgcaattg tcatagacga tagcagcgaa accgaaaact   122880
ttgaaaatgc tgggagtttt aatgaagact tactggcaac cacaatattg gaaacactgt   122940
gaattttatt gctgtattgt aattcttatg taaactaaat aggttctatt cgttcagaat   123000
gttccaattg attgggtctt tcccgtgctc agtaagaaat aaatttgttc gcacaaaatg   123060
attgcaacca ataaatggca ttcttgcagc tttcactttg ggtgatggat gtgcactttc   123120
taagacgaga tgtttctgtg cgtctattag ataagagagt ttccgggcat gtttcccca   123180 caacaagaaa acgagagagt tcatttgttc cgatagtctg ctgataatct tgtagctcag   123240
tgtttgccaa ccaaatgcct cgtgggacat tggtaatcca tgaactacag tgaatatcga   123300
gtttagcagt aggactcctt ctctacacca ggagtttaaa cagccgttgt caggggggga   123360
aaaattcggg atgcttcttt ccagttcttt aaatatattc tttagagatt ctggaatcga   123420
gcactctttc actgtaccga aggccaaacc gcaacctctg ccgtcgggat acggatcgtg   123480
tcccagaatc acaactttaa catcggtggg tttgcacaaa aaactccagg cgtggacgtt   123540
atccgaagag gggtggacgg ttagatgagc tctatcgttg tccaccaatt tataaacatg   123600
cttaagatgt gtaatttcta acttggagag ttgcaggaaa ctcaaccagt ctctgtttat   123660
```

```
gccgaagagt gaatgctgat catctattga aaggttttca tagttttttt cttcatcctg   123720
aacgtgatct aacatccact gtagtagggc catggttggg aaatgaaatg cagtggatta   123780
aattccctag gagcatttta tgtgaatggg acgtgatgtc atagccaatt atgtgtttct   123840
aatcagaatc gtagggcggg aacttcggaa aggtagttta gaattgtagg cttccatctg   123900
ttttagcagg tcgaattcta ctccggtttt caagtggaaa tactttaaac aattcaaaat   123960
cgtatcaaag agagtcaaag agttaaaagg gaacctgata attttgtga tgcctgtagc   124020 aggattctcc aagtataata aaaaccaat gttgctgtaa aaactgtctg tgttttctga   124080
aatgttaaac tcgagacctg caatgttatc aacaaaaaag ttattgacgt acgtaattct   124140
ttcaggcaaa tattttctac agttatcgct gatgcaggtt gttattccga cggaaggcga   124200
acatgtctgg aagccattga aaaagtttag ccaattgtcc cgagattctg ggtcccctat   124260
cagcgcaaac aatgtgcgta gttgctctgg gttatcctgc agaagtaaga agtcgctgag   124320
gaattcattg gttaccatta tacggctaaa aggcttttt tttgttgggg gttttagcag   124380
tattgacata acgtcttcat tatataccgg agcttggtag attggttcta gtaatagagg   124440
tacttcggat ctcgtgcaat ttattacagc tgcgatacag tcgtcaagtt tttcaaaata   124500
gaaagaattg tggtcgaaaa gaggcatcgc tttcgagaag gttagtaata tgagtgacat   124560
tacaaatagt aaaagttcca tggttatttt ttatttggag aagttaacac gacgggaaca   124620
acatcttata tacagtaggg aaaaagactt gtcgaaatgt tcatttggct ttttattgtt   124680 ttttttatg cggcatatat tggtatggct atcggattta tcggtagttc ccccgatgcg   124740
gagctgtctt cagaaaattc acgtatttcg tcttctgtct tattaggatg tttgttgtgt   124800
tgcacagatt ggtccgctgt cgtacctggg aagacagaga ctttcagaaa acctttgtt   124860 gcaatcatga ttaaaaagct aaaaagttgt tttgctgctt acctgtctga tttagagcag   124920
ggctcgatgt gtgatatggc aaacgcatcg ccgacaagtc ttgaattagg attgtcgaaa   124980
ttagacaaag aatcatgaaa ctattcgaag acattaatac tggttttctt tctcgttatg   125040
acgatcaata tagaggacgc aaagagagac caatttagat tcgagccaaa aaagtttatt   125100
ttgtcagttt aatagtttgc cataatcatc ccaataaata tatttgttga aagagttgta   125160
tatggtgatg tgttctcgaa ggagcatcgg ttgtgttacg ttcgcgatat tcagagtaat   125220
ctcgttggga tggcagattg caaaattgat acaaacgtga gcggcgcata ataaatcttt   125280
ttccgtcggc gcgtttatca tgagagagca aatgccgaca agctttttt ttgaggcgtt   125340 taccggtata ggagctacag cgttttttcg aagtgcgtcc gtatgtggga cggtccctct   125400
aaaaaactga ttgattgcaa tagcgactac cggttcatgg tgaaccgatt cagaaattat   125460
ttgctcgccc acgttaataa ccatgttgcc aatggacatc aatttttctt gcatggcgtt   125520
tattaagatt ttatttcggg aataaacctg tatttgcaca attgaagcgt tgtaacagcg   125580
gaataatctg taaatttctg acataaaatt tttaggtgag cacggggagt aaggtggaga   125640
tgtttcgtaa gattgaaaaa ttttgaaagc gttgactgca ttcggatctt gcctttggca   125700
ttccgtagac ttgacaattt ccttttctc cgtcgttgat gtctttacag gcatgttgaa   125760
tgataggtcg gcgagaggtt tgtccgtaaa tgcagaaaaa cgattaattt ctttatttg   125820 gtgaaacacg gcgtttgaga ttttccgtag tttggaatgg gcgtagattg cgttatttcg   125880
atatttttcc ttattaaatt ttatgtcggg cgaggtgtgc tggggaaagg ctcttgcagt   125940
ggcagaatcg acgggtttat cggttttggac ggtttgcgaa gatagattgt tttgtaatcg   126000
attatttcgt atagtcgttt tagtggttag atttttttc cgttctgtag acggtttcgt   126060
```

```
tgtttttcta gttcggcgag atttgacggt ctgtcttgtt ttagaggtgt ttttattacc    126120
tctgtctttc atctcttctg aacttaagcc atataaattt taactttaa atgcaacgat    126180 acacatcgaa atcagtagca ccataactga tattatcaat atcagaatta atggtacgat    126240
ccaggtaaat acggtttcgt cagaatttga gccttttacc gcttcttac tgtattcgtc     126300 gtgattttgc acagtgtgtt cgccggaagt tacgagagcg ctacgctttt ggttggtaaa    126360
ccagctcgac gctagacatg agatggtttt tccgacaaat tccagcttgg ttcgtctttt    126420
gaaagtaaag ctcacactaa cggttgacga tccgttttca ttctgtctaa ccattggtat    126480
gtctctctta tatacttctc caagaaattt aataaccaca tttggttttg ataagacgt     126540 cacggtacac gtaacgtcta aaaaattgtt taggtaacga aaatacaaaa cgacgatggg    126600
tttcataatg agttttaagc aactagtcgc agatgttttc tcgttatcca ctgtgaatgt    126660
acaggttaaa catgtcgcgt catatgctga tctggcttta attttcaaca gagatgtagt    126720
tctatcgtgt tttatgtgga aatacaattt actgtccacg tcaagattgt tgatcttatt    126780
tagttcgtgt ataaagacgt agccatcgtc agtgcccgat aagttgtcca tgttttgtac    126840
ctcatgattc gatataagtc ggcttttatt gtaccacgag acgctttgga tgtttgtcgt    126900
tgtgttgagg cgacaatgga aagtaacagt tgaccctatt tcgtatacta aagaaggact    126960
cgtctccggg cggggtacaa aatgtgcgct tatgataata catagaagcg gcaataatcg    127020
aagcatcaag ggactcatag tgtacacctg tgccaaatag cagtttctgc gccaaatagc    127080
ggtttcggat atatataagt cacacccaaa ataaaaaaaa gtcaaggatt tccgttatac    127140
tgttttattt ttttatttaa aaaaaaagtt gggagttaac attttgaaag tgtaagatat    127200
ttcgatttaa aatctctgct gacagaatta tagatagaga tagaattgtc accatcaatg    127260
attgagcaga cccgaaggac aatttcttta ggtttatctt tggcatactt attgcatatt    127320
ttagaagcca ttacaaagtc gatgggcgta gcggcgtaaa ccataagagt ttttacgtcc    127380
gaatgtctcg taaatagatc atgtgtgttg ttttcaagtt tatcccacaa ttcttgaggt    127440
ccttgttttt gtagttctat aaattgatta attgcatctt tgtcataata gttaggcggt    127500
gcatgattca tcttaaatgg ctctgaaaca gtgatgttgg gtcgaatcat taattctctt    127560
tgcatcgtct taatgatttc tgctacttgt tttgatcttg taaagtacat aatgatggct    127620
ccggtgttag agcatccatt agaacagatg ttgtatacag cttcttttag cttgttttca    127680
gggaaaggtt ttttggggat ctgtttgtat tcaaatgctc gtatggtatt tctaaagagt    127740
tttctaaaat cttttgtaga caccctgccg cgatgaattt taaattttgc cgattctttt    127800
ttttcttttc gtctaacata ttctctataa gacaactctt cttcaatttc acttatttca    127860
gaatctgttt tcttcgttcc agatattctt ttccttgaaga aattttgcat actggaatct    127920
gaatcatcat cccgggtgcg cttttttttg cattttgttg tgttgcgtga tatgttactt    127980
tggttatccc gtgggcgata aattgtgtta gtggtggtgt tcgtggtctt aggtgtcttt    128040
ttttgttctt gatcaatggc gttttctaaa tgattggatt gttcatgtgt gttagatgga    128100
ctagaattgc ctagggggaaa ttttcacct gttttctggg agtttctaaa catatctgca    128160
tgtctatgtt ttgattcgtg atttggagat ttgattttgg ttttgtctct tgaagctgat    128220
ttaggtcttg tttgttttc tagttgttgt agtctagatc taggtgaata tgtggcagga    128280
tcttcactgt ttttatatcg acttttgcgc caggattttg atctggaact ggaacatgat    128340
gaagagactg atgatgatga tgccgatgat gatctagttc tggagtgctg atagttaaat    128400
gttataagct tgtctgttcc ggtttctgta cgtgaattag atctggaatt ttcttcaata    128460
```

```
ctggaagaga tgcttgatga tccagatttg tgttttttc ttttggagt attgagtgaa   128520 tctggtgaat aacgagagta agatctggat ctagatgtag aactttctga atcggtgtaa   128580
ttggtggatt ctgatttttt tctgttggtt cttatatgag gtctgaatcg ggggttgtaa   128640
aattgatcat tgtggttaaa ggactggagt cgagctgcag tatttttgta gaaattgagt   128700
tcaggcccga accgaaattt gatttctgat acttcagctt ctgtactaat tgaggtgtca   128760
tgtggatata tttgtctttt attagaatcg caacaaattt gcctcggttt acgtttgttt   128820 gaagttttt cacaagtttg agggaaggt atgttggaca ttaatttatt gttaggggtt   128880
ttaccggagc tctgctggag gccctgctgg aggccctgct ggaggccctg ctggaagccc   128940
tgctggaagc cctgctggag gctctgctgg aagcccctgcc ggagcctgct ggaggctctg   129000
ctggaggctc tgctggaggc tctgctggag gccctgctgg aggccctgct ggaggctctg   129060
ctggaggctc tgctggaggc tctgctggag gccctgctgg aggctctgct ggaagctctg   129120
ctggaggccc tgctggaggc tctgctggaa gctctgctgg aggctctgct ggaggccctg   129180
ctggaggctc ttctggaggc cctgctggaa gctttgctag agactccgct ggaagctttg   129240
ctggaagccc taccggacgc cctgctggag gctctgctgg aggccctgct ggaggccctg   129300
ctggaggccc tgctggaggc cctgctggag gctctgctgg aggctctgct ggaggctctg   129360
ctggaggcct tgctgaaggc tctgctggag gccctgctgg aggtcttgct ggaggctctg   129420
ctggaggctc tgctggaggc tctgctggag gctctgctgg aggctctgct ggaggctctg   129480
ctggaggctc tgtcagagac ctcggtgaaa gttttactca gaggtttatc agagttttcg   129540
ccattagttt ggttagaagt ttcagattta ttttcggtgg aactgcagtt aggtttcatg   129600
tcagtacatt catcaccgtt agaagtgcta ttcatggtgc tgttgccact gttggatttg   129660
ttaaaagcag taaatgagct aggattggaa tgactccgaa taggtgaatt gtctgttaaa   129720
tttttgttgg cgcctgcaga gtgttttta gacgcacagt ttctgttcat agttgaagga   129780
gtttcttgcg tggggcatgc agaagttgat ggaataatag tttcattaca aaatagttgt   129840
gaaaatggct gaataatatt agagtcctct atttctgttt tatttgtatt ttcattggaa   129900
aaactgttta agtccgtatt ttcggtactt tcttctgttt tatggtttgt tttgctgttg   129960
ggggttgttt tagtgaaatt atcatagaat ttatctgata aacaatttcc ataattgctt   130020
tcactgttgt tgggggattt gtattggcct tcttcagagc tactgaatc atgtatacaa   130080 tggtgcgttt ttgattttgg tggtgtagat atctttcat tgtcgggtga ggttttatat   130140
tgttcatcag atgtttttgcc gtgtaggtta tgtgagggat cagactttt tgatgtattt   130200 ttggcggctt tccctgaaac attttaacg actacttccc taacgtcttg gtgtccgttg   130260
gagtttgcag tattttttt agatgtcgta cgtccccgag aatgtttcat tttaggatca   130320
ttagtgtctt ttgggtcatg atgtttttg taagagttat cttggtcgg ggctcttgga   130380 gcatgttttg atatgagaac tctgtcttgt agagaagttt tgatcggtg tatattttt   130440 tttgtgtggt ggagttccga gttagaatga attttagttt tatgaaccgc aaagtttaag   130500
gtgggctcag gtgtcatcgg aagaggagat agcagggat ctaatttga aaaatccta   130560 gcttcagtaa cggcttcatc ttcatgctga ttagattttc tctgtttaag atcagaacgc   130620 gatgaacat ggttttcatt atgttttgt acttatgtt tgtttattgt ttgagaactg   130680
tgtccttttg tcttttggat tgatctacaa cggatatgtg ttttttgta cttctgagta   130740 tccacgccac aatttgagcc attgtctatt agtgcttcct tcggtaacgg ataacttca   130800 gtgtcatata ttttttaat gagatccatt ttttgggaac taggtctgta tgataaactg   130860
```

```
attgcgtcag gagacgttga aacttgctgt ttttttgtgtt ctttgttatc cttagcattc   130920
tcatgttctt tagttttcgt agtttctggt gttgtctgtg attttgttgg ataattgtga   130980
ttgtcagatt gtacgtatgt ggggtctgtt gttattgaag tttgtgaaaa tgccatgcta   131040
tagtcttggg cttgaaaatt gaagttggtt gttagttgtg taacatcttt atagttattc   131100
atacggagat ctggattata ttgttcatag tttggatgca tgtattgttg atatgataaa   131160
tctgcggatc tgtttgagaa atcgtgtagt ctgtggcctc ttccgcgtct gttataactt   131220
ctgggaaaaa atcttccata tggctgttga tactttgagt ttggattgaa gtaattacga   131280
ctatcgtatt ttccctttcc tcctctgggt ctatgggaat gatgtctaaa gttagagtca   131340
tatcctctat cggtatttct agattctctg taggaactct ctatactcct gtatgcatca   131400
taattaggtt gatacggcaa cgaggtgaaa atttgcactgtg aatttgtagt ttggttctgt   131460
gatgcgtaca tgggctgtag gacttgatct ggcagttcgg aagcaaaacg catatggatc   131520
gaattgtttc cgtttgatgg tagattggaa gcagaggatg tgcattgtct gtggatctga   131580
gctgctctcc gtggatcctg gggagttctt gaattttttc tggaatcttg agaagatatg   131640
ggatcttgat gcgtattctc actcaatggt tgtctatgtg tgacgtccgc atcatggtat   131700
agtccggata atttcatggc ttggtggaca acgtcgttat gagcatttgc ttgtttggat   131760
ttttgttctg gaaaacatgt ttataaaatt caagcttaat agatagtatt tttccgtcga   131820
ttagtgatac gcttaatgta tttaataaat tatggataat cattttgatt atgatacatc   131880
ccgtgcagag aatgatgttt atacagattg tgcgtagtat gcaaatgaaa gttattccat   131940
cgttttgtaa tatgaaaagt ttcaaatata gtaaagaaaa gtacatatac gttttcaagg   132000
tgtgttctaa taaatgatg aataaaatag tagttttcta tagaacgtat tatagacttt   132060
tattgcataa taatcattga gtaaatacgt ggagacatta aatttgtatt ttgtttttta   132120
gattgttgag ctatatagat aaatttggat gataaagacg ttatagtttg tagtgaaatt   132180
cactaaatcg ttttaagctt ttatatttat caattaagta gtaactttcc gtggaaatgt   132240
cgcagaagcg gaataatgca tttactaatt ggaaaagatg taggagagtg gtaaaagcct   132300
attggtttct taaggatgta tatcgtgcga tgtgttatta actagttaga tgtggattac   132360
taataatggg ggggggggaat tattcgcata acatgcaatt aaaattcaat tcaaatttta   132420
tgaaattgac attatttgga gaaatttttat gggacgcatg atttatataa ttgatctatt   132480
aacaggccaa gcgacgggat ttagtgagca tgatattaaa tcttttcatt cagtagttga   132540
agttattttc gtggttgatt acattttga ataattaatg gtatataatt aataataagt   132600
agggctaata gtacaattta ttatcactat tcttatgcga tgagttcaag ttcgggcgct   132660
gaaaaattac gtgtaatgaa cactttttttt agagaactta tgttattaga gaatttatgt   132720
taattagtag ttcaataata gaatttatga tttatcaatc acgtgatatg ccatatattt   132780
ggaaatcgcg tgtaatagta tattaggtgt catatattaa tttcatttaa aactaggatg   132840
atcattaaca taaattatat ataatacctg atgaagttaa tggcaattga attggatggt   132900
atattaattt atatttactt atttgcatta gattatatta taataaaatt gttttaatgt   132960
taaaaattta aattattgat gcattcatta ttgacgtgca gtaaatccag tataatgggt   133020
aaaagtgaga tttattgaag gggggggggg aaatgtataa tatccatgtt tttaagatat   133080
ggtaatattt atcaattatc taattgtcta attctgttgg ttgtctacag ggaacctata   133140
gatatattca ggaataattg gagttgaaat tgctgaagtt tgtgactacc aaagggttaa   133200
tatgcataat caaatagata ctgatgctac cgtggggatg gatatgattt gataattaga   133260
```

```
atacaattat atattattta ttatgtatta tggagatgac ataatttaat ataatacaat    133320
atatgataat ttaaagttta tagtagacta gttttattat gtttctaatg tgatagcgcc    133380
ctccgctgtt caggtaaatt atatgatatt gaatgttttg agtagaatag tttgattatg    133440
tttatgatgt gatagcgccc tccgctgttc aggtaaatta tatgatattg aaagtttga    133500 gtagactagt tcgattatgt ttctgttgtg atagcgccct tcgctgttca agtaaattat    133560
atgatattga aagttttgag ttgactagtt tgattatgtt tctgatgtga tagcgccctc    133620
cgctgttgag gtaaattata tgatattgaa agttttgaat agactagttt gattatgttt    133680
ctgatgtgat agcgccctcc gctgttcagg tcaaaattta agggtggtaa atagacattt    133740
ttaaaatatt ttaaacctaa ataatttcat ctattgtgct ttttgttaag atgctgagtt    133800
tgtgtgtttg tgtgtgttgt gtttgtgtgt gttgtgtttg tgtgttgtgt ttgtgtgttg    133860
tgtttgtgtg ttgtgtttgt gtgtgtgaga gagaaagaga tagagagaga tagatatatg    133920
gggggggggg gggaatatat aaatatagta atttttgaatc tgtgtttcca aaattgggaa    133980
ttatgcgtag catcccactt tcaaagtgat ttcagttaat aagatgttgg attaaagatg    134040
gatttggtat tttagattta tactttcaag tgtttggtgg aaaacagata gaacaatgga    134100
acgttgtctc tgaaaaaaaa aactagtagt gtgacattta ggaaatgtgg tttggatact    134160
ttcatcgtgt aaaaagtcaa aaggttgaaa atgttttttt ttttttttcat gaataggagc    134220 tattatgtga atgttgaaca aaaacagatt aaatagacct gaaaggataa tattgtgtag    134280
agtgctacgg tctagctaca actaatgtaa tacatttttt agcagtacta tgatttataa    134340
aattaagatg tccccggggc attagtctta ataaactggt ttagttttgga aaagagaaag    134400 tgaaaatctg aatacttggc atctgtataa ggttttccaa gaatacaatt gtttatagta    134460
tcacatcttc aagaaagctg gaattaactt atggaaatat tgtatgatga cttataagtc    134520
agtttatgta catgacttgg aattaaaaag agaaagcaat gtctgtatga ctttttatta    134580
tttgtaaggt gatattgaaa ataaattcct ttgagaaatc acatgtttgc tgaggtttta    134640
cataatagaa aaagttacat ttgcttatgt aatttctaat ctatagcaac ataaagagtt    134700
acacagtatg ggaaaagtat gtattttaca acaatataag catatttaca taatacacat    134760
ctgtatgcta atgattgcta atcaatttac atcttggttt catctagcta ataaatttga    134820
gcattttctt cgaatggatc ataatcagag ggatagccat ctaatttaaa gacttccatt    134880
ttatcactgt tgcaatcact tctaatggta catttttcat tatcattact tgtaccttcc    134940
atacatctgt tctcatcatt gtgacatgtt gtgtcattga taatatttag tatgggggag    135000
ttatttcctg ttccctgcgg gtcaaatatt tgagtttcgg ctgttacaag actttgggaa    135060
tttgtcacat ttaaattttt ctcacatgca gtagaggtga taacagtata tttactgaa    135120 agatcttggc aatgtttgtc tatgccgtgt ttaatgatat cagttagatc cataaaattt    135180
tccatgacca tttctgtgat aagtttcttg gttggtgtta tgactcccaa gtctgttttg    135240
ctatcctgta ttttactata agtatatgag acattatcct tattatattc ttcatcatcc    135300
attttaatgg ggacaaagtg attgatgaag cagtgattgg cttctgtccc atcactgtca    135360 tttttttacat tcattttttgc agaactgtgt ataacacaat tgtctacttt gtgagttttc    135420
ctcagaaacc acaaccaatt ttttttggga acaaatttgt ttctgatatc atgggtaccc    135480
ggcattgacc ttattgggat ggtaaacact ggggatacaa aacctttact tttacaatga    135540
ccattattga tcactttatc ataatcactc aaatgtaagt aattatcttc agatgtacag    135600
tcatctgact cgctgctcga ttcagaatta ggttctgatt taatagtttt ttttaagatt    135660
```

```
gagctatcaa tattattgtt accatcctct tcatcttcac tctctgaact tataacaatt   135720
acgtttgtgg tttcaggtaa cttatctatc ttaatctttt tagatttgga tggtttaatt   135780
ggaacatttt tccttttagc tgtcctcttt ttagatttgc atttctgagt cacaggcaca   135840
attttctcag ttttgtcatt ttccttagaa ggagtgacct ctggtggtga atatagagac   135900
ttgctaaatg gtgtattctc attagtgtta ttcatatgaa tgttattagt tctgacagtt   135960
gaatcacagt ctgcaatgta atcagtttca tcattgttat cgctttcact ctcataaggt   136020
gctgagtgat cagtttcata accaaatgtt atcatttctg atattaaagg gttgtcatgg   136080
aaaccatcac atagattcac tagactttct acagctccca attctttgtc tattttactt   136140
tctggattta aagtatcctg aattgcatca tgacttttga caggagttgc tgagtcggta   136200
aaggtcatac aaggaagcgt ttcggtacac ttggagttag aaccttttc ctgaatcctt    136260 tcttttgtct gtgacctttg atcggggctg taagccaaaa tgtcttgttg ttcagacccg   136320
gtctctacaa ctactgagtc gggttgagtt tcaagtagtt tttctatcaa gacgtgttta   136380
caactttcaa ggccagtaat ggatttaaag ttattagggc cgcccagatc tgtcactgag   136440
gctgtacata cacagttagg gcttgtttgt ttttccta tctgtctgct attttcaatg     136500 aatgttttg cctctttgga tttccctggc acatctggag aaggagtatc tggatacatt    136560
ttttctacat cttttcatg tatgtttgta agttttgtc tagttgggga ttcattgttc     136620
tttgatgggg tgggagtatt attatcagta ggagattgta cttccatgta ttttaaatat   136680
tctacattgt catcatcttc atggatagat tcgatagaag attcctctga atattttcca   136740
tgttcatcaa attcagctaa ctctaatagt attgattctg aagggtctat gtttaaatca   136800
cagatggaag actctctatc tttatttata gcaatgtagc cttccattat atcagaggaa   136860
gttaaaggtt taatcaaacc agtatcatca taaactgttt ctaagtattc acatgcgtgg   136920
gtgatcatat tcattatggt aattttaaac tggtgtctgt gaggtttgag gtattgccat   136980
gaaaattcac tgctgcatag aacaatactt tggagaacag cagtgctaat attttttggcg  137040 gcagtaatta aattttaca attcacatga attttaagga atgttctatc acagttatcc    137100
ataaagattt gattcatctg cttattagca aattcctgaa acattttcat attttaaca    137160 tggttttcta ttatctcatt tctactttcc agtagttcct gtttaagtaa atttactcgc   137220
ccacaaaaat ccttattgga gatgtcagga ttggacatct ctttgttgtg tgccatcaac   137280
aacaatgagg tggaaaccat gttcaatttt tcacaatcta atgccacata agctttggaa   137340
aaaatgtttt tgatggctat aacaaattga ttgttcatat tagctttcaa atccatgagc   137400
aaatctctgg attctgatgc catctttttc actaacccat caaatttatc acatgcaaaa   137460
acaatgaatc gcggttcgca ccaattaaaa aaatccaagt ttttccaga taacattttt    137520 gcataacttg aaacaaattt agatgaaaca ctacttagta aattaatatt tatcaactgt    137580
cctaattgtt ctaataccag cccctccaac atggatctgt gcagcgttaa taagccagcg    137640
gagttaatta aatcgtcttc catgttagac agttcctgtt tcatggcagc cttcactgat    137700
gcaccaatac tttggatgca agtgccaacg gactgagcta ggatgtaaaa gaagatattc    137760
taagtatgct atatgttaca tgcttaaaac tatgtttttt tcttgttttc tatcttggga    137820 catataaat ataattcatg tactcaccaa ccaaagtttt gaattcttca gatgctcctt     137880
cttccacatt actggaatag gacacattct tggaagcgat gtcgttggaa gactctggga    137940
tgaaaagatc aaaggcttcc agttctggaa aaagcaggct ttcaaaggac acatcacact    138000
tgagactctc ttccaatatt tctttgatgg attcttccac cactggatcg ggatggtagc    138060
```

```
tgtaagtatg gatatttctt agtacttaga aaaactccca tatagtttta aataagatag   138120
atctaataag gactaatcat acttactttt gcatacgttc ctcattggat tccatgttgt   138180
ttccagaggg ttttccgaga atgaacatag aagtaggggt tgtatctttt gctgactcca   138240
ttgtatatta agatgcaaat tcagacaccg cctactgttc tgttagccaa tgaaaaaata   138300
tcttctgtca gcagatataa tactatataa ggagattacc accacctctt tctttgcaga   138360
gattattctc tgcttgaaaa tctgtaacac tgatcatgat gggatatgaa gaaaaagtgt   138420
cagctactgg aaagactcgt ttaaagatac tggcatgtct gatcgtttta atactagctg   138480
cggcaataac tatgttaacg ctggaaatta tatcgaacca aaaacgtacc actactgatc   138540
tcgaagctgt gactgtggcg ctgaagcatg taagcacatc tcttgccagc tgcactgaat   138600
ccactacttc tgtacatacc ggttagtgaa agatatgtct ttttatgtt aatgtattga    138660 ttatatattt gcatacattc cttaagaatg aaaaatcac ggatggtttg ttttagatt     138720 ctgtgacgag ccaaccccacg aaaaacaaag aatcgaggaa aaaattgaa gggaaatctc   138780 caagttgggt tcaggcttta actacagcat ctggaattat cctactgttt tgtataatga   138840
tgatattcat tacatgttcc tggaccacag aaaaagatac agagaagagt gaagtgcaat   138900
cttatgcttc ttcagtagag actttagact ctttaaatga ggctattata ccgaaaactg   138960
aaatgaatgt gtaatgtctg tattttctt tacagagatg tacggagagt ttatatttgg    139020
ggaaaatacc tgactgttct gcctatatgc gaatgttaaa gtatgtataa tataaattct   139080 tacctttaa gagtgattca aggtggaggt ttctttggag attgattcca ggtggtggtt    139140
tcgggtgcaa tcaatctttc ttctgggcgg gaagaaaatc cagcaatcca ataattgatg   139200
ggatgtaatc aatgtcacaa atctgtaaga ttaaatgtga acagtataaa ttctttcgtg   139260
cttatcaaat tacaattatg cgcatgaaaa tatcattaaa ttgttttaaa cattcttaaa   139320
ttcaatttaa aataattttt gtagcaattt taaatattaa tagttaaaaa attgacttac   139380
cagactgcag cgatataaga aagaatctct gtgatgagaa tgttctccgg agccacttct   139440
tgagaaaagt ggcactgaac tggctgtaac ttctgcttat atacaattct atagcgggtg   139500 tgatgtcacag gaaaatgacg aggatgaagg agccaatcgc tgtataatgt taaaccgcaa   139560
gtgtagaaat acacccttt tagacaaata tggaatggaa attagctgat gcttacaaaa    139620
atttagggtt ttgtcatatc ttactcaaaa acaggaattt gtggtctgga ttttttgagg   139680
ttttcttctt atggctgact tgtatttttt tatgagaaag acggagtttg cggttgaagg   139740
cgggataata aagaacactt tactgataaa ttgtcatgtt ttttttttaa aaacatctgc   139800
tacacatcat gaaacaggaa tgtggttttg tgttagcgc ttctcacgaa ataaatgact    139860
tagtcagggg aaaatgttgt aaccgcggta cacactgacc tttaacttta tgagaaaaac   139920
aggaactgcg gttgctctgt tagcagattt tagggttctc gttagcctgg gtaggaaaga   139980
ccccaaccac agtacccact aacctttaac ttaatgagaa aaacaggaac tcggttgctt   140040
cgttagcagt ttttagagtt ttaattcgca tgaacaggaa agacttcaac cgcaatatct   140100
gctaattttt aactttataa gaaaaacagg aactgcggtt gccgcgttac gagctttag    140160 agttctcatt cgcctgggca ggaaatactt caaccgcggt acccgctgat ctttaaattt   140220
atgagaaaaa caggaactgc gattgccgcg ttacgagctt ttagagttct cattcgcctg   140280
gacaggaaat acttcaaccg cggtacccgc tgatctttaa ctttatggga aaaacaggaa   140340
ctcggttgcc gcgttacgag cttttagagt tctcattcgc ctgggcagga aatacttcaa   140400
ccgcggtacc cgctgatctt taactttatg agaaaaacag gaactgcggt tgccgcgtta   140460
```

```
cgagattttg aagttctcat ccttattagc aggaaagatt tcaaccgcgg tacccactaa   140520
cctttaattt tatgagaaaa actggaactg cggttgctcc gttagcagat tttagggttc   140580
tcgttagcct aggtaggaaa gaccccaacc gcggtaccca ctgatcttta actttatgag   140640
aaaaacagaa attgcggttt ccccattag cagatttga agttctcatc cttattagca    140700
ggaaagattt caaccgcggt acccactaac ctttaacttt atgagaaaaa caggaactgc   140760
ggttgctccg ttagcaggtt ttagggttct cgttagcctg gtaggaaag accccaaccg    140820
cagtacccac taacctttaa ctttatgaga aaaacaggaa ctcggttgct ccgttagcag   140880
gttttagggt tctcgttagc ctgggtaaga aagaccccaa ccgcagtacc cactaacctt   140940
taactttatg agaaaaacag gaactgcggt tgctccgtta gcaggtttta gggttctcgt   141000
tagcctgggt aagaaagacc ccaaccgcag tacccactaa cctttaactt tatgagaaaa   141060
acaggaactg cggttgctcc gttagcaggt tttagagttt taattcgcat aatcaggaaa   141120
gacttcaacc gcgtaccca ctaaccttta actttatgag aaaaacagga attgcggttg     141180
ctccgttagc agattttagg gttctcgtta gcctgggtag gaaagacccc aaccgcagta   141240
cccactaacc tttaactta tgagaaaaac agaaactgcg gttgctccgt tagcagcttt     141300
tagagtttta attcgcatga acaggaaaga cttcaaccgc ggtacccgct gatctttaac   141360
tttctgagaa aaacaggaac tgcggttgcc gcgttacgag acttttgaag ttctcatcct   141420
tattagcagg aaagatttaa accgcagtac ccactaacct taagtttat gaggaaaaac    141480
aggaactgcg gttgctttgt tagcatcttt tagagttctc attcgtattg gcaggaaata   141540
cttcaaccgc ggtacccact gatctttaac tttatgaaga aaaacaggaa ctttgttgct   141600
ttgttagcag attttaaagt tctcatcctc attatcagga aagacttcaa ccgcagttcc   141660
cactgacctt taagtttatg aggaaaaaca ggaaatgcgg ttgctttgtt aacagctttt   141720
agagttctca tccgtatggg caaaaaaat ttcaaccgcg gtacccactg atctttagct     141780
ttatcagaaa aaacagaaac tgcggttgcc ccattagcgg attttagggt cctcacccac   141840
ttgagtagga aagaccctaa ccgcggcacc cactgacctt taactgtatg aagagaaaca   141900
gaaactgcgg ttgcccagtt agcaattttt aaggttctca cccgcttggg taggaaagac   141960
cctaaccgcg gcacccactg acctttaact ttatgaggag aaacagaaac tgcggttgcc   142020
ccgttagtaa ttttttaaggt tctcacccgc ttgggtagga agaccctaa ccgcggcacc    142080
cactgacctt taacttttg atgaaaaaca gaagctgcgg ttgccccgtt agcaattttt    142140
aaggttctca cccgcttggg taggaaagac ctaaccgcg gcacccactg acctttaact    142200
ttttgatgaa aaacagaagc tgcggttgcc ccgttagcaa ttttaaggt tctcacccgc     142260
ttgggtagga agaccctaa ccgcggcacc cactgacatt taatttatg gaaaacaaa      142320
ctttttttgtt catcatgcac ttttttatat atcattatat ctctatccaa tcagcactct   142380
tgagggtgca tacattaagg cagtgttgat ttttttttcat tgtacccact tacgaataac   142440
gaatcaaaag ccgtgaagta aatatttta atgatgtatt aatcatcatt tcctaccacg    142500
cctattaact tcagtattta taggataggc aatttgccgc tatacgccat tagctgttct   142560
tctgctagct tggacacagc ggtacagggt gagttatcag cgtcttataa tgtgatgtct   142620
ttttttttat tttcttgtcg gtattttaaa agtagtctgt taagatgttt ttaaatagat   142680
agttataaaa ttttttggaac cgtgtagtca ataaaacaat ttatagaacg gtttctggcc  142740
cagaacagaa attgatttat gtcgtctttc tgaattacag gaaaattgcg agggataact   142800
ttatcaaatg taaaattata taccctctgt gatagattta ttttgtggat atttgaatgt   142860
```

```
accatcgagc gtatatcaac gcaagatgtg gctatgatgg gacacggtcc tatctgtacg 142920
tggtcgtttt cattaattgg gaatattatt ttttgacccc caaggaggga ttttataata 142980
ttaaaatttt caaagttgat acttatgtct ttccaccaca agactaaaac ctgtccgtaa 143040
gctcttaaat ttttagtatt caaagatccg tgtaatattc catgtaacgg gatattttca 143100
agaatggctc ccgttaacat cgatttttcca catccgggtg gaccaataaa actaacggtg 143160
ttttttttcc ctcttctgtg gcttagccac tgatataata tggttcctgc taatataggg 143220
tcaaaagact gcagacagaa caactggtaa accgggtttt catagatttc aaagtcagtg 143280
tctatgtgcg ctataaaatc gatagctttt ctagttgctc ttattctttt tttagatata 143340
gatagagccc tatggattag cacgtccccg tgtgttagtg tcaataattg catgtatgat 143400
ctaacgtctc ttcgtatcca cgcgtcttcc gtgactattc caagatcaga cagccattcg 143460
atggttccca gaaatttaga ttttaaagat attctgttgg tcccatcctt tggaaacagc 143520
ataagtttaa cattaggttt tttattgaaa tgggatatga tgtgttttcg atgtatttca 143580
tcgcatacgt ctcccagttc gttaatattt gtccatgccc attggaactg tggtctaata 143640
atttgaagaa gggcaaaggg gatataactt agactgaaga cctgtgttcc gccaccattt 143700
ttctttgttt tggcatacgt gcaccaatca tctattttag gggcgttccc gtcgaagaaa 143760
tctttaatta atacacccct gatttccgtt gtgtgttttc ctatcgttgc ggtgggaatt 143820
ccatctaaag ctatcaataa tgttaaggag ggtctgccag ctttattctc cgcttgagcg 143880
taccactttg caggggtggg gacggcagtt ttattattcc agtaattgag tatgacatcg 143940
atcattttgg tacatgcagt tatccattta atatcgggcg ctcccggtga gtgcatatct 144000
ctaaaatgtg gcacgggcac gttagagaat ttacaaaaaa aatccgtaga tattccaggg 144060
atttctgcct cccactccac ggggcctttg atagtcaaca tgatatattt gtctttagtc 144120
caaaaatcat cacttggatt tattatgaaa acataccgt ttgtgccttc caagattttt 144180
atagttgtat acggaaaata aggtaattcc cctggcttgt cacctctaga tgtcttcaaa 144240
tctggaagat ttgttatggc aacaaattct cagtatggat ccggcggaac ttctgtcgga 144300
caatgcaatc tcgtccacgt gtgacgaaaa catcgcagct ggacatcatt ttacgcaacc 144360
tccgcacgtt gaaatgtcag tccaatcaac gacatcggcg ggtcatactg gagtgatgac 144420
gacacagtcg cagttttcca atggcgtacg ggatcaaaac cgcgaatcac tgtcgactct 144480
gacgggcctc tcgctggaaa gcatcaacaa tcaaatcaat gttcaaccca ctcagatgac 144540
ctttcaaccc atttccccgc cgatgcaggg tcagaattat gtctatagca ataatatgat 144600
caatcccatc aaacctagat caattatcaa atcacatggt cattcgatgg gggagatgtc 144660
atttgcagac cattccttgt atgttaatgc tcaaccgcct gtccaacagc ctcaacttaa 144720
atcccttgta ggtatgcatc catgcatgac cgctacctca cagggtaaat atgagacaaa 144780
taaaactgtg gggccaccct ctatttcagc ttcccaaatt actacgggaa atgccggtat 144840
aagacccggg gaatatcagt ctgtccataa tcaatcttct ggaaacgggt ctaagtctta 144900
tgagatcacc acggcatccg gcgatgaatg gatactgact acaccggcg ggcaatcctg 144960
gactctgaaa cggaaccccc ctaatcctcc gaataacaga actaattcag ttgtcaacaa 145020
ggcacaacag gtctcgcatg cccaacctta tgtctctggg tctagcgacg gtttctatca 145080
gggggctgct ctccaatcat gtgcgtatgt aaatacgcca ggtttcactc ctgtgtgcga 145140
aacacagaat atgaacaact cacaggcgac acaactaagc gcatccatga actgcataaa 145200
tgcgttatca actactatgg atgcgattgt cacttctact tccaagccgg tggggggtggt 145260
```

```
atcaaataat cggggtgcta attttggaat gggaggcatg gagaattata tggataataa  145320
cagtccatgg aaccaatact gtaaagttca agacattgta tctcaaaact gctcccaggg  145380
aaaagttgtt tcttcgacac cgggaatcgc tcctaatctg atgaagggca acggggttgaa  145440 tgtttatggc catgtggggt gtgtagatgc ggccatttcc gataaacaag gtggcaccgc  145500
taacgtcgca tcttctctat tgaatccgga acatcaagat tggatgcggg tgaccgggac  145560
gagcacaaat ctgttaaaca atataaatgc tgaaacaaaa atggagaact atggttttcc  145620
ggaaaatggg aatgtccacg gagccgtcaa tacagcttta ccactaactc tatccagtgg  145680
tcagccctac acatctgtgc cacaacatgg cgcatgtgaa ggaaatggaa caattcccgt  145740
ggtacagatc tgcagtccca atacggcgtt caaagcgcac tacagtttgc tcggtacagt  145800
ggatgaaaac aaccccttgt ccgtcagaga gagcatacag gacacaagtt ttagtaatgg  145860
atgtgctcct cagttgtcct cgcctggagg aaacccgaca ataattgcac attcaatgat  145920
tggaaataac ggaaccccga ataaagatgt atgcaagcct accccagcc tacgtgcaat  145980 aaaaaaatta aactttgact atgatgaccg aggggaaaat ataggatttc cttccaaact  146040
ggcagccctt ctgtctatgg gagaaaacat gtcaaagatg gacaatcctt gttatggaac  146100
ttctctagcg cagttcgagg aatcacatca gcagaatgca tcggagggta aaatatccat  146160
tgcggattta gagttttctg aagaagatga tgtgctttcc agtgcagcct ctgtcagctg  146220
taatgacaac tgcgtcatga agatcggact tcagcagcaa ggtaccactg tggctgattt  146280
acaacaaggg tttaagcaac aaatgaacgg agaattctcc atgtttgcag tggacgagaa  146340
cattaaaaca caggagatgt cgaatgactg cgcgacaaac gtcacggata atgtatgcgc  146400
cattcgacaa aataaacgta tgcactgtga aattggggatt tcagaggatg gccgggtgcg  146460
ggaagaggag aagtgctcag acgtcgcaat tcacgttccg cggaaaagtg cgcgtattca  146520
taacatgaag tccgaaggcg tgacttgcgg tatgtgtgtg acggctgcgg attccacacg  146580
gcaggatgcg tctggaggtt cgagcagcgg aaccaagaaa ggcgaaaagt tgcaaggact  146640
ttggaaggga taccaggatg acgacgattc ggaattaacc gaactgtcgg atacagacag  146700
cgacaacgat gtccaaaact gtcacggagt aagaaagacc ggttccaaga cgtactcctc  146760
agtatttttt aatcctgact atcgccaagc caagagattg cttgccgaca ttccatacag  146820
aagatggatt ccgacacat tcaacatgga agaaacgag ggtccattcc ttccaatagt  146880
gactagacca cccactgtgt ttattggcgg tagacgccgg aggacttacc tccggcgaag  146940
tgtcacctct atcggtcctc tgagtaaatt aacttacttc aaagaattac tgcagagcta  147000
cgtgttgaga aatagcaact gttatttaag tatcggttgg cctgccaaac acagggtgta  147060
tatcatgtca gaggagaaat tggggtataa tcatataccct accttgaggg agatgttccc  147120
actgccaccc ggatggatga ttgtccttgg aattgtcggt tcagagacgc ccgcggctct  147180
gtataaacac atggtggttc tcctgtgtga aaataaatgg gtgcttctgc ataattaccg  147240
ggactctaaa cacgagctgt atttcgccgc ctcggatttg aaacagttta tggaggaggg  147300
tctgtctaga tgtgactgca tatattatga aaagtcagtg ccgtacgcg tggccatgga  147360 agactctgtt cgagagttct tgagaaacag taaaacgttt cagagtctta tggagtatag  147420
gaagaatatg cacggatta cctggaccctt taacggaatg cctggtagac tgggcgcacg  147480
agttatacat atctgcaatc ctgaattggt taactcaatc ccagcagacg aggccatcag  147540
atatgaagga aaacctttgt attctttgc atttgtcacc actttcaaat cacaccccgg  147600
tagcaaggcc aacgtattga tcgctgcgga taagaactta gggatatacg gctatcataa  147660
```

```
aggtcgcccc aggatacggt acttgtgcaa gaacgtacag gcttttttta gagccggagt   147720
tagaaagatg tatttggatt atgagattcc atcgaaaacg ttgcttgccg tcagcaaaga   147780
tgactatctg tgtactctac aaaaagctcc ttgtctgctc ttaaaaccag ctgtgtttag   147840
aaagactttc tctcaggaag gtaaataaga attgctatgt caagagtttt ccttgacagt   147900
tcccaccctc ttttttttaat taaaacagaa aggccattga ttccatccgc taagagattt   147960
actgtttctt tgacatttat cagagatacg taatactcgg tctactgtgt attgtgtacc   148020
ttgtaatctc taggtaaact tctgctattt ttaatgttga ttaattggac attgttgata   148080
ggtaaactgt tctttcaaaa tgaccagaga ttctatgtac taatctcttt gtttttttt   148140 tctgtgtatt gtgatagggga aggtttgtaa ggacaaagga caaagttcag taagatttaa   148200
taaaataaca tgtgacacaa tttctgactc tcccttcag taatttttt attttaataa   148260 tgtccgttgc cataaggtga gggcaacgta gggtctgagg gataaaaaag taattcgttc   148320
atatgagtag tcggataaaa catttgtagt ttttttttcta aaacataacg attatctcga   148380
tgacattcat accggaataa atccgatata aacgtttcca tctgcagata tcttggcccg   148440
tttttgtgtg ctgacatagc actttcggtt aaatttctta tcacagctct cccgtagtca   148500
cttaaaaaaa aaacaaaaaa aaagacatat gaaatttat agtaggccta cctgcaattt   148560
atataagtac ggatgaaaac aaagaaacaa acatagtgga aataaaatga ttcgcatgtg   148620
aattaatacc taatgactag attgaaatcc atccatgtta cggaccaggg tctttggact   148680
tggtcttgca tagtatatac aattgttcta ttgtccgtga aaggtcgaca aaatttctgg   148740
cctgcatttt gaaacagact gaacaaatat caagttatag attaaccggc gatgtcctgt   148800
gttattacgc agactatacg cgtatacatc cacatacacg cacacacgag aaaatggtgt   148860
actaatcatt caagtttacc cgtggtgaca ttttccccga gtagatagaa cgacacttac   148920
atttcaccgt ctaggcaggt cggagtcgag gaagatacag aactcagtga attaagaacg   148980
acatagtgat cacagcacga agtaatcttc ggtaacgtgc taaaaaacgg tagcgcagcc   149040
actccaggat atgcatggaa atgtgttaaa atatacacag ccacgaaatg cataattatc   149100
tagcagcaat agtttgttat ttaaacaatg ttttttatg ttcatttaaa tatagtatga   149160
atatttacaa ctaaatatac aatcgactat acacatggtc gttaacgcac tattacatgt   149220
gttccaaaaa acagaggttt atcgggagtt atcgttatct acatcgataa agtgtacaag   149280
tctacatgta aacatcacag gaaaatatag aagtccgagg ccgtgtacat ccaaacacgc   149340
acaaataacg gtcaggttct cacgacagta ggttctgtag ctgccatttt gatgttctga   149400
aagtatacat ctctcgggtt gtaaaatacg tgcccaccct cgcataaagc ttgtccgagg   149460
tgttcatatc catatatttt ttttttcgaac atattttgtt tactatatct cgcttggaca   149520
gtgaagatgt tgttaaccat cagtagtccc gcatttctga aacgttgttt tgaagttccg   149580
gtctgtacaa agatggtgct gcggattaag aaaaactgca taaatataaa aaaaaactcg   149640
ggaaaagtca tttgtttaat tatggccttt cgtcttctaa tccaaagaaa gtgaaattaa   149700
acgtaaaaaa aaaactctac atacagattg atagtttaac agcgctcacc ataatgcggg   149760
actcatatgg gtcggactgg ctatatcgta tttaatatta gtcgttgtca gttttctgg   149820 caaagagtgc cacaatgcgc ttacgatggc cggatctatg ttgctgtgca taaccgaaaa   149880
agcaaaaaaa aaaaaaaaaa taaatataac aggttactaa aaaaaattcg ttcctatcaa   149940 tccctatta tttaaaactca ccgtatagat gttcctcgct gtccgaccag tgacaatatt   150000
tgtgaggcaa gtcgcattcc gatggtttcc atcagttcct cagtttcgta cagtgcattt   150060
```

```
ttaaacgctc tgtgagaaac acaagttaag aaatctcaaa tataaactct ttcaaacgat   150120
acatcgcaga tagtataaac tcgaactcac gttcaaagaa gagaaaataa gcttacttac   150180
agtacggaag ataaataatt cttcgtgtcg ttcttattca aacgtgaaca ccattcgtga   150240
ccttgcaggg tttgaaatct gacaaaaaaa gcgaatttcc aaattagaat ttcagaattg   150300
tgttccactg ctatatggca aaaccaataa aaaacataga tgtagttttt tttttaaaaa   150360
attagcatga atcactcaca cgacgtagct atcgtttgga caatgattat cgtttatagg   150420
gacgtatgcg tcaacgacgt cctgccacgg ttcgaaatac tcagtccgag tccatgagtt   150480
agaagattgt aacgtaggac gatcatggtg cacgtctcgg ggaggacaac atgtgccatt   150540
ggcggcaggt ttagacttca atatgtcctc tatgctaacg gacgcgaagc gcgtgcaggt   150600
ttcccaatct tgcccgtcgt tgtcttttcg aacgatcgca aacgaggtta acgttttgat   150660
agtctgtccg ccatggtttt gtatcttcaa gagttcgata ttgacgatca gttcgctgga   150720
ttttgagtgg atgaatacat gtgtgccgca caaagaggca agatacaagg aacgagaaaa   150780
aattttcttg ttacgaagct tccagcccca tagtttctgc tctgaaagga tgtaggtatg   150840
cgtgtggggt tgacacgtat gcgcgtacat gggtgtggtc tgtcttctaa gaggggggtgg   150900 agtggagggt ggaggagaag tgctgcgaca ttttttagagt gacaggtgca tccgagggcg   150960
gggcggggtg tataaatggg actcttttta gtgaattcgg gatatttata cggcggggat   151020
cttacgcttt tctatgtgaa taaatacaca atgcatgcct ttccttgtcg ataaaggaga   151080
cgtggcggga aggcacaaaa acttgtacaa gtactcacca tcgagccttt tccagtctgt   151140
agttttggcg tagctccaat ttactagtca ttggacaaaa agctatcgcc gtcatcgcgg   151200
ttagtggttt caggcgctcc atataggcca aactattata gttgctcccg aaagcgccat   151260
atagcagaga gaagtgaagg ccgaggccgc tagagagaat ctgtgataga cccataggca   151320
ttaatctgtt tttcaaattt ctcactcctc tgctttcggc cgagagagga acgcagatta   151380
tgatatctcc gaacatgatg ctgcggggaa ttaactatga ttattatata ttcatttatt   151440
tgttatctcg gcggattccg acatcggtgt ccgggagaat gagcgcgtgg caaataaaca   151500
agacgaaata aaataaaacg ctagatcctt accgtgcctc tgtctctatg agacaaccgc   151560
agctgttatc atcgcaaatg gcgtagttca ggaggtcttc tatatcttct aaggtagtag   151620
ttggggtata atctacgggg acaaaaactt taaggcctcc tagacgtgac atttcggagg   151680
tagaaaattt agagatgatt tcgggtagcg ttcgtcttct gggcgtagga tttgtaccgt   151740
cgtaaatgtt aaaataaatg ctgtcgtcat agtattttgc ggtatagttg tcttcgtcgt   151800
ccggcggcgg tgtggattcc acggttcccg catctcggta gaccgtagca ttcgacaggg   151860
ctgtcgccat ggaaatcgcg cacacgagta tcggcgcaga acatctcggc ggtctcatag   151920
cgcttagcgt tgcggtcgcc gttctccgtc ttagtcttgc gaaaatgcgt atccgcggga   151980
ggaagaggac agaaaggaag atggtgttag ataagatcta caggaggaga aacgggagac   152040
aaatcctacg aggacgggag agcataatag agcggtttgc atccgggaac attcgcgtga   152100
atgtaaagcc acaagaaatt aatgcaacta gagacttccc aaagatgata tatggctaac   152160
gagcaacgtc tggcgcgttc acactcgttt accgtgtgtg actgagacac gtagtcttca   152220
atctctgcct tgtaaaatca tacgtgggtg gaaagatcgt gcggtgtatc gtcgtcgggg   152280
agcgtactcg gagataagtc tggggcgatc atttttatct gcgacgatat aaaacggggg   152340 gggggggtggg atgaatcgat aacgaggaag aaatacatct gatcgtcatt tggcgatcag   152400
tagtttgtcg gtgatttctt ccgtaaccgg cgtgtgtgta gactttagtt ttggtggtca   152460
```

```
gatattaagt cttgatcaca cgcgtacccg cgcgtttgta gcggcttctc gggtgtctta 152520
ttttcacccc gcagctgaac cgcactccgg tcgggccact tcttttcata caggcgttgt 152580
ctgtctgctc cggggagctg ggctgcgctc gggccgggac acttattccc atacaggcgc 152640
tgccttctct gctttgggag gtcggactgc gctcgggccg ggatacttat tcccatacag 152700
gcgctgcttt ctctgcatcg ggaagtcgga ctgcgcccgg gccgggacac ttattcccat 152760
acaggcgctg ccttctctgc tttgggaggt cggactgcgc tcgggccggg acacttattc 152820
ccatacaggc gctgctttct ctgcatcggg aagccggact gcgctcgggc cgggacactt 152880
attcccatac aggcgctgcc ttctctgctt gggaggtcg dactgcgctc gggccgggac 152940
acttattccc ataccggcgc tgctttctct gcatcgggaa gccggactgc gctcgggccg 153000
ggacactttt ttgtgcgata ctgttgctct ggaagacaga tatcctcgcg tttcaaaaat 153060
tactttaaac tccccggggg ggttaaaaaa aggggggtat taaccctaac cctaacccta 153120
ggcctaaccc taaccctaac cctaggtcta accctaaccc taaccctaac cctaggtcta 153180
accctaaccc taaccctaac cctaggtcta accctaaccc taaccctaac cctaggccta 153240
accctaaccc taaccctaac cctaggtcta accgtaaccc taaccctagg tctaaccata 153300
gccctaaccta tagccctaac catagcccta accataaccc taaccatagc cctaaccata 153360
gccctaaccta tagcactaac catagcccta acctagccc taaccatagc cctaacacta 153420
atcctcgcat ctggccctaa cactacccct ctttcaacca ctcaccatca ccccacccgc 153480
tgccccccccc cacacacaca cacacacaca caccgccca ccgctaccac cacctctgaa 153540
cttcaccttt tccctccatc tcgccccact tctctctaca cttctccgcc cctctattct 153600
tactcctgtt ttctaggatg ccgctgccgg cgcgtgtcag ccacgccctg catcgtcttc 153660
cgctgtccca ctattggtgg ctactgttgg gtcgacactc ccttcgtcat gtccattcct 153720
accttcgcct gcacaaaggt ctacgccttc ctttaccttg gcccgagcaa gaatgcctgc 153780
atttacatcc taagccttac aagtttctcc tgcgttaccc ttgtctaaca agacaaccgc 153840
atcttcttca gggctggccc gcggattctt ctctatgtga gtgacattta cacttccact 153900
tgttcacatg atttattgtg ttttgtctgc tacaccaagc acatttcggt ttctctttta 153960
tacatttgtc tctattctct cggtctcagg gttcgaccct aaaccctacc atcttcggcc 154020
gacagcaagt tgctaccgct gggcctgatc acgctgtccg ccttttccat gcgcgtttct 154080
gagccgacac actgcagcgg cttccacgcg gcacatccgt ctctcagttg gttaacggga 154140
tcgtcccctt ggctcgtgct cctacaagcg ccaggagggt ctctgttctg ccacgacgtg 154200
ttccaaggcc gactctatct cctgtcgcac tccgtgtcgc tcttctaaa gacgggcctt 154260
cgccagtgtg aggccatcta tcgcgcaccg ctgtggcgcg tacggcccct gccgagccta 154320
tggacgtgtc gagatcccga cacggccttc ttgccgaaat tactggcgag aaccgcccga 154380
cgcggcctgg ccgctttcta tgccctgtgg agactgcatc tgggatcccg ctcggagctc 154440
tctcaccccg tgttggagtg ggagagaaca gagctggtcc tgacggatcg gagacgcagg 154500
tggccgtgta cgcacctcct gtccggctcg agttccagc gcgtttcctc gagtgacgcc 154560
ggagacacat ggaacgcagc gacagagaag gcggcggggg gaaaagagga ggcggagaga 154620
ggcgggcgac agcaagccac tgacagactc gcaagtccgc acctgacgcg ggcctccgc 154680
gactccggtc ggtcccttca gggtgaggag cccagcgccg cggaagactt tgcgaggtgc 154740
agaccgctgc tggacgaact gtgcggggag ggcggctggc ttcccttttgc gtttctcacg 154800
gcatctccgc acgtctgtct gatcctaacg gagggaggcc ccgtcctggc gcttgacctg 154860
```

```
aacgacacct ccctgtggcg catcgcggac gacttggagc tgctgctgcg cctggggagc  154920
ctgctcctgc tctcagggct ccggcttcct ctccgtcccc cgagcgggag cggcgaggcg  154980
gcgagaaagc cggggtacga aaggaagag ggaagaggga gagcggcgac ggcgagcgcg  155040
acggccgcga cgtcgccgcg cagaccgacc cgtccgaggg gggtgacgga gaagggacgt  155100
gtgacaaccg gggacgtccc tttctccgca catcccgaat ctgaggaaca gacagacggc  155160
caccacgggc gccaggaaag cggccacggc gaccagcgcg gcgggacgg acgaggacac  155220 cgcgatgacg gcgcgcgccg ccacgcgaat gacgaaacag agcccagca gcgcggagag  155280 cacgaggacg gggaacagac cgactccggg cgcgaggagg acgcacagga gagcgaggtc  155340
gcaagaagag acgagaaggg aacggagcag ggcggtagcg gaaggagctg cgggagggca  155400
aagcagacgt acggcgggag aggcgaacat ggtgcctggt cgtcgatccc cctgtctgtc  155460
cccaggcccg atcccgcgt gtgggtccct cctcctcatc tgttattccc ttcccgctg  155520 ccgtcgataa cgcccgtcga agacgagccg tccgcccgcc ctcggtgccc gccaggtccc  155580
gcggaggaac cctctaagtg ttctccgtgc ccgccctgcc cgtcgcccga cgcccgcag  155640 tccgctgtcc cgcgcctctc cgctctgtcc gtccctcgc cgtccaccgc gcgtgtccgt  155700
ttctccctct cctccctctc ctcctcctcc tcctcctcct cttcctcctc ctcccgtcc  155760 tactctccct ccccgttgtc tccgccctct ccgtctctc cctcgtctcc cagatctccg  155820
ttcatctccc ccattagatc tccgggactc cgagcaaagc cgcgggtgtc ctccgggcat  155880
cccgtggcgt tccgccggc gccctcgtcc gcgccgccct tttccaaaag agtcccgtcc  155940
gttccctcat cggcatctcc gtccgcgccg tgcatcggca ggtcgcggcc gccctccgca  156000 cagacgcgt gagacgccgc gtgaggtgac ggaggcggcg aagggacacg agaagaacat  156060
gcagaagaac atgaagacga agaagacgaa gaaacgagga cgaaaggagg ggaatacacc  156120
ggagaccgag cggcggatgg agcccgctcg gttttgcacg tccgcgatac cgagcggact  156180
ccgtcgccgc tccggaccct ccacgcccct ccgtccagga cccgaggtcc gacacgcccc  156240
cacctcgcgc acctcctccg ccaccaccgc tgacagtcac cgcatatcac ccccatacac  156300
acccagcagc agaggccggc gcacacacac gcgcggagca cgcacgagaa cacgcgagac  156360
atcggccgcc gaaattaacg gagtctatgc gcgcgccgtg acacggaaaa ccaagcggag  156420
cgagacgatc gaccgactcc tgctatcctt cctccctggg tacggtccac acgccagtct  156480
gcggagtcac ctgagggccg gatccgctcc gcgcccccg cccgatccgc cccgataaaa  156540
aaaaatcatc tgactcgtgc cagttcacac agatgcaacc gatgacaaaa aaaacacac  156600 caccacaagc aaacgctcgc cggcccgttc accgtccctc tcaccccac tcgaatcgcg  156660 caggcgcgtc ggcgggcagt cccccgaacg cctccacggc aacgctcctc ccacgccccc  156720
tcggtccccc ccccccctcc ctccatcccc ctccccggag catacacgcc gactctctcc  156780
gcagaggcgc cgaccacagc ggcagcggaa actgtaacgg ccacgttctt tgaacagtga  156840
cagtaacggc ggcggcggct gtcgccgtca cggtagtcgt ggcggagcac ccggggaggc  156900
gacgacgggg actaccgatg ctctcagatc atcgccatag tgaaagagta ccgaataaaa  156960
caagttaaat tttgttgtaa ataaaaaaaa aatactatgt ggaaattaaa aataaaaaaa  157020
aaatgaaaat aaaggctaaa cactgactaa acgtgcatcc ttctccgtac gtcccctttc  157080
aataaatggc ggacccgacc tctccataaa cggagacacg ccgggagact ccggccctcc  157140
caatccacag gtagcccgag acctaatcac aaaactgtac ctgaaaccga aagtatagag  157200
ggcggcctcg aatgccccac ctatgaggcg ggacttcgcg acgcgccacc cttcctatac  157260
```

```
gcccggcctt ccgcgtgcgc gcctatagga cgcatcccct cgccccgaaa ccgcaacgcg  157320
gcagagtcgg cgccacaccc ccgtcccccg agttcgcgat gggctggcgc cgaccctgcc  157380
gcggcaacga aggcgaaacg agaccccgac gcatgcgggc ataaagagcg agaagtaaac  157440
gcggggtccc gaattatcgc gagactattt gcccgggccc gccctcgtcc tcatgccctt  157500
ccccccgccc tcatccccg acacacccgg tgggaaaaac gaaagacaca taaataaaac   157560
gaattttgtt gttaaaaatg tttccacgtg acgtccccgg tgattcccgg agatgcggca  157620
cgcggcggat tcgcccgttt acatcggggt ccgcagacgc ggttctgcca gggcgttgcg  157680
gtgtcggttc cgcacagaac accgcggtcc gtcgtcaccg ttcaaccgcg cggtagttcc  157740
gcgattctat ggttcatctc cgctcacagc gttctctttc ttttattttt cactgagccg  157800
ctccaccacc aagagtgtta ctgactacac cgtatacatg ttttttttatc tctccacccc  157860 tccccatcac agaccatcaa acaccttgcc gtatcgacac tgactatact cgaccgcgga  157920
tgacaacggt cgttggtcac aacaagagct acagcggaca gcaaaaataa gataaataca  157980
gtaagagaga ggccccggtc cacataggaa gccaagggcg gacgaaaata aaaacccgtc  158040
cgtgattcac acacgaatcg ggggttatga caacgcgaca cacgcagatg agggacggac  158100
gcatcgcgat ccggcgcgac ggggcgcgat tggcccacgc gcgagcccgt gcccgcttcg  158160
agtggctgct cctggctcgc ggcaggccgt ccaaactgta cggctatacg agtcggcacc  158220
ggggagaacg gatccaccta ccgtggccgc ggtactggtg cctagaactc catccggatc  158280
cgtacaggga cgccaggagc gccaccgtgt ggggtcaccg ctggggttgg ccgccaacgc  158340
acgtgagacc cagatccgtt caagactgcg gtgagtgagc ccgccgcga ccgacgacgc   158400 tatgcgcaca cgggcgagcg gcggggaggg acgtcggccg cagggcgagc gggtggaggg  158460
cgagcgggtg gaggccgagc gggtggaggg cgagcgggtg gagggcgagc gggtggaggg  158520
cgagcgggtg gagggtgagt gggtggaggg ttcgtcgaaa accaccgaag acattggctg  158580
gcggagagtg gggacaaaac aacgtcacgt caggggcgga gaaatatagg gtgcgcagac  158640
cgtcaaagcg cgagttacgg aaaacgagta cggatacacg ggggggggg ggggaagga    158700 aacatggtga agtctgtgac acgcgtgacc gtcagccggc aacgcctgcc acggcctccg  158760
gcctcacaga cgactcacgg agtttcctcc agacattgtt tttttttttt gtattcatcg  158820
gtaatgcggt atacgtaaat tccccgcaaa ggtactttcc gttaaggacg gtacaggcgg  158880
tatgacttcc ggaacacgat gattacggat atcctgcata gtgtacagga gaccgctttt  158940
ttttaggttc cgtataaaac gtacgtcggc gacgtacaca caacggttaa aaaaataaaa  159000 aaaaagagg aaacagtaaa gctcctcctt tcctctgtgt tatcgcgttg agttagtagt    159060
cgccattgct gttgcgtatg cttttcgcgt taacggtacg cgacaggata cgaatgcgtt  159120
acacgccgca aaggcatccc tacgatgact ctatgcggca tctcccgttc gcgcagaaac  159180
gcgagttccc gggacgccag tcgtgacgtc cggccgatgg gatgcctttg cgtgtgcgga  159240
tgttttctgc tgtttatag gaacagagac aagagacgaa aatagcggaa cgcccactat   159300
aacgtgcatt tttctctgtg ttttgcgttt tcatgtttta tgattcttct acggtatcgg  159360
ccggaacggt catcctcgat ccttctcgta cgcgtgtccc gccccagccc tggactcgag  159420
tctgtacgta tgttgcggat acggagaaaa acttcaaccc gtgggcttcg taagctcgta  159480
tctgacccac tccccgctcg acacgcttcg cgtgctcctg gtcggtagag acggagccgt  159540
gtacgtccac cacatgaggg cggccagact ctgccgactg cgtcgaacg taacggagtt   159600 tgcaaggcga gggctgcagc gggacccccgt ggcgtatgag gaggacctag agctgccgga  159660
```

```
ccggcgtatg tgcggaacga acgtcagaca tctgttcgac gtgatcgccg cggccgccga    159720
cgaacacgac ctgctgaccg tcggcggcct gtgtcaaacg cacgccggag tgagctgtga    159780
attactagag accgtgcgag atccgtggac ggcggttccg ggcgtacgca tgactctgac    159840
cgtggcgcgg gctcagtatc gcttgtggcc cgatgcccgg agacagctcc gcctgcacct    159900
gtacgcggga cacccctgg gaccgtggat agtgtgcgcc gttctgtctc gagagaggga    159960
gacgcagacg ccgtcgcctc cgataggcag cggaggcgtg actctgggaa acgtgcccac    160020
gccggggcca cgcgaagtgg agacggcttg ggtgatcgtc acctggcggg accgctgtta    160080
tcgttctggc ccgataacgg caagatctgc cgtctggcga actcgttcgc cgccctgtgg    160140
aggatgggcc gcgggccatg agaggacatt ggacgtattc ggccccgggt agacatctcc    160200
ccgggaacgc ttggccactc ctgtgaacac gtgagaccgc cggtcggaaa acttcccgg     160260
caaagagcgt acctggatta dacgccacgg cggagacgta aggatgcgat atacggccag    160320
agacatgacc ggaggaagat catgacaagg atctcgaaat ataaacaaa aaaaaaaag     160380
tgaggagtgc gcaaacgcaa gaaagaaaa agcagaaccg cggtggagat gtctatccgc     160440
ctgcgtgtat gtgtggggtg tgtatatgtg cgcgtgaccg tatccctccc tgcctttaac    160500
ccgatgagaa ataaaatcgg cgaatgtaca caatcacaca caatgtgctt acgttccgtg    160560
ttactgacac cacataacaa aaaaaaaaca tacttcctgt ccgtgagaca ccgccgccct    160620
ctagcggagt tgctatagca gcgcccgatg ccaacgcgac acggtgagtc gcatagatcg    160680
ggactgcttg aaagcgcgcc acattcgcct tttatataga cgccccgggg agtgggagga    160740
gccaacatac acacgaggtc ggtctggggt tggagacgaa cgcggaaaat caacggcgta    160800
aaaaaaataa aaaaggcgga gacacatagc cttggcggga agacgataac aggttcaaag    160860
atagacagtg aaaaaaaaaa aaagaggaga ccatgacatt gaatacacgt gcggcggcaa    160920
tccaatcaac gggacgtgcc ggggcgcaaa aaaaagtata cggaagtgca tgcgacagac    160980
agtcacgcgg accgacgaca aaggccgact cctagcatgg caactaggaa aaaaaaataa    161040
gcaacgctgc aaaatactaa caaaggaaac atcccttcac cccctcccta ccccgtctac    161100
cacaataccc cccccctcc gtaatcactt ctgtccgcgt ttctcccaca ggcgcgtgca    161160
cacgcagaca cgcagacacg cacacaccac ctctatggca gtcgcgggcg ggcaggcggg    161220
gagcatacgg ggggcagatg taaagtcaat gaggaacggc atagcgcgcg acgtgccgtc    161280
gtctcggacc cttgctattc tggcacgacg ccaagggaag cctctggcgc aatctataac    161340
cctaacccta accctaaccc taaccctaac cctaacccta accctaaccc taaccctaac    161400
cctaacccta accctaaccc taaccctaac cctaacccta accctaaccc taaccctaac    161460
cctaacccta accctaaccc taaccctaac ccatcccca acgcgcgcgc gcgcgcctct    161520
atgggaggcg ccgtgttttt caccaaaacg cgcgccactg cgagaggcgc gtg           161573

<210> SEQ ID NO 2
<211> LENGTH: 153080
<212> TYPE: DNA
<213> ORGANISM: Human herpesvirus 7

<400> SEQUENCE: 2
ccccccgttt cgtatttcaa atcctaaata accccggggg ggtaaaaaaa ggggggagc        60
taaccctaac cctagctcta accctaaccc taaccctagc tctaacccta accctaaccc       120
taagtctaac cctgacccta accctaagtc taaccctgac cctaacccta accctaaccc       180
tagctctaac cctaacccta gctctaaccc taaccctaac cctaacccta gccctaaccc       240
```

```
taaccctaac cctaacccta acccctaaccc taaccctaac cctaacccta acccctaggtc    300 taaccctaac cctaacccta agtctaaccc taaccctaag tctaacccta acccctaaccc    360 taaccctaac cctaacccctg acccctaaccc tagctctaac cctaacccta acccctaaccc    420 taaccctaac cctaacccta acccctaaccc taagtctaac cctaacccta agtctaaccc    480
taactctaag tctaacccta acccctaaccc taaccctaac cctaacccta acccctaaccc    540 taaccctaac cctaagtcta acccctaaccc taaccctaac cctaacccta acccctaagtc    600 taaccctaac cctaacccta acccctaaccc taaccctaac cctaaccccga ggtctaaccc    660 taaccctaac cctaagtcta acccctaaccc taagtctaac cctaacccta acccctaaccc    720 taaccctaac cctgacccta acccctagctc taaccctaac cctaacccta acccctaaccc    780 taaccctaac cctaacccta acccctaaccc taaccctaac cctaacccta acccctaaccc    840 taaccctaag tctaacccta acccctaaccc taagtctaac cctaacccta acccctaaccc    900 taaccctaac cctaagtcta acccctaaccc taagtctaac cctaacccta acccctaaccc    960 taaccctaac cctaacccta acccctaaccc taaccctaag tctaacccta acccctaaccc   1020 taaccctaac cctaacccta acccctaaccc taagtctaac cctaacccta agtctaaccc    1080
taaccctaag tctaacccta acccctaaccc taaccctaac cctaaccccca acccctaaccc   1140 taaccctagc tctaagccta accccctaaccc taaccctaac cctagctcta agcctaaccc    1200
caaccctaac cctaacccta gctctaagtc taaccccaac cctaacccta acccctagctc    1260 taagcctaac cccaacccta acccctaaccc tagctctaag cctaaccccca acccctaaccc   1320 taaccctagc tctaagtcta accccaaccc taaccctaac cctagctcta agtttcaccc    1380
caaccctaac cctaacccta gctctaagtt tcaccccaac cctaacccta acccctagctc    1440 taagcctaac cccaacccta acccctaaccc tagctctaag cctaaccccca acccctaaccc   1500 taaccctagc tctaagccta accccaaccc taaccctaac cctagctcta agtctaaccc    1560
caaccctaac cctaacccta gctctaagtt tcaccccaac cctaacccta acccctagctc    1620 taagtctaac cccaacccta acccctaaccc tagctctaag tctaacccca acccctaaccc   1680 taaccctagc tctaagccta accccaaccc taaccctaac cctagctcta agcctaaccc    1740
caaccctaac cctaacccta gctctaagcc taaccccaac cctaacccta acccctagctc    1800 taagcctaac cccaacccta acccctaaccc tagctctaag ttcaccccaa cctaaccct    1860 aaccctagct ctaagtctaa ccccaaccct aaccctaacc ctagctctaa gtctaaccccc   1920 aaccctaacc ctaaccctag ctctaagcct aaccccaacc ctaaccctaa ccctagctct   1980
aagtctaacc ccaaccctaa ccctaaccct agctctaagc taaccccaa ccctaaccct    2040 aaccctagct ctaagtctaa ccccaaccct aaccctaacc ctagctctaa gtttcaccc    2100 aaccctaacc ctaaccctag ctctaagttt caccccaacc ctaaccctaa ccctagctct   2160
aagcctaacc ccaaccctaa ccctaaccct agctctaagt ttcaccccaa ccctaaccct    2220
aaccctagct ctaagcctaa ccccaaccct aaccctaacc ctagctctaa gcctaacccc    2280
aaccctaacc ctaaccctag ctctaagcct aaccccaacc ctaaccctaa ccctagctct   2340
aagcctaacc ccaaccctaa ccctaaccct agctctaagc taaccccaa ccctaaccct    2400 agctctaagt ttcaccccaa ccctaaccct aaccctagct ctaagcctaa ccccaaccct    2460
aaccctaacc ctagctctaa gcctaacccc aaccctaacc ctaaccctag ctctaaacct    2520
aaccccagcc ctaaccctaa ccctaaccct agctctaagt ctaaccccaa ccctaaccct    2580
aaccctagct ctaagcctaa ccccaaccct aaccctaacc ctagctctaa gcctaacccc    2640
```

```
aaccctaacc ctaaccctag ctctaagtct aaccccaacc ctaaccctaa ccctagctct    2700
aagtctaacc ccaaccctaa ccctaaccct agctctaagc ctaaccccaa ccctaaccct    2760
aaccctagct ctaagcctaa ccccaaccct aaccctaacc ctagctctaa gtctaacccc    2820
aaccctaacc ctaaccctag ctctaagcct aaccccaacc ctaaccctaa ccctagctct    2880
aagcctaacc ccaaccctaa ccctaaccct agctctaagc ctaaccccaa ccctaaccct    2940
aaccctagct ctaagtctaa ccccaaccct aaccctaacc ctagctctaa gtctaacccc    3000
aaccctaacc ctaaccctag ctctaagtct aaccccaacc ctaaccctaa ccctagctct    3060
aagcctaacc ccaaccctaa ccctaaccct agctctaagc ctaaccccag ccctaaccct    3120
aaccctagct ctaagtctaa ccccaaccct aaccctaacc ctagctctaa gtttcacccc    3180
aaccctaacc ctaaccctag ctctaagcct aaccccaacc ctaaccctaa ccctagctct    3240
aagtctaacc ccaaccctaa ccctaaccct agctctaagc ctaaccccaa ccctaaccct    3300
aaccctagct ctaagcctaa ccccaaccct aaccctaacc ctagctctaa gcctaacccc    3360
aaccctaacc ctaaccctag ctctaagcct aaccccaacc ctaaccctaa ccctagctct    3420
aagtttcacc ccaaccctaa ccctaaccct agctctaagc ctaaccccaa ccctaaccct    3480
aaccctagct ctaagtttaa ccccaaccct aaccctaacc ctagctctaa gtttcacccc    3540
aaccctaacc ctaaccctag ctctaagcct aaccccaacc ctaaccctaa ccctagctct    3600
aagtttaacc ccaaccctaa ccctaaccct agctctaaac ctaaccccag ccctaaccct    3660
aaccctaacc ctagctctaa gtctaacccc aaccctaacc ctaaccctag ctctaagcct    3720
aaccccaacc ctaaccctaa ccctagctct aagtctaacc caaccctaa ccctaaccct     3780
agctctaagc ctaaccccaa ccctaaccct aaccctagct ctaagcctaa ccccagccct    3840
aaccctaacc ctagctctaa gcctaacccc aaccctaacc ctaaccctag ctctaagttt    3900
cacccccaacc ctaaccctaa ccctagctct aagtctaacc caaaccctaa ccctaaccct   3960
agctctaagt ttcacccccaa ccccaaccct aaccctagct ctaagtctaa cccaaaccct   4020
aaccctaacc ctagctctaa gtctaacccc aaccctaacc ctagctctca gtctaacccc    4080
agccctaacc ctaaccctag ctctcactgt caccctaaca ctagctccag gtcatctgtt    4140
ctagatccta tccatatctg ccctgactcc tggttccata ccgctccgag ccccacccct    4200
cgtcccgccc tcctcctgtt ctccatgccc tgccttctca acccttcctc ttccacgccc    4260
acattgcctc tgcactccgc gctctcttgg ctgtgcgccc tgccttccg tgacctactg     4320
ggagcgccgc caaatctgtt ttgccccgcc cctgcgcgcg cgggaactgt cggcgccgcg    4380
ctgctgctag cccgccttcc agagctccct ccctccgtct gcctcctcac ccttgccact    4440
cacccttcca tctcttctat cacagactct gtgttacacc acctatgact gctgcaacca    4500
cagaacattt tgctctccgc gcggcactca atcgttactg gtggctgctt ctgggacgac    4560
acaagctcag tttggtatgc aactacgtca cagctcatcg ccaacagtta ctgccgctgc    4620
cgtggcccga acaggaattt ctccaacttg acccggcccc ctactccaat ctccgcaacc    4680
gtgtcgctca ccatctccat cgcggctggc cagcggcaca caacacatgt aagctaccgt    4740
acatctcttt cacaaaccca aggctcacat agagacaagc acaagctcgc gcaatgacat    4800
taaaacctcc catcattgtc ctttcctgtc gctttgccga taacgtcttt gctctatcgc    4860
aggtttcgac ccccgtcctt acttccccaa tgctaaagtc aagctgcttc cgctcggctc    4920
catcacccctt accagatcat tctccagtga cgagcctcat cctattggtg atgatgtgca    4980
tcacagtcat gaccgggggtg actaccatac tgttatctgc agctggctca caggaacctc    5040
```

```
cccgatccta gtgctgcttc aaggaccgga cggcagcatc tattgccacg acgtgtaccg   5100
cggccgattg tatctcgtgg cccactctgt atcgttgttc gccaggctag gccttcgcca   5160
ctgcgaacct ttatatgcgg cacccagatg gaagcacgtt cctctgccca gcatgtgggt   5220
ggcgagcccg ccagcgtccg ccaccctcac gcaaacactc gccgtgagtg ccacgcacgg   5280
tctggacgcg ttatactcgc tgctaaaaat ccacagagga actccgtgtt cgctaatcca   5340
ccccgtgaac ggctacgtcc tggacatgat actgacgggc cgctcattcc aagaagcacc   5400
ctgccaaaac actcgcacgt ccgttaaaac aacgccacat gtaatggacg cagtctgcgg   5460
tggccgcggg tcatggctgt ccatcggcta cctagtaaag atgccgcaca ttcacctggc   5520
ggtgacccga acatgtctgg tcaccgccat agatgtccga caaaactttc tctggcgcgt   5580
ggcggacgac gcgctgctat tcctggtcac cggtagtctt ttactactgt cgcggccgac   5640
cgcagacttg acgtcttggt catgtttaca gcaagaacct gtgtggagga actgtctaga   5700
tacgcgcgga gaacaggatg agacagaaga ccaagagatg aaacaaagca caagcaaaaa   5760
gcaaaatgag aataaaaaac tcaacacctc aaaaaaacac acccgcgtat cgtcggcaat   5820
tccgaccttt cccctgagtc tccgagaaac gccgccagaa gccaggagcc cagccgtcct   5880
cgccgccgcc acccagtctc acaaaactcg agcgatctcg acgcataatg ccacgacaac   5940
aataagaata ccgcgccttc ccagttacct gctggaagcg cgtctgttgt ccgtgacagc   6000
tatcctgaaa gacacaaaga aaaaaaaaac ccagcctcag gcgtagcagc tgcgacgctc   6060
agcgcggtgt ctgaaagctc gccaaggtct cgcgtaaaag aacagatgtg aacttcagat   6120
gtaccaacca aataatacgg gttccgctat aaaaagtgca cctctattcc cgttcttatc   6180
cccgttctaa ctcttccttg tatcatacct tgcatgttaa ccggatcccg tggatcttac   6240
acacatacac acacacacaa acttggtgag gtaaacacag aaatctcact aactcataat   6300
cccctacacg cttaccacca cctaaaaatg gttatgacca aaactggcaa tagtctatct   6360
tcttttcttt tccattcaca gccaatgtgc agtactcgtg ggtccacaac aacgaaagag   6420
actgtagaga cacttccttt aagtagacct tagagacaca ccaaatacaa ccacaaccaa   6480
aaaaaaaaca gaaacaaca caaagccaat gagtgcagaa atgctccgcg ctgttcagct   6540
ccagccaaga cgccggggac attcctcatc tcccacttcc cctccactcg aaggagagcc   6600
cagtcccaag agactccaat cgagcaacag tcaccaaggg cgtagaggca gacctaaacc   6660
cagagctaaa acatggagcg aagctttatc ccaccggtcc ttcctcaaca tttacgcgtg   6720
gctgtctttg agtcgagggt ctccgcgaaa agtgtacgga tatgccttca ggcacagagg   6780
agaactcgta gcattgccat ggccgcctaa ctggagcctg gaacttcacc acgatcccta   6840
tcgagacgcc agagcacaaa ccgtttggag tcaccgctgg ggatggcctg caacacacgt   6900
gacagctcgc acggtgcggg actgcggtga gtgtaagcag tgtgacacat tgttatcgca   6960
attgtcttac ccgattaact ttttattaat gtattaagca ctctttcttc acgtgtgact   7020
gttgtgtttt ttgttgttat ctacatcccg gcagccctcg acacgcatat gtacgtgtgc   7080
tgcggacgcg gagaaaagtt gcagcccgtc ggatacgtac gcaacagagc cgcgccttca   7140
gacctgaact cgttacgcgt cctcctcata gccagggacg gagcaatgta tgtgcatcac   7200
atgagaacgg cgcgactgtg ccgcctagcc agcagtgtga ccgaattcgc gcgacgaggg   7260
ctgcagcgag aatccgaggt ttatgaagat gatgtttcct tgccagaccg tcgagtaggt   7320
tcggcaacgg ccattcacct gtttgacgta attaccagg cagccgatgt ccacgaccta   7380
ctcaccgtgg ccggactgtg tcagactcac accggcgtca gctgccaact gtggtataca   7440
```

```
gaccacgatc cccacaccgt cgctggggcg gcacgcttca cactgacggt cgcacggcag    7500
cagtatcgat tgtggccaaa cgcacgacgc aaactgctgc agcacctaca tccggaccac    7560
ccacttgggc tgtggctgtt gtgtgccgtg ctcacgtacg atgcaaaaga gacgaatcgc    7620
gcagtgccac ccgtaacgcc aggggccgaa accgtgtggg tgatagttac tggcaggggt    7680
gccattctag gattctggcc agagagcgcc aaaatgtgca gattggcctc gtctatgaaa    7740
ggactctgga aaaacggagc gcgggcgcta aaaggtcact ggacatacgc agcacccggc    7800
cggcatagag cgggagaggc ctggcctttg tgtgcacact accaatctcc tagatagaac    7860
aaaattaaaa agattaaaaa aaaaagaaa aaagtacaa gagtgttatc gcgaaacagc    7920
gtgtcaaaaa aaaaacaat ccacatactc tagaacaaac tgtacccaaa aataagtccg    7980
tgtgcaaaac tgggaaaaaa aaaatcacct tcctcgttgc cactagaggg agtaccgaaa    8040
gtgtaggcaa gaaggccacg ctgtaaatga ctgtcagcgt ttggcgctga aaacattgct    8100
gttcttgctg gctcaagcac aatcacgtga ttaagattcc tttcgttttc aaagtgtgcc    8160
cgggaggcag acatgccctt tctcgtgaga cattatgaga tttgcctgcc agagaaccac    8220
gtgacttgga cttactttcg ttttctaaac gtgccctcta ggcatgaatg ctctttagcg    8280
ttagccatga ggctagcgtg atcctgtata gtacataagt ttctaagaat atgttttaa    8340 caataatcat gtcccaaaaa gtcgcgagtg actaaaattc tctgtaaatg aaggcaaatt    8400
aaacaggata cagacagttg tggcagtggt ccgtttcgtc tttctgtgtt ttccttacgc    8460
ggctgacgag gtaaagtgtc tcagtccata ttgttgtctg tgccaccgta gttagcggtg    8520
gcatactaaa aactccgata gatgcagaac aataacaccg aaaccacgc tgtggaacca    8580 gaccacactt tataaacaaa acggccttat cacctggaaa aaaaaactaa aaataaggca    8640
atgatacacc tgactttcca ttggaaacct gccgtaaccc tgaccacaaa tcccatgcta    8700
aatcccctga aacactgcca aacgtcgcta caaggtttt ccgggatcga gccgcagcaa    8760
gcttaaactg aggtcacaca cgactttaat tacggcaacg cacagctgta agctgcagga    8820
aagatactat cgtaagcaaa tgtagtccta caatcaagcg aggttgtaga cgttacctac    8880
aatgaactac acctctaagc ataacctgtc gggcacagtg agacacgcag ccgtaaattc    8940
aaaactcaac ccaaaccgaa gtctaagtct caccctaatc gtaacagtaa ccctacaact    9000
ctaatcctag tccgtaaccg taaccccaat cctagccctt agccctaacc ctagccctaa    9060
ccctagctct aaccttagct ctaactctga ccctaggcct aaccctaagc ctaaccctaa    9120
ccgtagctct aagtttaacc ctaaccctaa ccctaaccat gaccctgacc ctaaccctag    9180
ggctgcggcc ctaaccctag ccctaaccct aatcctaatc ctaatcctag ccctaaccct    9240
agggctgcgg ccctaaccct agccctaacc ctaaccctag ccctagggct gcggccctaa    9300
acctaaccct aaccctagag ctgcggccct aaccctaacc ctagggctgc ggccctaacc    9360
ctaaccctag ggctgcggcc cgaaccctag ccctaaccct aaccctagcc ctagggctgc    9420
ggcccgaacc ctagccctaa ccctaaccct agccctaggg ctgcggccct aaccctaacc    9480
ctagccctag ggctgcggcc ctaaacctaa ccctagccct agggctgcgg ccctaaccct    9540
aaccctaggg ctgcggccct aaccctaacc ctagggctgc ggccctaacc ctaaccctag    9600
ggctgcggcc cgaaccctaa ccctaaccct aaccctaacc ctaacccaaa ccctaaccct    9660
agggctgcgg ccctaaccct aaccctaggg ctgcggcccg aaccctaacc ctaaccctaa    9720
ccctagggct gcggccctaa ccctaaccct agggctgcgg ccctaaccct aaccctaact    9780
ctagggctgc ggccctaacc ctaaccctaa ccctaaccct agggctgcgg cccgaaccct    9840
```

```
agccctaacc ctaaccctga ccctgaccct aaccctaacc ctaaccctaa ccctaaccct   9900
aaccctaacc ctaaccctaa ccctaaccct aaccctaacc ctaaccctaa ccccgccccc   9960
actggcagcc aatgtcttgt aatgccttca aggcactttt tctgcgagcc gcgcgcagca  10020
ctcagtgaaa aacaagtttg tgcacgagaa agacgctgcc aaaccgcagc tgcagcatga  10080
aggctgagtg cacaattttg gctttagtcc cataaaggcg cggcttcccg tagagtagaa  10140
aactgcagcg cggcgcacag agcgaaggca gcggctttca gactgtttgc caagcgcagt  10200
ctgcatctta ccaatgatga tcgcaagcaa gaaaaatgtt ctttcttagc atatgcgtgg  10260
ttaatcctgt tgtggtcatc actaagtttt caagcttttg gcaaggcatg aaaaataaca  10320
ttactattgg actgtttata cttatcttca aatgttcact cacagcagcg aaggggacac  10380
tagaaaacac tcccaactag aactacgagg cggaacagca atggaaaccc agacgtgttt  10440
ttacttttat tttctgaaat catttaatag catacaagta cggcctctcc gaatcgaagc  10500
taatctgaga gcaaagacaa agagcactgt aaaactgaag gcaaaaaaac cccccgctta  10560
aaaaagaatt tcataattcc gcagctcttc cgaagccccc cgaaaacaac acagatcgct  10620
aagggtgtct ggactgagct cagtatcccg gtaagcctcc aaagcagatg gacataaact  10680
atattctcgt ggtaattgaa ctaccggaac gtggatgcaa gtgacgggta actgcatggc  10740
ccaagcgttt ctatcaggaa agcgatagtt tttaaagagt ctcctggcgc ccatggccaa  10800
aaaaaccta aaactacaag ccaagttaac gacggctcct ccgcgaacat ccagagcgta  10860
gacagcaccc aagcgatcca taagaacccg ttgctttcga agaagaccac gaccgaggca  10920
tcttccgaca aactttccga taaccacggc aacgccacgc ctaggaatga acctccaccg  10980
ctctccatgg tcctccggga cggaaaattc gaacagcacg cctttaggcc acggaagagg  11040
cacaagagcc ttgtcgaaag caacagcgaa attcaaaaca tcctccaccc cgcacatagg  11100
gccgaagaaa aaacccccg aaacgatgga ctcgaaaaaa gcgtacacag gtcaaatct  11160
gcgcagacca cgcttccaga gaccataagg ggtgtccgca actctgtaaa tggcgttgtc  11220
cacggaacgg ttaaatgcat aaaattcacc ccgatctcca ataagcatca aagcagataa  11280
atcagaatag agcaccagac cgatgaccca aacttccaca aaaggacagc agacaaaatt  11340
tctggttaac ttgcagactt cgtcttccga aatgccaagc atctccgaag aggcaaacct  11400
caactcagcg ccggaaggcc acacgagagg aagtcgatgg tgagcatatt gcaaaacaaa  11460
atgagcaacg tctccgaaag atacggtttc cgcagcgaag ctctgcaaaa acgtggtcca  11520
gtagacctcc ggaacaggtg attcaactgt attcgattcc agattaaaca aaccgttcga  11580
tgcattcgac tcaacagccg tttccacacc ggaatccaaa agcggagaat ctgacatact  11640
agcaacatgc aaatgatcag agaaaaaaaa acaagtgaaa tgcacagaga caaatacaat  11700
caaactcata ctctaaagca cgaacgctgt ttattaatta ccatgtcaat ttcaaaaccc  11760
accagcaaac aaggcaataa agggagagag tcacaaactt agcaacgaaa atctggggtt  11820
ccaacatcag gaaacgctgc ccgctcatct gctcttgcag ccaagaagag aaggtcgcag  11880
tcgccctgtc tggcagtttt cagataaaag cgcgacgaaa aatgacacaa tggtttctgg  11940
caccatttgg gctgagccgc gtaaaaagtg tgatgtttat agaagttacg cacaccgaca  12000
aacctaaaaa cctgaaaact ctctgcgatg aaagtcaagt tcccgtcggg atcgttatca  12060
ttaaacccat aaattttttcc cgagcagtca gcgtaaaggg aaattctagc tccgtctgaa  12120
aaacatttca gtccgaagct cgcaagaaaa cacatatcag ctaaaacact ttttatctcc  12180
gggtcagaaa caaaatgaaa actgtctttc ctgtgatgaa acaggatatt ctctctcgcc  12240
```

```
ggccatcgca actcaaattt ttcaccaaga tgcctgtccc gaaatgccaa aatttcagcg   12300
catgttgtga tagcttcaat ctctggatct gatacctcaa attgcagaca cttacacaaa   12360
acgtatgcgt acagacatct tttgagacct ttcctcaaaa aactgtcaat agtgtcaccc   12420
acgcgacata gttgatcagg aaataacgtt gtatgtgcat aaacgcggcc aactttccca   12480
agtaagataa ccacatcatc agtctcatac tcaagttcgt aaacagtcgt cacagtatgt   12540
tttatgtaac caagaacagt aagttcttca ggacaacaca ccaacgcggc gtacttttg    12600 agcttatctt cctcatatcc ctccacacca taagtcaaaa caagttcaaa ccctctgga    12660 aaaaccaaag gcaccctcaa atgcggattc agaaacaaaa acattttag actattaaaa     12720 tttgtataaa cacgtagaaa atccacgagt ttagccttag cagattcaaa gattttctct   12780 tttcttttt tatcagataa aaacgttttc tcaacgttgg caaccttcaa atccttttc     12840 ccgtcaacat gagcaacata ttttcgtata aacgaatttt cctttttaa atcttttgcc    12900 acaactctca aaacacgctc ttcaaaattg aagtcagacc ccaaatctgc catacttaaa   12960
tcgtacctag cgtattaata atctttgtgc accggtttcg caaagggca gaaagccaac    13020 cgcggaatgc gacgcgactg gcgaatggta atccgcggt gctgagactc tttaaaaagc    13080
cttttcctca ccgaaactct cctttgtcgc atcctgtgtt caagatcct aacctcaaaa    13140 gaacctccac ccctaaccgc atgcggcact acgtttggaa acaaaccact ccaaagatgc   13200
gtcccatata aattgcaatc ttgacaccga aaaaacgca ctggattgtc catgtagtgc    13260
agctttaaag gattcgtaaa tccttccaaa atatcgtgcc ttaactcccg agctaagtgt   13320
aaaagaaagc acgaacaagt taaagctacc ttcttttgac acaagtgctc taggagagct   13380
ctcactctat gattctgttt actgtaggaa gctactagaa tagaagccac ttcaagaaaa   13440
gcggaacagt gccgaggaat ggacatcaca ttgtgactgc taaagtgact acctaaaact   13500
gctaacttcc tacaaacgtt ttcaactcct tcaaaggta gtatccttat ttctaaaaag    13560
actaaagact gcgcgaaaaa acgcgctatt ttgtccaaat cacgagagat gcgttctctt   13620
actctgcgcg ccaggaaaag acataaaatg atattacaat aaatctttaa aatgtttctt   13680
tctagatgac tattccctaa aatttcatca tgtagaattg gcaatgtttt cgattccatt   13740
gctttcagta ttaactccgc gccgagatct ttgtcaatac tctctctaac gcgtaaagct   13800
tcatcattag ttaaatgtaa ttgctggaga atcaagtcct gtggactaaa gtcctgtata   13860
tcggacaaat gtaggacgcc cctttctctc cgcttcaaaa aacgagaaaa tagcgccttg   13920
cgacattccc cgcaactaca aagattagat acaacaaagt gataattcat cacgaatgaa   13980
aaaaaatttt tgtcgtctaa gaaattttt aataggagat tggaaggcgc tacgacttca    14040
ccagctattt ccttcggatt tggaagtaac tcaaacaaac tcaacaatat atttgaatca   14100
cagcgatttc taagcataaa aaattgtaaa acaatgaat ctaagagctc cattaaacga    14160
ttaaagtgag acgaaagagt gtcgcgcttt tctccagcta caaatattc cgctattgta    14220 aaatgagcca agctgtagc tttagtcaga actcgataaa acggagaagt gcactcttca    14280
aaccttagac tttgaagaaa cgcgagaaaa ccgtctaaag tcattgttgc cttgtccctc   14340
cttttaaatg aaacggagtt tttctccact aaaacagccc atagtagact gtcatcgtaa   14400
aattttaagc ctcgagtttg gaacaaatct tctgaagtga gatgaccgct atccgcaatc   14460
atctcctctg tcagctcatt caagttgacg tctaactcgc atgagttaaa tgccgtccat   14520
gacagataag gatgattcgg tataacatac gtaatgcgat tccttagcgg ccctttacaa   14580
acatcataat cgattaaatc cattacgcaa atccttgtca aaaatgttta ttcatttcca   14640
```

```
tcactagcat cgactccaac acaggctaac gtttctacat tggcaaagta acacaagtca   14700
ttctgaatct tgtcaagacc ccccagctta taccctacag ctcttacatc tttttctgga   14760
ctggtctgga aatttccatt cccaaaattt ccaaaatatt tgagaccact gaaaaaaagt   14820
gccattgctc cattaatgtt ttttgtgtta cttaaatatt cagcttcgat gttcacgatc   14880
gatctctcca gcacatctat gaagctcttt tccttagcat tcactatgaa gaaacctggt   14940
gctagattat ttgcagcaac caagtccgtg tgcttcgcag gctgcctttg gatgtaaaga   15000
tgatgcaaat aaaagctttc catgaagttt gtttcatcat agttttgta atacggaatt    15060
tcaaagctca tctttatcac ttctaagcag ttgaaaataa agtttgagga tgtgccaggg   15120
tttctgacaa tatctttaac ctgcttcaac atattgaaat aaacgatatt gttcatacaa   15180
cccttactgc ccagtttcat ttcacattcc atgctagact ccaagttctt taattcatct   15240
aagtacacat cataatacat tttcagttca gtaaacaaaa cactgttaag agtttgaatt   15300
atgaaaagca aaaacacaat gttactaaga atattcaaca gatttctttt gtcctgaccc   15360
atatccacag taaccgagat aggaaacctg gaatgttcaa tctgcccctc aataaaactt   15420
aaacacaaat ctttggctac aaacatagaa agattagaat atttctcaga taaatgtgga   15480
aaaataggta aatcgatctt acccaaagct ggaaagaaat gtaatttgac agagccagga   15540
ttctttttca ttgtgcctac attttttaaac ctgaaaaaat tgtatcgaca ttcttcgcaa   15600
ccacaaaata gtaaaagtg ctcaagtaag tacaactgaa aacgatcaaa aaaatcgcgt    15660
ctgaagaatg attctgtttt gttttgcatt tctgtcttaa aagattcgct ccaaaatgca   15720
cagctaaagc cccctaactt ctgcttagat tctttactca attccttcaa ttttccatct   15780
agtttaaaaa ataacataga aaggtactca cataggtagc gacaccagta tccaattcca   15840
ggcttagcac ccaaattaaa caatgatgcc ccagaataga accctacagc tgcaagttta   15900
gtaatgcact gccatttggg gtcaaaatct tccataaatt ttaaatcgcg caactgcaaa   15960
agaaatttat cagcccttgt gaaagttgat ggatacttga acatttcgta ctcatagtct   16020
atcaacctat tccaaataac accatctgaa cataatctta gcccttttat tccaaagcgt   16080
ccagcagctg atgcttgaag gccgttgatt agtctggatt ctgtcaccgg aacaatgtac   16140
ttcagttccg tgtctccgtt tggaatgatg attggatgta gaaactttgt aacactttga   16200
acaagaggat tactgatttc agatgagtgc actgcaaaca gaatacttgg catgttcttc   16260
aataatctga aaagaacat ccatggaacc atcagtaaga gtattgtgta gagaataccg    16320
aaaagaagaa ctttgatctt tacataccta tcacaccttg gatacatatg ccgtggtttc   16380
ttccgaagaa tcggagactc tccatttaac attctgttca aattttccgc ctcactttca   16440
ctcacataaa tcaaactgtc atcatgccag ttcagggcat atctttcttt gtataagagt   16500
tcttcaaacc ctcgcctgat aaattctcta atagaccttg caactttgtt gatcttgtta   16560
tcacaataca cataaatgtg aaaattggga cctagtagga tgacagctct acaatttggc   16620
tctacctgac atctcgcgca gttcctatg acaacatact ttcttcttag tattttttcg    16680
agaataccag aacctgtgat gtaatggatg tcattcgaag aacagaaaga caaatcaaaa   16740
ttttgaaaag catcgatacg aattttttga ccacattggc gattgacaaa attctttaag   16800
gctggaatat ttttttgtaa gagtacgaac tcctcaccgc tgcatttggt ttctccgtac   16860
cacagtctgt ctagctcaat atctaattca atccttgcaa aaggtgggaa atttctcagc   16920
ccgatactgc aaaaatgtgc aggagattcc gctatgatgt acaattcatc tgtgaccgta   16980
tctaatgcaa gcatcttatt tgatgagcag tacatccacaca atggatcaaa gtccgggtcc   17040
```

```
ggttctcggt aatttggatg tgcataacca acagcgcaaa gaaattcgtc tgctcctacc   17100
aaattactcc aatcataagt gatgacacta cgtctacatt tgaaatgata aaattcgcca   17160
aaaataagca catagtttgg cggccaagca agacagcact ttataccatt gcgaactatc   17220
tccatgcctt ctccatatga agacagcagc aactcaacgg caaaatcaaa agacggtaaa   17280
tccggagtcg gttcaatgca aacatcattg cacacaggaa caatttctgc aaaattaact   17340
tgtgattagt acttccgtca ctttcagaaa aattaaaaac cataaaaagt actgttactt   17400
acttagatac caggagtact gttgaaccgg tgcacttcca agagttgata atcttccaaa   17460
tctggcagtg acttttccaa ttttatcata accaaaatct ccacaatatc tcgcgaagcc   17520
gatccttgca aaagtcagta aacaatcagc aatccgcgtc aacactttat caatccaatc   17580
ataataataa attgctcctg tttctccaat gcatagaatt ggtctcaaac catagtcttc   17640
ggctgaaata tttaaaaaac ctaaacaac tactttttca aacagtgcct cttgttcttc    17700
aaatcttttt tggtctgagg tgccacagtg tatgttttc ctgtcttgca ggattaacgc    17760
tgtaaagatt ggagtttcca aacgaagttt taaaccagtg tttatagaaa cgaagtgttc   17820
aatctctgct aacgttttac accttgccaa ttcatctaat tcggagagca ttgaaatata   17880
atttctcctc aaagctttta gtgccaaagc tgttttcctg ttaaatctta gactagaatt   17940
caaattaagt ggttcctgta ataatcctaa gtctttaaga gtctccaatt tttcaaactt   18000
tggaccatca taataaaagc gagtataaac aggttctgag caagtgatta catttgtacc   18060
tagaatacca aatctaacaa atttgtcaaa gtcttcagct atgtaataca aaacatcatc   18120
ctccaaatcg tgacaaaaaa ttcgactcga tttccccaca aaaattggca cgtctttcct   18180
tccaatttga atcgctccaa tcaagcacaa attttcctta aatccttggt aatggtcatt   18240
cagttctgcc aattgttgtt ctgagtaacc agcaacgtca actggctgtg caagccttaa   18300
ccacaaattc tttggccaaa tcaaagacaa gcattcattt cgatgtcgtt cagtaagaag   18360
gcgaattcca gggaaatcag taaaacgaca taaattcttc aattccctta acaatccatc   18420
atttagttgt ccaacacaag gcaaagtttt atattgttct gccatcgtct caaaattttt   18480
cattgaagtg aatgtggtaa gaagtttgta ttctcatcca tttctcaaaa actcaaccag   18540
ataaatataa gagaaaaaaa tcacatgaca ggaaataaat tttaaagctt gcagatttt    18600 ttatttccca ttacaggaaa cattagagtg attaaaacca taagcctggt gttatcggat   18660
taaaaacctc ttgtcgaaag taggaatcgg atttttacct tttttaaaga tcgatttta    18720 gaacattcac ggtaacaata caaaactaac agtgtcatta atattacaaa ctcagaatct   18780
gccactgaaa ggaaaatccc ttttcgccct aagtaactac acttaaaaat ggctatagca   18840
gaaagcggag cgttcgaaat aaatgtcaat cttggaaaat ccatcgcttc catacaaaaa   18900
aatcctataa tctacatgcg tagacatctc tcttttatg tggagttatt aaaatttatc    18960
attcatcaat atgagcaatg ttttttacca ccgaaaggaa cgatacttta ccacaatggc   19020
ttaatcgaac taaatacttt aattatcgat ctgaatcaac aaattacatc gaaacagcag   19080
atctatagtt ggacgagcat tactttgcca aaaatatttt cgactaaaga attatatttt   19140
attgtcgcgt caccagaatc ggaaaacata actctcaatc cagctgttac taaaggagga   19200
tggttatctg ggagttttag cttttccattg agtttaagtt gtgcatacgc cctcactggc   19260
gtatcttcaa caatctatat gttaccattt attccatata aattcccaat gacttacgta   19320
gacttttcga cacttcgaac atacgaggta acaagtgaat atggatcaat ccaaattata   19380
aaacagcgga atttttttatt tttgggaatt atacgggatc tgtcatggaa aagtcagagg   19440
```

```
gataacaaga attttatcct gaaagcaatg ttcgttggaa actggttagg gatacaaatt   19500
ccagaagctt ttgcattgag acttttaat  aacacacggt tttctattca ggattttgaa   19560
ttctccatta acatacaaaa tataaacctt actagggaca ataaaatttt gggttctctt   19620
tccacggttt cttgtgatca gatgccacca aacttgtctc cagagaatct cccaaactat   19680
ctagttattc agttcgaatt ggtttcaact ctcgcaaatc ctgatcatct actgttttct   19740
tgcaatccca aattgttttt cacaggagat attctgaaca gcgctataaa tttacaacat   19800
agtcctaatc attatgagct tacagtgtac gcaccacata atttacattt ctatcccagc   19860
tgttttcata tagtaacatt accaattcag ttttcatcca gaaatgatag acagatgttg   19920
gtgtcaagct atcctaatga aggctacttt gaagtacaaa tgtgcccatg ggtacagaat   19980
tctcctcttc aaattgttat taaatctttt tcaaaaaatc tagtgctacc gcaaggcacc   20040
cctattgcaa ttctcttata tatggaaaaa atgacaacag gaaaaaattc tttacgggat   20100
caagaattaa aaattaataa agacattacc cgaataggaa acgtaaacct tccaaaagaa   20160
aatttcttac attataatag ctaatcttta ttcaactgtg ttttagacga cgtcttcttc   20220
tgagtgtgtt aaatgcgata ctagtttatt aactatatca tcatcttttt gaacagaatt   20280
ttcaagatcg attaaatctt tatcgccatc ttcttgagcc ttgctagcac cgaaaatggt   20340
attttgcgtc tctttgcctg ttaaaagtga acctgaatca aaatcctgga tttcagcatt   20400
tggtaaaaaa aatggagacc gcacaggctg catcttttca gtgaagctaa aattttgaaa   20460
taaaggatct ctcttctgg  agttcagtaa attcttcagg ttgttgtcat tgaaagtcgc   20520
aatgttagaa acatctgttt ttttcggggg ttcgagtacg tctttaagc  ttcgctcttc   20580 taaactaatt gtatccgtaa aatccgttaa taatttctta acttttttcac ctagtcctga   20640 ttcaaaaagt tctttttgaa gaagatcgtt ccttctacta agatccagta atgaagaact   20700
cggagtccac ttcacatctt tgactaattg attttttttta gctgaagaag cactctcttt   20760
ttccttcatt gaagcgttta cgtcattagt acctatcata tttaaagtct tggtggaaga   20820
atttgcttta tttccatttt tttgcttaat gcttttttga tcttgtggag gcaatgacat   20880
ttcattatgc tcgtcatcaa aactttgtaa gttctcgtgg acaatttctt ttctgcgttt   20940
ttctgaagga agtttaaaaa tgtcttcatt attttgttta attgttttga ttcgttctcg   21000
tagctccaaa atttttctgca agtcattggt cgagttttta gacagttgat cgcgtgattg   21060
cactccgttt tgtctgttta cttcgttttc tggcagaaaa aaggtagagt gataatcaat   21120 tttattttg  ggtagctgaa ctacgttaac ttttggtgag ctaacaatgt ctattacttt   21180
gtttgagttg tgtagatcta gtttgctcaa ggtatctata acttggttaa taccgtctgg   21240
tgccacagca atttcattga attggtttac tttgtcctct ggtctgtgca tagtttgatc   21300
agttaaatca agtatttcag tctgtagtat tctgtgcatt ttttagaat  tgtttataga   21360 cgtgaatttt cttggctcgt ccaatatcat ggaatccttt tttaccgagg ataacaaccc   21420
atcttcagag cctacaaata aatctttgga tagcgtgttg ttactccgtt gttcagtttt   21480
tataaatggt tctggattaa atgatgaacc atacgaagtt ttttagaac  tactctcaaa   21540 ttgattgctt aaagacgatt tcgacaaatc tgttaaaact ttgaatgtct gaatcggttc   21600
aggagtaaat tttacacgat catcccatgt actctttacg ggaagagcat gtaactcaag   21660 acttttgtt  ataacatcaa agtcttcggt taaaatttta aaaaagaag ttactctatg   21720 actagttaat ggcaaactta aaatttgata agaatatatc gaaacaaaat ttttgttgtt   21780
ttcaatcgcc tttaaaattg cattttctct ttcattaatg gtatttaatg cgagtttctc   21840
```

```
catgttcatc caggatccat gtaatgtaat taataaattc ccaagataaa gcaatcgatt   21900
gatgttagta acatagtagc cattttcatt ccacggatca actatttggt aaattgtgaa   21960
agaaagcata ttgttttttg cctttgtaa attctcgcca atttccgctc tttcttctgt    22020
ggtaagattg acgtaatcgg ctgcgtgtgt cacagtgccc caacgaagaa aactgcccag   22080
tttaagcaaa tcttttgcta cgttttaaa ttctgtttca aagccaactt tgttaaaaga    22140
tgttaaacta gaataatcag taatcatctg tctttgctct aagtaatctt tcagaatttt   22200
ttgcaccttt agtatttctt gccaaacttc ctcatagtct ggtttctttt tacacaaggt   22260
ttgatgaaaa taaatccaaa gaatcaaatt gttgtaaagt gttttacat tgttaatgga    22320
atttccagtt ttaacgatac attgactcaa aatccatgga ttttcgcgaa tatcaacaac   22380
tggtaaagac gatatgtttt caaaaaatcg agataaaaaa cactttgctt catccgaaat   22440
ccaagcaaag ggtaaatgtg acattttcat gactcgtttt ttctgttgag cattattgaa   22500
cacttcttaa aaaattagtt taatagtctc tattttctct ttgattagat acatgcgctg   22560
ccgacatgga cactctaatt gatttccaaa aaatcctggt atgataatct aatgttatga   22620
tttgctacag ctttgctaaa aatgttacct ttgcatttt aatcatcttg caaaactttt     22680
tttcacagca tgatgaagag tacaagtaca attatacgtg tattacgcca acagtacgga   22740
aagcccaaag acttgaaagc gtaattaacg gaattatgct aacgctgata cttcctgtta   22800
gtactgttgt catatgcact ctgctaatct actacaaatg gacaaaacag acaattactt   22860
ctccatatct tatcacactc tttattagtg attctttaca ttcattgact gtgttacttc   22920
tcacattgaa ccgagaagct ctcacaaacc ttaatcaggc tttgtgtcaa tgtgtgcttt   22980
ttgtatacag tgcgtcctgc acatacagtc tgtgcatgct agcagtaata tccacaatac   23040
gctatcgaac cctgcaaaga aggacattaa acgacaaaaa caataatcat attaaaagga   23100
acgttggaat tttatttctg tcttctgcca tgtgtgccat tccagcagta ttatatgttc   23160
aagtggaaaa gaaaaaaggc aattatggaa aatgtaatat acacatctca acgcaaaaag   23220
catatgactt gtttatagga attaaaattg tctattgttt tctctgggga attttttccaa  23280
ctgtcatttt cagctatttt tatgtgattt ttggtaagac cttgcgtgcc ttgacccaaa   23340
gtaaacataa caaaactctg tcattcatta gcttactgat actatccttt ttatgtattc   23400
aaataccaaa tctcctagta atgtctgtgg aaattttttt tttgtatata gcaaatactt   23460
cctgcttagg caccatacaa agagaaattg tgcaaataat atctagatta atgccagaaa   23520
tacactgctt gtctaatccg ctagtatatg cattcactag aacagatttc cgattacgat   23580
tttacgattt cattaaatgt aatttgtgta attcatcttt aaagagaaag agaaatcctc   23640
tgacaataaa aaattgaaca gtgaagcttg cttaaaactt tgaaaatttt ttgtgatttt   23700
aaataaaatt taaaatcaat ttatcctaag cttttcaggc tatgactttg aatcaacagc   23760
catctaattg cagactaatt acagctaacg atccagtact tgcatcgaat tttacaatgc   23820
agcctacttt taaaatagcc gataagaaag ttgtactcag agatcataat tacattgcag   23880
tcaaagattt tgttctatca aggtcttttca tgcattgcat tcgatgtcag gaaaaaattg   23940
aaaagaagac atccgatagc attagagcat attccattaa gccagatttc atgttttatg   24000
actcagacga cgaagttcgt tcgtcaccat ttttataaca atatttaaag tagctgaatt   24060
gtacgttctg aaacagtctg aacggatccg ctgaacgcag acacaatgga acagcaaaaa   24120
ggattttcga ttccattttt tgtcactgac gaaaactgca actttgtgcc tgaaatatta   24180
cctcgtatac atactaaatt tcttaaagat gtcttaattg ccgattccta caactctgtt   24240
```

```
agttgggcaa acagttttat tcccatgcct attcaaacgc ttgaacaaat tatggttctt   24300
ataacaaagt tcaagttttc tcgctcgcgt gattttttat tcccagtaat tcgattagct   24360
gttcatatca ataggttcca cacagggaag aaacagctga aaaccatgat agaaattatg   24420
aaaagcttgt ttaacaccga agaggctatg cgacgattcg atgaagcatt gatgattcta   24480
ttttctaatg agcaaaccaa tacttacatg acaaacatag ctttatcgat gcatgagaat   24540
ggtcttccag attcaaaatt tatgaatgct ctaaaaatga tttacagagc tggaaattct   24600
tttgataatc aaccagacaa tgatatagaa agctacaacg agaaattaaa aatctacaac   24660
tacctaatta aaatacctaa gtacacacta aaagctggag ttgatttata taatgaaaat   24720
ataaaagatc tttcgattgg aatccaaaga caacctactt tattattcac atctcgtaat   24780 gattttcat tgaaagctat ttataatgac gtgttatttc tagtttctgc atggaatatg   24840
atcatcaact ataaaaaga acaagaaga ctctttagtt ggataacatt tgaaataaac   24900
tctttaatgg agaatgttgt gcttgcagcc tttcagttac cagatttaaa agaaatgaca   24960
cttgatttaa gcgctttgat tgccaacatg aatctttaa aaccaaatga tgattacagc   25020
ccccatttta aactaattat caacaaattt tttgaaatcg aattttgt cacgaaatca   25080 tatatttgta ttttgccttc ttttgtcaaa agccaactca tttcgtttga aaacgtttta   25140
agttcaaaca gacatgcgga agatgtgact ttcatactaa catcttccaa ggaatctgat   25200
gatgaatatg atgaagataa acctccacga caagtagatc cagacagagt ggacaacatt   25260
ttaatggaat cagattttt taatgtgaaa ccggaaaacg ccttttcaga aatcgcatta   25320
atgccaattt cacatgacaa aattatagat gtcaacaact caaacataca agttcttgaa   25380
actgaattgg cacatacaaa tttatttgtg tatagcgcaa tagctcaaaa atatgatttg   25440
cctttaaaag aatacgtaga gcgcttaaac gtctacaatc ctgatctatc atctggaaac   25500
tctacacccg cgcggaattc taattctatt cgtacaactc cagttctaaa tatatccaga   25560
ccaggaagca ctacaccctc tgggaactct gcaagatatg gaataacac acctagaagt   25620 ataactccgg ttttagagat ttcaagatct agaagtgcta ccccttctgg aaattctgaa   25680
atctatgaga atagaacatc cccaacgttc cgtgtttcta ggagtgcaac tccaatagaa   25740
agaagttcga gatctgctag tataatttct ggagaatctg ttcctggttt ttttaatgac   25800
caagaacgtt tgagcaccaa ttcgcctatt tccataaatg gtaatactcc aagacagcaa   25860
agccatgggg acaatgaaat acaaactata gattccacgg atgaagactc aatgaatgcc   25920
ccacaatcac cccaatccat ctattcaatt tctagctatg tttcaacaga cgatcaactt   25980
ctacattcac cgacaaatag cccatttaat cttttgact ctgtctcgga aatgcaagaa   26040
gacaccgaat aattaattgt ttttattta gctaattcat tgtatgacaa cacaagggca   26100
attgtttgat taatttccac gttttttagc ttttgaataa tctcaattaa acatctctg   26160 gtcagttgga gtcgttctat gtatgaaaaa acattatcg cgttttcatg ctcatcgtct   26220
ccaagcctca gatgactttc ttctagaaac taaagaaaaa aaatgttaaa agatctttta   26280
cagaagaaca tttattattt ttaaaaatga tttttcttac cgcataaatc atgtttaaga   26340
aaagttgctt tcatgctttt gttgtcatca tatacaataa tgctgtgatt ttcctgaaaa   26400
taaaagagcg gggttagaca ataaaatttt gaaactcgtt tgtgtagaaa taatagaggt   26460
ggactcaccg ttttacaggt atgtgtgtga attgagcgac gatataacaa tcctcagttt   26520
tgtggacatc tagattgaaa atctgcttga tttcttgcca tctcttaata ataaacaaag   26580
cttcaatcac tacagacttt gtcacagttg tggttaatgt taatccagaa aaaataaatc   26640
```

```
tatatgttgt attaaaatcc atttgaaaaa gatattttat atagattgtc tccactttag    26700
atataatatt agataacgtc atcaatatct gtagtggaca cagctcgcga aattcctgta    26760
gtcgttgtct tctccaggtt tccatttctc acaaagaaga gtctaccctc gtagaagaac    26820
actaactaaa tgaattttt taggcgaacg cttaaaaaac tcttttactg gcacaccgcc    26880
tataaaaacc cccaaaggaa attttatgt aaccacacag aaccaaaaaa agattaaccg    26940
ttattagaaa gtgttcgttt taacgatttt ttattggcac attttgaccg ggttaaatt    27000 cgtcttcatc agatgtatcc acttctctga aatcctcact taaatatata gctaatccgg    27060
cagcgtgtgg gcaggtcgga taaatttcat gagtaattgt taaattcctt ggaaaaaatt    27120
tgtatgtgcg atatgttcta actatcccct gtcttaataa acattcaaaa ttttctgcaa    27180
ttttgacaca gggaccgatc ccggttccaa ttgcgtcaat accataaata aaacctttta    27240
aatccatcat taaaaataaa ctttaggaa acattaagtt tttaccgacg ctgccaatga    27300
tatgtccata gtatggcata ttgtcataaa cgtcagctag aaaattccat tctgtgcgat    27360
tagggaattc ttcttttctg gttagaaaca aaactagttt ttcatccatc ttttccctct    27420
tcaaacgaag agtgtacact ttcccactgt tagccgctat tatttcagca aacttcacaa    27480
gattatactg tgcatgaatg agactttgca aaacgtgatc gatagacgtt aggaagggaa    27540
tgtcactatc ttgataaatc ggatcaaaac ggtgcaaccc gaaataagca aagcgctctg    27600
ttgattcagc aagcaaatat aaatttctt tttcgaagtc caaagcatag aaacgctctt    27660
cttctccgag aagaatgatg gtttagcag ctgctgttgt tacgtcgttt ttagcactca    27720
gaaaaccgat gacttgtaac ctttcattgc aacataggag atagcaacct atgaaaacaa    27780
caaaaactta ttagaacatc atgacacatt ggaaatgttt tgactgcttt tgcaacttac    27840
ataggtcttg cagctcggtt tcactagtag ttctgaaagg catatcccgc aaaggcgaaa    27900
tgattatttt cctactctga ggccatctta tgaagatttc acacccacta ttttgagtaa    27960
cgaagtcact aagagaatcg cgataaaagg cttgtttaac aaggcttaaa tttgcgagtg    28020
catgcctaaa tcgaactttt tgttcacttt cggccatgtt gaagcacact ctaagcttat    28080
gaaaacagca gttgtgacta ggttttata tattactgaa gcatgacgtc gctttatgct    28140
taagctggaa agttctgaaa atatacagct atcttaaaca agtctgttta caatagggat    28200
ttccttttcc tgtaaatgct gcctgatact agaaatcatg tccgtgaatt ccagtatgga    28260
aatctgggaa attccaaaat atatgatata taaattccta cttttccatg cagcatcatt    28320
aacgccgaat cgaatataca cattttcaga gctgcagttg acatactaaa atatggctat    28380
taagatcacc gtatgtcttc gatactttaa tcgagatcgt aacgaacttg gaaacattac    28440
ttttaatatg gaatacaaag acaggagagt cgctgtgaca tcgagttata ttcgggtaca    28500
ttttgttttt aatcagcgtt aactgatcaa acttagaaat gtttcctta atacaaaatg    28560 cggaagaaaa agcttacact tacctcttct ttatattgag taaaaatgga ccgcgggggg    28620
aacagatttt aacagttcta gattacactc ggtttaaatt ttttgatggc tcagtgacca    28680
ttgcacactc aaaaaaaaat tattttcttt caggttctct cagatataag aaagatgatt    28740
atgacgttat tcaaaaacaa aaaggtaagc gaattacatg taaacattca aaatttattg    28800
tttgttaaac atgtagaaac tcacaatgtt ttctctatga tccagcaaag acttgcaaag    28860
acagaaattg aaatgagcct gacagtcacg taaaagtgtt caaaaaagat tccggatgat    28920
aatcgagaat aaatcaacca acattcttgt caactttgcg ccgatttact atcgacaaac    28980
agaaaaacaa aaaagtacc attgctgatc cgccgacaag aaacactaca ccaatagttg    29040
```

```
tcgcttgggt tgatcgagg aagctttcgt aatcattcaa gaagatgaca ttttaccctc    29100
catatgaagc gctgagatct tccaattctt tgtacttgta ccaatcaagc cacgatgact    29160
tccaagtttt gcgcaaaaat cttttataaa tagtttcatt gcgtactatt gtaaagtttg    29220
gatttaagac tttcctttga tatatttcat cagataaatg aggacatatc attgctacga    29280
aataacaatc ataattaaat ttttgattta gaatttcaag tgttttgttt ttatcttttc    29340
cgacgcttct ccacttaact gcaactatgc cagatcttag ctgcaaaaga aacttttgac    29400
cccctgtcat aatagtgatg gaaccacccg aattatgacc ttctaaccaa cattcaagtg    29460
tactgttagc ccgagaagca aagtgccatt ttttggcaat tagtgctctt aacataactc    29520
ctctaaagta ataattgatc agcactctca aataggttaa tttatgagat gttgtagtaa    29580
gatttactag actcatttcg cgaaatcctt cagtttttaa agacaaagaa atcagaaaag    29640
ctgttcttac agataaacaa ctagaattcc ctattagcat ttcattaaca taacacgtgg    29700
tgacacaaac agcttctaat ttattatcta gaaatattat attctggtga catttcaaat    29760
ttgacatgag tgtgagagat aagcaaatca aaagacaaa aacatcatc tcttttccca     29820 tggtcccttta taaagacttc acaatttctt caagaaagtc cacggtactt ctataaaaca    29880 aaaaaacac aattaactat tgatgaacat tgcagcattt ttccaatgca ttgccataca     29940
taccccgaag aaatttttcc tttgaaaaga tactctagat gtgaaaattg tgttgaagaa    30000
agaagttccg tcttagtgga catacattca aacgcaggct cagggagttt ttgaatggtt    30060
gatattctgc tatcttgttc tttccccctt taaatggcca taaaaagaa attatcagtt    30120 aaagacagcg aaaaatttaa aataagtaaa aaacaataag gcacctactc ggtaaattgt    30180
tcgaaattca ccgggaaacc cgaagttgaa gtgtgttcca agtttttcag tggcgagttt    30240
gctatttctt cataggtttc caatgagaag tttgaactct cttctagcat atctaaaggt    30300
gctgtctctg tctcgttagc tgtgtttacc tctttatagg gatacatttc cgctgtggtt    30360
tgcggtttgt aacaccgttc tttaaaaaaa atgtcatttt gtgatgtttg agtactgcga    30420
gtaaaatgtc cgagtcccgt ttgcgtagat ctggacacta aaattgtcac accaggtgta    30480
tgacacattt tgtaaatctt gcaattattt ggaagattgt catttctga gtatcctatg     30540 gacatataca tttttctgc ctgtgtctct ctatcattcg aaagcttgtg accaggaaga    30600
actctttgaa atcgcgcagg tagttttcca ctaatattga ttgttttttg tcgtattcga    30660
tgatagtagt tgataaatct ttcatggcat tcatctctcg acatcttctt tgacatgcca    30720
tgtgtaattg cattttgaca gctaaattcc aatttcgtgg tccagaaatc ttcaaatgtg    30780
ggcgataaat agaacatcac accatcttca taagcaaaca catgctgaga caaggacagt    30840
aaaaaaacta tttgtcttcg cggcgtccca gaagctgaca cccattcttc ggcaacccca    30900
aacatcacca tctttccctc aaatggataa aatccgatgt taactaaacg tttaagtctc    30960
ctttctggaa gaatgtcagt catatcacaa attcgaatat tgatacacat tatgtgttga    31020
atggacacgc catccttcat tatttcttga actgttttt caaaaaactt taaatctttc     31080
gaagctgcaa ttaatttttc tttgcagcgc agcatcgtcg ttaagccaca ttccttagac    31140
ataatcgtct cttcataaaa aatactgaat tttaagcgta tatattcaac ccccggata     31200 tgggcgtgga aattaataaa aacacttcaa aaagcaaact ttttattgaa actcattaat    31260
gacacatgaa atctaaggtc ccgtgaattt gaagatctgg agaatcctta dacaggcagt    31320
ctgaatctga aatttccatt ttttcagttg cacacaaatt ttccacagat atataatcac    31380
agggatcaat ttccatgatt actttaacac tatcagatct atcaaggtcc ttacgcttat    31440
```

```
taagaacagc cataacatgc agccaaattt caaaaaacat ttttttaaca gtgattatag  31500
aaaaaataaa ggcaagtata ggaatgatta aaagtatcca aaaaacttca aagtaattcc  31560
cgtgtttgta agttttgtga aacaaatttt gaaaatattc atctgaatta ttaaattcaa  31620
ggacgttaaa agagtaatta cattttttgat gaattaccac acattgataa ttagcggact  31680
ccgtgttaat agatttaaaa aaaagtaga attttttccc ttttaagatg tccgatgcca  31740
aatattcttc tgtcaaatca tcaggaacca gtttattttc tagcttccat tgaatactca  31800
atcccagtgg actataaagc tgcgccgaac acgttatgtt agatccacgt tttgtgatgg  31860
acaccacagg tggccgatat ccatcttgac cgaaggtcac atgtgcagaa aaatctgcga  31920
gttgtttaac acaaaactgc tgcacataaa atttgagaat aagtaataat tcaacattag  31980
catacatgtt ttcgtcaaaa ccactgctag aaaaatccaa caggttgaca ttcagtgtcg  32040
tgtcattatg aacttttaac aaataatgac ttttcaaaac ggtgtcaatt tcacaaatga  32100
attcagcgtt aaaattgtgg tgataatgaa cactgcgatt cctatgtgac cagacaaaat  32160
aagagaaaat gctgtttaat gtagattcgt ccttgttggt agaaaagacg taagacaaag  32220
cattaaattt cgttggaaaa tctgtgagga aagacgaaat actagtattg ccgacagaca  32280
gattcttata atgtgccagt tcatagttat ccatcatcaa ttcatatttc tcaagatgtt  32340
ctttattgat tattgacatt gtcaacttat gtgccacata tttggtaaaa tgtacaatga  32400
aaactaaaag acatgttttt ttcacaaaca ttgctgtttg agagattctt ttttaggtaa  32460
cggttcttgt ccaaacatca agtttgttag attgattatt ttctctgata ctggttcttt  32520
ttgtatgtgc tgtaaaggcc acgtcagaac tttctgaaca ccgtctaaac aggaaactcc  32580
taataaaact accgctgtaa caaatgcaag gaataatata gcaatcaatg tgtagcaaag  32640
catgtctacg aaaacattac tagacgtttt ttcactatct aatagatcca aatccacatc  32700
aggtaatgtt acctgtattt gtgttcctgt gttcttattc gtacaggtac aaacatatgt  32760
ggtcatttct actcttagaa aaattagacc ccaaagcaca tcactaccat acaaaggagt  32820
aaaagcaccc gtagagttga aaccaactct tttccactct tctccaaacg gactttttat  32880
cttttgcaga acttctaagg agccgaaacc gctaacaccc catcctgtat atttacaaac  32940
tgctaccttt acaccattct gtctaaattt cgaaaatgaa caatctatgt tattagttct  33000
atatcgttgt tcatttcttt gttcaatcat aggattaaag ccttgcttaa atgtagcttc  33060
gaatgttttc gcgagtgata ggtactttct ttgccaaaaa aaagttgat tgaagtcatt  33120 ttcacaagaa ttgatcagaa agtttttagc gtgtgtcaaa gtgtgccaaa ttcgataagt  33180
gaagggatca tcttcaccta aatagttttt aatcgctacc cacgtgctgt ttctttttatt  33240 ttgcaagtag aatgtggttt caagaattct aggagaaatt ccagtttcat tcatacgtct  33300
cagacggata aaacttttaa agggtgaaca gataatttga atatgaatgt aagactcgac  33360
atcaagacag agtttatcat atcgcttcat cagtcctttt gttttttaa agttcttaaa  33420 caaaaaatga tttagtgtag aaaatacttg ataacagttg aaagccaaat atttgccaaa  33480
atcggtttca atttgcgttt cgctgttgcc aaaaagaaa gcattgtctg tcattgccgc  33540
gactgcagag tgtctgattt tatcgtctga acattgtttg ctcaaagata tgtcgaacaa  33600
tagcaaatca tccactgtag cattcacatc aaaatccaca actgctaagg gacagaaatc  33660
cggatagagt tctccataaa tcacaggaac gcaaacagc aagatagtcc acatgttgaa  33720
ttagaaaaga gtgatgagaa agaaagcttt tatttcttaa tatatatttg acgactgaac  33780
gtcacagtta cgcccatttt acggtgataa acgttagggg ttccgcaaaa atgtgtgcat  33840
```

```
tgatctttct gtgatgacac agtggttagc aaagcacatc taacataata agtctgtttt    33900
tctcagtcat aggattccac aacaggataa gacatttgtg ctggtctgat tcctaattac    33960
atgagctgta tttacgccag aattttgttt atttccttta attaccctca aaaaatgaaa    34020
acattgatga aacatacttc ccagtgaaac gctttcaacg gagatcatgc gttgatggta    34080
gataaaacac aacaaggaga actttgccca aaaaacatt tattaatccc agacaccaat     34140
aaaggcttgg ttattgtatg cattttcgg tttcttagaa tggttgcgtt tggggttttt      34200
aattagtaaa actaacaacg ctaacgctac aataccaata aaactaactg ctgcaattaa    34260
aatcacaagg aacaaaacga actttttaa agggctattc aaaagttgag gttttgtcag     34320
ttctggagtt gaaattgtca gtgtgaaaaa ttcagatgca ttcccactgt tttcatgatt    34380
agtagtactg ccactggaga atgtcgaggt ctttgtaaaa tttaaggatg tagattcgac    34440
attctcttta gttgttgcga tagtcgtagg tatactcata gacacagaca ttaaatcgct    34500
cgtactctct gtatctgatg tgattgacgt ggaactaaaa tctgaagttc ttgacatttc    34560
cagagtgggc gtactagaaa cagtactcat gttaacaaag gtaaccattt ctaaaaaaaa    34620
taaaattcca ataacatttt taaacactgc gcaattagaa gaagcctagt ttaatattgt    34680
acgtgtgccg actaaattac tgtttttaag caacgcaaaa aagtgctgga atcggtgtaa    34740
aattcagggc ttcgtacccc catatcgaac attgaagatg tgtagaataa gaatcagaca    34800
taagataacc gatattatga gacatgccag tattataaaa gtccctcttc ggcgcacatt    34860
tttgatttca gaactagaag ttgaatttat tgttcttggt gatagatttt cctgatgcaa    34920
aaaaacggaa tgatcgtgga acatttgcaa cattacatca ttataagaag gtggcggtgt    34980
ctcatgagtc atcttctagg gatatttaga gcacctgata aatgataaca tattctctgc    35040
tattgaagga cttatataat catgatatgc aatgcaagcc aaaataaaca gaacaaacaa    35100
ataataaatc cctttccaac aatcttcata ggtctctggg aaaaaatggt tgtacttata    35160
aaacattatg tgcagaatta ttttttctac caacactttt ccatagtaat ggttgtttaa    35220
atatgttcct ttttttcctt ttacaagtat ttccccatgg acagttgatc tgccgtgaaa    35280
gctcttcttc cacatttcta acatcgtttg ttctttcaaa ccaataccca tgtagtcgac    35340
gattttcatt aaatcgtaaa caaccgattt tcaaaaattc agttatgtta tgtgcgagaa    35400
aaatgatttg ttcatcatct acaccaaaaa ttttcccatt cacatcgaat attatcacaa    35460
gttcaaacca cttcccaaaa acgttgtgtt ttacacaaaa aagaacatct acaatgttgc    35520
aacgaatgac ccttttccaa cggtgaaggt cttgatcagt ataaggtgtc atgggaagtc    35580
tgcaaaatcg tgtgtatgtt ttataaggac tacttttcaa tataaaacaa acgtttatat    35640
tttcatccct ataatgatc atatcagaga aagatttgct atgctccacg attttgctac     35700
cagtttcaaa gtccacgata aaatcacaca attcgtagat ggggtagaaa aacttcaatc    35760
ctactaaaaa gaaatcttgt aagtttgatg aaacatagta aagactttg tcaaaaaaac     35820
cattgtagac atacaaatgc cctctgtcac cttgtaaaag aattggtcct ctgcaagttg    35880
attttttaac atgatgtaac acaccaacaa cgatcaacgt ttttcacaa cacaagtaag     35940
tgtttcgaat ttcttcgatg tcttcctttg aaatttctgg gattgtttct aatgagtgaa    36000
atgtaactcg ccattcttct gggaaaggca atacgaaaga tgtaccttcc ttacttaaga    36060
tgaattcttc gagaagagta agtttattga cacagcacaa attcgctaag aaatccatgc    36120
ttcagtttta aaattcccca agaaaaaaca aaggcataaa tatttcaatt ttttttttatt   36180
tagcacattt agaagctgca aatttctctt agaaaaaaat tacaaagcaa gctgaacaat    36240
```

```
aaaaaaggtt caacaaatcg cctgtaaaaa tatcttttct acccactgtt tttgaaattt    36300
gagcaaatag agcgctataa cctaagccaa gaaagaactc aaacaacaat gaaaagaaac    36360
aatgttctgt tattacccct gctaacaaac acagaatact acacagaaca agttgatata    36420
gtttagtgat aaacaaatta ctatgtaaga ctgccaagaa aaataaatgc tggcaacttt    36480
ttcttggtaa atacaatttt ccaaaccaaa ccagcagcgt taaggttaaa aattgcagca    36540
aataaacaat aacatctttt atagccattt ggtacgggcc attcggttta tagatcggtt    36600
tgtatcgctg aagacacatg gcaaactgat gagagttaac cagaaactta taactggtta    36660 catatgcgt tatcagaaac actgtaacaa gcaatctgta atgaaccaaa tctgatattt    36720
ttaacacaat ggcaattagg gtgccgaaat aagatgccat tgaatgcgtt ggaaatatta    36780
gcatgcatct acagactatg gctctcaagc ggatttcaga aaaaataaa aacgagcaga    36840 ttaccaaaaa aaattcatcg gtcatttgca acacgagtaa tgataaagtt ataattttga    36900
gatcgttgaa aggacaatag ttaaacaaat tcacccgacg gtaagtcaat agcaaacctc    36960
cgctaaaaag gaatattagc actacttgtt caaacagcgt tttctttatc ataagatgga    37020
aacagctttc tcccggaatt acattcccta aaacaaggcc catagaaaaa cttatcatta    37080
cattccacat ctttgtcttt tcgaatttgg ggtatagtca aaatgtgcag aatcgtcact    37140
ttcgctgtcc tctttctcat taaaaaaatt tgttcctgtg ccaccatttt tagtgggcac    37200
catgtaactt gtaattttgt gttgcgtttc ctgtttacaa aaaaattat ttccttcctc    37260 caccttgtga ttttctctc cttttcctc tgttttgct tgacgttcaa attttgggtc    37320
gtctttaacc tgctcttgac ttaaataagc ttctacggtc agaaaaacat ttttagcgat    37380
taaaaataat ttgtattctt tgccagctat tgctctaaga ctacgaag actttaaaac    37440 tgcacaagta ctaaatgctt gctgtagatt tttggaagat agtacaagtc tcatgcattt    37500
tgcgtcgtga acacaacttt tcccgctatg agcaaattct atttcgttta agtcggttag    37560
aaattttata cttggcgggt taacttgcac aactatttgt gccaacgtca tttcattttt    37620
attactgcgt ttgttctttg tgaccggagc aagccatttt aaaatctccg ttacagttga    37680
atggtccaag tctattcgaa gtgcagattt tccgcttct cttacaattt cttgaccatt    37740
gacacaagga atagatgctt gtgcacaaat atctgatgcc gtgactaaaa accgcgtata    37800
gagatcgcta tcatgttgaa tatacagttt agtgacatca ggatttgata taatgcccat    37860
aaaactatca aataatggaa caaagttatt tatcgtttta gtcgaaaaat gatctgtatc    37920
ggttatatat aaacattctg catgaataat cagctttaaa accaaatggt ttttgcaga    37980 ttgaattatg attgccggtt gaggagtaaa agtaactgta gtatttctc gcaaaagctt    38040 tgcaaaagct cttagaggct tattgattgt tttccaagtt ttcatgtgaa aagccatggt    38100
gggaggctct ttggaatctc gatgttgcgcg atgatctcgg tgactatggt gttctctgtt    38160
gctacgatcc atgctgcacc aaaaatagat attaacagga agagttgtat gagaatacta    38220
aaaaatcaca gagatattca aaccattata tactgtgttt ttttggcgcc aaatttttat    38280
tacatcactg aaatacatgc atagtactca tcaccacacc atcagaaaaa ccactcagca    38340
aatcaaattt ttttgatgga ttgacaccgt cacacttttg atttttatac acagcttgat    38400
aaattcctgt tttaaaccca ttttgataca aacatactaa aatgtccctc atattttctg    38460
tcttatttat gaaaaataca tttgcttgtc catgatctgt aaacggcaac gcaccgacgt    38520
acatatttag catttcattc acagaatagt caaaagcatt gagaaaaatt gtcatttcct    38580
gcatttcttc ttcggaaaat aaattttgt tgactttgga cacatcataa tttacagagc    38640
```

```
ttaagtactc taaatggttt ttaaatctgt ttaagaacag gccattgtac actggtatgt   38700
ataatgtctg taattcagta gaatagacag acagatcact atggaaaaca ggattaggat   38760
gcaaaacttt tatactagat cgctttaaaa tcttatttcc ctctatggga caaaaagatt   38820
gtgagcaatt taacaaatcg aactcttttg acatggccga accagacaca aaggttagat   38880
ttctaagccc atatttttt atgtcgcttc ttaaattcgt ccataaaaca tttggtaatg   38940
tatattcaac attatcatac aaatcgcagt gcaaatccc ttgtgcatat ttggatcttt   39000
gaaaaaaact gcaaggttcc gctccttttt tgcaacaatt catacttgtt ctaacactag   39060
aatagtaaat gttctcgcat actattcgat ataattggca tccaagttga gaattaaatg   39120
gcagattcat tgacattaat gctgaatgta atccagtaac acagatagcc aagcttcttg   39180
cattgactat tccatccatt aaaaaatccc tattttccaa agcataatct ataacagcat   39240
tcccaatcaa aactaactca gtcactgttt ttctcatttt ctttaaattg aaaatttat   39300
ctctataatg aaacatatct atgttagtat gggacttttg ttcttctgaa cgttttcga   39360
caaaataaga aagatttaag gcaattctga aagctgtatt caggccatat tcaaaggaa   39420
ttacatccat agaatttcca agacagtagg aagctatttg aggtaacatg gagtacttat   39480
gtatatttt cctaaagatg aatcccatct gtcctctgcg taggcagcga caaatattat   39540
ccagcaacgt ttcagttttg attctggcat gttcagcggt gcgttcacat tcaagatatt   39600
tacttgtaaa atcagattca tcatataacc ctaaattaat tgccagagct ttgtggaaaa   39660
ctgaccaata agaattttca gttttcagcc gttccataaa aatttctggc agtattagac   39720
aaaacttgac ttgaacagtt gttggcaaaa tttcacagaa gtccagccac attaataatg   39780
acaggtgcca aatttcaaga taaattgtta gaccagttgt tttatttgtg tccttctcta   39840
caatttgtaa ctgagacaat agcaattcca taagagactc tgcctcgtag tgataacgag   39900
tcagatttac actaacatat gatccattta acatcgcagg caagaaaaaa ccactgttaa   39960
tgtccaaaaa atcttccaga gaaaagttac tcacattatg aaagacagtg tcaaaaacac   40020
tctttttc agacactaaa cccaaattac tcatacaagg aaaaggtaac atacaaactc   40080
tcttatacaa taaaatcaaa atttcttcca ctagagggca tttgtgacta acaaaacttt   40140
tttgtaaata ttcgattttt tttatttgac tggccaatgt cacactgatt cttagaaaaa   40200
tcgttgggat gttttcttcg attccgttaa atgaatttga atctcatcg agaaatctcg   40260
atgcagctaa tactcctggt gaaaacttcg ctctccagac atggatagct gcttgcaaga   40320
tttttcaag ttctactttg gagtcacgta caaattcaat caattctttt tgtaaaatat   40380
tttcactttc taaataagt gagatggaat caaattccga agcagagttt gttttgagat   40440
agaactggcc taacaaacga tcaacgtgcg gtgcatcatg cattgctccc agtgctgaaa   40500
ttatggcatc acgtaagcac cacatatcta agcccgaatt taagcgccgg agaatttttg   40560
aaatttcata taactgctta taagaagag ttttgtgatg gaagcgtgaa tagcaaaacc   40620
gttttttgtt atattcatca tgacaaagac atttcctcaa gagacccatg ttttatta   40680
tggaaacttt attgttagga tccataatca caagaaaatt tttctttcac acaattcgac   40740
aaagacgtct ttgagtctta taatggttaa tgagataccc tgtaagtcta aaattcctga   40800
ttttatgttt tgggttttac aatgaccaat tcgttgaagg cttccaaaat agtttagatt   40860
tccatcaccg ttgatcaaat agttcataaa cataaatcgt tctttggaaa acttgtttct   40920
taataaatct atcaatactt cttcatgtgt cagctcagat aaaacaatgt agatcccgta   40980
ttctatttta ttaaatgctt gcctatagat ataacagagg taaatgtact gaattgcatt   41040
```

```
ttgtcttggt tcccagtcag gttccaataa taaatctttc aatatgacca atccatatat    41100
attttccttt cttacgtcat atacatgacc ttgcattaca caggatatta gacaattagt    41160
cccttgagag atataattag ttactccaaa caaagacacc ttttcttcta agtaagaaca    41220
actatctaac attgtgttga tactgtcaac taatgaagtt ttatacagat tagctaaaga    41280
agtcctcgtg cagaaagaca cattgaaggc attcatggct aaaaacaata cactaatcaa    41340
caaaaatttt ggactctccg cgtctgtttc aagtctgaac ataagcattc ctaaatggtc    41400
tcgttcaggt cctaaaagtt cgcaaggagt aaaacttcgc gaaagcacac actctttggg    41460
aacaccaaaa gctagcaaac ttctgatctt ttttttctca ttttcaatga gattatttaa    41520
ggaagtttca tcaattgtct gatgtttcct tttttgaagc atttccattg ttcgcaagcg    41580
aaatggattg tacaaattta caatttgagt caatattgaa tttacttaaa acagatgtgt    41640
ccgataatac attcttaact ataacagcga aaattgaaat ttttctctt gcggctgaaa     41700
gtatcacagc agataagata ttgtcatttg cgaaattatt accaatacac aattatcatt    41760
tcaactttat taaaaatcat atggtgtttt atatattaaa ttatagtact ctaggatttg    41820
ccaaaagatt ttcaatagct gaaacactat gtagagaatt aaaaattttc cacagaacat    41880
tccaatcaac gtctaaatta caaaacttaa ataatgcaga agtcctttat caatttgaaa    41940
aacttattga atccattcaa gtattcaagg cggaattggc atcgcctatt ggtaaacttc    42000
tacgtcaaga aacaatgatc tatgacaaac ccacagaaaa atcagttaaa tatgtcatta    42060
ttcagcaaaa tttgataaaa attaataact taattcaaga ctgtgaatcg ataaaaaact    42120
gtagactcat agcggagctg atagatgaat tatatcaaaa agtttatagg tggtttatgc    42180
aaattttcac atacgacgat attatttttcc ccaatgacaa tttcttagat agacttttaa    42240
aaatggattt ctgctataca tattacacgg catctaatca gcatttatta tcactttttg    42300
aacagacaat tgacaatcaa attttttatcg acccttctcc atacttcgaa ataaatccag    42360
tatattctcc cgaattacaa tttatgagca catttagctt aaagatattt tcaaaaaata    42420
tttcagcgaa aaacgaagat ctatatatttt atccacttttt aaaaacaaac ttttccatac    42480
ttacctttct gagtttagaa aatatttttt tccatcatgg atttatatac cacatcttgc    42540
atagaacaaa tatcacacca actgaagaaa aaaattagg aaaaataaat ggattcttaa     42600
acacggttat tcagcaagtc ctaattaaaa agaataactt acaatcact ttcccggagt     42660
tgcttgataa aatctatcat ttgcatagaa taggcttgaa tatcgaaacg gcacaaattt    42720
ttttacaaat gttaacaaca tacaaaccag cgacgacaaa taataagttg cagacatttt    42780
tcacgaattt ttcaataata attttttcgg catatatttt ttttctatgt attgagttat    42840
tcagcccaac ttttatttttc cataataaaa aaaaacttat cctcgagaaa caaaaatcca    42900
tcatactaat tctcggtgaa cagttctctt tcatttggaa agaggtaaat gaaattgtag    42960
atttgttatt tagtagcaca gttacagaaa cctatttcaa attttattct aaaggtgccg    43020
atgactacga aaagattttt ctttataaag acttaatgga aaaatggggt gaattgtttt    43080
tcccattaac ttattcaatg acaacgccac agaaatatac cgacaagcat gtatcaagta    43140
cagttttgaa aaatttatgt gatacagcat atcaaagtaa gatggaaaca gcgtatgaaa    43200
gtctattacc atatattact cacccagagt tcaaattcat ttttattaca cattcgtca    43260
gaccttcttt gtcattaatc acaaacttaa cctttgaaga aataaaagat aatcgaagat    43320
tactaatact aatattcgcg tgtaaactgc taatgccatc aaattatctt ttatcacatt    43380
acttattatt gttacacgct ttcacactac aaattttcaa agtagatctt ggccatttt    43440
```

```
caattataca tgcaattact caaaaaattt ttgacaatat taattctctg acccaaacta    43500 ttttattcc aaaacaaat tttttagtca gccttttatt aacagcatac actgtgcata    43560
tgcaaactta tgtgaatcct tggatacaaa aaacaatcag tgaaaatata gcccttctta    43620
aagaatacat cgatttcaca aagaaatgtt caagtacttt ggcaactacg tgctatttga    43680
acttagaaaa ttttgcagta aatatgtatt ttgggaaaaa caaggttgga agtacttcac    43740
tatcagcttt ttatagaact tgctctaagc taattgagga atctaaactg tttaaagata    43800
ggcttcaaga aatcaaagtt tcaaaaacat tgtttataga gatgctgcaa aatgttgtga    43860
aaaacatcac aaaatttaag gatttagtct caaatcaaac tttgcaaaat tttataatta    43920
ttgttgaaag aatctcctct catgcaaata aacatatca agatgttctc aatagcatag    43980
atgaatgcca tttttcaaac atgcaactta tccaatcttt taaaaacatc gtgtatgtca    44040
ttgatgttct gaatactaaa aacatcttta acttttctct cgcatcacaa ttaattgaag    44100 cgaaaaact tgtaaaaaaa caggacacct ataatcaatt aaatgtgcaa gatgattttg    44160
tcactgtatt aaagtcacat ctaaataatc tgtttgaaaa gcagaagcct acaattaata    44220
ttgaaagaag atttatgtta gaaggaatac ccgacataaa acagattcca ttcttggatg    44280
tttttgatga aagatataga ctaataccac aaattgaaaa gtatctgcat tggtacattg    44340
catatagtga agctgcgcag gctgatttgg tcgagccttt actcttaaaa cttggttaga    44400
tgagaatcat agcaggaagt acaaatcaaa acgatcctaa atacggacca agagccggaa    44460
agcaatgtat gtcaaattgt ttttcttct tgcatacagt ttatttgaac ggaataaaca    44520
atgtgttaaa taaagagtct attgacataa tcatggaaaa tggagcatta ttggataata    44580
tcagtacaac gacattgaaa ctcgaaactg gcaatatccc agaatatcga ttttcacag    44640 aaatcccaaa aaaattagt tctaattttg gcgaaacaat acatgaatta tctagaccct    44700
ttaatggtac cttagaatca caacatatag ataatgaagt ttatcttgga ctgttagact    44760
ttctattgta tgggaaaaat aagaaaccag ctttttattgt catcactata ggggtaatgg    44820
cacgagctat atttatagtt gatgaattgt tttaccttt tgattcacat gcatcagaca    44880
cagaaaactc tgcagccatc tatatctgtg aggatattga cgaattatat gctctattgg    44940
ccatagagaa tgttgcggaa ttttactatg atgcagtttt ttcatatttc attgaaacga    45000
ctgatttatc tcttgaagac ggagatgcaa caattttgat tttaaagact tacaaagatc    45060
cagatatagc tcttagtttg aatgattttt tatcaatgta ttcatctaca tcctcaacaa    45120
agacagcgga aacaaacact ttaatttcaa acaatcacc aagcaaacgc aaacaagaaa    45180
aaaccagtct aaattcaaat tctctagaaa aaaaaggaa gcagggctca tcactcaaat    45240
actataacaa tgaagtagat ttagtaccaa gttttttatga gcttagacct caatttaaca    45300
atattttatt tgagctttct aatttcccaa ttgtaaagga aaatgtaaat tggaccctt    45360 acatacagaa atttgcaaca aagtctacac agccatttac aaaaccttt atatggaata    45420 gggtattcca tctattttct caagtggttg acgccttaat tatgattaaa aacgatcatt    45480
gggatgagac acaacagcaa aaacaattct tcacacattt cttgccgttc aaagaatttt    45540
ctgaggaatt tgaaaacgct ctagaggctt gccgagaaaa taatcttgat ctaatattgc    45600
tttataaaaa ctatctttcg aaaactactg cattcaaaaa ccttgaaaga attttattaa    45660
cgaagtttag cgccattgtc agtccggtgc atgaaaaaca ctacacgctt gtaaacacat    45720
ggctaactaa cttaatacaa aaactagtca aacatcccga ggataccaat gctttcatca    45780
atgactacgt gttaaaaaac cccttaaatc atttcatttg tttgaataag aaggaaaagc    45840
```

```
agagcatcgc tctactactg aataaaaaaa gaatgagtat gctaaaagat gtggaaatcg   45900
aaaagaatgg ttttgttcaa ctccaagcat tcatcgagaa cataggagaa gctccagcaa   45960
attatttaga tccggaaaat gcacgcaaag tgaatgttga agaagtctca gaaaaagaca   46020
tcccaacatt atccacagat aaagtttcca tacccaatga agtatgttc acatcaaata    46080 aaaacacag catagaaaag ttaatacatg ctaagctgaa agccattttg agtacaatgg    46140
ggcaaagatt aactagaatt attcaagaaa attataataa catcgctgca ggttttctgc   46200
cggtgaacga tcttaataat ctgtttgcct atttggtcaa actctatttt gatgtctata   46260
gcatcaccat taacggattt gtggtggaaa acgaattgat aaaaaatatt gaacaaattt   46320
acgacaatac gcaatatctg agatttggat tgacacgctt caatatgcaa aatttgacac   46380
cgtttactat atctgtccgc aaaatgttcc tggatttttt tctatcacaa aaaactctga   46440
tagatagagc tgaagaaatt atagagaacc ttgagtttaa atcagttaca ccagaaggaa   46500
aacaaaaact tgccacaaag aatatgctca gagaacaatt agaacagttg aatgctatgg   46560
atgtggatga tacaataaat ctgaaaacag acacattaac acatcaagta ttattttcag   46620
accaagaatt acgcatgata caagacttca ttttacaact ctccattcac aatattccaa   46680
gcattaactt tgtgaaatct ttgaaattac atattatttt agaaaaaaga cctgatatac   46740
tattagctct acaagaaaaa gtccagaata ttctatattt ttattttcaa gatctagtta   46800
acgagatacc tgctcaagaa atgttttgt caacaatgtt atttataata gagcttttc     46860 cagccgacag tagaatacat ctactagaaa ccggatatat ttccagacat attgtaaaaa   46920
aatggctaaa catgaaatca ttgcaagatg ctgaggattt aattcgattt ataaatatta   46980
ataaagaaca actaggaaaa tttgaacatc agccatttgg aaaagaaatt caaaaactaa   47040
ttgaaaaaat acacttgttc tataagcaaa aagtaatcga gtatcaggaa gatgtctgga   47100
gtgaaatggc taaaaatata attttaactt caccctctga attatctcaa tttttagctt   47160
cagctcccac tcaacgtatc atacaaaaac acaaaaataa tttagatcag aaactttaa    47220 tacatatgga aaaccaagcc aagcaagcaa tggaagatga caaaaaaaga gttgcctgtt   47280
ctaaaattaa tctggaacga cacctgaatg atttactgct cttattgaaa gacagacaat   47340
ttgcttccat acaggcttct gttttgattg tgtgcgaaaa tatatttaaa acgataccag   47400
atgataacct aattattcaa ttttcacatg ctctgctttc agttttactt gacattgaaa   47460
aggatttaaa aagctattca tcagaaatat tagagaaaat actaataaat aggcccctcg   47520
aaaccagtag attattagtg tttaaagacg cttatggtaa tctgaaagag ttttttaaacg  47580 ccttaaaaca atcactttt gccacagcgg atgttcaaaa caaggctgat tttcttatcc    47640
aaattttaga ttttaccat aaatttagac ataagacaaa taaggtaaa cttctacatt     47700 ccatttataa tgaggatttc aaactatacg aagaaacatt aacagagtta agaaaaaaag   47760
caacagatgc aaaagagtcg ttaactaaac tttttaaagc atccgaacaa aagatcgagc   47820
tgtcgcgtac gattccgtta aaggaaatct acctgaacat agaaactgtt aatttccaag   47880
gttatggcaa cgtagttttt cgagaaagtg cttttaaacg cgcaatagag gtagaaataa   47940
aaaattacga aatgaaatta aacgatctaa taaaacactt taattcacac ttaaaaacaa   48000
aaattgacca catgcagatt cttaatctat cttttgataa caaatggaaa gattttgtct   48060
ccaagtcaaa aatatctttc ccaccagaac tgacaataag ttcacaagag ttgatcaagg   48120 atccccattaa agttataact gaaactctaa acaaagcctc aaacgattta gcgtatgtga   48180
ttagtgaaaa aatattgaag tggttaatag ttttttgtcaa agaactgaat accttttttg   48240
```

```
tagctacaat gtcagaattt ggagaagtta tcccctttga ctataaacat ttcagagctt   48300
tggaatacga aattaattct aagtacatag agattgaaaa taaaataatc tgcaacgaaa   48360
ttatcgaaaa tactgacaat atagaaaaac tctcaacctt gataaaacaa atagatccaa   48420
atcgtattgc tggtggtaaa cagaaatttc aggattatct gagcaaaatt ctaacagctg   48480
aaacgaacca gcaacaaaca cgctataaag aacagttaaa aaaacagtac tttgaccttt   48540
tagataacat cgcccatttc cggttcgcat tcgattttaa ccatcaacaa atttaatttt   48600
taaaactgaa agacaaattc aaaactctta gaacagacac tgtatttgaa agatttccaa   48660
atttagatga tacttttgtc agttcaatga atgtcgagaa cttttttgcag gcacttgagg   48720 ctttaagcca tttcgtgcag gcagcacaaa attttctaca aaacgtttta acagagcaag   48780
cggatttatt tccacagacg aatttcattc ctgtcgaact ttccaccgtc aaaacaattc   48840
caaaatcaga tataaattta cgtatgaaaa tacacacacc ccaaactttt tttcaggttg   48900
attcagtttt taatacacag ttgatagttg atgagaaagg aattccagtc caattttaca   48960
atgttttcca caatattgtt ttcaagtttt ttgctctaaa ttataagaaa attatcgtac   49020
ctgataaagt gctgaactta gtatcaacca agtataagat cttaaccaca ttaaaaagca   49080
ttctgagtgt tgtaaaaagc ttttggaaag agattataaa tttcgattta acttcttatt   49140
tccaagggaa agcagaattt acttttcaaa atgttttccc aataattaat cttaaaatat   49200
ttatttacat tattactcag gcctggtcag tcacatctga tgaaacacag cattcgtttg   49260
aactgccact agaaaaattt tctcttttaa ttatagcaaa taatccagag tttcttttg    49320 gttctctgca gtgtccagtg gacctagcta ttaattctct aatacccctta ttggaaaaga   49380 aaaaatattt cactgcattt accatctctg acaatccacc caagctatct atggatgaat   49440
taaaaattgt gtgtttggat ttgaacacct ggagtgaaat aacattagaa aaatacactt   49500
ttaaaaagaa cagtttgatg cagttatgta tgggcaaaga gaatttttt atttaccttt    49560 tatcagcgtt ggttcttcct caaaattttt tgaattacat ttggattcaa tacaaacctt   49620
cgtgctgtgc tcaggattca ttccaacaac tcattcaaga tttatgtttc gagtatacac   49680
accagaatca cataaagccc atttcattaa atctccaaga accaaatgca ttaaaacatg   49740
gtgaaagaat cctttcgaaa ttcgtgctgg aaaaaaatgc aaacacttct cttttttagta  49800 tcttttagg caagcagttt ttattagatt atctattatt ttcatactta accgcaactg    49860
aaatgacttt ttcatattat gtggattcca tcaaaaattt tcttcttacg atccgacatt   49920
tggaaaatgt ccagcaaaac gtagacttta gaacgatatt gcaatctcga aatttcgatc   49980
taaaatatct tttaacacaa tcatggacac aaaatgtttt agaacagtcc atctttcacg   50040
tgcaacttga taaaatcatt gctgacatca acaaccaca actaagtctg aagaaaattc     50100
cactggtttt gtttaacggt gacaacgaag tcgtgtcaac ttatgtgccc cctgaacaag   50160
caagccagac agagcagagc tttcgcatta agaatatttt cccaaatcct gtgcaagagt   50220
atagtagcaa aaatgtgatt cttttttacga actatccaaa aaacaccaaa tttttattta   50280
actctcctcc acctaaaaca gcggcaaaaa gttacaaact accagacact accgatgaca   50340
taaacacgga acattatca agtcccacga ttcaaagaat ccctatcaaa ggacttgtac    50400
ccaaagaaaa cgaaattgtc ttttttaccag aaaaaaacac tgcacacaca gactctaaag   50460
agacaaaaac gcatttaata gacaccttca atatattgtc tcaaacaaag ggtgaaatca   50520
aaacattttc tacagatttt gatcaaacaa tttccaaatt aaaacatttg acttttaag    50580 atgattcgct aactttgcta tttaatctat gcaaagcaag catgcgtaaa aaatcaagtc   50640
```

```
tgaaggctgc ttttttcaatg tttccggtat tttgttttgc atattttgct agaaacgtcc   50700
ctgtgacagg gtgtgaaccc atagaagaat gcaagcctag aatattcgta aacatttgtt   50760 gcttttctt  ttcttcttct tttttgaac  tgttgccaga aatctggttg atttgagcag   50820
tgatttcatc accacgtgtc gcagccatgt tgcgtgcact tagctaattg agaaatttta   50880
cagcctgtac aaatttctcc acagtcctct agatcaagac acgtttctct gtagatattt   50940
tgacaatctt ggcattgaaa ttctgtggag tgagaaatta gtttcaacag tttatttatc   51000
gttagattct gcagatggat catagagtaa caagttctgc aagaacatgc aacaatggca   51060
tcaaatttaa cactatcgtt taaaatagtg caagcggaat tagttccaat tatagctttc   51120
catgatacac ttttttacttg aatgcctgaa acactatatt catacaattc atatactttt   51180
tcaagtgtca aacgttgccc gccacataat gaacaataaa gcaaatctgt gtgcatactg   51240
taaataatat ttttttcctg tctatctcga taataaaaca tcgagcttaa agaaaaagtt   51300
tgtttccctt taagcctctc tttgccggaa tttaaacaat gtccacattt agaacatatc   51360
acagtgagat aactatcaat tttagcatat ctgagacact ttgttttgca aaaacataat   51420
accggtaaag agatgatact tgaagttaag cttcttttca agactgtcgt caaagcaaaa   51480
gttagaattt ttggaagttg atgttttttct tgtttgttca aaacaatcgg caccaagtta   51540 ttatttttcta gcgggattaa aaaacgatcg aaactgtaac aataattttc tatcatggcc   51600
atggccatag caaagataaa atttccacat ggaactgtta agaacacccc atgaaatata   51660
tcttgatatg tcaggttgct tgctctatga gcgtatcgca gtgtgatgtc attacattgt   51720
tcaaagttac gtaaacaaaa gagtttcata caaggaatat tacaatgagt tgaaattggc   51780
aacattaact gttgctgaaa taataataaa tagagatcat taaaagacac aaacgacggt   51840
atttccaaca actgatttaa cttatgtatt gggtattgtt tgaatctctc cacaatttgt   51900
ttccaagtaa gacgttgaat tttgtaaaga gccagaattt ttagaaccctt gcattgcctg   51960 tacaaaaaat acaaatatgc caaaagcaaa aagaaatttt ttgtcatcat cattttatta   52020
aaaatagctt taatctgatt tcttgaatcc agatcacact ttaaccaaac ttttaaaaac   52080
ttccggtaga aattatcagt taaatctttta ctcaaaaact ttttattcgt tacgaacatc   52140
gataatacgc aattttcaga tttgctgaca tctccaataa gaaataactg caaatgactg   52200
tacgaaccat gtttacacag cggagaaatc agccgacaaa gcaaattcct taaagatgac   52260
atagcataca attagtaagg cggcaaccaa aaaaccacaa agaatattat ttctccgtgc   52320
aaaaatagga acagtaactg ggaatactgc tgcgtctttt gtgtttccca tgtaatttat   52380
actcctgaat gatgtcatct ctcctactga cttcaactgt aacctcaatg gttttttttat  52440 gtgccttgca gctctatgtt tctctaaatc ttggcgctct aaaaattttt tctttaagat   52500
tatcgcttta agaagagcga tatactcaga ttcactctcg ggaccaaaag ccacaaattc   52560
aactataaaa gccgcatctc ggtttcgtct aataatgcac tttgtcagta caccacttga   52620
agaaggttta atagcttcaa tgtcattcaa acacacagat aaacactcat tgacatttaa   52680
gatgttgcat tctttgacaa tgttctgact ttccttgtttt atgggagcgt ggagataaca   52740
agacatggaa acagcacctc ccgtattttt aaaaataaat ctcgcttctt gttttgtcaa   52800
atcttcccag agactcagca aatattccag gctatatgca aaatccaatt ttaaaagtat   52860
atcacataaa ggaaatttag gatttttaga aaataaattt ttatctgtga cacgaaagtc   52920
tgcgggaccc aattttaaaa cgcggcacgt ggaaagaatt aattcatcgt acatcttttc   52980
tttcaacatg tttatttttct ctttaaaaat ttctgcagtt gtatattatg tatttaaata   53040
```

```
ttcctgatgt tctaaaattc cattcacatt taacagtttc gataaaattg aagtgagtag    53100 tttgatttt  tttttgataa tctccgagtg actgcattga tttgctctgt gatgtaaata    53160
ttttaaatag gttaagtgtc tgtatccaac attaataaaa tgtagtcggg catctaatga    53220
aggcagcatt atatcgtaca gttttggtaa catagggaga aaagctattt caatttcaac    53280
tcgggaagat aattgttcat aaagaatttc tatatctgtt ttggcattgt cgttagacat    53340
ggcttataag ggatggaact ccgattcctt ttctatgaac tcagaacttt ttaatgaaat    53400
tcttttatat gcacacttag attcaagtgg aatagattct gatgatctta acacaaatcc    53460
caatacactt gaaaatgaaa ttaactccgt tgaaaaaact ttaaatattg aagaactgaa    53520
aaaaattaca actgctttaa atattgacaa ccgatgcaat atatgttcaa ttataaacat    53580
ctgtttacga catgaaaccg ataaaatgtg gatctatgac tatgctcttt tgtgttacaa    53640
atgtaatgct gcacctagaa ctcccttggc tgtcgtaata atcgccaccg aatttatgca    53700
gttgattcaa aagcatttct taaacataaa tttcgatggg ttatttttaa acaacatttt    53760
gtcaatactc gattttcatg tacactttt  cataaacagg tgtttctcaa acaccaacga    53820
tgatctatta cataatgaaa acataacctt atatcacatg ccatattaa  aatcacttct    53880 attggaagac gaatctatac caaatataag aataaagaaa tttaaattaa aaggaaaacc    53940
aacgaaaaaa cagcatggaa atgctatcct tgaaaaacaa actcttccac ttaacacgca    54000
ttttacacat ttaattttt  atatgtgggc tgggacaaac atattcgatc gcatttcact    54060
aactgatcta gccatcaaga aacgccaaat tttaaaagcc atttactcta ctaaaaatga    54120
gctcaattgt tctgcgggac caatcctact atctcaaata ccgatctcca tcactaagaa    54180
cgccaccagt agcgtatgct tattatgtga actaatgaca tcttctcaga aaaatttcga    54240
cttgctacag ttcatctaca ccagtgtcat taattactgt caaaataatt tgaagatgat    54300
tgacagaatt caattcgtac tcgcaaatct tttagattta gctagaatat atactaacgt    54360
taaaaccaca tcagattgct caaaaattgt attagccaat gaacaagaat tttcaaactc    54420
tgattttgta attgattgtc atagtttttt aattctaaag caggttggac ctgtgggatt    54480
atacaaacat ttcttttgtg atccactgtg catagcaaac attaagacaa taaaacccca    54540 tatttattc  tatacaacag aaagctgtat actacaagac ttcaaagttg caatttgtta    54600
tcagaatgag tatttaaaca gtgttgaaaa acatgtttgg ttagccattc attttttaa    54660 agcatttcag gtttcaaaat taaaccacaa aaataaaacg cttatatctg atttcttaaa    54720
ggatttcaca cagctcttag cagatcaaaa ctttgaaatt gtcgatccta catttaccat    54780
tcattattac gtttagcatg attattcaaa gtacacgtag actgagacga gcatctagct    54840
tgttaaagaa aagcaaacct tacaacaaag aaaaaactaa cttatcttta tctttgtcac    54900
ttaaagaact ccattcggtt ttcaaattat ttccagagta tgaattgaaa tttctaaata    54960
tgatgaaact tccaataacc ggtaaagaac ctatcaaaat tccattcgat ctaagtctac    55020
atcatcaaca tacgtgctta gacttatcac catatgccaa tgaacaagtt tcaaaaagtg    55080
catgtgttaa ttgtggtaca acaaacattc caacagcttc agatgctatg gtggcatata    55140
tgaatcaaat ttcaaacgta atgcaaaata gattatatta ctacggtttt cagaaaaagg    55200
ttgaactgat tcgtatgtca gccaagcaac caacgctttt tcaatttttt tatattcttt    55260
caagcatagc aagtaatttt ttaccaatca tgtttgaaaa taacgagaaa ttaaatatgt    55320
atgttgtttt ccaaacaaga actcttcata tcccttgcga atgtatcaat cagattatga    55380
cagtctcctc cggatacact gtacttttag acatcttaca cgacagcatt gtactacatg    55440
```

```
ttctttgtaa aactattgag actagcaata ttcaaattga tattaatgtt cttcagcgaa    55500
aaattgagga aatggacgta cccgatgaaa taggtgacaa gttcgaaaag ctgaaacaca    55560
ttctaccgtt tatttaaaac agatcacaga acatctgtca ggtcacaaaa gctttgatct    55620
acatatactt ttaaaggtag gattgaaagt aaaaacttt ctttcttaat gcccgttttc    55680
ggaaatattg gagagatagc atttgttaca gctttcatta tttgttcaaa atatttatct    55740
gcattgattt ttaagttgtt ctcaatagca tatgctggat cttctgctaa ctcataatta    55800
tgaaatgttt tttttacggt ttctgtgggt gcaattaaaa tgtacataac tctatctcct    55860
atgtttggca actcttcctt tctttgagct aacctttta caacagccaa atgtggtaaa    55920
tttgcttgct tgtaggcaga aatgtctttt gataagactg aagacaaaac caaactttta    55980
atgttaaccc tgtttaagaa aagtgcgtct cgtgcgtcac acaactttt aattatttt    56040 tggataccat cgggaactcc attttcatag atttcttgta ttgtcatatt agagagcttt    56100
tcagcagact tttgtacatc gacatcccaa aagagaagat cgatgatgtc tttaactacc    56160
actttaacaa aatcgcaaga agtcttgcga actaactcca caccttaaa aacaagcgtt    56220 gcatcatcta actttccaat gtaacgtttc ttgcatatta aaattaatgg aaataggatc    56280
ttttcaaatt ctaatttgat aggatgttta aataacgtgt ttgttatgtg gcttgcaata    56340
gaaggagcta ttcttttcaa agctttggga caaacatttt tgaaagtaac aaaaagactg    56400
tcagtatcac cataaatcac ctctattcca aatgtccctg aaaaatcacc gcgtgtcaat    56460
ccaaatttct caatgaaaaa agtgtccgaa tacatggcgc tgtcaacgta atcaacagtt    56520
ttacaaagca tttcacgccc aagacatgtg acagaagctg ctattgccac acatggaagt    56580
aagctatgtg ttgccccggt gactccgtag actgaattac aagtagtttt taatgcaagc    56640
tgcttcttat ctaaaagcat ttccatcacg gggttgttac acattttcat ctgcattttt    56700
acttcttttc ttttatccag ccatttttc aataaactcg ctaaaattga ttccctgact    56760 gtcttttaa caaacctgtg cgttacaggt ccaacatgca cagtgagaat gtcatctgca    56820
tgtaaaccaa ttactgcatt ttcatcaaca accagggtac tataacacag attatgagcc    56880
atcataatac ttggatacaa actttggaaa tcaaaaacta ctgttggagt agcataataa    56940
cctattttcg gttctaaaac tgtagcacct ttatagccca cattttcttt gcctttatta    57000
aagttagtgt tcatacttgg taaaatcata tttaaatttt tagcttcgtg taaaatgcat    57060
gggaaatttt tttttgttg tccctcaaat acggcgcaac gaatagtaat ataagcgaga    57120
cttgcaacct cagccatttc atagtgataa ttaatctttg taaaaagctg aacaaccaat    57180
agagaatctt gtatacaata tctgccaacc acagctctac ctttggaacc atcaataaat    57240
tttttaggaa tttccttgta agagagattt tttttttcct gatttaaaca aagtttggct    57300
atagtgtcta atttataatt ctgagctgag attttagatg aatacacatt atacatgtcg    57360
aagcataaaa tcccagacat gttaacttta gttaaagaat tcaaaaactt cttatgctgt    57420
tcgtagggaa cgatgacaga aaactttcca cgttttagtt tcgaaaaacc ccctatctca    57480
aaattatata ttttttccat tctcgtacat aaatacttta aatcgaaatt tatgatgttg    57540
tatccagtaa ggatttctgg tgatttacat tttaaaaaaa ggaaaaaagc atatagaagt    57600
tcaaattctg atgcaaactc atagatgaat acccccttcga tttgctcgca agtgcccaaa    57660
gtaaacaaat gttactttg gtaatttcct tcagaatcaa aatcgatgac cgaaatttga    57720
atgatgatgt cacccatttg ctcagcatct ggaaagtttc catttggct tagacattca    57780 atatcaaaag aacaacaatc atataatggc caagaatctt cctttaacaa aaataaatct    57840
```

```
gacacatgac aatttaattc aatttcaaca ttactgcttt ttgcaaattc ttgaatagat   57900
agataattaa tttggtacca accaaagctt tttaagttgt tatcaatgaa gaaacgattg   57960
agaatctcaa cttctgcttc ataaacagaa acgccctcat ttagtaaaat ttttccaatt   58020
cgattactga tataaaagtt tgaaaatgat aatttaaata aatttttgat aggttccgtg   58080
ttataaccgt agaaattgta tttagttaca gattcaatag aaaatgagca tgacattttt   58140
atttcagaac tattcagaag tgaacagatt ctagaattca gctcttttt acattgatat   58200 tcacagtaga aataactatt ttgtccaaat acattgatac aaactttttt accacattct   58260 gttttccaa aaagttttat gacattacca gatggaataa cgaaatgtct atattggaaa   58320
gggatgtttt ctatagaatc agtaaataat aaagattcgg atgcatcata gatatgaaat   58380
tttaaaggcg cacgcaattc ttttcggct acttgagaaa gcgatggcca tgtcatatca   58440 ttttgagaa tgtattgctt atcttgatag aacattctcg gttccgagtc acaaagagtc   58500
ttcattaagc cgggtgctcc atcgtgcatt ataccgcgcg gaaaaatccg gagaaaagta   58560
gattttgttt tttcttagt tcgtacattc tctagatacg gattaaagaa ggacaccaga   58620
tccatcacag ttcttctgtt gaaagttttc gatagcccct gtattgaatc ctttcaagta   58680
ggcttggtct ctgtgatttt tttgcctcag cgatttccgc ttttttatat gactcatcta   58740
ataatttaat agcttttcaac attttttaaag cttccacttg tgaatattca ttagtgtgtg   58800
ttatgtcatc accttgcggt tctgtgtctt tgttagtttt taaataaggc ggagatgaat   58860 ctaaggttc tttcacttgc gcttgaactg attgcgttgc ttgaagtacc gaatttgttg   58920
attttgatgt ataaggaaat aaaatatcaa tcggtgtttg tgctaatcgt ttatgtctta   58980
aaaataagaa aataactaag ccaatcactc ccaaagttag taagatagtt agtgctccac   59040
caaatggatt tttaagaaaa gagaaaactc cattcaccac atctcccaaa gcaccagccg   59100
ttacacccag cacagccccc aaccaagac caagagcgcc aagacctttg aaaaatgtgt   59160
caatccctcc tatatatgtt ggagtaacag ttgcaattt tgtttctata tggtgtagcg   59220
cacttttgta agaattgtat tctctaagaa tggtttccaa atcaaaaacg ttcgctttgc   59280
tcagttcatc ttttgtatac aattccaata atgtaaaatc tgcattttct aaaggatcta   59340
tgtttaagtc aacaaacgca tctaaagctt ctatttctgt tatcaaacta gaattaacgt   59400
acgtatagtc tttaaaaata tgagcgaatt taccagacaa aaaaattttc gtgttagatt   59460
gttcacattc ttctgttctg tgatttccca gtaatatctc attgtctaaa ccaagttgtc   59520
ctaaataagt ttccttcgaa gaatttgcaa atgaatatgt taacaatggc cgagaataac   59580
atcttagagc atcgtaactt gaatcttttg tcaatctcat acttttatgt agctgaacag   59640
aagtctggtt gacttcaatg cactttgaga ctgctaatac atcaccaatt aatttagcgg   59700
acatgggttt accgtacact gctgaaatga ttccagaagg acttatttta ctaagctcgt   59760
gcaacactgt gatagtgcgt ttttgatcta aacaccaggc ttcagcaagc ttacctagtg   59820
ctgtgttaat gtaatctttc agagtgtcgt ataggtattg tagttgaaca tatacgatgt   59880
ctttgttagt ctctaattcc ctcttcctcc tttttctaga agcattagaa aaattttcca   59940
aaaccgttaa tttccgttgt attaacggtt gccaaatcag aattaaatct ccctcagttt   60000 taaaatttc ataactacca tttttgtcat gcgaattgtt gtattgcgtt tggtaaatct   60060
catccaaaat tgaagtataa ttgctgttaa tacaattata ttttgaatca gaaagcgtat   60120
aattactttt tcctgtgaca aaagaagcag ttagttcctg cgcaataaag tgaaaactgt   60180
tagcattttc tgcccgtaaa gcgtgtggga ttgtcatcca atgctttaac aaacaaatgg   60240
```

```
aagactcttc attctgcact tcccatgaaa aaatagtatt tcccttttcc agaaaagcca   60300
ttttagttaa cgtcacaaaa tttccttttg atccatcatc aaacgttttc agcatagtat   60360
aattatttct aaacaaaatt ttttccgttg gttcattaaa tgttttagaa ttaataccat   60420
tataaaacgg tgacccttcc acggtttccc ctgttgataa agcaaaaaaa tcaaaaggat   60480
atttagtctt tgcaatgcag tctgtaacta tgcaatttat cgatgtagat gttgaataga   60540
accagagggg accatttctt aaaaatggtt ctttagtagt tatatatctt ctgacagtat   60600
cagatttaaa atttaacgga atcaaatcca acgttttatt cacatattca tctttatgat   60660
atgcaacata ctcctcttcc tccgaacgtt ttacagagat agaggacaaa caacgcgcct   60720
cggtgtttac catgtgcact tcttcaattg gcattggcaa agttgtaaca gttcgatcta   60780
agaaatacac agtgccaaca tcgcgatatg ttgtttgaaa tgtaagttct tttttaaaag   60840
ttctgacaga aaacgtgtgt gcttcaatct ttgttttgta aattatcaaa ataccttcgg   60900
tagttttaat gttagagccg taagacgcgc aagaaacctc cctgtcaaaa cgcactaaat   60960
ctgtcccggt ggcaattgaa caaattcgaa atggtaaatg ctgattgtgt ccagtcatga   61020
caaagtcagc ttctgtttgt agagatagct gtaagctaaa agttataaaa acactcagga   61080
atagaatttt cattttgtct acatagatct aacagatttg gagccggtat atgggaaact   61140
tgcttagttt gtgaaatttg aacaggatcg cattgagtct ttaaatcgaa atacaataaa   61200
gagtacaaat cattaaattt tgtcgtgttc gttccacgct tgaatagtaa aggagaacca   61260
ctatcaaaag ttaaagtat ttttcgaca gtttctgtct cttcgccaaa cttgacgatt   61320
gataattgtt ttccaaatac atcattatat agtgcaacag acaaaactaa ttccctgata   61380
aaattccaca tttgtctttg catatcgttg atattatgca aaccatcaaa attgaaaaat   61440
ttattatatg tacacagcat ccaattttcc gggtagatcg tgccttcaac acatttagcc   61500
agatcttctt tcatatgtgg taaaaaatct gcaacatcgc aagcatacgc catggatatg   61560
ttgctggaca atggaaaaga agcggtgtga taattcgaca atggaccagt caacaatcga   61620
tacatttctt gacttaaatt aggtaaaagt tcctgaggca attttttttga aagtagattg   61680 tttttaatgt ataagtgatc atcataagta aatggatcag cagagaaatt tcctagtgac   61740
tgcagttgtc tatttgcaaa tgcgttcatc attttcgaaa gactttcgaa aatgtgattt   61800
cctaggatat taatattcat taacttattt attaatgctt cttgctcttt gatacacagc   61860
attactttac tataacccga ttcggaaatt ttttggtaat aagcttttt tctaatgtga   61920 atctcttgtt gtaaattgtg atcttgtgtc attgaatgcg ttacgtattt ttttgggaca   61980
gtttcatgag ctgaattttc aagttcattt aataaagttt ttattttagt ttgtatttca   62040
tcttcctctg ccagctttgt aaaaaccgga tcttcttcta agttttttat actaacattg   62100
gtaataatat caacgagtct gcaaggggaa ataaatctcg atccgatgta taatttgtca   62160
tcatttgtaa cattttcttc gttaaaattg aaaacatctt gaatagtttc accatataaa   62220
aacttactaa tttcattttg gagatcagca taaagtgaat gacaaagatt tagttgattt   62280
agagttattg aagcttttg aataacagat tctgaaattt tagaccaata ggtgaattca   62340
ctcaacgaat aaattgtatc tggaattttg ctaaaaaggt caaagttgat taaagtgttt   62400
tcagcttctt gtaaatgtgg aggttttgaa tatagttgct gttgaaaaat atttgtgatt   62460
ttcgccatat actcttttac aagaccatat tgttttgtgg aaaaatccaa atctttctca   62520
atgatgtcaa cgtttttttc taaattggat accatatgtg tttcagttag atgattacaa   62580
aatttgccag ctagtctttt acgaatagac tttccttgat tgggcactaa agataattct   62640
```

```
tcataacatt ttaaacatgt agtagtttca gaaaaaactt ctggcttcat cactacgcaa    62700
acgccacaca aaattgttag aaattcaata atttgactgc aagcattaat gccatccagt    62760
ggtgaaatta agccaaaaat acaattcatc ttacataaaa gttttcaat  atcattgatc    62820 gtagaaatgt ctacagaaaa agtcaaataa ttattaagag ccaagtccaa ttttaagtgt    62880
tgcttgcatt cattgagttg aatatatttt tcaaatatt  tttgtttgtc attatctaat    62940
agaaattgat gaattgaagc atcgagtaat aagacttgat tatacatagc ttttaataaa    63000
atctgtaaat aaatggttac aggagatgca caattaaaat tttgatgaca gagttcagca    63060
aataatgtct taaacaaatg aattattaca acaccgtttt tcctgaaatt tgtcatatct    63120 ggataagtg  tgacagggtc acaaaatcgt aagcactcta attctaaagc acattcactt    63180
aaccttgaac acaagacaca caatgattgc aaagaattca ttttacaat  ctagctttt     63240 ttaaggaggg ttcctcattt tcatgctcag tctcttcaca ttttaatata ccaaaacctt    63300
gctcattacc ttctaccaaa agttctgaaa aatcatagat ggcagcacta tcttctactt    63360
gttcttcaaa aactgacaat aaagttgaaa gagaaaaatc atgtacattt aaatccgtta    63420
aatgctgaat cttgttcatt acggattttg ctagaggctc tctaccatcc acgtagaata    63480
acatatcatc catagtaggc ttactatctc tatctttcat cacttcagct aatatgagta    63540
gttctggatt tacagaattg gataaacttt caataatgtt gagcaccttt cctcgaatta    63600
cttccacatc ataaacaatg gcttctctct taactttctt cacaataatg tcacacagtt    63660
ttgtagcaat cacaaatttc tgacgcataa aacggaaatc ttgcaagccg gaggaaggag    63720
ggtttaaatt gcgatctaca ccacttccag ctatccaacc taactgacca aagtggaaat    63780
aatctctact agcaacactc acaaattttt cgatcattaa accaaaggta ataatagatc    63840
ttcctgtgaa aatgctccca aaatttggtt cttttgttaa tgatgcagtc ataggttctt    63900
taagtccatt ccctaccaac ttttttacgt gcatgacgta ttcctgcaca gaagaaaatg    63960
ttggatgttc tttaagaaaa actgggaata acatagggtt tgaggaact  agtttagaag    64020 ttaatgcatg caaacttgtt agataatctc tataaccaag aactgataat aatttattat    64080
gaaagtaata ctcgataaag gatagtaagc attctggttg aatatctaac aaatcaattt    64140
catcatatga attggtgaca cgaaaagtaa acttgatgaa agaacgcatg tcttcaacat    64200
tacctatatc tatggttttt ggcatgttat taagcaaaat acgctgccaa aattctaggc    64260
aggatatttt taaatttgga aagagccgtt catgatattt aaacagcaaa aatgataagc    64320
aaccagaaag tgggttcttt ttctgtttga ccttttgaa  aaaaggatta ttttgtgtgt    64380
ttttgtttgg cttattgaat ggtctatttt ttactcgaaa atctttcaaa cattgcatgg    64440
aaaggcgaca gagtttagct tggatagagg ttttagcata tttacccgat ttaaacaaat    64500
tgaaatcaat gtattgttcc atgtctacat ttgaagctat ttttacagtt ttcatattca    64560
aaaaaccttt tttaaaatga ctgttgtaaa atgctccgta gagagattgg tattgttgca    64620
ttaaccattt agaaattaag tttccagtac aaggcctatc tacaacatag cccgtaccga    64680
ttattaaagc caagttctgt aaaacaatta gtataacttt gtaatacgtg aaaacaaaga    64740
atggagaaaa agccaaagac agaggtgtcg tatcaatgtt gaaagattgt agacagtttt    64800
cgatttgttc tctggatgtc tgcgttttc  tcatttctga aatacatttt gaaactgctt    64860
cctcaatgca ttgaattaaa tcattaatca tattcacaaa atcatttga  cttttaaaat    64920 ttaaattgtc ttccccagtt attgcatcaa tcaaattatt tttcttacaa taatcgtgaa    64980
tcattcctaa gaatttgaat ctatctaagg aaggtgtggt ttgagcttct ttcattggat    65040
```

```
ctttgctttc attaactccc tttttcccaa aagaacctag aacatctaca tctgcataaa    65100
aacgagaaaa cattgtcata acaataggtt ctttttagt cgttttagaa atctgaggta     65160
atctgctgtt gattctgatc aatgctgttc cgatacacga atggcaacac ttaccttcac    65220
aaaactcaca gagattagag gaacaattta cgatgtggtt atatatttca gaatttccac    65280
agttcgtgtt ataaatagac attctgttca aattccatat tatatgcgat aagatttgtg    65340
gacatgtcgc acatgcgtaa gctagatgaa aagcggaaaa tttatcttct ttacaaggtg    65400
aagaattaca ctttatcaat tttctggcat cgttataaaa atcttcgtta agagatgaca    65460
aggaattaca aaactggatt gaacgcagta atgtttcttg agtgatcgca gagttaaaag    65520
cttgttttgt gttagatata taggccaatt tgttactgta aagtatcgaa ttcgcagcaa    65580
agactaaagc agctacatgg ctagatagat ggagcctcaa ttttttcagt tccacgattt    65640
tctcttcgtg ggtttcagcc gatttgatga tgggccactc tgaaaaattc atgatttgat    65700
tattttcata aatagaatca agatactctg ctgtgtaact gaaggttagt tccgtgatta    65760
cagcgtccac taacattaaa tgatcttttt caatcggtga tagttttga ccaggaatac     65820 cgtgatatgt tttattcggt gcaagcttga cagtttgttc agtatcttgg ataaattgtt    65880
tcagaccggc tttaatcaat tccagggtat tattaaatcg caaagtcatt ccccatgatg    65940
taaagattaa gtagaacaat acttcgctga tctgaggcgc ataaaagccg ttttcttgaa    66000
tgaattcagt gcaagtatcg atgcacaaag tttcttccga ttcaaacaag gtagccgaat    66060
ataacggaat ttttattgcc aagcattcac caacctggac ttgaatctgc tcttctacac    66120
atgggattaa taatccagca aataaaagtt ctttgaaacc attcccaaca actatatgac    66180
atagaacgtc atctgcattt cttccaacac tttcacagat cttcctata tccacaggct      66240 ttcgatttcc gttaacgaca aattcttgta gattgaattt ttctcttgtt tgtttgcaca    66300
atttatcaag atttccatgg tcttctgctt cttttaaaaa aacatctgta ccgtggaaaa    66360
agaagcatac aggcataaac gatgtgattt tggtaatgac tgttccgccg taattaataa    66420
tgggtgtttt aacggttggg aagaagtcat tttcaaccgt tagattaagt aacaagggtg    66480
agatcactac tgattttctt ttttccatta acgataatgt agtcagaatt tctattaatt    66540
tttgttcttt cggcagaatg tacagccatg ctgcggtaca tattgggcc gaaacaacag     66600 tttcattatc atcagccatt cttgaaacat gaagacccca gttctgcaa ggggtgtttc     66660 tgctaaacct tatatatttt agttgacgta acaaaactta gcgtcatcat acaacggaaa    66720
ttaagttttc tcgttctact gttttagtgc ggagaactaa aaacgatata ctgactcgga    66780
tttgatagtt tatgcaaatt agcgtccacc tcactcgtaa tagtatttat ttttcatggt    66840
ttttaaaata gaattgcagg caaggaggat caatgaaccc tcccacttcc gcaaagtaag    66900
caacgaccaa tcagaagttt gcattgcaag tatttaattt gttgcagcaa agcattagct    66960
agaggacagg cacagagatg ctacatattg ggaaattaat ccgaatcatc agaatcagtg    67020
tcattaatgt cggtctcaca agtttctaca tcttcataat ctaaatccag ttccatttca    67080
ttatcagagt tttcctctcc attgttttct ttaattttcg ctgatttcat agaagtatca    67140
ttttcaataa atacaaagcg agtttcatct tcctgtagag tcgtgtttgt ttcaaaatct    67200
atagaatcaa cttctttact ccagtctttt ttcagtctgt tttcgcgtag ctcatttgtt    67260
ttctgtcctt tattcgtttt atccgcagta aagaagctttt tacatttggc ttgcttttg    67320 gtttgtaaat tcaattggac ggtttgctta gattgctgtg aagcaaagct gcaagacgga    67380
gttgtagaac atgcaacatt aaagctgttg tactcttcag gcatgttagg atgcagacca    67440
```

```
aactccacaa attctttggg aagataggta cagaaatata agcttggttt ccaaggtgac   67500
atcatgcgtt ggattctagt ttgacaaccg atgtcatcac attgatgatt gttaaattgg   67560
tctccgacta atctggaaat catgccacat tgatattgtt cacttacacg atcttggtca   67620
aaatcgcgta tgaactgagg ttgtttagtt tgaagaatac gttcctttat ttgacgtaaa   67680
atccttgcaa aagttactat aaatgataaa gcttgctgtg ctggatattg aaaagatcca   67740
ggagtctgtt gctgtacttc atattccgtg ttaggcatat cacggtcata taccggtttt   67800
ccacaaagtt gtctgaaaat acggtattct atgtcaccat gtccattgtc attaaaaaca   67860
caacaaagtt ttgccatatt caacttgttg aagtattcaa acttcattat ggtaatagta   67920
tacataaaca gatcttgagg gtcaataggt aagttgtgca caaaatgata tttatagtaa   67980
atgcaagctt cctcaataat cgcaagagaa aatgctaacg atggagaatt cgtcaatgaa   68040
aaaactcggt ctccgagtat ctgttgatgt tgttctctat tgagggagtt taagcagttc   68100
ttatatcgta gtaacaagtc tgttgtcatt agttcttctt tttccaaata gatttttca   68160 tgattccggg gaaatcgatc tcgaatccta tgagctggat ctcgtgcttc accggaatac   68220
ttgcgtaaac caagggcttc cgcggtgtag ctagagccaa aaggtgctgt tggtaaattg   68280
gcgaaaaaag tcaatgcatg cgtctgtgca cgcttttctt cctgcttttc ttcaatgatg   68340
agtttcagct gttctagttc tctgagactc aaagcgtcta attttgattc atcaagctgc   68400
ttaataggaa tgatgcgtct gtgaaattgt ttcgtaaagc ggctgacata cttgttagca   68460
ggtttatgaa caagagttcg tttaatggtt ttcaaaccat atcgttgccg ccctaataca   68520 ttcttttta ccccgcgtgg atacatgttt ctgtcgaaaa tgagaacctt gttcataaac   68580
ggccttttat attattttg tctcgtgtag cggtgacgcc tctgtggttt ttaatataag   68640
gaacatttga catataaagc tagacacgaa ttaaggtgcg tctaaaattt tatttacaaa   68700
acacaaataa ataacataaa aatgtcacat attcaaagaa tctaaaacga cagatgaatg   68760
cacttgctta ctattagatt tacatttcgt agtaaaacat ttgctccata atattatcaa   68820
aatgcgattg ttatctacct taaattctaa gtacactaag acattttcac ggtttccctt   68880
atgattcctt gttaaacaac tgaaatcact tagttttccg ttttgcaatt tttttagttg   68940
tatatttttg tgatcaattt ttagaaaagt tacatgttga aattgtgtag ctgttcgtgc   69000
ttcacagtgt tggatgttct tttttaacat ttgtggccag gcaattgaac gagtaaaagt   69060
cattaacaaa tcatcacggg aaagacaact tgtttccgaa aaaccattga catgtaaata   69120
tttcaaacat aaagtctcca gtgaactttg ttttctgtga tacagttgct tagtcctaga   69180
atctataaaa gaaaactctg ttggacaggc cttatcaaaa atgctgtaga ttatctctgt   69240
aatggtttgg tctttagttc catgatgtaa aatattattg agatctagtt gcatgctaac   69300
gaaatcttga aaattctttt tcattttttc cgggacaata aaaataggct tcagacgacc   69360
atacaaaaat ctgttattct cttcgtcaac tttatacatg aaacctaacc gtaaacaacg   69420
tcccgtatta tagattcctg tatcaaaaca ttcaccagga aaaattaccg agttaagaat   69480
ctgcattaaa tcgtggttta gacacattaa atgattgaat attttagaaa gttgttttaa   69540
tggctcactt ccaattattg cagtaccttg agggattgga atagcaattc gaagaccaat   69600 ttttttttg caaacacaaa aagctgtttc aacttcattg taacatacat tgtggttcag   69660
gggattctcc ggattactac aggtagtttt gaaaaaaaag atggggtagg cgtctttgtc   69720
aataaacgga atatttttt gccatgcatt gatcagcaca ttccgcatca atttacacat   69780
agagaaaaat aacgattccg ttattatagc tgaatcctgt aatggcagat ctaaatcacc   69840
```

```
aatataattt gtaaccggaa ggtattcatt aaagatttca tgcctggtta cgtaaaactg   69900
tttttctatt tcgtcgctta aaaggtcgt gtcctgcaac caaaatgtac ttgttaaaga   69960
ttcatccgaa atgtactcat tgggtaaaaa ttgcataacc tggtcgaaac ccatattttt   70020
gtaccaactt tctgcacttc caaaacaata aagattttg taagacattt gaactctaaa   70080
cataggaatg gggttgctga attggtcatg tagatattgt ctccttgtaa caggtttacc   70140
atctatcaaa atagatttat tagatgccaa aattttaaa aatccttgta agcctaattt   70200
aattggtgta aaataccctt caccgtgttt attgcatttg ttaaccatct ttgaaatttg   70260
gtctgaattt attacaagca tgatatttct attactgttt atgtcataaa cgtactgttg   70320
catttgaaat ttgttgttta acatcctttt tatttctaca taattttgaa ataactgtc   70380 ttcgttaaag tactgtttca tgattgaaat gagatccgag tgtaaagaat ttcctaggat   70440
gtacatattt tcctgacatt gagaagtatc agatctggta ggatcataag atgtcagttg   70500
actatacttg atgaatttat ttttttctaa tgctgtactg taagcaatgt agatatagtg   70560
gactcgaaaa ctgtttgtga gatgcacgct gtttctaaaa atatctattt gcttatcaag   70620
ataaagaaat tcttttcgat ctcttatgtt ttttgtttt gcatattcag aaaaactaac   70680
aaattttttc cgatagttag atttcaaagt aatattaatg aattcagaca tggaggaata   70740
agtaaatacc atatctccta atttatcagt gaaacactga acataattct tagttgttgc   70800
tatggtgctt ttctgctctt caaataaata ataatacatc gttaatagta gcattccttc   70860
tgtttgaccg tatgttgata aaaccaaaa cggtgacgtg ggtaagagat acttatttgt   70920
tagatgttta atgattatag tcttgcaaaa aaagactaag cttttaaatt ctatattttc   70980
acttccttct ggaacatgag aaagtaaaaa atctttatac agattttctg tttcttccgt   71040
atttaaacag tgaataatat cctcagactt aatgggtaat gcatttttta cataatagct   71100
gaaattcaaa gattctgcgt cgcaaacaaa taccgtctca attcttttgg aaaacttgca   71160
tttctgtgtc tgcatacaaa aatatacatt ttttgatggt ttatatttaa cgattattgg   71220
aaaaattaaa tgttcactag ggttcttaca taagatattt actatcacgt gcgcggggtc   71280
atattccgtt gcaaacacag taatagtcat tgtgaatgtc tttcagttta tcttccaaca   71340
gcttttaata taagcaaata ggaatcatgg gaaattgctt tgtaaaaaaa atctcttctg   71400
acatcttcaa ctctaactac cagatgctct attctgagct ctcagagcaa gaggatttac   71460
tggatttttt agagacaaaa tatacagatt ttggaatttt aaaaaccgat attctcaact   71520
atgaaagaga ctccgaaaca ttcaaaactt tgttgcaagt gttacctatc tataaaaaaa   71580
caaagctgag gtataatttg attgaacgct gtttaaataa ttgtcccct cacgttaaag   71640 atgcattgat tattgaaatc atgaaagcta agaaaatttt agagactctg gatgttgtgt   71700
tcatgaaaat tatgattgga gaatttacaa tttgcagtga caatgtgaat caattgctca   71760
ataaattttc aatagaccaa acaacattat gtgacatgga aaaataaat actttaattg   71820 acttagacga agaaaatagc aagcgtcttt tgacagagat cgatcctttg ttacatcaag   71880
aaacaggcct gtatcaagcg ctgcctaatg cagttacgga tccaccaagc gaacagagag   71940
ccgcaactaa aaaatgttac gaaggattta ccaaataaaa ttttattccg tgctgtactg   72000
aaaccaaagc atcgatgttt tatctaacac tgcaagctga ttcaacactc gattaggtaa   72060 tagcttttaaa ataaaatgac cgcatgtgaa aatgatggtt gcaatacaaa ttcctgcttg   72120
cacaaagatc ctctgagaag tgggattaaa aatctttaca cttggagttg tgttctttaa   72180
ccagatatta gtttcaacca ctaatccatg acagagaatt tctttgtttg ctattattaa   72240
```

```
agctttcaat tcatcaggac aatcaaacat gtaatcaaaa ttttggattg tgtaattatt     72300
ggattctaca tagaaatctt tattggtaat tagtgaaaac ttgataaaat ttggagaagg     72360
aaaattataa gtttcccagg gttccggtat atagcatgga aggatgttaa tcactaattc     72420
tatatcacca ggtaacaaca ttactgattc acttgacagg tttattaaag aaatggagat     72480
aacgttttct gttgtgatga gttctgttac acattcgcag agagtgtcgt taactgttcc     72540
agtcaaaatc ccaaaaagtc cgtcgggaat gtttaatgac acgtttaaat taaaaatgcg     72600
tacttgttca caaggcaccc atataagttc tctatttacg agtacaattt tatttgtatt     72660
tagaattaca tccatccgac ttttctcaaa atgatttatt aaaattggaa gttcgtttac     72720
tcgaggaaca ttttcaaaac caaatctgct agatctgttt cttggaaagg tgagatattt     72780
cttttcattg tccatatgtt ctgcaaagaa ctcatcgtaa atttttttcac aggatttgaa     72840 taaaccgttt tgaggaattc caagtaaaga aaatggtcgt tgataaaccg tcaattcagt     72900
gttcacatat tcatttaatt gctttgcatc gatttaggc catgtaagag agctctcttt     72960
tgtttcgcta aagttccaga tatcatccac atccgttaca gtaaacagga aaaagtgcaa     73020
gtatctggac ataggcaatt tgttaagtgt aattgtttca gagatttttt cagaaattat     73080
tttcttgttt gtttcagatc ttctggaggg tagactttgc attttcgttg aagccttcgg     73140
atgattagga aaaatgactc tatacaagat tgtttccaag ccaattatat tgctggcatt     73200 ttttttttacc cgagttgttt tcacaaatga agtcgacggg gaggagctgt tttataagcc     73260
tacttgtcat tcagatacat atgaaattat tttaaaaaaa ttttcttcta tttggatatt     73320
ggtcaacaca tttatttttat tatgttcatt ttcattattt ttaaagtatt ggtgttttaa     73380
gactctcgcc aaagaaactg taaagggta ttaaatctat atgaagaatg tatgaaaatg     73440
ccctcagaac tgttttaatg tattttttctc catgcatatt tgaacataaa tattctaagc     73500
caaatatttt tctcgtgatt agtctgcgtt acttctgtca ccacactcat attttttcatg     73560 gtatttgtta gaatatctgt ggcttttgct ttccatcatc acgtcatgct gtatgttgaa     73620
gttgaacaat ggtgtgtctg tggttgaatt tgttacgaac gcttaataga aattattgta     73680
catttttcta ttagtatgag tgctatgaaa atttcctaca aaagttctgt tttgagtgtt     73740
aattaaagtt gcattgaaaa gaatggcggt tgtactgtaa tttctcaaat caaagtttta     73800
aagtatgctt tgtcacggag atactctaca ctacgaagtt ataagtccgt gttttgctga     73860
tttatgtgct tgtgttacta tggtttgtcg tgaaaaggt cgtaggaaat gatgaagtct     73920
gttgtgaagc ttgcatgctt gaggtgcctc gagtagatgg aaaaaatttt gttggttcgg     73980
aagtaacagc gttcggaatt gctgtaggct tagtaacttt ggtcttattt tctaagaaca     74040
tcaagttccc cttaaaactt tgtattggtg acatgattcc ccttaccaag agaagttgg     74100 taacaccaaa tggtgttgac acattccgcg tgttcacaga attatagaaa aattttgaaa     74160
tagaattctt gcaatctgtt cgattgtaaa caaagtagta aataaaattc gtaaagaaa     74220 aagttgctc agaattttcg cgtgaaaata attgagcttc agtatggttt tggagatctt     74280
ggaaaatggt ttcaatcttg ttttggctaa agttaatttt aaacaaatgt gaagcaagta     74340
cttcaaacgg tattttattg acacaagagt catccatcgt tttgaatgct agtgtagcaa     74400
aaactaaata caaaaaggaa atattatcta agtaaacgtg acgttttctg tttgttttag     74460
tgggaaattc aaaatgtaat gtccatcgcg gaaaattatc tagatagagc atatttattt     74520
tagaaaggca atattctttt tctgggata gacggaatga ccaaaataaa atctgtttaa     74580
aacagttctt agagatgggt atgtcgcaac tctgaatata tgttttttca aaagactcat     74640
```

```
aatgaaattt tgcgaatttc ggccacatgg aaaaattcgt taaatttaca aacgagattt   74700
tttcagagca aacacttaat acaggagtcc atatgatcag ataactataa aaaagaaaag   74760
aaatcaacgt gaacactagc attgaataca ttttgttttt cataaatgtg aattatttag   74820
gaactgtaaa tatcctaaaa tagttattca ttttttttaac caggatcatg attgcaaaat   74880
gtaccttgtg ttggacagta tttgttcacg cgctaatcat tttaatgata cttttattaa   74940
ttcttcgttc tctaattgga tttaacaacg atctttggtc gcaatcacaa ctagctttta   75000
cttgtctgaa taaagttta tctcatgttc cagcataata tcaaaacaat ctaaatacat   75060
gataaatacc aaacaaaact ataattatga taattaaata cagaagaact aacatgattg   75120
aaacttgact tgattttaga tctaatgcgg taatttcgaa aacagagcca tttcttaaaa   75180
acaataaata atgtgttcgt ggattcacat cgataaaatt tgtgtccgga tctattaatt   75240
ttaatagttg cttgtcatcc attatgtata caaattggat aattccgtct atgtcgtcat   75300
attccacaac caagctttca caaacacac aatcgtggga tgaaatatta tagattggtt   75360
ttatattttt caccgaatat ttataattag taggtgtgca ggtagagttt aagggaacaa   75420
cagtgataat aattgtagtg cttatgacag tactcgtgac actgaaacta gtaccggcta   75480
aaatatattt tgaagagatg gtgtaagtaa tatttggtaa tgtgaggaag gcagcttgtt   75540
catttgaaac acaggaaatg cttttaaaca tatctaatct cttttttcta tatacagaaa   75600
gtgtgttcat caccttgttt gtgtatgcgt ctaggttttt ataggataaa atgttgttga   75660
caactctttg agttaaatct ttgcgcgtgg ctgttgcaca aggagaaaac atcgtttcaa   75720
tgtccatgac attatcaagc atatgtgtcc aaaaatacat ttccaaagga ttgcacagac   75780
ttgcgagcaa aacatgaatc tttcgcttga tcttttcttg gaagactaga ctgtttccaa   75840
tttctgagag taaaaacaaa tttgcacgtt ccggttgggt taaatttgta aacaatttat   75900
gtttttcata taatgtttca atattgtttt ctatttcttt ccatttgttt tgtggaactg   75960
taacgattct tccatctgct aaagataaaa atgctagctt agcagagata ggaattgtca   76020
gatcagatgt aatataagaa taatctacta actggaaatt ctgaagtttt tccatctcag   76080
gatataataa atgactctta gtcatttga agcacttttc taaaaaccta cccatcgtaa   76140
tgatgctttg gtgagtatta aggatttcca acagagggag gagtccatct cctcgagtac   76200
tatatagaaa atgagttaag ccgaataaaa acattaaatg gaatgtgtct tgttaactg   76260 gttttccgca aaatccctcc atgatataaa cagttgctaa cttattgaat ttggctatta   76320
aaaacgagat gtcataattt tgtttccaaa tatcatccag aaagtctatt ttgagaaacg   76380
gataaaatct ttcaattgtt gttttttttg taattaacag gagatcgtct gagacagtct   76440
gtctatatat gaatgaactt tttcgaaaag gtgctttaaa aaaaatacga ctaacatttc   76500
caaagataaa aacgacatca tccattcctg tttccactga aattataaaa aacgatggtg   76560
tcaaagctag catgaacaca gtatttaagt aattataatg tctcataaca catctttctg   76620
ttattgggaa tagataatca gtcaagccat ttgaaagtgt gcaaatgtat tggttgtaat   76680
agagtttgcg aatttccgaa acatttgcaa agtagacatc cttttcataa aataaaggta   76740
ataaagacac tgtaatcgtt tttgtatgcg aaacaggttt gatatttgtc tgaaattttt   76800
gtgcatagat tttcacagct ttctctgttg atgggttaaa aaaacgtgta atccgatgtt   76860
tatattgatc aaatgattca tcgaaattca cagaatcaaa taaattcgag acaaaagtat   76920
atccgaataa gcatttggga atctgataaa cccgagtttc gttataatca tggaaattaa   76980
acgttattaa accaggttga ataatagttt gatttgtttt ttcatttacg caaattgaag   77040
```

```
aattgagtat attccagtgt ttccatccat ttattgacac gatgagaagt agactattta   77100
tgtaaaaata cattttctcc aatttagagc ctggaagata aacgggaagt ttgttgtagg   77160
ctacgcctta actttacata ttaaatacat aacgggatag gaatcataga gatattttgg   77220
gtaatatgtc tttagaatac ttgcccctg ttagaagacg tattggtcaa tataatcatt    77280
tgagaatcta caaaaaaatt ctgttgttaa aatccaattt tgaaaaatta aattttttt    77340
tgggcaatct ttttccagaa gaactgcatg attcaaaaat acatgtatat tttgaagtta   77400
gattagggtg ccgtattccg gattgcatta ttgttttag gcattttggt gagaaattat    77460
taaaaacttt ccattgttat tttttgaat tcaaaactac ttttgccaaa tcaaatctgt    77520
tttcaattca aaaaatagg acacaaaaaa ttcaatattt acagggacta aggcaactac    77580
gacaagcaac agattatcta cagcaatttg tcatcaaaaa tgaaagctta tgtaaggtaa   77640
accctgtaat ctgctttttt agacagcatg gtttaaaatt ggactttgtg aaaactttca   77700
tagctaaaga attgcaactg tcttccacgt ttctttgcaa ccttttacg aaatatcaaa    77760
atgacacagt taagtctatt ttatcaattt ccaatccaac caatttcga agggcatgtc    77820
agaaatactc taatttgtac cgaggaagat atgcaacaac tccaaaactt gggaattcga   77880
aaacttcgaa aagaaaaaga agaaattcaa aaaaacaaga ttttaaaaaa cttgttaaaa   77940
actgaacttg atgttttgca agcacatgta cagacagaat gccagaaatt aaatacaaat   78000
ttaagagaca ttgaaaatgc attgctttta gaaaatcaaa aaataattcc ttctagtgaa   78060
acacgttctg tcttggaaga gtctctccag gctaaaactg tcacgcaagt cacaattaca   78120
caaattgatc ctgctattca tttcacggaa aatttccgac ctgagatgat aaaaactttt   78180
tataataata ctcagatgtg gagctatacg tttggagctt ggttttacaa attaaagcga   78240
gctttcttta ccgattctaa attaaaaaga atgctaaagt taacatatgt tgattctctc   78300
tctattacac aggaattgct gtctatttca attaatgcat tggaacaaat tactatttat   78360
cctatgcatg ataatttagt gtccgattta gaagctggtt tgtgtctact gactgctttt   78420
tttgcatcgt atcctggaac tttcttaacc gaaaatatta aattcgtgga tgtcattcaa   78480
aatttgtctc aaattttag atatctaaac accgaaattt tagctacgaa aaacgcgtca   78540
ccacaggatt tttattttgg attcaatgat ccagacaaaa tgaaatattt tattccgttg   78600
tgtaaaggga ggcattatgc aataaataca ttcagtaatc atatcttaat taaaattttt   78660
ataaaaaaag gtgtgataaa gcaagttccc ggagatcaaa tgtcgaaagg acatgttgta   78720
atagaatcga agttgacagg cacgttaaca gatgataaat tattatattg gactcaaatt   78780
ttattgcaac cgaaattggg aaaagaggtg ccgatatttg tccatcagca gcagtatttg   78840
cgttctggaa ttgttgccat agaatcctta tatttacttt ggcaaatttt aaactcagaa   78900
agcattttg gaaagagaac tgggaaattt tatctaacga caattttccc ccatgtaaat   78960
gcagaagatg ttacagaaac agaatttttct tctgtcaata tccagaattt tgagtttctc   79020
atgaaaaact atgtcgtccc cacatattta gccaataatg aaagtactat ttccacttta   79080
tttccggggt taatcagcat tgtagttaac gaaagtgttc gtttaggctg ggatcataat   79140
caaaatactt tgacacaaac taatgctttg catagccaaa caaaagacaa tccgtttgtt   79200
gaatatatcc gttcacaatt agaagaaacg gcagaacttg cggtactcga gaaacatgat   79260
aaaattcttt ttcatttga aaatggcttg aatgtgacac tctctttagc acttccacga   79320
cataggttgt tcgctatggc atcctcatta tttaatgtgg ctgatttgta tgatttcttg   79380
tatttttgg tattaggttt tattccagta gcaactgtta tttgaagacc aggtgacgtc   79440
```

```
tagacatttg ttttggatat aaatacgcgt ggaagtgtta aggagcttca ttttaaaaaa    79500 gacaccttc  ttaagctttt gtaaacatga aaaatatcga tttaacaaat tggaaattac    79560
tggcagaaat atatgaatat ctgttttttt tctcgttttt ctttctttgt ctgctggtaa    79620
taatagtggt gaaatttaat aacagcaccg ttggtcgaga atacacattt agtacttttt    79680
ctggaatgtt ggtttatatt ttattgttac cggttaaaat gggaatgtta accaaaatgt    79740
gggatgtatc caccgattac tgtataatct taatgtttct gagtgatttt tcatttatct    79800
tttcgtcctg ggcgttaacg ctgttggcac tggaacgtat caacaatttt tcttttttctg   79860 agattaaggt aaacgaaact aaaattctaa aacaaatgtc tttcccaatt atctgggtta    79920
cttccatctt tcaagctgta caaatttcaa tgaaatataa gaaatcgcaa atgaatttag    79980
aagatgatta ctgtttattg gctattgaac gctctgcaga agaagcctgg atcttattaa    80040
tgtataccgt tgtcatccca actttcattg tttttttcta cgtgttaaat aagcgatttc    80100 tcttttaga  aagagacctg aactcaattg ttacacattt aagcttgttt ttattttttg    80160 gtgcttatg  cttttttccct gcttcggtgc ttaacgaatt caactgcaat cgattgtttt   80220
acggtctgca tgaattgctc attgtttgtt tagagctaaa aattttttat gttcccacta    80280
tgacatatat aataagctgt gagaattata ggctagctgc caaagctttt ttttgtaaat    80340
gttttaaacc ttgtttcttg atgccttcgt taagaaaatt gcaacaacct acaaaatcta    80400
cacagtttta aaattgtaga ggtccaatag aaaacaaatc tgataaatta cactctgtta    80460
cttttgcttc tttctccact atgccacaaa aaactttgaa atcattctga ataaaagtaa    80520
ataatccatt cctgtgttct ggtttctgtt gactaaaagc accgtgagaa attttgatct    80580
tgtcaaaaaa aattaaataa ccaaaccaca gatgcttaca aattttttcgg ataaaaggtt   80640 catatacttc ttgcccccag aacttgttga aatagcgaca taattttaat aaacggtgat    80700
tgtagatggc accaatagaa acattatat  tcccatcgtg aataatttca gctggaattg    80760
taattgaaag accaaattca tccaaaaaga aactttctat gatttgttta acaattccag    80820
tatgatgtaa ttttttcgag agctgagctg cattttcttc actgaagata tgtttaagga    80880
tttctgatcc agatctttgt ttaatcatgc aaaagatctt aaaccaaaat tcatcaggta    80940
cctttcgatt cagaaccact aaatcactca ctccgatatt gtgcaaagtc tctctcaaca    81000
gtaagatttg gatgccgtga gaaaacatta gggtacacac attctggatg atcaaaatct    81060
cttcttgttt tagattaagt aaagattcac cgcttaccaa tttcttagtg atatgtaata    81120
ttaaattgga ggttgagttg ttcgagatta tgtattgacc tacttgtgtc atcgtaataa    81180
tggaaactgt gctagtggca ggcttcctat gtgtgtatga tgataatgat ataaatgata    81240
acttttatct gccaaggagg acgatacaag aagaaatcaa ttccggaaat ggtttgaata    81300
ttccattgaa tataaaccac aatgaaaatg ccgttatagg cacagtctct tctttaagtg    81360
atttacagca cggtttgttc acggttgccc gtgttcaatc aaaggaattc cttacaataa    81420
ttaagaaaat agctgtaaaa tctaagctga taaccaacac ggaagaaaaa actctgccac    81480
cagatcccga aatagagtgt ttaaattcaa ttttcccagg tttgtcatta tcgaacaggg    81540
ttggtggcaa tgaacgtgat ccgttttta  aacatgtctc tatctgtggc gttggtcgtc    81600
gacctggaac aatagctatt tttggacgaa atttaaattg gattctggat agattttctt    81660
ctattacaga agcggaaaaa gaaaagattc tgagcacaga tcaaagctgt gttcagtttt    81720
ttgccgagga acaatttaaa gtggatttat atgatctgct agcggatagt ttagacactt    81780
cgtacataaa agtacgtttt ccaaaattac agtctgataa gcaacttagt ggaatttcaa    81840
```

```
aatctactta tattaaagcg agtgaaaatt taacggctaa caaccatact attaacgtga   81900
attcaaaagt cacaaaggag acagaagcaa cagacagcgt ttcacaagat gattgcgcag   81960
tccatgcacc agatttgata agtacgattt gctcgacaac gcacacaacg catcacgacc   82020
tagtcagaat gaatggctca gctactggca actcagctag tcttcccgct cctcagtttt   82080
ccgaatgtgt tttttaccg aaagatacat tttgctcctt actgaatgct acagctgggg    82140
cccaaaataa aaacgtaacg ccagctgctc cgatatttaa aactgatgaa tatataactc   82200
cgtacccaga atctctgagc agaatggatt atggaaatag aatgaattat cacataccac   82260
ctccatattg gtatccctct atgcctggat ttaattataa atcttatcgt ggttcccaaa   82320
aacggtgcgc tccaacagat tcggatgatg aaatgagctt tccaggagat cctgactata   82380
cgacaaagaa aaagaagcgg tatagagaag atgacgatcg tgaactcact aaagacaaaa   82440
atgatattaa agaactagtt gatgcaatag ggatgctgcg tcatgaaatt tcagcgctaa   82500
agtatattcg gtctcagtct cctcagagac agcattgtac agcggtagat acaatgccaa   82560
cgattgaaga aaaaacgtg gcatcaccta aaccatcggt tgtaaatgcc tcgctaactc     82620
caggtcaaga caggaatcaa aatttgatgc aaagtgatca atctttattg agtttgaaca   82680
aaaaattgtt tgtagaagct ttgaataaaa tggacaattg aatacaaatt atgcgttaat   82740
gtctctgtct gttcccactg ggacaaggaa ccgtttgcag cccaatgttg ccttctaaaa   82800
cagttaatgt gtgtggtaag gcagtgattg gtagaaatgt gcgaaggttg tctgttctca   82860
tgcgatatct gactggtaca aggtgttcct tagctatgtt taaatgaaga gaatttagat   82920
taatagatac gttagttgca gctgtgatat ttggtactgt agatagtaca ggactatcag   82980
cgacaggtgt tgtttccgat ctaaagacac ttatttgatt attttgattg gaaatcaaaa   83040
ttctgcttgt ctctgtccag ccaaaatcta tatttgattg atcgtgtgtt actatttgac   83100
tgggtaggaa aataagtttt cccagttcct gagaataatc aatacggcag ttttttttgt   83160
aggctctcat ggttacttga agatgagttc tctctttcca agtgaaagtg tttaatgaaa   83220
tcccgtttat taatctcgga ataaaaagtc ctgcaaattt ctgtttagaa tcaaaaaatg   83280
ttggaaatgt acatgagaag gggtcagtgg tattcgaatt aatgttttt gtagaaccta     83340 cggttatgca tgtgccatcg tacgtcatta caggttcttg atttctttcc atcacaatgt   83400
gaggaatggt ttggataaaa tttacttgga aaaagatgtc gctaggaaaa ttatcaggat   83460
ttaaaagata attgttttca taagatgctc ttataacaag gatttttca tgcagcatta     83520 tttgcttaaa ataaacattt ctgctggata taaattccac ttttgcactg ttaaaaattt   83580
gatctggtgg agttgtttgt aaatctatcc aaaattcaca cgcgtacatg taatgcgttg   83640
gttcttcgtg ttgtaattct gtccagcgta ttctcttaat atgggctctt aatttagttt   83700
gagatccata aagaataaat tgagcacggc actctccatg tggaatgtaa ttgtgctcca   83760
tgcgctcaac tatttggaca ggaagtgata ccaaattaat gctaggaaga aaaaggcaa     83820 aaagattaat aattaaagga aattgtttta aatctaaatc tacatcagat atattttgaa   83880
cagccaaggt tacattgcca caatctctta gatcgtata cgtaaagtag gctgctgtaa     83940
agcttccttc atctctgcac atacacacaa atgttgattg ttgcgaaagt atgcttagcc   84000
ctgtccttaa gcatcttatt tcacgaggtt ttaaaaggat tggtgctgtc aattttagtt   84060
gtagaaaata tgaagaccag accacataac aggattccat tcttacttta aatcttttat   84120
tgttgtaaaa tacttaaaata gttgatatta caattgcata cgtttgaagc ggggtgttat   84180
gttcatagag ttatgtctaa tgttttctgt ctcttgtatt tgttcgtagg gaaagtctgt   84240
```

```
catgggatga actgtcaaaa ttgggagaga gtctgaaaaa aaatcgttcc ctaaaaagtt    84300
aattcgaaat gaattgaaag cggcttcaac ttttgatttg caatctgcgt gtgctgtagg    84360
atggaaagaa tgtggaaatt gttctctact gataaagtag acatgaccaa ttatatcatg    84420
ctccgttaca aatgtctcat ttcggcagta cacgtaaatt ctaaaagtct cacgcggttg    84480
ccaaatgaaa ggaaatgaga gtacattaga tttctttgga atgaatagcc ctacagcagc    84540
aggattctca aaggttcctc gtaaattgat ttgtgtgatg tgattaggtg tcagtgtcat    84600
tctttcaggg aaataaattt ccattgtttt gaattcttca gaaatattga aatacggcat    84660
gcaaatgtta agtgcaactg attgcatatt tggtttagaa aatcttaagc gtaaagaaca    84720
ctcatccaca cagaaacgtg aattcattac tttaagatac cgtagaaaga caaataacac    84780
cggtgatcga tattcaatct tgtacaccga aacattgtgt tctgatatca tttccacgtt    84840
gcagattggc gttgcgctcg cgaaaaaaac attccaatat ttgcagtatg ttgtattgaa    84900
ggtgaagatg cagtacatgg tttccagtct ttgatcattg gagtttttca gtaaaggttg    84960
aaattcattc ttttcccaag taattttagt tactgtggca tttacgatca gatcaccatt    85020
tttcacagaa tataaaatta taggagttgt tcctaaaccc ttttcaagat aggcaaattg    85080
atgaaatcta agaggatcca tattttcttt aaagtaacaa ttatcttgta tcagcaggga    85140
tgacgtaatg ttaaaaattg gcagggcaaa aatattgaca aagtttatcg attgtatcat    85200
aggaaaaaca ttaattttga tcactttttt gttttttaga acgtgaccca ccaaagttac    85260
gcattctgca ttgttttcag ttccatcggt aattagcaac agtacaggtc tttcgtgcga    85320
aagtatgcag gtaatctctg cgggagaaaa attgagttct ggctgcaaat cattaaaatc    85380
cacagtaaac tgaattaatt gcgataattc agagactggt gttgaattca tttttacaaa    85440
gaaaactaga atatacaaat gattcttaat tgttttcaca cgttttatag aatctagcaa    85500
gcttctaagg cttttttaaaa ccgcaatcta ctttttgaag gggcgtggtt atttatattt    85560
gatccagatt gcaattttt tttacgagcg ctccaacctt ttcttaagat taaatctggc    85620
aaatcagaga taaaaatttt gtctgctaaa aagtacagtg cgtcagattc tggatcttct    85680
gagttaagct caatttcagc agcaaaacta tccgtatagt tgggatcaaa tttagttcgt    85740
aaaatatgcg ttgggataaa ataaatgctg cctattatgt catttgtagt cactctctgc    85800
gatctatcac tagtcacttt tgtggtaaaa cttgtagtgg gagaccagaa agaagcaata    85860
gactgcactt tggaatttgg gtctggaacg tagagagcat tagcattaaa attataaaaa    85920 gtgccttaa aatgaagttt tttagtttcg ccctcatcga aaagcatcgt gtcttggaaa    85980 aaacgtcaa ttttttctttt atcgctacag attttaaagt aatgcatatg cacagttaga    86040
gaaatttcgt ttgggattat ttcgttgaca aaccaagtt taagcatgca atcgtttgga    86100
accatatacg tgttatttt agttacctct gtataacatc gaagatagat ttcgagtaga    86160
ggaggagaaa agatcatttt aagtacggaa actgttgggt ctgaaataga aaacactttg    86220
cacgttggaa aatctgaacc actccgaaca tcgtgaaacc aaaaaggtaa attgtttatg    86280
ttaacagagc agactgtaca tagagttgtt aatggatggc caggtgttct ttcaatcgaa    86340
cgttgataag tacttagttt ccattcaatg ttaaacatcg tgacggttat ttcgtttact    86400
ttatgtgggg tttgcgtcac tatgaccttt tcgttttga atcttatcag actaggaaaa    86460
actcccatct gctcttgttc tttaacatca tggtttggga tgatgacgat agagctgtta    86520
atttttaaca acgaaaatcc aaaaaacaag acttttgatg gataaatgtg tctattcaga    86580 tttttttaaat gtagttttag ttgttgttct tccattaaag gacgagcaga aaaaaaggag    86640
```

```
tcagaattcc ttgaatttat ttcagcgctc aaaagtaaaa ctggttcagt ttttgattgg    86700
acatactcgt caaataataa tgtaacatta tcttacccct ggaattcttc tttgtatgga    86760
atttcaatct gaacatattt taagatatca gaagttgcga gagacatgga gctgaaataa    86820
aatctgttac aacagacact atttcaaaga acttttattt cactctttaa atatacaagt    86880
tgccagccta ttgtcagcag aaacatcagc cacaatgaaa aacgttttt cttgtgtaag     86940 ggaattgatt tggttaatca tggtgaaaac cgttttaatt ttctgtaatt ctgttttaat    87000
ttcagtggcc ttgaaagaac taggttcttg agaaaaattt tttttgcta ggagttcttg     87060 acatttaatc aataacatag actgatcttc taaagataat cttctatat atgtttgaac     87120 tatatcagga gccatggtgg caatcataga aaagaaatg catgctgttt tcatggaaaa     87180
cgtggactta caatcattga taacatctgg taacttaatt gttacatctc tgtactgcaa    87240
agtgcgcagc tcatctataa ttatttgaac ttcttcatat tttctatgta tggaaaggag    87300
gctgatgcaa agcattcgca cgtttatttc cgttgcgacg tctgtaggga tcagtaatgg    87360
cagaatcagc tcccagttag gtaagacaag taattgttgc gaaggcttca gaaatggtgg    87420
cagtaaactc aattgatctc ccttttccag aggaaatggt ccggtatttt tgatttcata    87480
ctggtgtcca atttttggac gtattaatat taattggttt ccttctactt tttgtaagat    87540
tgttaacacc attgttttta agatatccct tatttgaata taatcggtgg ttgtagataa    87600
gaccgtgtaa agtcctaaat ttgtgttgcc aattaaatga cggtgcgacg gtattgggat    87660
gacggcatta gtgagtttgc ataaagttcc aatgtcagaa agagtaagct ttgatcaaa     87720 agtacagtag attgaatcca tttctatagc agggactcaa taatattttg taacggaata    87780
cactccccta tagcgaaatt tgcaaaatgc gtttcactta actgtgtcat tccgttctta    87840
gatcgactct ctaatagagc ttggttagag gagcaatgga ttggaaacgc aatttgtaaa    87900
aactgacaag gacgatgagt gacatcgtct gttccttcgg aacaagaata ctgaatatca    87960
gtgtcgctgt ccaggcatgt tttagtttt atggaataat cactgataag tttaaacata     88020
aacttatttg tcttaaatat ttcagtgtct gtgaaaaaga ctgcgttagg actgtaactt    88080
tttggattat atcctaattg atctctgtga tttatattat ataagacatc agataaagat    88140
ccttcttgag atgcccaagg atttgttgtt gccacaaaag cgtcgctatc aactcgagaa    88200
tgatcataca aagattttct agcttctgac tcattatggg gatcgacacc catcatacac    88260
gaagcccttc ctctaggatt tttaggtgtt ttatagaaat taatatcgga agtcactgga    88320
gtaatgacaa cctcgcagat tgcttgttgg ccatgtaaaa gtattgattg tgattgctta    88380
tttatcttac cgaaagaaag gatgtttaaa gcatcggttt cggaaggatt gggtttttca    88440
atgccaacgt gatgcctaac ccaactattt acagtagggt tggtgtatgc gtgcattgga    88500
aagaccgaaa atagatcttg cactttactt cccatatcag ttttaccct tttcaaattt     88560 gcgattgcag tgctggaact aaatcctaat cccatatcaa gaaaacttat atgctgcgta    88620
aggttatatg tggttgagat gtcttttact tctgtagata ccgttgggtc atcaatcatt    88680
atggatgttg cagatttgga gctatacagt aagcaattaa tgtcgaaaca atctgttctt    88740
actaaagtcg cagcgaaacc aggatgaatt ttttgtctgc tttgaagaat gatagctatt    88800
ggagacaatt tgcaatgcat agtagctaaa gtcatgatac ttagcaatga atttgaacaa    88860
caagaagcat agacaaagaa cggtgttctt tgccaattat ggaattcatg agataatgct    88920
tgtggtagag gaaaaccacc gtcatttctt tgatagtggg gaaatatgtt tagataggtt    88980
tgtacttcaa tattcattaa gccacaaata atagggtctg agaaaaaacg attaaaagga    89040
```

```
attggcttga aataccgttt caacacatta attggtgata ctaaacacag tccattatat    89100
aaaacatgtt gtagagattt gaagtttgaa gaactaccat gtctttgaga aggatctaaa    89160
gaagattcaa tttccaaaat ttttgtattc tccgttaggt ataatataga tttaaagagt    89220
tgtttaccaa tgcaagataa atctgtgagt gcatgtgagg gaccaacagc ttcagttatc    89280
aattcaatca atacattgtt cgtaatcggt aattcgcaaa agttgtcatc aggtaatata    89340
aagggttctg tgtagaagaa atctagaatg aaagatttca catcaaaacc tgcaccacac    89400
atcttgttat ttgtcagtgc tggtagaaag cagaaataaa aaattttgct taaaacaatc    89460
gtttcaaaag atggtctatc tacgtctgtg aatatttctg ttgaatccaa taaattcatt    89520
ctattcaggt cagatacttc atagtttctt aatttcactg tattttgggt aaggggagtg    89580
ttaccagctg tgattattgc atttgcttca ttttttggaa gactgtttag aaatggaggg    89640
aatagacgat tatcaaacaa agcgttcaca aatccaacca atggttcccc acacagttgc    89700
tcattaaagt ttgaaataga aattgtcctt ttcactaatt ttaagattga aattatattt    89760
ttgtaatgtg tataagcaat tcctggaatt gactcatctc caagataggt tgtaattaac    89820
caaatcattt caaaattatt gcaaaacaat aatatgtgct ttatattata ccaatacgta    89880
atacattggc tgacaacgtc tttaagaatc tgaaacgctg tcttattacc atggatgaga    89940
agttctatga tatatgctag ttcgggataa gctgtgttag ttaaacttc aacgacgagt    90000
ttcagggtgt agtcataatt taaattattt gtcttggctt gttcgatcat ttgattggtc    90060
ctagcttcat gaaaagatga aggtgctaac ggcagaggta tattgcctaa caaaattctt    90120
ggtgaacaca aaacatcagt tgatctgttt ttttgaatat aggtgaaatc aaaaaatgga    90180
tgtagctctg tctttaaagt aaaatttttca gatttataga aatcttctgt ggtaagttca    90240
tttttaagca tattcgtcgt cttaggtatt tcttttttca tttcatataa gttgtataaa    90300
tttgataaaa aggtgcttgg aggttctcta acaaattcaa cctgacacag ttggttaaaa    90360
gattcccccg taggttttgc agcattttta aaaattcgct ctgagacact acaatcaaaa    90420
ataattggat ggcacaatga tggcaataga tcactatagt ctattctctg caaaagctta    90480
tccttattat agaaatagat agatgtgggt agattgtttt ccattgtatc atttagttta    90540
agcctgctat ccatagtgct aaaaccacta tccttcgaaa tgtataagcc cattgggaaa    90600
aaaaacgtca attccaattt tgttccaaa ggatcctcaa tgttagtgtt tttatacact    90660
ttctttaaat gatctaagac aactgttta tcactcagtt gaataatgtt tgtctttaga    90720
tcagcatgtt gagtttggtt ttcaaagatt tcagattttt tgttttggtc ttgtgtttca    90780
gtcgcaacgt ttttggtata atttgaaaaa tccgccataa tagcctggta tgctattgca    90840
gtaacagcat tttctttccc cataacaaat gtgccataag aaacaggtac agacattgtc    90900
atttgtgaaa tgtgttgcga tagggcattg gacaaaatct gaatcgtatt aggagttccg    90960
agtaaaacgc cgttaatagg tgttccatct tttaaaacat agctattggt gttatttaaa    91020
atgctttcag tggttgaatc aaccatttca cacagatatc tgtatataaa gcttacatta    91080
gaagttctgt tcaaaaaaaa taaggaattg atgagtttgt ttttaaagtt ttgaaacata    91140
ttgcttcgct gtactttaga aagaatctgt ttactgttga ctttgttttc taacatggtt    91200
ttcaggataa actgtggcgg tgccttctta agaatagttt taatgaaagc atatattaac    91260
cctcgttgta acgaatcagc agaattcttc agcgatcgta acaccgtatg aatcgcattg    91320
atgttgagca tttgatctaa aattgtgttt taaaggtgt ttctaaatg cgctaaacaa    91380
gcagcactta attcaaacga tatattgata ggatgctttt ctgaatactt ggtaaccagt    91440
```

```
acggttgttt ctttaggcgc agttacgtcg tttcctgtag cgactctagg taattgtata    91500
taaaacagaa ttttcccag tgacattttg tctaggtcgt tgaaacggat aacatttgca     91560
gcaaccgcta tggacgtatg aaaaaaatct atccattcag tccgattaca gtaaatccca    91620
agtaatgctt cgaaacttat gttataacga tcagagtcgt caccgtaata caatcttaag    91680
ttttcaaaaa gttgttcagc agtttgtgtt ctgatatcat caaacacgtt tggagaaaca    91740
tctagtttg ggaaaatttc agctgtgcgc caatttccca tggttagtaa taatgataga    91800
ctcaatatct gaagaaactt taatagtaaa gagctacacc gttaatcact gtgctaaaaa    91860
tgttccagtg tttattaact cctatgattt aaccgcagaa gtggccaaaa atgaagacgt    91920
gcgattagcg cgacaagttc aaatttcatt agagaaaata gatgaagtta tagaatcaat    91980
tttttctgcg tctggtccta gcgttgaaaa tgtaaaagat caggcaaagt ttgctttgtg    92040
tcgtttactg cttggtcctg tgagtattcc gtgctactgc gaagaatggg atgtcaattt    92100
ttatctgaca aaatgtagtt ataattgcga aggcccggtt ctatatatct ataaaaatgc    92160
ttctcaatgc tgtgaaagca catatcgttt ttctatcatg actaattatc attccactca    92220
catctttaga ggattattat cattacaaga atggaatagt catctatcaa atatcttatg    92280
tacttgttcg aacgtaacag gtgataaata tactgcaaca atctttccaa acaatgcttc    92340
aatttacttg gaatattatc cgtatttct atgctatcta tgcaagcatc tgtctatcat    92400
tgatattgag caatgtacta atgaattgat agcttttctt ggtccaaaga cttctcaaag    92460
gattataatt cactataaac tgttattcgg gtttcgatct aaaccaatga atttcactgt    92520
ttctttgtta gaacaggttt tcacccttga atccaaaaa ctctactatt ccgttagtaa     92580
gcacaacagt acaacagcag atttttttcaa tgtcattacc gctaaatttg cagaggacaa    92640
atattttgtt ctacgaacat ttaaattgtc tgcgcaaatc actcctggta ttcaaagttt    92700
ttgttcattg aaattcaaac tccagacctt atatctaaat ttgaaaatta tgaaaaacac    92760
aaaattatcc atttctaata gttttttatca tggtaaaact ttatatacac tggatgaaaa    92820
gcaacttgtt tggagaaatt tattgttaat ttactatggt tacaatttaa aagcaaatgt    92880
aaaacaaaca caagaagaga gtttgttgtc gatgcattac atacgaatat tggaaagatt    92940
gtctctaaaa agttttcgcg aaattaatca acaatttaga tttgaaattc cgagttacca    93000
agagaaaact ttgcagtttta ttccaggtgg aaatgatttc gcagaaatca catcggtcac    93060
gcatggagaa caactgtga atgcatttaa tacaaatagg gtcatgaatg tgaaagctgc    93120
tctttcagga gaaatacact gtgttttaca tcgtattcct aaaagcatga cacatagttt    93180
tgtgatgtat aagcgcactt ttaaagaacc ctctttaaca gtgagtacct tcatttcaaa    93240
tgatgatttc accacaagtt cattgaacat taacattcga ggtccctact gtgattttt     93300
atatgcattg ggtgtgtata gattacatgt taacatacaa gattttttt tacctgcttt     93360
tgtttgtaac agtaataatt cgatggattt gcatgggcta gaaaatcaag gaattgtgcg    93420
aaagcgtaaa aagaaggttt actggataac taattttcct tgtatgatct ccaattctga    93480
aaaagttaat gttggttggt ttaaagcggg aacaggcata atacccaagg tttctggaac    93540
agacttaaaa aatgttcttt tgaaagaact cataagcatc ggagaaattc ccaatattac    93600
ttttgatatg gatttacatg ctttgttaac tcttttagag aaacgaaata tgcatcaggt    93660
tccattttctt attaaacaat ttttttatgtt tcttcgtttta ggtcttttag tgggatatgg   93720
acgtaaacag gaaagaaagg tccatcacat tatgctattc ttaatacaaa agggttttt     93780
cgatttttcg aagaattcag ttgccaacag taaaattaaa catgcatgcg ctctagttgg    93840
```

```
aagtcgactt gccaacaatg tgccaaaaat tctgtctaag cagaaaaaaa tgaaactgga    93900
tcatttgggt cgaaacgcaa acgctttaac cgttttacgt tttattgtag aaaatggtta    93960
ttataaaagg aagacaattt ttcgcaaact tttgaagtat ttagctacta catcttttaa    94020
tgctcatgtt caaactgaaa gtaatcgttt actcaacttg atgcacaatg acagcaaaac    94080 aaattttttcc agtttggaaa gactgtacac tttacgttaa caatgagaca gcaactgtgc   94140
atgaaatctt gaattccgat ttaagtgaac tgttacagtt aaagacggaa tttgtatcta    94200
tgacagacct atgtgtttac attactggat gtataaatca gaatatttcc agcatcacga    94260
tatattggca tgcttacagt gaagtaattt atgctttaac tggaattata cactgtgaaa    94320
agatttctat tgaatgtgga attaaatcca cggacaataa cattttgtat gaaaagccca    94380
aactgttttt acttcgagaa aatttagcac caactgaatt aaggtggaaa tctttaataa    94440
aaacaaagac tataaaaagt gctctgtctc caaatcaaaa tgagattttt cccaaaatag    94500
cacacaagcc gtcaatcctt ttagagattg aagaagcacc ccgatttaag gaatggtgt    94560 catgtatttg gaagttagtt gccgaagagg cgaccataac ctcaaaaagc gagaatgata    94620
ttgtcaaaac atgcaaaaag cttgctgaat cacaaagata tactttgaca aatggtactg    94680
tgttgcaaaa ttttatatta gtccatgcct gcttatttaa gcttggagct gttaattttt    94740
gggaggaaat gaatggaaaa ttacgtcaac ggccagaact aatgtcaaaa tcattcactg    94800
gccatgagga atgtttctat aattgttatt atttatgcac tttgttaaat tccatttata    94860
gttacaaaac tttattgcca gaaattgtag acaataccag atccattcat gtagtagtga    94920
aagcatatta ttcagagcac atagatgttt cttacaaaat tctttcgtac tcaacaaaca    94980
tgatgaactt attctctcag tatttaaatt ttacagattt attgccatat ataaataagc    95040
acattaaaat tgatgtttca gcatctaagc aagatatgat taaattctta aatgcctgtt    95100 tgggactttaaa gatttcttta aatgaagttt gtttaccttc atggcacata taaatagcca   95160
ttataataga aattaaaagg tcatctgaac aggtttgttt tttggcatta taggttacgt    95220
gttcatttat attaatttgg tgaagattct taatttgttc aatcacatac tctattgggt    95280
catacgttat ttttattgta aaggaaatta gttcttgtga cgctttaatg taacctgaat    95340
taaaattcga aatgaaatat tctacggcta atctctttttc tctccccagt aaataaaatg    95400
gttgtgcaat ttggctctga tctaaagtat ggaaaaatgt tatgtgctta tatcttataa    95460
ccgatatagt ttgtttcaat atgcatgcaa tttttcaccgc cgatgattga ttggaattac    95520
cctcgataat aattttgagc tcagtaaaaa aagggtgtaa ttctaaaaca gctagtcatca   95580 tatgtgaggc acattcagca attgaagcat cggagtttga tagtaaactt tctagaaaat    95640
agtgctccat tccatatatt atatattgat caccatatgt tccgatcgct gctacccctg    95700
ttccagaagc acgtcgattg attgtgtatg ctggatcaat atatatgtag agctcttttgc   95760 ctaagaatgg aattatctgt ttgctaattg tgctatatcg gaaaaggtcg aattcaatga    95820
gtccttgctc tgttatcaag gtatcattta ccacattgca gagagaacca cccattattt    95880
cgtgtttgaa agcaccttct aaaaataggt cggcggtttt tttgacgtca gcgttgatgc    95940
tgataaattt cggtttatgt agtcggtaac atgcacaggt tgttgcattt cctctgtcat    96000
ttagtatgtg cacatgatct tcacaaacat aagatactac agttaacatt tcaaggggg    96060 aattgcttag ttttgtcaag aaggaagtag agtgatttcc ggaatttgtg gatgatataa    96120
aaataatttt agtcgaagat tgtggcagaa atccaagaat tgtgctaaac gcgtctttt    96180 tgataaaatg gctttcatca acgatgagaa gattaaagct ctgaccacgt atactctgag    96240
```

```
aagaaaatga acggagtttt aaacgatata aagactgagt ttttatgtaa tactaaaaca  96300
gatcttttaa cgttgataca aaaaatttgt ctgaactgtg atttcattct tgaaccggta  96360
gaatcttttc ctaaaaaaac cgagttggtt gcggtgatgt atgatacgct cgcggtggaa  96420
atttttaacg atcttttaaa atataatgaa caaaaaaaag atggacttgc ctaaatgtca  96480
gtcaatcaca gttgcttgtg aaggagaatg ttcgcaaatg tacaatttgc ataatcctct  96540
gacatttgaa atgggtttgg gaaacatctt tatatgtgtt cggtgtttta agatacattt  96600
ttgcaatatg ctagaagact gcaacctgat aaatactcat gaaggatgcg tgtgttcaaa  96660
aaccgggctt ttttataacg gatggatgcc agcctattca catacctgta tggaacctac  96720
tgaagagcca aatatggaga ccgttaatgt agttgtagtg ctgttatcat acgtttacag  96780 tttttttaata caaaataaag ccaggtattc aaacattatt cgcgacatta taaaagatgg  96840
aaagtttata gaacaagtag aaaatgctgt ttttttgtaca tttaataagg tgtttaagaa  96900
ctccaccttg aataagttac ctcttactac tgtcagtcaa cttttttgttc agttaataat  96960 tggaggccac gcggaaggca ctatttacga taataatgtc attcgtgtta gtagaagaaa  97020
gagggaggat aacatactta aaaaaatgag gattgaatat ggaaatgcac ttgctctgtg  97080
aaacaatgtt tacttgcaga aaaaataata ttttaccggt acatttatgt attttactgg  97140
atgatgttat acataaagag aaagtaaaag ctatagaagg gatctttttt cagtgtgtat  97200
tttttaaaga aaagcttgta tacggaat ggacaaaaat aaagtttact tatgtgttac  97260
atgatcttgt aatttctcaa atctttaaga atgcctgtat taaagaagta atacatgggg  97320
cattaattct ttcagttccc ataaatattg ataacctaca ttttgataca gatattttaa  97380
ttctaaaaat tatttaccca cattttttgc acgatgatat tgtcataaaa ttatcggaaa  97440
ttttgtctgg agcacctcgc atacaaaaaa cagtggaaaa aaaacaagag gtggaaaaac  97500
cttttttcca tattcctgca aaacttggag atctcacaaa ggaagaccct atttcgttca  97560
accatcatgg tccgttagaa cctccatcaa ctgttagagg attaaaacaa tctgcgaacg  97620
ttaggcatag tcatccaata tcaaggcctg aaaaagcgaa cgtaaccttt ctaagtgatt  97680
cgtggtacag ccaaaatcta aagtgtgact tcatatctga cattcaacaa agacatgtgc  97740
ttgtcatttt ttggtatgag ttatcgaaag ggatacaaat gcaattaaa aatattcaaa  97800 ttcctcctga aaatttgttt tcatcaataa cgaattattt agatagagtc aacacatatc  97860
tagacgagat tgctgaaaga acttttcgat gtattactac taacatggaa attcagaata  97920
gacatcttcc acaaaaattt aatagtcatt ttcaaataga gtttaattgt actcacttaa  97980
tttatggtat ggaattggcg agggattttt ggattttgtc tttagataga aatagttgtg  98040
ttttaaaagc tatggccagt catttttcttc ataaaaaaaa agggagaagc tcacttagtt  98100
cgaatgaatt ttgggctgac ttaattgatt gcactaccgg aaaaacccta tatggagaga  98160
aagtacggtg gcaattaaat tctgaaacga gcttatactc cacattcaga aaaaatcaaa  98220
acatttcatg ggaattacag cctaattgtt atgcactata tatgtctgag aatttaaagc  98280
tgtattgggt attacccggg gggttctgcg tgtctggaac ttttaaatta aaagagaacg  98340
atgaattttt cttcgattgg caatttggga tgtcttagga gttttttaca aaatgagtgt  98400
aattggtttt cggtgtgtaa aaaaaagttg taccacgaat atcgttgtgt ggcaacatct  98460
tctcctgttt tcgctgttga taaatttaaa gattgcttgc actgtaatat aattattta  98520 aaaaagaatt tggattttgt ttttagcttg gccataaacg gaatacatgc cggacagttt  98580
gcaacaaatt ccattaaact aaaaaaaatt ataataacaa acgatttggt gtactacata  98640
```

-continued

```
ttagaattgg gatctttaac ggtaacggat ttacatttca ttccaaaata caatagtgaa   98700
catgtgctga atgtgcgacc tattacgcca aatctaattt atgatacttg ttcaattgtt   98760
agttatgacg aagctaaact tttaactgtt aaaggacctg agaaaataa attaattcct    98820 ttggggttgtg gttcttggtg tctcaacaac attggacgtt attatgtgta cacttttgtc  98880
ctggtgtacg atttatatct ggcttgcttt gaaaaaaaca ctttgccatc attatctaaa   98940 gtagttttg atatgatttc ctgcaataat aaacattgtg ttttttgtaa ggatcatagt    99000
aaacacgtag aacaaactgg caaaaccgtt ggatgcactg ataatcaaga aacatgtttt   99060
tgttacaccc catgcaagaa aaaaatggct aagatttcca accaagatct gtcttcatta   99120
ttatgtgatc aagagctcga tttacttgat ctaatttacc ctgaaaagcc cactagtctt   99180
tcaactgata taaatgctta cgtacatgga cataagaatc aagaaccagt cgttttaagg   99240
aatacaaact ggatattaat tcgtcttgac ccagcaatta gcagattaat actccttttcc  99300 tgtccagtct gtaaacgcat agtaagtagg taagaaaaat tgttacttta cgtgagtgtt   99360
gtaacaacta gcaaacagtg ctgtactttt tattgtttcg tgttcgatag taatcacatt   99420
atcttgacag gtgatattct tttgcgggaa aaaacgtcta catttaaatt caacatcttt   99480
cataacaaag tgcgaaacgt gttttttgatg tgcaacataa ccaatgctga ttccttctaa  99540
attctttaat aaaaaacaaa taactggtat catgaaccat gttttaccgt gtcttctggg   99600
aactagaaaa acactagctt tctgtttaag tatgtttacg ctgctttcgt ttataaactc   99660
tatgtcaaat ttatatttta agtaatcaag gacatgattg gccagtgtgg gtaatttcgt   99720
aacagagatg aaaaaaatta tgtgtataag aatgctcttt tgaaatggct ctagtttaat   99780
tctttccttt ttattggtgt tctcaaaatc accgcagatc catctttgaa aatcttgaat   99840 aaattttcg atctgtaaaa acatgggatt tctgtaaaaa cttgtttgta gctctagatg    99900
tttttgatat tgtacttctg tattttttctc tatgattgca gtaaatttga gctttgacaa  99960
agcgcagttc aaggggtcgc atattgcaat tttagatttt acgtgccgtt ggcgatcaca  100020
aaagagatat aaaggtttaa catgcctgca atatgcatgt gtaaagccaa gttctggagt  100080
taatataata aatcgttttt ggcaaaatat cgcgctgttt ggaaaagttg aagaaatctt  100140
tacgtcctgt tcatgtttcc aaattataga ctgatacgct ttctgaattg catctatatc  100200
gcatgatcgc aacatggaca cagatattgc tctagctgca atttataaag aaacgactaa  100260
attaaatgaa aaggatgcta aaattttctc ggaggcagtg cagaccgcac taactgtgtg  100320
taaagcaacc gctcctaata cacgtctaaa actcgttgaa acaccaacta ataacttctt  100380
actagtaaca aatgttgttc catcagaaac ttcgaaagca acgactgaag caaatcttaa  100440
tattgatgca gcgttggaaa aactggcgtc ttccttttaat acagcggtac ctgtaaaatc 100500
atccaaaaag tatttgttgc aaaatgtgag aaaaatgacc agtgagaaca tcgctctaac  100560
tggatcatat atcatctata cgaaaaaaca catcgaggtg gcgtttctgt tagataagtc  100620
tgattttgtt caggatattt tacgttatgc tgaaacaccc agtcttctag gacataccga  100680
tgtacgtgat ttagaatgtt tgttatggtt agcttttttgt ggtcctatga gttattgtca  100740
ggctgataat tgttttggac taaataaggc ggggtataac gccccttttcc caatattgtt  100800 tccaccatgc atgtatgaaa gaaatatgaa ccttagtgta ttttttgggt tattgcaaat  100860
ttatgtgttc tcttttgtata gagattttag tgtcgaaaat tcaaatttac agcaaggtat  100920
taaaaagcgt attaagttgg ttctgtcaga tttacgggcc aaagaaagaa tttgtgagga  100980
agagatagga aattttccat tggcggctca aatatgcctg ttttgtgcat tatatagaca 101040
```

```
aaataggctc tgtatggaat atgccgcaaa caatctaagt atgagtgtgt tcagtccaat   101100
aatattaaag gactgtacat ttatgcaaac aacagttacc ataactcaaa tcttgccagg   101160
ttctaaggaa gcaataattt tcccagttta cgatataggc aaattattat cagctcttgt   101220
tttttcagag aacggtgtac ttttgaaact ataatgtcac tgcatgaatt aataaaacaa   101280
actatgtcca aaaatttaga aaaaaaacat tatgagttgt taaaattaaa acttggtgaa   101340
gatcatcctc ttagcgttcg acagcaaatt cacgctctca atcaaaatct tgtatcagaa   101400
aatctcgaac agtcccagat aattacttct ttgacaaaaa tgttaaagga tcaaaagctg   101460
cagctgaaag cgcaaaggaa aaatgctgct cagctagaat gtgtagattt ggatgacatt   101520
ttggatacgg cagcggaagt gaaatccgtc accgacaata taaaagaaac tttactggcc   101580
ggattagaat cagactaaat atggagcagc ttaagacacc ccaaaatcaa aaacacgtc   101640 caagaaatat gcttcctaaa aaaaaggaa aagaacttaa aaaaaggcct tgtaaagtaa   101700
aacgtaaatt atttggttcc gaaaacatca gacctaacaa aaaaatacct ctggcttcag   101760
acgtggataa cgaattggaa aaaaaacggg gctcgatgat acgaaaacgg tctgagacgg   101820
acttatgtcc agatccatct gtaacagacc tcctatgtca tgaatctttg actgtatctc   101880
caaagtttga acgagatgga ttgagtgcat gcacggaatt tgagaatttt atggatacaa   101940
ggaaaatcgt gttaagtcga aatgaaaagt ctgtgacaga tttaagtgca cattaccccg   102000
ttttatgtaa tcttggaatt tttgagcgta ttcattcacc cttttttgttt tcaatacaca   102060 ttgatactca gtcattttca gttgtctatg ttccacataa ggaaagttcc tgttctcagt   102120
tttgcgagcc agaaaaaaac atggcacgga ttttaggaag cggatcatat ggaatggtat   102180
atgatttgaa caatgttgca attaaagctt ctgatgactt agagagctgc atttcttctt   102240
atgtgtctgg agtagttcgt gcaaaagccg gagctcaatt aacctcacgc gaatgcgtgt   102300
ttaaaagtct tttgatatgt aattctgtct gcctgaacca taaaatctcc ctttccaaaa   102360
cttatgatac agatttatat aaatttacag actggaaatt ggaaaacgtt gaaaattatt   102420
actctatttt ttgcaacctt gcagaagctg ttcgttttttt aaacatggtg tgtaaaatca   102480
accattgtga tatttcacta gcaaatattt tgatacacca caaggaaggt attattttgg   102540
aggctgtgtt agctgattac agtttagctg aagtacaccc acagtataat ggaaaatgtg   102600
gaatactaag acaatttgat cataggatcc agattgtgcc taaaagttat aataaattgt   102660
gtgacatgtt taatccaggt ttcagaccca tgatagctca caaaataatt ttggtcgaag   102720
tttatgcaga atttgatggt aagggcaatc cagtgagaca ttgtaatcta gatctttgtg   102780
cactagcgca agtattttta ttatgtgtca tcagaatgtt ggatgaacgc ggatgccgtg   102840
aggcgcaaaa atattatgaa aatcgattgt tcacgtactc aaatgaagct tgtactttga   102900
atccaatcaa ataccccttta gaatataaag atgcttgttg caagttttta gctgagcact   102960
tagttttatt tggcattctt ttttatcgtg aggtggtgga tatgtttgaa aacttgtatg   103020
actttctgca cgcaagtggt gatttaagcg taagagattt actcgaggaa acatatgtaa   103080
atgacagtag agatgttaga agacaaccaa tcaggtatag gcacgcccaa ttacaaagac   103140
acgaaattgg tcaaatactt ttaaatgatc tgcaacaatt gctttccatt ataactatttt   103200 cagatttaga gaaggatcca tattctgtat ttcgggtgta acatggcaat agattacgca   103260
caaatttctt gtaatttggc ttctattata gaagaggact cggtcttttt atttctaata   103320
gacaaattaa acaatctgga catttcaaga aggaaaattt catttaattt tatccgtctg   103380
tgttatactt attatatctt aataaagttt aattctcgct tcaaagatac cttcttagcc   103440
```

```
agatcgttca ttgattatat gcatcaaaac atatcagatt ttatcgatga gaatgttgag    103500
ctatctgatt tatatagcaa tatttatgtc cgcttacaag atgcgagtcc aaaagttgtt    103560
aagaatctat ttaaaatatt agaacgagag acaagaggac agtcaacaaa tccactctgg    103620
cacgctatgc gaaaaaattg catcacggca actaaaattt atgacatcta tatctctaaa    103680 tcttttcgg gtatacagga gcattcttat ttaggagatg cggttttata tggaattaaa    103740
catgaacgca tcatagaaca cctgttaaag acattctttg tgaaaaagcc ctggatatct    103800
aaaacacttg gtttattatt agatccttca tctggagtgt ttggtgcatc catagattct    103860
tattatggaa tctcttttaa tgacaacaac ctgatagaag taggggataa agttgttata    103920
tttgaattga aatttagata taaatatctg agagaaaaaa acgatctatt tgtttccgag    103980
ctgttacaaa atccgtcaga aattgcttta gctaaattca tcttatcaca tccaatacca    104040
gctatagagt atagagaaaa tggaaagatg ccctcggcaa gagaatattt aatcactaac    104100
aatcctctat acgattctgg taaaaaacgt cgtgcttgct tgactcccaa aaatttgacg    104160
ttcgacatta cacgactaat tcccatgaac gaaaaaaatg tgtcaacggc aattattttt    104220
gatgtcgtta aagactgtat attaaacaca ttggttgcat accaaaaagc tattttact    104280 attgatgctt ttataaatcc taggcataga tattatttc agagtatttt acagcaatat    104340
gtaatgactc aatttatat acaggatcac gataatccag aaaatattga aaagagaat    104400 ttaccctcgg tttatattgt atctgccata tttcgaaaaa gagaagacga cgaaaaaac    104460 tgtcgcttgc taattgagga cacagaatat ttagaagaag aaatccctt aattttattg    104520 attactccaa ttactattga cgctgaattt acttcacgag taatcaaaga tatatgctgt    104580
atctgggaaa ataaaattgc acaacagaca aatttaaaaa tatgggctca agtgctgta    104640 agacaataca tggcggcatc ttcagcaagg ccgaagacac cttagtagac tataaaggaa    104700
aatatattaa tcttgaaaaa gaattttctg ctttaagtga tactgaatct gaagaagagt    104760
tgcaactaga gaagccactt ctaaataaac aagattctag cgtttcgtta acccagaaga    104820
aacttgaaaa tcaatccaaa taaacgtcca ttgattaaaa acccttatt catttgcttc    104880 ttctaataca tctaggtctt ccactgttgt aggtaatttc ttataattat gatgtttccg    104940
cataaaaaat ctaattaatc tgcatataat aaaggaaaga caaactatgg tgatcacagc    105000
tagattgact atgaatttga cagtccattc cgttttaaat agtgaatcat attttagtat    105060
tgggtaggtt aagcctagga taccaaacaa aattccaaaa tgtaaaccaa attgaaccct    105120
aacatactga tgtaaaatta attcaatcac caaagagtat acaaaagaca taacaaaaaa    105180
ggtgttgata gatgcgaaag ccactgttga tgatttaata tagaaattgt tacctaaacc    105240
tagacaaatc gtaattgcaa acaccatact ggaaaaaccc aacattagtt ctatcatatt    105300
gattatgata gttttatatt ttattgtgcc tttgagtttt gggtggatcc gtttcaatac    105360
gaagaaagat ctttcagagg attgatactg tgttatcata gtcaatgtga agctgtgaa    105420 gcaaatgaaa acaggcaat acgtaaaagc tgcgagggtg actagtcgaa aagaaagaca    105480
ggtgacaaag aactgatatg tatccatagt taaacaaat tggaaacacg ataaactatc    105540
ccccatccaa gttatatccc ttgtagattg attgatgttg ggagttttt cggaagagaa    105600 tacttttacg caacaaacta tatagtatac taagatgaag aaaaagcaga tatccatgaa    105660
aacaacatag cagataagtt ggataggatt taggtagagt tgtggcgtta ggctgcggat    105720
gtcattccgt atagagaggt tgatggcttt catatcattg atttcataat atgcgcatgg    105780
gaatcccaaa ttgggaaagt gaacagccac taaatgcact gtgacgttga catacgttaa    105840
```

```
acaagcacag attatactta agacccaaat tctcatatta atcacatcta ctctgctcaa   105900
tgccattgtg gggatctgtc aaatggaaac tcagcttcaa aatgatcaat tattttggga   105960
atggtttgga caaaatttgt tggattgcca cttgcacaa aacgtttcag tgtatttgca    106020
agatgcttca atggttcatt ttaaaacctt ttctgaacaa ataaaaatta taagagctcc   106080
aatgggttct ggcaaaacct ctgcattgat agaattcttg aaaactgttt catatattga   106140
ttctgtcctt gttatttcct gtcgtaaaac ttttgctgca gaacttttaa atagattcaa   106200
gaagaatgat ttgaacgatt tctatctgta cagcgaaatt aaagagcgtc aaatcaacaa   106260
gaacaaactg ataattcaag tagaaagttt acatcgtgtt accaggaatt atcatgtttt   106320
aatactagat gaaataatgt ctattataaa acagttctat tcaaaaacca tgactaaagt   106380
caaggaagta gatgctaagc ttttaacgct cattagaaat tcaacacaga tcgtagctat   106440
ggatgcaaca gtcaatcgtt atgtggtgga ttttttctct ctctgtatgc cgcatttaa    106500
gtctgcattg atcataaata cgtttgtaag cgcgaatttt tctaatagat ctgcttattt   106560
ttgtccaact tttatagatg ggaatcttgc attttatgga attctaaaac aaaaattagg   106620
cttaggaaaa aacatttgct tattttgtag cacagttaca tctgccgatt tcatgtcaga   106680
attgttaaaa actgatttcc cggataaaaa aattttgctt ttaacttcta agcagggcaa   106740
atgtcattct gtcgagagtt ggataaaacta taatattgtt atttatacat ctattgtaac  106800
ggtcgggctc agttttgact ttctacattt ttcagctatg tttgtttaca ttcatttggt   106860
aaaaggtggc cctgatatgg tttcggtttt tcaatcaatg ggtagagtta gaaaggtcac   106920
agacaacgaa attttatttt atttgaatcc tgcattaatt caggtgcctc tttctgtatc   106980
ccctatttcg attccacaat gctatgattg acacttttt gaaaagtcaa tcctacaatg    107040
cagctgtatg gattttaata aaaaatgtct cagtgcacaa aactacttgt ctaattccat   107100
gataaaacaa ttttttagaa ttaggcatta tattgaaaaa actacgctat taaatcttcc   107160
tgatagtctc tatcttttat gtcttttatt ggatagtaat tcaattaaag ttcacatcga   107220
tggagacgtc tttcctatag ctaaagaaaa attctacgca tttacaaaaa tgttggttca   107280
aggttgccat ttttttgaaa agaagaaaac agactttgta gaaaatacta tgacactgaa   107340
agaattgctt tctaatacaa atattactgt taacggagaa ttctatgaac ttggaaattt   107400
ccaagttcat aaagattaca ttgttaattt aaataatttc cagaatttat ttttgaaaaa   107460
tgatgttgac attttttgtaa ttgaagagat tatgcttact ttaaaatctg aaattaggag  107520
gtttgttttt ataaatgctt tgctacaaaa atatgttgcc accggtatcg atgtggaaaa   107580
gattaaagcg ttttttaaat cccgaatcaa aacatttact ctacctgaaa actatatatg   107640
tagcaagttt tatttattaa gtgatatttc aggcgtacat gaatgtggta tgttgatgga   107700
tgtagctttt ttagcagaat ctattagagc ggatttaaat ttacagtcct gtacagatac   107760
gcaaactgac atctcagaag atgctatctt actttgcgct gcaagaagat catctgaaat   107820
ccttaggatt ttacaaattg ttttttacaac gcacgtgcaa ttatttgaaa aatacaacag   107880
ttatacgtta tatttgttca ataggttaaa gggaatgcaa ttaaatacct ggtcactgtc   107940
gattgcaaaa ttcagtgttt caataataag gatgtttttc aaatgtgcct ttaatatgaa   108000
tctggttaag agtaaaccca gatatatcgt tgggaagcca tttagaagtc taacgaaaag   108060
ggaaatagaa acttacttg acatgtggca cgtatcaaga accaatctga aaacctacaa    108120
agagttacgt aaggctctga cagaagcttc aaaaaaaaga caaagaaaaa aaatttataa   108180
attactaggt cacaatataa gttcttatat cagtgaaact ggttgtctct tccagcatgc   108240
```

```
agatgcgggg atgtgtttgt catctgggtg tctattgcgt tcataacgat tggaaaaata   108300
aacaatatag agtaccaatt tatcaatgcc tgttttttaa tgctgagact cactccttgc   108360
atactttttt ggttattgga aatgagattt ctgaaaatct ccttgataag atttccattt   108420
caaaagaaaa aatctttatg tgggatttga atgaacaaat aatgagtata actcaaaaga   108480
cagagtcaat ctgtgaactg atgtttggca acaaacaaat aattcaaaaa ctatccagaa   108540
catttatttt cttaacaatt attttaaatt ctaatatgta tgaaataata gatgtctgca   108600
tagacagtaa tgcggttttg tacatgccag acttaagacc aatgataata agatgtgttg   108660
gaaactattc gaaatatctc tctgaactat tgtcagattc agactgcaca caggcgacaa   108720
agaaaatgcg atttgattat cacgtcacaa acttttgttt ctcattaaat gtcaatggta   108780
aaaaagtact gttttctagt acagagtctt cagaaagtat tttagaaaaa ttgcttgagt   108840
ttttcacaat acaaacatat aaattggcag aagaacaatt cttaatggtg acacctaaaa   108900
acttttttac cgtcttattt gatgaggaca tgtgtctact tttgctgcaa acagttgtta   108960
gttttttgta tgacaatcta tttcgaaata agttagttgt gaaacaagtt catgattaca   109020
ttggtccaga tttgtggccg caaggacatg agagggcagt ttattttgta gggtttccta   109080
atatgtggtt tttatcgatt tacgatctgg acaacaagat accttgtatt aaaaatattt   109140
gcaatagaat tttactttac tgtggcctgc cagatagtct aggaccagat ggttgccaga   109200
gtgttccaag tacgcagtgt gtggatgaat tcgaagacct tcccaatttg ggagcattac   109260
aatatttgaa atataatagt ttggttgtta caatggaaac agtagaaaat tctgagaatg   109320
tgtattattt ttttggagag caggatctgt ttattgtcaa attggtagac attattcaat   109380
ctttgttgga actatatgtt cctaaaagtt ttctcccaga ttttagcgat gcttatataa   109440
aaagtgaaat cttattgaaa tttatatctc gacttcacaa aaaatctaac aacatttttt   109500
gtaagatcgt aaaaaaaatc acagagtttt tgagatgttt tttaaacgcg tgtcgattaa   109560
tggatcttaa ttggatgttt attagaaaca tgcatattgt gtattttata ggtccaaaaa   109620
aggatccttc tgtagtactt cctctgttaa aaacgtctgt ggaaagttgt tggaaaaaaa   109680
ttctcaattc ttcaagaact ccagtagtga acataaaatta catccctggt tacaatttcc   109740
tacacagctc atgtagcttt ttgacaagcg gagacatcaa tagtgaagat tctcattgga   109800
ctatcacagc tagcaagtgt ttatataatt gtttaggggc aagtcagatt acagtagatt   109860
ttaaaaatat ttacacaaat ttccagcaga tggttagcgt ttttctaagt cacagatacg   109920
aaaataaata ttggatcgaa tattttgagc ccaacaacta ttttctagag acacacgaag   109980
gtttactaga ctgtaataga tatacagctg tctggacaac agaaaacaaa ctaataagac   110040
aatctgttgg ttatccatta acggataaaa tagattttat tcattacatc caggttgtga   110100
tagaaatttt caaaaagtgg ctcttaacaa aatatagtca acaagagtat gcagaaactg   110160
ttagattagg aagtaagatc atctctgatc atttacattt gtttaatgta aactagtttt   110220
ttctatttct gtcatcttat attcctttga aaaggcatcg catatagcgc ttttttaaaaa   110280 atctattaaa tatttagagt cgtcttgcaa acgtctcgtg tttagtgata gagtacatgt   110340
gtcgtcattg tcgtgagatt tgaaaaaaag atttaacatg tgtatatttg ctgttttga    110400 ctcataatag agctgaataa tgggtggaac tttatccagt acgtcttgct gtttgtcatc   110460
gtaaaaaatg tatcttaaaa tactaatcaa tttttgacag gtgcaggcta aagtttaga   110520 gactggcaga gttacactga tttttttaat aatatctcgt aatttaagta gtgtctgccc   110580
ttttattggt agattttcta gagcatatac aataccacag agtaaaaact ccgtgtcttc   110640
```

```
ctttaaaatc aaataaatga ttcttcgttt acattgagtt ttactcagcc gaatctcttc    110700
tagcgtatct tcggaatcaa gaagaataat gccaatgaag cctagaaacc ctaatgtttt    110760
ctcacatatg cttttatagg atttgccatt tacaattgtg ccatcttcca aatgaaacca    110820
tacatcatca tttccaaccg aaatatcaat taaaggtaaa ttttaatgg aaacgtgttc     110880 ggcgtgtttg tttagttcac agatattccg gacgcttgat atattgaata tgtctagagt    110940
ttcgaatcct tttaagcttg ctggcaacgt catcttgcgg atattgaaaa tcttctgggt    111000
ttgtggatcc taaatcaggt gtcaaagtca aatcactttg tttctgagta tgtattaaat    111060
gcgaaagctc gttaatctgc cgtatataga ttaatcttaa ataatgctta attttacagt    111120
ttgagtacac agctaacata atctctttta gagagaggaa cagaaactct tctgggagca    111180
gttcaaaatg tcttaatttt agaacatgtt tcatgaaggg tataagaagc aattctagcg    111240
tgtaatttga atatgagatg ctgtcttcct gtccttgatt gttgacattt tttcgtagac    111300
ggaatgtcct tgtgtattca gtttcccata attgatcaat tttttttgtct gcgtattcaa   111360 tatctggaat atattgtgaa aaaaaactgt ttgccacagc tctggtgtcg tctattgata    111420
cactagtgaa tgggagactt tgaactttgt tcagagcttt agcgagagac aagctttcaa    111480
tatctgaatc taaagtaaag tcatgtttag aagtttcgga taaatttatt aatgaatgca    111540
tgtctttaat cttatttttca aatagccgat ttgcagtttt cagtgttttcg atttcgtcca   111600 gttgtgattg aatctgttcc tccatgcatt ttatgatttg ttttttgaag atatctctaa    111660
tatcgcgatc attattgtcc tgcccacgac gttgcaaatt cctttgctg attaataatt     111720 tattttggtc aattatagac ggcgtgatgt cttgtaaaaa accctcaata ctatctgtta    111780
ttccaatttt agatttacta tcggacaagt ttaatagaaa cttttataaga cttttttcg    111840 catcgctggt tttttcctct cttttctataa gttctagaat tttttttgtta tcaacactgt  111900 tctttgatgt agttaaaaact ttaattggaa aagtattcag caattgacac attttacggt    111960
gcctgtgtag gttttcgtgt ttattcaatt ctgagtataa gtgagctagg ggtgttgtaa    112020
acagcaattg attatttatg aaatatggtg cactgtaaac aaagtactct agttccttgt    112080
tattggagag acaggttata ttgccgtttg acttgtttcg ataaatgttt atgttggtga    112140
aatcggcaat agatgttgag gagatctgtg ttaaaatgtg cagtagaaag ttctgtttgt    112200
ttcgtatgat ttcttgaatc aatctagagg aaatactttt tgctaagggt gtcagcgtaa    112260
ccttgttttt tggtaatgtg acaattggtg ttattccaat cgtacaaatc caatcaatgt    112320
atttattata aatgtcgtta tcgagatttt gaaggatgta gtttatcgtt tgcaaaatgc    112380
cttccaggat tacctgtttg attgcataat accagatatt aaaatattct tgaaatgaca    112440
tgcctttact gcggaacgga aatgcttttca gatgacgttg ccattcagca ttgatctgct   112500
ggatggatat actattcaag agagtgtgtg acagtgtgta aaacatttgc ttcttaaaga    112560
cagccgagtc tctaagaaca ctgtgtatag attgtcccct aaagaattct tttttaccgt    112620
gtagcatttc tataaatttt atagtcttaa tagaaggaaa taaaatgtca ttgtcttcat    112680
tattcaatgg taaatatgac acaaaattcc ttttaaacat gtcatctgct gctaaggtgg    112740
agttgattgt tgagaaagtt gcagctttag ctgatgcctg tttagagacg ccgttaccaa    112800
ctgactggtt tcgtaacatt cttgatcctg aattagaatt taatagcaat tttgaagaaa    112860
ttcattctat aggtgatgaa gaatttgctc aaccgttgcc attttttacct tttagagtat    112920 tattaataac cggtactgcg ggtgcgggca aaacaagcag cattcaaacc ttagcagcta    112980
atagtgattg tcttataact gctaccactt ccattgctgc tcaaaatctt agtggtttat    113040
```

```
tgaacagaac caaatctgcg caagtgaaaa caattttaa aacatttggt tttaatagtt    113100
cacatgtatc tatgaatgaa agaattagtt gttcagtaac aactttagat tcgattgcgg    113160
atcagcaaaa acatgattta tctacatatt ggaacgtcat cgcagatata gcggaaagag    113220
cttttgaatgc agcaaatggg aaagccaaag tgatacctga tctatgtgaa agcagtgtga    113280
ttgtgattga tgaagcagga gtgatcttaa ggcacatttt gcatacagtt gtcttttttt    113340
attggtttta taacggtctt cataaaacac agctctataa aaatagagtt attccttgta    113400
ttgtatgtgt tggatctcct acacaaagtg gggctttaat ttcatcgttt aatccgttaa    113460
cacaaaataa agacgtaaag aaaggatttg atatcttatc cgctttaata tgtgacgaca    113520
ttctatcaaa ttactgtaaa atatcagaaa attgggtgat ttttgttaat aataaacgat    113580
gcactgatgt ggaattcggc gaatttttaa aacatataga atttggtttg ccattgaaac    113640
ctgaattgat tgagtatgtt gataggtttg ttagaccggc aacttatatt agaaatccta    113700
caaacgaaat tggaatgacg cgtttatttt tatcacatta cgaagttaag tcatatttta    113760
aagttttaca tgagcaggtc gaactgacaa ataaagataa tcttttttact tttcctgttt    113820
atttcataat tcagaataaa gcatttgaag attacaaaaa tgaaatttca aattttactt    113880
tagagattga accatggttt aaaactaatt tacacagatt aaatacttat tcccaattcg    113940
ctgatcaaga tttgtctaag accatacaaa tcgaagaaat tgtattagat gatggttcgg    114000
tagaggaaac tttgataacg tgtcatttga acatataaa acatagttct attggcgtta    114060
cttccagaac aaaatcttca actgttgggt tttcagggac atatgaaaaa tttgtggagc    114120
ttctgcaaag tgatttattt attgaaaaaa cagcatgcga atatagcgtg cacgcctatt    114180
ccttcttgac aggtttaatg tatgggggta tgtattcttt ctgtttatcc gaattcacga    114240
cttctgaagt aatgacagaa ataagaaaga tcaaattgcc caatattgat tttctacaaa    114300
caatgacagc tgaagtttct ttgcaaacct tcgatgaatc agacgaatac tatgatctac    114360
acattgcacc tacagatgaa gaaatgttag cttcggatcc gtgcccagat cctttttttt    114420
taaagtacaa gcaacttcca ttaacgaatg ttctaacatt tgaagaaatc agttacccttt    114480
atacagtatt taaagagatt ttcatttcta gatttgcaat tctacaaagg cacagtaaag    114540
aaatgttcgg caagagtaat ttaatcacat ataataggaa taatgtttcg agcaaaagat    114600
gtggggagat atgttcacat gttaaaagct tctacggcat gttaacatat gctgtgcctg    114660
ctaataatta tactttggaa ggatatactt atgataatgt gattttctta gggacggata    114720
aaatgcttcc tccgataatt tacaaaagag gtttacccaa aattgttatc aaggatgaaa    114780
tgggctttat ttcgatctta gacaacaatg tatcaaaact tactgacact gtcaatggta    114840
acagttttca tatctgtaca accatagatt acgccatagt ttctaaagtt gcaatgactg    114900
tgacaaaaag tcaaggctta tctatacaaa gggttgcctt agattttgga aatgatccta    114960
aaaatttaaa gttgagttct atatatgttg gtatgtcaag agttgttgat ccaaataatt    115020
taattatgaa tctgaaccct ttacggttga actatgaaaa tgataatatt attgcttcac    115080
atattgtaaa ggccttaaaa aataaagata ctatgcttat tttttaaatg ccagagtttg    115140
tgttgattga cgtattttt taaactaagt tgaaattaag tttttcatgt atcgatgtgc    115200
tttttttctgg tatgtttta atggttggca attgtaaaaa taaagacatg aatcaatgat    115260
ttggtataca ctatttttatt gcgaaaatga taaatactct gggtccggaa gttgaggctt    115320
ttagaaatct ttcatcttct gaatctgcaa agaaaaaaaa tgcttagaat cttttgcaca    115380
tctagataaa gtaggtaaaa aataaatata aacaaaattt accgtctgcg tagttatttg    115440
```

```
ttccagttga atgaggactg cagtattctt atgccaggtt tttcaaagac gcagtctaaa    115500
agtaaaggga aaaacttttc cggagtatac aaatgtactc cggattgcgc aggcgtgttt    115560
attctacatt taaaattgat ggcagttagc ggtgtcaggt ggtatgtatg gtgtctattt    115620
taagtatgtc agaaatcaac taaagttcct tttccacaca ctactgaagg ttgtatgaat    115680
atcacaattc acaattttat aacaatctag agttgctttt taaggtatgg aaaaagccta    115740
tgaaatcatg caaaatgctg ataattgtac attcagaaag ctaaaactac ttattcttaa    115800
tatctatgac ttaaccttaa aaatctatga caaaacctat tgattattct aacagctat     115860 tattaaaatt aaaagtgatt aactattctt aaaaactatg atttacccc  attccccacc    115920 cccaccccca cccttcttga ttatatcccg gaccccacta aatggattgt ctttgtatta    115980
tgttggtgtg ttgcccacta cacactgaaa catagtacaa gggctaactc ttaatggtta    116040
caagtatgca gctcaaaatc gtaatggttc tgatctttct tgtacatgtt caagttttcg    116100
gcggttaaga tgcttagag atagttcaag attttagatt caaacatca cttatctcca     116160 cagatcattt ccaagcaatt gtacagaaag atagaatgtc aatgagaaca gccgttctca    116220
ttgtcttcac aaagtgaggt tcagatcatg acatagtagc cgtaaatggc tactgtggtt    116280
tacattataa atgagaacag ccgttcccat agttttaaaa tgaggtttaa aacatacagt    116340
agccattaca tggttactgt ggtccaaaac gcggtatccg aatcgcaatc cacaatacac    116400
agtcccgttg ttcaaaaagt tatgcagttg gcggtcttaa tcaggtatga gatggtatgg    116460
caatacacgt tgtaaaaatt ctgagatttg aaacaatgat gtcactgttg taggatatcc    116520
tgtagttttt gatggttttt tggttgatga cttacacaag atcaaaagtt actggtaatc    116580
cttagtgtta gatcttacat gatatgacaa gagaaaaaaa gctatatatg gaagggata    116640 acccatatca aacaagaaaa gttaaagaga agaaactatg agatgggaga acctataaca    116700
aatacacttt taagattggg gtgggtgaac agggcataac tgtagcaata aaaccagtga    116760
ccgacagtta cattccttca taaaaactaa cgtgatagca aaaaaatat acataaataa    116820 agaagatggc ttttcaagtg ataatggcag tctagataca cttatattcg tgagaggtgt    116880
gtcagtccat atacaacttt tcctattacc tcgtctaaaa aaggcaacct aaaactggct    116940
gttttacctg ggatgattta aatatagaat aaacattcac ctaccttgtt ttcttctctg    117000
aagagtagta gtgttgactg cattgtctcc gtgtatcttg atccaataga gctttatcta    117060
ataaatacaa aaaaggaaaa atccgtatat tccataactt gttaagtaca atttccataa    117120
aaattgaaaa aatatatcgt ttagatgtta tacaaaagtt tatcgtttta actaatcatt    117180
gtctattttc agacatcgat acagagtttg atatttacga gttttcgaa agattaaatt     117240 tcaatctcac ctctttcgct gtcttaacag ttcatgtaga tcgcgggctt tataaacaaa    117300
tgctttccag ttttccacgc cctggggat atgacgcaat ttccttcatc cgtgaacttg     117360
tcgtgtttgc ggttaaactc gcggaagtaa accgttattt tttctcgaac ggtaaaatac    117420
aaaaacggtt tatgcgaaac aatttcaggc aaatatcatt gcgacttttt aaaaacgatt    117480
taagttatga gggttttgt tggctacatt ccggaaatca attttcatgt cagaaagcat     117540
aaaagggaga tgcttttgtg tcaggaagca actttatcag tcaagaactg tgaagtacat    117600
tccttgagaa atcacttaga ctcgtagtaa gaagtgagtt tttcagtgag tggaagcagg    117660
taagtataaa atttccctat tctatttcaa cctgtactcg actctgaata cgttatttct    117720
tttattgaca gaatgattgc ggaggataga gaatatggaa cgtttgaatc tgtaacccag    117780
gcttatcagc agatcattag tcatacttta cagctgagac gatatgaatt tgaaactggg    117840
```

```
tgcatgatta tgttttctgc taattctgga aaatgtgaga tgctctctaa tggttggatt    117900
tcaatgattt catggacttc agaaaccgat acggccggct cattgacatt ggatatttgt    117960
actgagggag ggcagtgcaa aacttacagt gccagaggtc atatattatg ttctaaaaac    118020
atcacttcaa tttctcagaa aaacgaggga aaggaaaaag ttttgacgat tgtcatgac     118080 aatggaaaat tgcatttaac ttatatcaca gttctaaaaa gcggccttga ttgtgatatc    118140
aaagaccaaa aactggagaa actgtttgaa aaagaacatg cagaacgaaa aaagcaagat    118200
gatgattata aaaaaaagc tcttaaacaa aaagataaac gccgttctga gcaaaaaatt     118260
ttggaagact gtgataaaaa agatgaaaaa aaaagaatgg atgacaccga aaaagaaaa     118320 ctacaagagg accgtcgaaa cgaaaaacaa gacctaaaaa aagagtaga tgacaccgaa      118380 aaagaaaat tagaagatga ccgtcgaaac gaaaaacaag acctcgaagg ttagttgcct      118440
tttttctaaa tcactagtcc taaatatgac ttgttgaatt tttgtagtgt ctaaggtttt    118500
tacataaaca tgttttctta gatgcatcca aagaaaaaag gatgaaagtg catcacgaaa    118560
aacgtcatgc ggaagaacaa gcaaacgaag aggttgcttc ttcgagtcag ttatcaagta    118620
gaataccaga gggtgcgtta tcgcccacta tttctattga tcttcaggaa tatcaagaat    118680
ttgaggattt tgacaagcgc atttgtgggc aggtgggtgg agttttgggt ttatgatgca    118740
tttttattgc agttttttat gtggttaaag atgtttcttt cttttagggg aagaatcaag    118800
acgctgtatg caagaaagtc caaagtgatg aaagttttg tataaataaa ccgttagagc      118860
agtttagaga gaaactaata aaaattactc atgaagctgt acaacagtca ctgttacaat    118920
cgcggggaaa aaatgaggat aataaaaaag atgttaccca aaatgtaaaa ttcgctgatg    118980
aaaatatgaa tttcgcaggg ggttctaaat gtacttctaa aactaagcat attgaagatc    119040
aacaaataca gtttggggca caaatagat ttgttcctat atgtgaaata aaaccattta     119100
ttgatgtcaa ccttttaaaa tcaaatgtaa gaggtagaag gagtactcgt ggaagaagaa    119160
actcaaactc cgctagattt tcggcctcta cttttgaaca accaattgaa acttctgaga    119220
tgctgacggt ttcgactcga tccagaggac gttccagggg aaggccaaga ggcagaggca    119280
gatccagaaa catgtcaatg agacaaactc caagagaagt tgaagacatg ttaccgattg    119340
ttttggacag tgacagtgac acggagactt taaggcgtaa tgaagattta ttggcgtctt    119400
ccatattaca gactttataa atcgtttgtt atgttccaat caattggaca tttgttgtgg    119460
atttgtaaat atttatttgc ttttaaaaaa tgaccacaac cgataaaagg tgttttgat     119520 ccttttgttc tcggagatgg atgtgcacat tccaaaatca agtgtttctt tgaatctatt    119580
aaagacacga gtttgcgagc ctgtgatccc cacaacataa aaactaagtt ttgcatttt     119640 tctgatagtt ggtaataat tcggttgctc aaaacttgcc atccaatcgc ttcatgggac      119700
attggtactc cccttataac tgtgaaaaca gtgttgagta acaaaacgcc ttgggcacac    119760
caagatttta aagatccgtg ggctggagct ttaaaattct ctattgttct ttcaagttct    119820
gcaaaaatgg ttttttaaaga attcggaggg gaacatcctc tcacagtgct gaaagctaat    119880
ccgtgacctc taccatcggg ataaggatct tggcccacta ttatcacctt aatctcttca    119940
ggcgaacata ataactcca gctgtgtaca ttctgaggat cggggtagat aattaatctt      120000
tctctgtcac gctgaaccaa tttgtataca ttttgtaatt gtacaatgtc agaatctgat    120060
aagtttaaaa acttaagcca cttcacattg atttgaaacg tttcatgttg ttcttcaaga    120120
gacattttta ttgagttgtc atctgaaatg ttttccagca tccactgtag taatgccatt    120180
attgaatggg agaagcagtg ttcatgggct ttttattaat gttgcctgaa cacgtgacac    120240
```

```
ataagttgag cgatctataa agcatgcgtc agtaagttct aatgagcaaa ttcgaaaact   120300
cgcttcggaa tggaagcact tcattatatt tttccatttc ttgaattaac gggaaactaa   120360
agttgtaata cctagaaaaa tatctcaaac aatttaacaa agcatcaaaa acattaattc   120420
catggtgatc aattctcaca attctctgtg tgcgagtctc ttcattttca aggtaaatca   120480
aaattgacat gttaaaattt atcatatttg atggtatatt gaattcaaat ccgattatat   120540
tttctacaaa gatgttgccc gtgaatttga gttttttcata agagtatgat ttacacacat   120600
tatctctaca ggttaaaagt gtgttatctg aaagacatct ttcaaagtta tttaaaaagc   120660
caagccagtt gtgccctgat tctgaatctt aattaagga agtaaggtg tgtagttgat    120720 taggattatt atacagtagg taaaatgttt ctaaaaaatc ttcatcaatt aaaacttgat   120780
ctctccttga gatataggga gtatgatata ataagcgaga aattatatcc gaatttggta   120840
taggtgcctg atcaataggt tccagaagcg acagagtttt tgattgggta caatttagaa   120900 tgttttttgat acattcttgt tctaaattag aataataaga gttattaaat aaagcatata   120960
tttggtttag aatggagata agaaatataa aaaagatgtt agttttcatg ttccataaag   121020
ttgtatacaa acaccagga acttaaatat ggaagacaca tttaaatgga atctaataat     121080
ttacataccg tttttgaagt gagctttcta attatttcgt gattatagaa attatcattc   121140
tgttaaatac tctgaaacag aaaatctgga attcttaaca gtaggttttc cttacctgta   121200
ttagtagaag ttgtattttt agaagtcgaa tctgagtcaa gatctataga aaatataaac   121260
tttatatcat tccaaaagtt aagcaataaa tataacgt aattcgagtc aatcagagta     121320
cataagtttt aaaatatact atgtctttaa tagtttacca taatcgtccc agtagatgta   121380
tctattgaaa gtattataga tgattaaatg ctctttaagt aataaaggtt gtgttaactt   121440
tgagacattt agtaaaatgt cagcagggta acgaattgaa aattggacac agagatgagc   121500
agcacaaaat agatcttttt cagttggggc atttatgtac agagagtaga caccactatt   121560
tttcctgtgt ttgctgttga cattcacagg catcatagct tctttttctag tcagttcagt   121620 atgtggcact gttcctctga gaaatctgtt aattgctatg gcagttttct gttcatggaa   121680
aaagatctca gaaacggttt gttcgccttt gttaacaatc agattagcta tttccatcaa   121740
tttttcgtga agtgagttta caagtaatcc gttacgtgaa taaacttgaa tttgaactac   121800
agtcgaatta taaaatcgaa gtaatttata aacttccgat aagaaatttt tcggcgaaca   121860
taaaccgcat ggatgcataa aatcacaatt aaaatctgta taattttta tttcaggaga    121920 gtggataggt ttggaatcgt taaaattgct gtgaacaata cccttagatt ttgttgcaaa   121980
gtttgtcgtt gagagatttt cttttacagc cttaaatatt tttctcaatt tagaatgttt   122040
atagatggca ttcgtatatt tgtccgcctt aagtaacatt tctgatttg aaatgtttat     122100 ttcagaattt attttttcag gaattgtaca ttttatggct ttttcattaa acggtaacgt   122160
ttttgaaaaa cagttacatg tatatcgagc attggcttta gtacacatgc agcttttaga   122220
agtgagttta cctttggcct tacaaacagt tttacgtttt ttgcccctca tattcaagta   122280
ctgaagcttt caaaattttc aatgttgatg agttcctagt ttacacagaa ggggttgaagc   122340 tattataacg aaaagcagga cactggagat tattaaaatt atccacgcca aatcgttgtt   122400
aattaactct gactgtttaa gagaatcatc acttaatatt gtatcattat agggttttc     122460 aaatggttga ataatcgagg taacattctc gtctatctct ccgccgtaag acagacaagt   122520
gatcggtttg ccaaagaacg tattgctgcc ttgtcttta aaaagaaagc tgagtgtcgt    122580
tgtctgcgag ccgttgtaat tttcacgcac tgttggactg tcctgtctat atatcttatc   122640
```

```
taaaaataaa atggctacta atggctttgg atacgacgtc acagaacatg ttacatccaa    122700
aaaattttgc agatggcgat agtacaaagc aattattggc ttcattgaaa gatgcacaca    122760
actcatagta gacaatcgag tcttggcgaa gaatgcacat gttaagcaac cagcatcgtt    122820
aattgttcga gatttaaatt tcagcaatgc tgtgatattg ttagcattga agtaaataat    122880
gctttctttg tcacgatgtt taaattcatg aactattttt tcactcatgt ttttcaggtt    122940
tttggtattt atggtatgat ttaatatcag ttcgtaatgt ttaaaccata ttacagagct    123000
gagattttta gttgtatcaa cagtacactg aaatacaatt gtgtttccta gttctactct    123060
atgatgcatt attggagata atgcatatat gattacagaa aatccaatca tctttatgaa    123120
aattgcacct aagaaaggca ttgtgtgaaa ttgtctgatt ttggattttt ctgcatctat    123180
attatctgga cacaccctaa aaaccacta ttttttctct tttactttga ttttttgtgtt    123240
ttttttttaa aatgtggacc cacccattca aaaataaggc gtttggggta aagcaaatgt    123300
aatctttatt ttttttttaa aatttacaaa gtgctgtgta ttttgaaaga aaatctctac    123360
ttacaggatt atagatggaa atcggattat ccccatcggt gatagagctt aatcgcagaa    123420
caatttcttt tggtctcttt tttgcataat tgttacagat tttagctgcc atgaaaaaat    123480
ctattggtgt tgcagcgtat attataattg ttttgagatc tgaatgtctt gtatacagag    123540
tatgtgcact attactaatg ttctcccaca attcatgcgg tcctttttt tgtaattcga    123600
tgaaattctt tatggaatct ttgtcataat atcgcggggg ggcgtggttc attttaaagg    123660
gttcagacat ggtgatatta ggtcttacca ttagctcttt ttgcatggct tttatgtctt    123720
cggcaacagt ttttgacctg gtaaaatata ttataagcgc accggattta gagcttccat    123780
tgcagcacaa agcataaacc gattcttca atttggcttc cggaaacggt ttttttggaa    123840
tttgtttata ttcaaaagcg cggattgttt ttcgaaacag ttttttcaaaa tctttagtgg    123900
gaacacgacc acgttgtact ttaaatttag ctgattgctt ttgctcttgt aatttttacat    123960
actccctgta ggataaatca ttatcagata gttctgagtc agatttttgg gtaccagata    124020
tccgctttt gtagaaaagc tgcatgcttg agtccgaatc atcagaaaaa cgttcctcg    124080
catttctgcg tttattttta aaaatttat tagtactttt cttttgttca tactcattcg    124140
gaatactttt ggccccatga gtaaaatcta tatctacacg cttgctttt tgtgtagatc    124200
cagaagacca cgaatgatta aacagcttc tttccgatct tttttgcaa tctgattcag    124260
aagacctgct tctacttctt agagtttctg aattcttatt tttacaggat tgataagtgc    124320
tttcagaaat actgtgttct gaatttgatc tagatataga tatcaaatgt ttgcattgtg    124380
tttccgactg agaatcttgt ttattgttag aacacacttt acatgttctg gatttagatg    124440
cagatctaga tctcgatgta tcagagctgc ttctagatct gtgttttgg cgatgtcttg    124500
ttttagtact ttctgaacat gattctgact cagtgtttct gtgttcgtgc cgtctctttt    124560
tagaagagga aaaggattgg gattgtaaat ctgaattggt atccgattct gactctgtgc    124620
tcggtggtct cttttccctt atgtgagggc gaaatcttgg attatacaaa tgttcattgt    124680
tttgatctaa ttgaagtcta gattcaacat gtttatacaa atttagctct tttccacacc    124740
tgaattcaaa ttctgacata tcaactttgc taacaaaatc acactgtcta ttgccattag    124800
aattaggaga ttctgtatat gaaggttta actctgtaga ggaacaacta tttctactta    124860
atacagaatt tttagaagat gctgagctag atgacttaca actgcattta ctgcttgaac    124920
tgctgcttga actcgatgta tccgtatcag agtcactgga tgaacttcgt gtagattttg    124980
gactcataga tctatcactt ataggaaact tttttgtttc agaggagttc tgtgtgcatt    125040
```

```
gtaattcatt atcaaagaat tcaaatagcc cattctctgt gtctgattta gctaaaaatt    125100
cttgctcagg acttacaaaa tttttgtgcta tttcatctgt ggtttgagaa atgatctgtt    125160
ccatgtgttg attttctatg ctgtgtacat gttcaacttc tgactgtgaa taatcattta    125220
ctggtgattt atattgtcct tcctcagtac tacttgaatc agatcgtgtc ctttgtgtaa    125280
gattgtcgtt acacatggaa tctgttgtat ttgatttttc agattctaca ggggattat     125340 cgatagaagg tatattacat ggtgctgtga ctttcccctc aaaatcgttg tccttagcat    125400
ctattttgga attaacagta gttttttgctt gtctaggtct acctacacga tatgaatttt   125460
ttcctgtaca ttttgtatca gagaaaacag tactagaatt acaatttaag gcagtactta   125520
ctgtacagcg tgaagattgc ttaatgaatt ctatatcaga agcagaaatg tctttgtcat    125580 tttttttctag gagtctttta aaattaatca acttagttgg agctcgttga tttgattcct   125640
gtacgtctgg tttaggagtt aatggcagtg gagaaagcat tggttctagt tttgataatt    125700
ttctgagatt ttctatagct tcatctggtg atttgtcctt tttctttaag tttgaagaac    125760
ctttgtccaa gttgggacaa tgcttagaat ctgtagtcga tgtgatttgt ttttcttttg    125820
atgtactagg tcttgttcta gctttcataa aagtcttttc ctgtgaagac ttgttatatt    125880
tacatttgtc tacatctgaa gtcgaagata gactgtcttt agccagggga actatatcag    125940
cattataaat tcttttaatt agatccatct tatgagaact tggaatatat gacaagctta    126000
caacatcctc attttgtggt gttttgtctt tgtctgtctt tttcctggca ggttttttcca   126060 aattgttcac gtttgagatt aatttggttt ccttgtgatt tgtctgaatt ggtgtatttt   126120
gactgtattc acttttcttt gataatgtaa gacctgatga aatacattct ttttgaaggt    126180
tttgactatc tgtgatcata gagctgcttg gaatttgtga aaaagccatg ctgtaatctc    126240
tgctttgaaa gccatagtta ggacaaagtt gttgataatt gtctctgtaa ggattatgtc    126300
taaaatctga attgtatgag tcatatgact gatctcgttg catatattcc ggaaaggtaa    126360
attcatttct gttggaaaag tcatgaaatt tagcatagcc acgtccacgt ctgttgtaag    126420
gtctgtgaaa atgttaccca taatgatttt ggtatttga gttagggtta caataatttc     126480
tactgtcata ttttcctctg ttgttgcgac ccctgtaatg atgttgtcga taggttgtat    126540
cgaacgaatt gtgacaaagt tctctatttt tatagtccaa attgttaaaa atatcaactg    126600
aagattgggg ttgatatggt aaagagataa aattttctcc acttgcttga ggataattat    126660
aatacaatga ttgcagtcct tgatgtggca attctgatgc aaatcgaaat tgtccagttt    126720
cagttgtatt tggagaagat tcagaagtaa aagtacttct tgatttaaga ggaatagcac    126780
gtcgcggatc ttgaagagtt tttgatgtga ctatttcttg gttgttaaaa tttgaataag    126840
ttatttcatt ttctggtttt gtatgatcgt gaatttcatt atataaaccc gaaagagtca    126900
tggcttcacg aaccacgtca gctgtagtgc tcatgggtgc atgcaatggt cttttttctg    126960
aaaatgaaaa ataaaaattg tttattttaa aatgttatta aattagcgat aatactaaga    127020
tgatatatac ctttaaatag agtggaaatg tactttttaat tgtctagaaa atataacgca   127080
atatgttagt taaaaatgta acttgttaga ttgatatttc atgggccctg aaacctgcat    127140
atgagctaat gtgtgtacaa atttgtgaca ataaatatta aagtggaaac attccaaatg    127200
tagcaattta catgtaaacg gatatgtaaa tgtaataaag atgtgtatgg ttatgtcaaa    127260
agagctaatt tgcaaacatg cagttattaa ttgtaatgga tgtacaaatg ttgatacatg    127320
tttgtgtctg ttgctgtgta tatgagttta tgttaaatgt ttatgtaaat attatatgtt    127380
ggtacatatc aatgtatttta tgttgataag cagatgttag tatgtattag tatcaatgga   127440
```

```
ttgtagtatg ctactgcatg ctattaaaca agtagagtgt ttacttgtat tagattatat    127500
ttacatgaca ttgtcatgta aatatatagt tgcatacatt tttcatgtaa caacacatat    127560
gtgttcatgt acatattaca taatatatgc tagtaaatga ttacatgcac tagtaaatat    127620
ttgcacatgc taatgtgttc atgtgggtat atgtacatat tacataatat atgctagtaa    127680
atgattacat gcactagcat atatttgcac atactaatgt gttcatgtgg gtatatgtac    127740
atattacata atatatgcta gtaaatgatt acatgcacta gcatatattt gcacatacta    127800
atgtgttcat gtgggtatat gtacatatta cataatatat gctagtaaat gattacatgc    127860
actagtaaat atttgcacat gctaatacat aacagtacat gttaataact tttgatctat    127920
gccgctacat gttagtacat gctatactga taatgcgtgg aagtttatta tttggatttc    127980
tgtaaggtca tgtgtattct atgaatgagt atataaatgg gtatgttaat atatgttagt    128040
atggttgcaa gtaaagatat gttaatgtgt attagtaagt acgtaatgta tgtgaatgta    128100
ttcaattttc aaagaaatga tatagaaatt tctaaacatg ttattgtgga aaatgtagat    128160
cttgtgatct attataataa tataaacata aattaaattt ttaagttata gctaccaatc    128220
tttgcctatt tttcttgggg ggcatacttt ttatatgatt ttatatgtac ggaaatatat    128280
gtacgtagaa taaagaataa aatacttgaa atcaaaccct gttataagta aatttactta    128340
gtatcatata tgtataaatt ttgataattt atgaagatgg cataaatgtt gaaaatattc    128400
atgtgtttgt tataagaatt tcaatgttac taaaataaaa ccaatcacta attatctttt    128460
atatgcaaaa atgtgtcttt gtatatattc aaattaaaat ttaaaactta tgtttttaatc    128520 atgtgaaata cagatgtatg aatatgtagc atggaaactt caaaaatata aatcatatag    128580
acctattgct ttaactatat ttaagattta catatttaaa tattacataa taaaaatttt    128640
aatatttaaa taaaaatatg tattataaat atgttatttta ctagtacagc tttataaatt    128700
aaagaacata tgtatttaaa gtttaaaaac taatgaaatg tgcttctatg agttaattgt    128760 aaaatgtcaat tttgtgattt taatattttt ctaaataatg agattcaatg ttgttaatta    128820
gatgtgtgca gtttgagaac atgtttatat ttacaaaaat ttgtatatat ttaaaaatat    128880
gttaatcagc atagccttat ttataatgat taattttaaa ttctatgtaa ttaaatctta    128940
tggacaaaat aaatttcaaa ccatttattt tgaaaaacat aaatgcagtt tagaactgat    129000
acaatttttt ttttcaaaag gggtacatac ttaaaagatt ttttacagtg gttataaaag    129060
tattagaaaa ggaattaaga tatatatgaa aaaatttcca tcctgcttat ggaactataa    129120
tatatcaaag caatttattt atgaaaattc caagtctatg aaagtaaaga tacccattca    129180
agtgaaaggc tattatagtt aggagggcta gcaatataag aaaacttata ttcaatgtat    129240
ttttttttaa gctatgaaag taaagatacc tattcaagtg aaaggctatt atagttagga    129300
gggctagcaa tataagaaaa cttatattca atgtattttt taagctatga gataaatttg    129360
ataggtctaa acatttttat ttataagaaa aaatgaaaaa attttatttc atagatacaa    129420
taacacagat gaaagttaca tttataatgt atctatccaa attcttataa tgtgtaaaca    129480
gtaagttaaa ctaatatgta aaatatttaa gtaaaaaaag tataaaaaac ttaaggttta    129540
tttaaaagtc catattttat aaaagttaat gaaaagaaa ctgaatagaa atagattgat    129600
aagtccatat gcaaaaacta caatttcaac aaaaggaaaa gtgatgttta atagatttga    129660
gcattttcca aaaatggatc atatccctgt ggataacctt caagaaagtc aacataagtt    129720
tgatcagaat ctgtgttttc ttttcccataa ttttgagtgt caacactctg ttctaaaata    129780
aatgagttca tctcacttac atttttattt gcatatctct ttttttaattc ttcataatgt    129840
```

```
ctattaatac cattttaat catttctgtg atttccataa aattatccat gataatattt    129900
gttaccatgg ttttagtctc tgaaatgctg tcaacctcaa taaaattttc ttggagtttt    129960
ggaaatatat atgagacatt ttcccgccta tattcttcat cattacttct tattggaata    130020
aaatgattat taaaacaata acttgcttgt ttggtcagtt ctttattttc atctttttc     130080 atgcctgtgt ctggaatgtt aactttatga gtcttacgta aaaccacag gcagttttt     130140 ttaggaacaa ttttaactct gacacctctt gtcacccccc gtatggatct gataggaatt    130200
gtgaaaacaa cactagggaa tccattgttt tcacagttat cagaattgtt aattagtttt    130260
gatctgtaag gaatagaatc tgtagacatc tctgtattaa aattactcat gttttcattg    130320
tctgtatcag tgcaagaatt taactccata ttattgcagc cctctttaac aattagtttt    130380
tttttttttg ctttgctagt tttcaacttg ctttcacttt ttctctttaa ttgttttttt    130440
ttaacagcac tgaaatcatg tgctgtagtc tgtgagtcac tgaaggatgt tagactgaca    130500
ctactgaatg tagaatttgt atcagtgctg gagctctcac tttcatatat ggttgattta    130560
tctgtatcat aaccatatgt ttccatctca gaaatcacca gatttgtatt atctgtatct    130620
ctactgttat tattggaatt ctgctccaat aaaatcaatc cttcagcggc cacttttcc     130680 acatcacttt ctgtgtcaac atcagctgtt gatctttcta cagctctatt agttgaaata    130740 tccttttct tatctctgat gtaaaaggtt tcattaggaa attatctgg aataattaaa      130800 tcttttccat ctttatattt gttttcattt ctgttaaggt tatgaaaatt tacattggag    130860
gttttattgc cctgactaac actctgttta tttttaatca tttcttcttg ccctgataaa    130920
gacttatctg ttttaatttt aacatctgtt ttgtcttcag acagattgtg acctttgttc    130980
tgattatcta atgtatgatt tgtcatggta aaaagttcaa agtactgttc tttatcttgg    131040
gtgtccttat taaatattga cctttccatg agtattccag ctgggctatt tgtttttta    131100 tctgttctgg aaaaggtagg aggaaattca tttgaaaatg tcaaagagtt attgacgcaa    131160
atttcctcag ttactgacct ttccatgagt attccagctt ggttatctgt tttttatct    131220 ctcctggaaa aggttgtatg aggaaattca tttgaaaagt tcaaagagtt cttatcttga    131280
taagtttcct catttctttt aaggttatac aaactcatgt taaaggcttc attgttctta    131340
ctgactttct gtttgttttt aatagtcttt ctctgtcctg ttagaatttg atctgcttta    131400
gtatccctgc agcttttcat agtagcctct ttgaaaaaat cctgtgtggc tgctgcttcg    131460
gaaagccccg tctcatttt tatagcattc acttcagaat ttttctcaac tgagattata    131520
ggattatcag ataagaatct gcaaatagta ttcctggaaa aatcctgtgt gtctgttcct    131580
tcagaaacat ttacctcact ttcttcagta ctcattccag gatttgtttc agctggatac    131640
atgagacagt caggtgagtc ttttgaaaca acctttttgg caagattctg tgtatctatc    131700
tcttcaaaga aatctaattt atattctctg gtacaaactt caggatttt tccagttgtg    131760 ttttagagt gtgattcatc tgatgcttgt gaaacagcca gagttgtttt aatggtttgg    131820
catatgtctg aaaaatttga ttgaacattg tactgttcag actttgaaac acactgtgta    131880
ggactgacat tctgatgtac actttggtag gattgttcag atgtttcaga acattcctca    131940
gaatactttc cataatcatt aaaatcttca atttctggtg gagtcgagtc agaattatat    132000
aagtgtgact caagcaaagt ggaagagtga tgtccatttc ctgtgacata tccatttcta    132060
atggatattg aatttaacac tgtaacttct cctgtgacat catatagctt ttctatttga    132120
tcacaagcat cattaatcat atgcataagt gtgatcttaa attcttttct atttgccctg    132180 aatttttgc atgaaaattc tttagagcat attacaatac actgcagtac agcagctcct    132240
```

```
aggttttttg ctgcctctat taaatttata caattgaaat gtattttaag gaatgtttcg    132300
tcacacattg acatgaacat ctgattcatc tgtttgattg caaagtcttt catagtttga    132360
gctattctgc tgttttttc  aattatttca aatttacatt ccaacaaatc ttttttaatc    132420
ttatttgttt ttatgtagaa tgcctgattg gaaatgttta tatctgttat gtctctgttt    132480
tttcccatca ttaataacat tgttgcacat ctgttaagtt tctcattact gcttataaag    132540
ttgcccatac ttatgatctt ttttatacat ttgataaatt ctctatccat attatttctc    132600
aaatctgata atattctct  acaatctgca atcacttttt taacaatttc atcaaattta    132660
tcacaggcat atacagtgta tcttgattca caccaaagaa aaaattctaa ttgttctcca    132720
gataagatat cttcataaaa agatataaat ccagaggaag caccactaat taaattaaca    132780
tttagcatct gagataattg ttctaaagca agatctgtaa gcatgtgtct gtcattcgtt    132840
aaaattccag cgtggttaat taaacaatct tcaatgtctg ctttttcctg atccatggca    132900
gcattcacgg atttaagaat accttggatg caggcactaa tggactgagc tagaatttaa    132960
agaaaaagt  ctaaatatga aatctgtaca catatatcat attttatatg taagaaaatg    133020
aaaaaaaaat acctgctgcc agtttaatat ccgaggaagc tccttcttca acatttgtgg    133080
aataggaagc atttgccgtt gcaatatcat tagatgatat tgagtcaagg aaatcaaaag    133140
aatccaattc ttggaagaga gtattatcaa aggaagggtt gcattttaaa ctgtcttgca    133200
atatgtctct gatggtctct tccacggtgg tatctgggtg atatctgtaa taaaatttat    133260
aaattttatt acagagaaat taaatctgtc ttttttgtat taaaatattt aggtttacct    133320
actcaatatg tctttcgtca ttcgatgcca tggtttcaga tggttgtcca acaatcaaca    133380
taggtgaagt agctccactt cttttccatag ttttatctgt atgtttagcc acacctacaa    133440
taacaaacca atcagaaata ttaaccccat tccaaactca atataaggcc agcctaaaaa    133500
tactttcaag cagagttta  aaactctgct tgaaaaaaat gtatactctg gaatatgaaa    133560
aacgtgtatc aaggccaaaa cttacttatt ggatcatttt ggcaatatta tttgtttttt    133620
taataataac tggatctgta ttaattgtaa ttgaaactct gtcaattcaa gaacgactt     133680
tgaatgctca aaatgataaa acaagtactg ttgttccaga attaacatct aattctccag    133740
gtttgttcag ctataaaatg tcattgttta aaaaaaagt  ttgtaactct gttaatatga    133800
atatttttc  ttgtagatca aacaactgtg acaaatttt  ctgcaagttc taaaccaact    133860
cttagcagta aacaacccgg atggatacag gcactaacta cagcttttgg aattttaaca    133920
ctgttttcag ttatgatgat tattataact tgtaatttt  ggctaactga gaaaaatgac    133980
aaaactgcaa atccaacaga atactactca gaagacatat tagattatac aaatccaagt    134040
tttacagaaa ttgatgaaga cagctcaaaa gtataacatt gcttcagaaa taacaaaatt    134100
gtaagtaaat ttacttgatt ttcttacact atgagatatt taatggtttt aaaatagaaa    134160
atgtcagagt ttaaagtaaa attaatgtaa tttatgattt tttaaatgtg tcttacaact    134220
agaaaataac tttaaattat tattagtatt gtaataattt aaaattatta atattagtat    134280
tgtaataatt taaaattaat aatattagta ttataaacag ttttaaaat  ataaaaaaa    134340
taaatttaaa atttatatta aatgatttta aatttactta ccagatggca gcgatatatt    134400
ggaaattctg tgtagcagaa ctgtatcttc aagctcttga agaaaagtg  gcaaaatagt    134460
tgatctgtct tcttattata tacatttga  agcggatgtg atgcacagga aatgacgtt     134520
aatatatcaa ccaattaaaa aaagccaaaa aaattataat actaaaaaaa ttagggttta    134580
accttatttg tacatgtatt ttttttaaaat attatttttc caataaaaac cacaatggat    134640
```

```
ttatatttta cgtaaacatg attttttgcgg ttattttatt tcgaattggt atttaaatct    134700
ttgaaacaac aggaattgcg gttgtcttct cagcaagttc tacacattcc cactcgcttt    134760
aggcaggaaa gaccccaacc acataaccca ctgacattta aacccgtgaa acaacagga     134820 actgcggttg ccttctcagc aggttttacg ggttctcacc cgtttaggca ggaaagaccc    134880
caaccacata acccactaac attttaatat gtgaaaacaa caggaactgc ggttgccttc    134940
tcagcaggtt ttacgggttc tcacccgttt aggcaggaaa gaccccaacc acataaccca    135000
ctgacattta aacccgtgaa acaacagga  actgcggttg ccttctcagc aggttttatg    135060
agttctcacc cgtttaggca ggaaagaccc caaccacata acccactgac atttaaaccc    135120
gtgaaaacaa caggaactgc ggttgccttc tcagcaggtt ttatgggttc tcacccgttt    135180
aggcaggaaa gaccccaacc acataaccca ctgacattta aacccgtgaa acaacagga     135240 actgcggttg ccttctcagc aggttttatg ggttctcacc cgtttaggca ggaaagaccc    135300
caaccacata acccactgac atttaaaccc gtgaaaacaa caggaactgc ggttgtcttc    135360
tcagcaggtt ttatgagttc tcacccgttt aggcaggaaa gaccccaacc acataaccca    135420
ctgacattta aacccgtgaa acaacagga  actgcggttg ccttctcagc aggttttacg    135480
ggttctcacc cgtttaggca ggaaagaccc caaccacata acccactgac atttaaaccc    135540
gtgaaaacaa caggaactgc ggttgtcttc tcagcaggtt ttatgggttc tcacccgttt    135600
aggcaggaaa gaccccaacc acataaccca ctgacattta aacccgtgaa acaacagga     135660 actgcggttg ccttctcagc aggttttatg ggttctcacc cgtttaggca ggaaagaccc    135720
caaccacata acccactgac atttaaaccc gtgaaaacaa caggaactgc ggttgccttc    135780
tcagcaggtt ttatggattc tcacccgttt aggcaggaaa gaccccgacc acataaccca    135840
ctgacattta aacccgtgaa acaacagga  actgcggttg ccttctcagc aggttttatg    135900
ggttctcacc cgttaggcag gaaagacccg aaccacataa cccactgaca tttaaacccg    135960
tgaaaacaac aggaactgcg gttgccttct cagcaggttt tatgggttct catccgttta    136020
ggcaggaaag accccgacca cataacccac tgacatttaa acccgtgaaa caacaggaa    136080 ctgcggttgc cttctcagca ggttttatgg ttctcaccc gttaggtag gaaagaccca     136140 gaccgcataa cccactaaca ttttaatatg tgaaaataaa caggaactgc ggttatagtt    136200
tcagtacatt ctagagatta catcctgcta aggcgaaaaa cactttaacc gcaaaagcca    136260 ctgatttta aacttgtgaa ataacagga  aaccacagaa acgtcaggaa aaaaacgttg     136320
ttttataatt atgtccataa aacatgcaac ataatccaaa ccggccaatg attttttctgc    136380 ttaaatgtaa tttaaataat ttattcatac gtaagttgtt atagccacgc ctacgcagca    136440
atgtatataa gcagacaccg tcatttcgca gttagtctgc tggaaagctt gtgaagacta    136500
cataaaggta aaaatttgac atttgcaaat gtattttata attacattat tttagtttaa    136560
aaaatccaaa attcttaata gaatttatt gtgaaattta aagatttttg taaatatgca    136620
ttaatatcta ttaaataatt gttatttgac agatttacta aatgtagtgt aaaatatcaa    136680
aaaaatttaa aattaattta ttctgaagtt taacattttt taaatatgtc tatttttagt    136740
ttcatttgat acattgcgta ggtttggaaa tgtgtttcga aaattgctgt aaaaattatt    136800
gactcttttt taaatttata gaacattgga tgtaattgca cattcctgga aaattcaaaa    136860
aaagaaaata cagtaagtca atttatatgt attgatttta aatggcctcc aataaatatt    136920
tttagccagt ttaatgtaaa acaaagcata aagtttatgt agttttaaaa tgatgccata    136980
ttttaacgaa attcatttaa agacagtatc tattaagaat ttaaatgcag ttctatggct    137040
```

```
ttaaaaattt gtacgtttta tttgaaaagt ttgctctatt tgaaatcaaa tgttttagat    137100
atttcttttc ataaattcag ttgaaatatg tttcatttat aataggtatt tttctgtttc    137160
taaaaataga tgataaaagt cactagatag aaaatatctt ataaattgtt atttagtaga    137220
ataaacatct ttttatataa caaaaacaca aagtacatga ctttagaaag ccaactaaat    137280
gcattattat ttaaaaatta cagaatcaac gagtaatgtc actatagttt tttaaagtaa    137340
cttttaattg ttcacttcta gttgtaatca aagaaggat ggagagtggg gatagtttcg    137400
gaaataatca ccaagtctca tcgaattcag atgcttttca attccggcaa tattcaacaa    137460
ctgtagatac ttttgcatat tcatcaatgg atccttcaaa ttgcatgctt aatgaacaaa    137520
ctcatttaga aacggtacta gtttatcctg tttacaacat gtcttcccag caaacagtgg    137580
agagaaatct ctatgccaat aatataggaa atggaaatgt gctgagttat tgtagacaag    137640
atagtttgca aggaaaccaa ggaacatatt ttccaacata tcagggattt cactcaaaca    137700
ctcctcataa cttttctata gagaatttta attttggcac caatgtcatc aggcctatac    137760
catttagaaa tgagggagta gacgcatcaa catccaaaga ttatgacttt aaaccttgca    137820
ttacaacgat gcaaatacag tttagtcagc catctgcttt tcaaacttat tctttaatga    137880
atggaaattt tagtgaaaat ggttatggat acaatactaa gattggtgaa aattgtgcta    137940
tgtcttatgt tgagcaagag tctgtagact caaaatatcc aaacaaagaa gttagtatct    138000
cttatcaaag aaatgaacat tatgatgaga atctcccgac gagagagctt aatacagatt    138060
ttccgcaata taatcaaagt tctgtgttac agcacacctt tgcgaatgtc caaagcatta    138120
tttcacagca aagtccatat cagttgattg gaaaagaaaa cagctttaac aactatctgg    138180
aaacagctaa cgttgatagt gattgtcaat ctaacggggg gcctaaaatt ggcctagaca    138240
cagatcaatc tgtttttttca gatgaagtga ctggggcgtg tgtagaaaat gttcatttc    138300 caatgaatcc taaaaatgag tatgtaaata acatatcact tgatgtacaa actgaatttc    138360
ctgtgactga gaatcctctt gtaggagaaa gtcaggctac aaagaacaag gatgtggaca    138420
gtaacgcaga ggttaataat cattctaaat atcgtctatt gaaacgcaat attcaccga    138480 ccatgggtaa tattaaacat ttaaatttta gttgcaagat atctaccgaa gaagaaagga    138540
aaacattttt taacaggttg agtgagctat tgaaaataag ggatgatata aaaaacacta    138600
aaatttcttc aaaagtggat tttattcaat ctgaagcttc tacatcattg gacatttgta    138660
aaaatacatt caataacaat tcggattcat cggatgtgga cactgatatc cttgcagaca    138720
acccattagt gatatgtgaa aatgaactga tttgtgataa caatgaggaa aacatcaagt    138780
ttccgcctaa cgttgaaaaa gaggctgtcc ccatgcagac ggttaaacgc agctttccag    138840
aaatctgtcc agagcatttt aaaaaaagaa gatttataaa tggtgatgtg atttatgaag    138900
atttaaattc tgtttataaa gtgatgccag caagtgcgac atatgacgat gtgcgtttcg    138960
gagaagtgga ttatcaaacc tcttcggctc agacaaaaat ttccaaccac cagttagcgt    139020
tgttgccaac aaattatcag cacatgatag ggcaggaaac agacatttca tcgcgggatt    139080
atcacaatga cagtgctcaa attatttaca attgctcatt tcaacgacag ggaaaaaggc    139140
ttcttgctga tattccatat agaccttggt taaaagaaaa tgttcccaca ggggaatatg    139200
gaaaaagatt tgtcaaaaca gtccctagac cagccagtgt tttattttt ggaagatgtc    139260 gaaaaaaaat gctgagggaa agcgttaaat ctttatgca tttaagcaag ttacagtata    139320
ctaaagaaag tctagaagca tatgtactta gaaattgtaa caagttttta gattttgagtt    139380 ggccgatacg acacaagatc tatattatgc ctgatgtgag tagaaattat aacattgaag    139440
```

```
aggttaagaa tttatttccc gtaccggaag gctggatggt aactctaggt tttgtaggaa  139500
cagaagaacc ggtgaccaaa atttataaca ttgctgtatt gttatgtgaa aatgggtggg  139560
tcatgattca caagaatgat aaagtggaac ctgaacttta tttagctgct tcgaatctca  139620
atgaacttat agaggatgga ctggcacgct gtgattgtat ttacgagaaa aggtctgtac  139680
catatggaat tgtcatggaa ggaaaattaa dacagtttat ggacaatttt ggctcactgc  139740
aaagtgtgct agcctacaga aagtatttac atggttttct gtgggctttt aatggcacac  139800
ctggaagatt ggcagacaga gtgttccata cttgtgtacc tggggttcat aatgcccttc  139860
ccttagatgc tgtgattaaa catgaaaata atcccttgta tttcattgga tatgtaacca  139920
cctttaaaca gcaaaatgat ttcaatgcta atgttttcat cgcggtagat ggaaatttaa  139980
gcatttatgg ctatcatctt atatctcaaa aaacttggtt tctagcaaaa acattttcaa  140040
cttttctgaa aatgggaact agaaagatgt actatgatta tgagattcca cttaaaattc  140100
atttaggaga tagtgcagat tcatttctgt cttgttttaa aaatgcccct tgtctgctgc  140160
ttaagccaga agtacttaga aagcaatttc ctaaacctta gattgttaaa acttggataa  140220
ccaaactata ttgaattatg tatatcttttt tattgaatgg gacatgtttg taaacatttt  140280
tgaagcttaa ataaagagtg ttttcaaata tctctgtttt gtctctttac agaggacttg  140340
aaaaatttt tactgtctttt agaacttgcg aatacttgtt gagcttttct ttccgggtaa  140400
cgcatctcca cagtggtgca ggtcgcttcg taaatataat caaaaaattc ttctacttct  140460
agtagttttg gtgtcggatc ttcattggcg ccataatttg aattaattct agcagctttt  140520
attccttccc aactaaaaga gaaaatgttt aaattacagt aaattgcaat tggcattcct  140580
tggaaaaatg atgctcacct gaaggctttg tttaaatcaa tccacggtgg cattggttga  140640
gtctttgtag gtttgttgtt aggcgtaggt ttaatttcat gtatgattgt tgtactcgta  140700
tatataggag tgcagtatgt aatacctccg gcctgatata tgctgcgaac gagaaattaa  140760
gaaatgagtt tgtttctaag acgaaaagta ttgtcccata cagtaaaaac tcacatgttt  140820
ccgtcgtcac atgtcagttc tatcacatca ccgtctgtaa atcgcaagta ttcatcacag  140880
caggattcta gtttaggtaa ttgaagttcg ctagctagaa ttaaaaaaat tctatacaat  140940
atatagatta atctatatat gcacatcatg gacgcatttt atggcttcga gctatacact  141000
cttttgtttt attcatttct ttaatacttt gtattttata gaaactaaat aagaagtttt  141060
aatgaaatgc atttattaac cacccataac attttgtaac ttttcggata cagtattgtt  141120
aaaggcttga gttatatttc cactgttaca cagttgagca tttaaagatt tgttcgagat  141180
gagttttttt gttgtccggt catctttttt taagaaagtc aataacagcg tatcaatagt  141240
gagtagtctt ccgttgtcaa actctgtttt tgcactgtcg gttttaattt taattgagct  141300
ggtatgaaaa aaaaaacaca ttaagttttc ttgttagatt cttatccccc ccccccccga  141360
caggagagtt ttcaaattac caaggtccga atctttaga tggtgttagt agtacatcgt  141420
attggagatc cgttgtagat atcttagatg gaaagtcttg ccacatagca cttacgatgg  141480
ctggatcgaa ttctctagga tgaagaagcg aaaattagat tatatctagt tttgcttttct  141540
aagttaataa tatttacaat ttacctgtta ctaaacgact gtcggtgcgg atgtggaaac  141600
atgtcttgta cagtctttttg tccaatagtg tcgaataagc gttctatttc tagtagtgct  141660
attggaaaaa gactgcgaaa cacaatttat ttgcttattc tctccagttt ttaaatttcg  141720
agtaataaaa gacacttgct tttcttacat tacggtggtg acgtagtttc gtgcagttgt  141780
atcgttttta ggcgagcacc aaatttgtcc atatgtagac tggaatctaa aaaaaaaaat  141840
```

```
attgtcaact caacctttt gtcattttgt tgattgcatg tatgtgcggt tttcctctttt  141900
tttagtgtgc ttgttaatat gagcagtttt gtgcgacagt acttacactg tagtgtttgt  141960
taagcacctt tcgtccgtgg gtatctgtct aataatgtct atgtctctcc agggttcgat  142020
ggttgtctct gtccagggat gttctgacca tcgccacgcg tatgtcgtgt tttctcgact  142080
tttgttctta tccgggcaac aagcgtcata caatggtttt tctgaagtca tgttcacttt  142140
aggtatgtta aaatcttctt ctttccattg tgaaaattgc atgcaagttt cccattcgta  142200
gcccttgttg tcttttcgga cgattgccag tgatatttgt gtccgaaagg ctattccgct  142260
gtagctacgc atcttttaa aatctgcgcg tatctgtaat tcactaataa gcgggtactt  142320
tacattcaaa ttcttggaga aaaaaataac tatagatagt acctttttt gcttaccatt  142380
gagcagacga ctgggtgtat tgctcacgtc tttcccaacg gtggcgagca gggaacaaaa  142440
ccaggctcgt caaaatgttt gcggtgttca ttcttttcac atacaacaaa ctgttttgtt  142500
tacttccgaa tcctccatta agtagagaat agtgtaagcc tgtagttact gacaagactt  142560
cagacagccc tttactcata attttttctc ttaatccgcg cactcccaat gagttctctt  142620
ttagtggaat gcagagtgtt gtttctaata atataaccct tagaagaatt aaaagtaagg  142680
tgtgagaaat ttacttaaaa agctcttcaa agtcgtcata ttgtagaaat cagtgtaacc  142740
attttactt actgtgcttc gtctggccat tcacattcgc aggaaaacga tgtacatctt  142800
gtgtattcta acaagctttg tctttcctcg gaacttagac caatatatct agtagagctt  142860
gcgttgtgca tgttttcatt tattaagttt tcgattatat cttctagagt tattgccgtg  142920
cgtgcttttt caagtgggac cgtattggta catatcttta tgagtaatgc gaaaattata  142980
taatgcagtt gcaccattat ctgcgaagag attttttttg cagcgtcttt atgtgcaggc  143040
ttattccccc ccgtttcgta tttcaaatcc taaataaccc ccgggggggta aaaaaggggg  143100
gggagctaac cctaacccta gctctaaccc taacccctaac cctagctcta accctaaccc  143160
taaccctaag tctaaccctg accctaaccc taagtctaac cctgacccta accctaaccc  143220
taaccctagc tctaaccctaa accctagctc taaccctaac cctaacccta accctagccc  143280
taaccctaac cctaacccta accctaaccc taaccctaac cctaacccta accctaaccc  143340
taggtctaac cctaacccta accctaagtc taaccctaac cctaagtcta accctaaccc  143400
taaccctaac cctaacccta accctgaccc taaccctagc tctaaccctaa accctaaccc  143460
taaccctaac cctaacccta accctaaccc taaccctaag tctaaccctaa accctaagtc  143520
taaccctaac tctaagtcta accctaaccc taaccctaac cctaacccta accctaaccc  143580
taaccctaac cctaacccta agtctaaccc taaccctaac cctaacccta accctaaccc  143640
taagtctaac cctaacccta accctaaccc taaccctaac cctaacccta accctaggtc  143700
taaccctaac cctaacccta agtctaaccc taaccctaag tctaaccctaa accctaaccc  143760
taaccctaac cctaacccctg accctaaccc tagctctaac cctaacccta accctaaccc  143820
taaccctaac cctaacccta accctaaccc taaccctaac cctaacccta accctaaccc  143880
taaccctaac cctaagtcta accctaaccc taaccctaag tctaaccctaa accctaaccc  143940
taaccctaac cctaacccta agtctaaccc taaccctaag tctaaccctaa accctaaccc  144000
taaccctaac cctaacccta accctaaccc taaccctaac cctaagtcta accctaaccc  144060
taaccctaac cctaacccta accctaaccc taaccctaag tctaaccctaa accctaagtc  144120
taaccctaac cctaagtcta accctaaccc taaccctaac cctaacccta accccaaccc  144180
taaccctaac cctagctcta agcctaaccc caaccctaac cctaacccta gctctaagcc  144240
```

```
taacccaac cctaacccta accctagctc taagtctaac cccaacccta accctaaccc 144300
tagctctaag cctaacccca accctaaccc taacccctagc tctaagccta accccaaccc 144360
taaccctaac cctagctcta agtctaaccc caaccctaac cctaacccta gctctaagtt 144420
tcaccccaac cctaacccta accctagctc taagtttcac cccaacccta accctaaccc 144480
tagctctaag cctaacccca accctaaccc taacccctagc tctaagccta accccaaccc 144540
taaccctaac cctagctcta agcctaaccc caaccctaac cctaacccta gctctaagtc 144600
taaccccaac cctaacccta accctagctc taagtttcac cccaacccta accctaaccc 144660
tagctctaag tctaaccca accctaaccc taacccctagc tctaagtcta accccaaccc 144720
taaccctaac cctagctcta agcctaaccc caaccctaac cctaacccta gctctaagcc 144780
taaccccaac cctaacccta accctagctc taagcctaac cccaacccta accctaaccc 144840
tagctctaag cctaaccca accctaaccc taacccctagc tctaagttca ccccaaccct 144900
aaccctaacc ctagctctaa gtctaacccc aaccctaacc ctaaccctag ctctaagtct 144960
aaccccaacc ctaaccctaa cctagctcta agcctaaccc caaccctaa ccctaacccct 145020
agctctaagt ctaaccccaa ccctaacccct aaccctagct ctaagcctaa ccccaaccct 145080
aaccctaacc ctagctctaa gtctaacccc aaccctaacc ctaaccctag ctctaagttt 145140
caccccaacc ctaaccctaa cctagctct aagtttcacc ccaaccctaa ccctaaccct 145200
agctctaagc ctaacccaa ccctaaccct aaccctagct ctaagtttca ccccaaccct 145260
aaccctaacc ctagctctaa gcctaaccc aaccctaacc ctaaccctag ctctaagcct 145320
aaccccaacc ctaaccctaa cctagctct aagcctaacc caaccctaa ccctaaccct 145380
agctctaagc ctaaccca ccctaaccct aaccctagct ctaagcctaa ccccaaccct 145440
aaccctagct ctaagtttca ccccaaccct aaccctaacc ctagctctaa gcctaaccc 145500
aaccctaacc ctaaccctag ctctaagcct aaccccaacc ctaaccctaa ccctagctct 145560
aaacctaacc ccagccctaa ccctaaccct aaccctagct ctaagtctaa ccccaaccct 145620
aaccctaacc ctagctctaa gcctaacccc aaccctaacc ctaaccctag ctctaagcct 145680
aaccccaacc ctaaccctaa ccctagctct aagtctaacc caaccctaa ccctaaccct 145740
agctctaagt ctaaccca ccctaaccct aaccctagct ctaagcctaa ccccaaccct 145800
aaccctaacc ctagctctaa gcctaacccc aaccctaacc ctaaccctag ctctaagtct 145860
aaccccaacc ctaaccctaa cctagctct aagcctaacc caaccctaa ccctaaccct 145920
agctctaagc ctaacccca ccctaaccct aaccctagct ctaagcctaa ccccaaccct 145980
aaccctaacc ctagctctaa gtctaacccc aaccctaacc ctaaccctag ctctaagtct 146040
aaccccaacc ctaaccctaa cctagctct aagtctaacc caaccctaa ccctaaccct 146100
agctctaagc ctaacccca ccctaaccct aaccctagct ctaagcctaa cccagccct 146160
aaccctaacc ctagctctaa gtctaacccc aaccctaacc ctaaccctag ctctaagttt 146220
caccccaacc ctaaccctaa cctagctct aagcctaacc caaccctaa ccctaaccct 146280
agctctaagt ctaaccca ccctaaccct aaccctagct ctaagcctaa ccccaaccct 146340
aaccctaacc ctagctctaa gcctaacccc aaccctaacc ctaaccctag ctctaagcct 146400
aaccccaacc ctaaccctaa ccctagctct aagcctaacc caaccctaa ccctaaccct 146460
agctctaagt ttcaccccaa ccctaaccct aaccctagct ctaagcctaa ccccaaccct 146520
aaccctaacc ctagctctaa gtttaacccc aaccctaacc ctaaccctag ctctaagttt 146580
caccccaacc ctaaccctaa cctagctct aagcctaacc caaccctaa ccctaaccct 146640
```

```
agctctaagt ttaacccccaa ccctaaccct aaccctagct ctaaacctaa ccccagccct 146700
aaccctaacc ctaaccctag ctctaagtct aaccccaacc ctaaccctaa ccctagctct 146760
aagcctaacc ccaaccctaa ccctaaccct agctctaagt ctaaccccaa ccctaaccct 146820
aaccctagct ctaagcctaa ccccaaccct aaccctaacc ctagctctaa gcctaacccc 146880
agccctaacc ctaaccctag ctctaagcct aaccccaacc ctaaccctaa ccctagctct 146940
aagtttcacc ccaaccctaa ccctaaccct agctctaagt ctaacccaaa ccctaaccct 147000
aaccctagct ctaagtttca ccccaacccc aaccctaacc ctagctctaa gtctaaccca 147060
aaccctaacc ctaaccctag ctctaagtct aaccccaacc ctaaccctag ctctcagtct 147120
aaccccagcc ctaaccctaa ccctagctct cactgtcacc ctaacactag ctccaggtca 147180
tctgttctag atcctatcca tatctgccct gactcctggt tccataccgc tccgagcccc 147240
accctccgtc ccgccctcct cctgttctcc atgccctgcc ttctcaaccc ttcctcttcc 147300
acgcccacat tgcctctgca ctccgcgctc tcttggctgt gcgccctgcc tttccgtgac 147360
ctactgggag cgccgccaaa tctgttttgc cccgcccctg cgcgcgcggg aactgtcggc 147420
gccgcgctgc tgctagcccg ccttccagag ctccctccct ccgtctgcct cctcacccctt 147480
gccactcacc cttccatctc ttctatcaca gactctgtgt tacaccacct atgactgctg 147540
caaccacaga acattttgct ctccgcgcgg cactcaatcg ttactggtgg ctgcttctgg 147600
gacgacacaa gctcagtttg gtatgcaact acgtcacagc tcatcgccaa cagttactgc 147660
cgctgccgtg gcccgaacag gaatttctcc aacttgaccc ggcccccctac tccaatctcc 147720
gcaaccgtgt cgctcaccat ctccatcgcg gctggccagc ggcacacaac acatgtaagc 147780
taccgtacat ctcttttcaca aacccaaggc tcacatagag acaagcacaa gctcgcgcaa 147840
tgacattaaa acctcccatc attgtccttt cctgtcgctt gccgataac gtctttgctc 147900
tatcgcaggt ttcgaccccc gtccttactt ccccaatgct aaagtcaagc tgcttccgct 147960
cggctccatc acccttacca gatcattctc cagtgacgag cctcatccta ttggtgatga 148020
tgtgcatcac agtcatgacc ggggtgacta ccatactgtt atctgcagct ggctcacagg 148080
aacctccccg atcctagtgc tgcttcaagg accggacggc agcatctatt gccacgacgt 148140
gtaccgcggc cgattgtatc tcgtggccca ctctgtatcg ttgttcgcca ggctaggcct 148200
tcgccactgc gaacctttat atgcggcacc cagatggaag cacgttcctc tgcccagcat 148260
gtgggtggcg agcccgccag cgtccgccac cctcacgcaa acactcgccg tgagtgccac 148320
gcacggtctg gacgcgttat actcgctgct aaaaatccac agaggaactc cgtgttcgct 148380
aatccacccc gtgaacggct acgtcctgga catgatactg acgggccgct cattccaaga 148440
agcaccctgc caaacactc gcacgtccgt taaaacaacg ccacatgtaa tggacgcagt 148500
ctgcggtggc cgcgggtcat ggctgtccat cggctaccta gtaaagatgc cgcacattca 148560
cctggcggtg acccgaacat gtctggtcac cgccatagat gtccgacaaa actttctctg 148620
gcgcgtggcg gacgacgcgc tgctattcct ggtcaccggt agtcttttac tactgtcgcg 148680
gccgaccgca gacttgacgt cttggtcatg tttacagcaa gaacctgtgt ggaggaactg 148740
tctagatacg cgcggagaac aggatgagac agaagaccaa gagatgaaac aaagcacaag 148800
caaaaagcaa aatgagaata aaaaactcaa cacctcaaaa aaacacaccc gcgtatcgtc 148860
ggcaattccg acctttcccc tgagtctccg agaaacgccg ccagaagcca ggagcccagc 148920
cgtcctcgcc gccgccaccc agtctcacaa aactcgagcg atctcgacgc ataatgccac 148980
gacaacaata agaataccgc gccttcccag ttacctgctg gaagcgcgtc tgttgtccgt 149040
```

```
gacagctatc ctgaaagaca caaagaaaaa aaaaacccag cctcaggcgt agcagctgcg  149100
acgctcagcg cggtgtctga aagctcgcca aggtctcgcg taaaagaaca gatgtgaact  149160
tcagatgtac caaccaaata atacgggttc cgctataaaa agtgcacctc tattcccgtt  149220
cttatccccg ttctaactct tccttgtatc ataccttgca tgttaaccgg atcccgtgga  149280
tcttacacac atacacacac acacaaactt ggtgaggtaa acacagaaat ctcactaact  149340
cataatcccc tacacgctta ccaccaccta aaaatggtta tgaccaaaac tggcaatagt  149400
ctatcttctt tttctttcca ttcacagcca atgtgcagta ctcgtgggtc cacaacaacg  149460
aaagagactg tagagacact tcctttaagt agaccttaga gacacaccaa atacaaccac  149520
aaccaaaaaa aaaacagaaa acaacacaaa gccaatgagt gcagaaatgc tccgcgctgt  149580
tcagctccag ccaagacgcc ggggacattc ctcatctccc acttcccctc cactcgaagg  149640
agagcccagt cccaagagac tccaatcgag caacagtcac caagggcgta gaggcagacc  149700
taaacccaga gctaaaacat ggagcgaagc tttatcccac cggtccttcc tcaacattta  149760
cgcgtggctg tctttgagtc gagggtctcc gcgaaaagtg tacggatatg ccttcaggca  149820
cagaggagaa ctcgtagcat tgccatggcc gcctaactgg agcctggaac ttcaccacga  149880
tccctatcga gacgccagag cacaaaccgt ttggagtcac cgctggggat ggcctgcaac  149940
acacgtgaca gctcgcacgg tgcgggactg cggtgagtgt aagcagtgtg acacattgtt  150000
atcgcaattg tcttacccga ttaactttt attaatgtat taagcactct tcttcacgt  150060 gtgactgttg tgttttttgt tgttatctac atcccggcag ccctcgacac gcatatgtac  150120
gtgtgctgcg gacgcggaga aaagttgcag cccgtcggat acgtacgcaa cagagccgcg  150180
ccttcagacc tgaactcgtt acgcgtcctc ctcatagcca gggacggagc aatgtatgtg  150240
catcacatga gaacggcgcg actgtgccgc ctagccagca gtgtgaccga attcgcgcga  150300
cgagggctgc agcgagaatc cgaggtttat gaagatgatg tttccttgcc agaccgtcga  150360
gtaggttcgg caacggccat tcacctgttt gacgtaatta cccaggcagc cgatgtccac  150420
gacctactca ccgtggccgg actgtgtcag actcacaccg cgtcagctg ccaactgtgg  150480 tatacagacc acgatcccca caccgtcgct ggggcggcac gcttcacact gacggtcgca  150540
cggcagcagt atcgattgtg gccaaacgca cgacgcaaac tgctgcagca cctacatccg  150600 gaccaccac ttgggctgtg gctgttgtgt gccgtgctca cgtacgatgc aaaagagacg  150660
aatcgcgcag tgccacccgt aacgccaggg gccgaaaccg tgtgggtgat agttactggc  150720 agggggtgcca ttctaggatt ctggccgag agcgccaaaa tgtgcagatt ggcctcgtct  150780
atgaaaggac tctggaaaaa cggagcgcgg gcgctaaaag gtcactggac atacgcagca  150840 cccgccggc atagagcggg agaggcctgg cctttgtgtg cacactacca atctcctaga  150900
tagaacaaaa ttaaaagat taaaaaaaaa aagaaaaaaa gtacaagagt gttatcgcga  150960
aacagcgtgt caaaaaaaaa aacaatccac atactctaga acaaactgta cccaaaaata  151020
agtccgtgtg caaaactggg aaaaaaaaaa tcaccttcct cgttgccact agagggagta  151080
ccgaaagtga aggcaagaag gccacgctgt aaatgactgt cagcgtttgg cgctgaaaac  151140
attgctgttc ttgctggctc aagcacaatc acgtgattaa gattcctttc gttttcaaag  151200
tgtgcccggg aggcagacat gcccttctc gtgagacatt atgagatttg cctgccagag  151260
aaccacgtga cttggactta ctttcgtttt ctaaacgtgc cctctaggca tgaatgctct  151320
ttagcgttag ccatgaggct agcgtgatcc tgtatagtac ataagtttct aagaatatgt  151380
ttttaacaat aatcatgtcc caaaaagtcg cgagtgacta aaattctctg taaatgaagg  151440
```

```
caaattaaac aggatacaga cagttgtggc agtggtccgt ttcgtctttc tgtgttttcc   151500
ttacgcggct gacgaggtaa agtgtctcag tccatattgt tgtctgtgcc accgtagtta   151560
gcggtggcat actaaaaact ccgatagatg cagaacaata acaccgaaaa ccacgctgtg   151620
gaaccagacc acactttata aacaaaacgg ccttatcacc tggaaaaaaa actaaaaat    151680 aaggcaatga tacacctgac tttccattgg aaacctgccg taaccctgac cacaaatccc   151740
atgctaaatc ccctgaaaca ctgccaaacg tcgctacaag gttttccgg gatcgagccg    151800 cagcaagctt aaactgaggt cacacacgac tttaattacg gcaacgcaca gctgtaagct   151860
gcaggaaaga tactatcgta agcaaatgta gtcctacaat caagcgaggt tgtagacgtt   151920
acctacaatg aactacacct ctaagcataa cctgtcgggc acagtgagac acgcagccgt   151980
aaattcaaaa ctcaacccaa accgaagtct aagtctcacc ctaatcgtaa cagtaaccct   152040
acaactctaa tcctagtccg taaccgtaac cccaatccta gcccttagcc ctaaccctag   152100
ccctaaccct agctctaacc ttagctctaa ctctgaccct aggcctaacc ctaagcctaa   152160
ccctaaccgt agctctaagt ttaaccctaa ccctaaccct aaccatgacc ctgaccctaa   152220
ccctagggct gcggccctaa ccctagccct aaccctaatc ctaatcctaa tcctagccct   152280
aaccctaggg ctgcggccct aaccctagcc ctaaccctaa ccctagccct agggctgcgg   152340
ccctaaacct aaccctaacc ctagagctgc ggccctaacc ctaacccatg ggctgcggcc   152400
ctaaccctaa ccctagggct gcggcccgaa ccctagccct aaccctaacc ctagccctag   152460
ggctgcggcc cgaaccctag ccctaaccct aaccctagcc ctagggctgc ggccctaacc   152520
ctaaccctag ccctagggct gcggccctaa acctaaccct agccctaggg ctgcggccct   152580
aaccctaacc ctagggctgc ggccctaacc ctaaccctag ggctgcggcc ctaaccctaa   152640
ccctagggct gcggcccgaa ccctaaccct aaccctaacc ctaaccctaa cccaaaccct   152700
aaccctaggg ctgcggccct aaccctaacc ctagggctgc ggcccgaacc ctaaccctaa   152760
ccctaaccct agggctgcgg ccctaaccct aaccctaggg ctgcggccct aaccctaacc   152820
ctaactctag ggctgcggcc ctaaccctaa ccctaaccct aaccctaggg ctgcggcccg   152880
aaccctagcc ctaaccctaa ccctgaccct gaccctaacc ctaaccctaa ccctaaccct   152940
aaccctaacc ctaaccctaa ccctaaccct aaccctaacc ctaaccctaa ccctaaccccc   153000 gcccccactg gcagccaatg tcttgtaatg ccttcaaggc actttttctg cgagccgcgc   153060
gcagcactca gtgaaaaaca                                              153080
```

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 3

```
gctctagact gccacgtgag cgaaagcata cac                                33
```

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
ttacttaagt catcggggtc actatcttcg cag                33

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccggatccga gttaatgcat acatgggagg ccagg              35

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggaattcct gtgtaccgtc atggcttgt                     29

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacatgccta cgcggcctca ccgag                         25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggacgcgtgt agaaacggcc aacg                          24

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtactaacat catcacatgc gcggag                        26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggactattc agattcctta cagag                         25

-continued

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gactcagatc tcgagctcaa gcttcg                                          26

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ccttctacga gcggctcggc ttcac                                           25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atggaaacga caaacagccg gcgtg                                           25

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctatcgaact acgtcgtgca cggc                                            24

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cggcacgttg accgcagagg atctg                                           25

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctccggtgct cctgcaacct gatgtc                                          26

<210> SEQ ID NO 17

```
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaagtggcag tgcatcacta aactggc                                         27

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccattcagtt cgccggcaca gtcc                                            24

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccaaatcta gctgctgagg ttccc                                           25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgtttgcgg tgcgtctgga cgaag                                           25

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gagggcggaa agcgagtctt gtgtg                                           25

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
catcctcgaa gaattgtctt ttcggg                                          26

<210> SEQ ID NO 23
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 23
cgtagccttc gggcatggcg gacttg                                              26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccttcagctc gatgcggttc accagg                                              26

<210> SEQ ID NO 25
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cttatgagta tttcttccag ggtactcgag gctgggtagt ccccaccttt ctagattttt        60
tttttttttt ttt                                                           73

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctgggtagt ccccaccttt ctaga                                              25

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cttatgagta tttcttccag ggtactcgag                                         30

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagcgtttcc tgatgttgga acccag                                             26

<210> SEQ ID NO 29
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 29
gcatcttacc aatgatgatc gcaagc                                          26

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ttggatcctg atcatttgca tgttgctagt atgtcag                              37

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gactagtctc cgaatcgaag ctaatctgag agc                                  33

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgattccta ctttcgacaa gagg                                            24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctccgtacca cagtctgtct agctc                                           25

<210> SEQ ID NO 34
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcgtcgacag ccagttgacg ttgctggtta ctcag                                35

<210> SEQ ID NO 35
<211> LENGTH: 35
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 35
ttggatccat gccttctcca tatgaagaca gcagc                                    35

<210> SEQ ID NO 36
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggactagtca gatttgtcat gttagtttaa tagtcg                                   36

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaattccgc aagatacgga ctatattaag cagg                                     34

<210> SEQ ID NO 38
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgacgcgtcc attgcgtatg caaccgacga ttctc                                    35

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggggtaccct gagccgggca gttcatcgtt atgg                                     34

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ggactagtca ctgcgcaatt agaagaagcc ta                                       32

<210> SEQ ID NO 41
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 41
ggaattcgat gatgaacaaa tcatttttct cgcac                                  35

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgacgcgtca ccaaaaattt tcccattcac atcg                                   34

<210> SEQ ID NO 43
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ggggtaccgc atggatttct tagcgaattt gtgctg                                 36

<210> SEQ ID NO 44
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aaaaaaaaaa aa                                                           12

<210> SEQ ID NO 45
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
tttttttttt ttt                                                          13

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ggactagtca ctgcgcaatt agaagaagcc tag                                    33
```

RECOMBINANT VIRUS VECTOR ORIGINATING IN HHV-6 OR HHV-7, METHOD OF PRODUCING THE SAME, METHOD OF TRANSFORMING HOST CELL USING THE SAME, HOST CELL TRANSFORMED THEREBY AND GENE THERAPY METHOD USING THE SAME

TECHNICAL FIELD

The present invention relates to a recombinant virus and a recombinant virus vector, and more specifically to a recombinant virus, and a recombinant virus vector, originating in HHV-6 and HHV-7, which are members of the herpesvirus.

The present invention also relates to a producing method of such a recombinant virus and recombinant virus vector. The invention also relates to a method of transforming a host cell using such a recombinant virus and recombinant virus vector. Further, the invention relates to a host cell transformed by such a recombinant virus and recombinant virus vector. The invention also relates to a gene therapy method using such a recombinant virus and recombinant virus vector.

BACKGROUND ART

Accumulation of knowledge and various technological advances in molecular biology and molecular genetics have greatly contributed to the recent progress in life science, providing rich information on various living phenomena.

Currently, there have been ongoing active research and development in various fields of life science, with particular interest in the analysis of gene functions. This has led to the development of techniques and vectors for introducing isolated genes into cells and individual living organisms.

For medical applications, there have been developed various types of vectors used to introduce genes into mammalian cells. Among these vectors, vectors using viruses (virus vectors) have drawn many interests.

Virus vectors have advantages over other known vectors in introducing a foreign gene into a cell for protein expression. The central idea underlying the gene transfer using the virus vector is to introduce a foreign gene into an infected cell and transform the cell with the foreign gene under control of promoter sequences, taking advantage of the infectious capacity of the virus (productive infection, latent infection, abortive infection).

Conventional transfection techniques include non-viral methods. Examples of non-viral methods include: simple addition of a target gene construct as free DNA; incubation with a complex of target DNA and a specific protein that is designed to uptake the DNA into a target cell; and incubation with target DNA that is contained in infected genes that are encapsulated by liposome and other lipids. However, these non-viral transfection techniques suffer from poor efficiency, and the expression efficiency of introduced genes is generally poor.

One conventional transfection technique uses recombinant viruses, and recombinant virus vectors, that are manipulated to include essential target genes, can infect target cells, and therefore enables the target genes to be expressed in the cells. Various types of viruses, such as retrovirus, adenovirus, and adeno-associated virus are used for this purpose. However, these viruses have the following drawbacks.

For example, the retrovirus is carcinogenic, and its carcinogenicity in a gene therapy has been reported. Another drawback of the retrovirus is that it can incorporate only small genes and is selective as to the types of cells that can be used to express the genes.

As to the adenovirus, it can trigger a strong allergic reaction when used in a gene therapy or the like. Some fatal cases in gene therapy have been reported. Further, the adenovirus suffers from poor efficiency when used to introduce genes into blood cells. It is therefore difficult to use the adenovirus as a vector.

The adeno-associated virus allows for introduction of only small genes, and its gene expression efficiency is poor. Another drawback of the adeno-associated virus is that it is difficult to produce a vector. Further, there is a potential risk of causing cancer when incorporated in the host gene.

To this date, eight broad kinds of viruses have been identified that belong to the herpesvirus family, taking into account only those infectious to humans. The herpesvirus is a large DNA virus, and is broadly classified into three sub families $\alpha$, $\beta$, and $\gamma$ according to the phylogenetic tree, with distinct biological characteristics in each sub family. For example, $\alpha$-herpesvirus is a neurotropic virus that exhibits latency and reactivation in nerve cells, whereas $\gamma$-herpesvirus is oncogenic.

Human $\beta$-herpesvirus includes human cytomegalovirus (HCMV: human herpesvirus 5, HHV-5), human herpesvirus 6 (HHV-6), and human herpesvirus (HHV-7).

Of these viruses, HHV-6 and HHV-7 in particular have drawn many interests as the candidates for virus vectors used for gene therapy (see Non-Patent Document 2, for example), since the disease causes by these viruses shows mild symptoms (see Non-Patent Document 1, for example).

Using the herpesvirus, and HHV-6 and HHV-7 in particular as a recombinant virus and a recombinant virus vector has certain advantages, which include low pathogenicity, ease of gene introduction into blood cells such as the T cell and macrophage, and introduction of relatively large genes.

Using HHV-6 as a recombinant virus or a recombinant virus vector is advantageous in the following respects. First, it allows for gene introduction into a macrophage, which is difficult with other vectors. Further, since the gene can be introduced into the macrophage in latency, the allergic reaction seen with the adenovirus does not occur.

However, it is difficult to produce a recombinant virus, and a recombinant virus vector, that originates in HHV-6 or HHV-7, and, today, no method is available that can produce such viruses and vectors. One of the factors that makes recombination of HHV-6 and HHV-7 difficult, beside technical factors, can be attributed to the characteristics of HHV-6 and HHV-7 genes.

The size of gene in HHV-6 and HHV-7 is smaller than that in HCMV, and HHV-6 and HHV-7 contain essentially no genes that are dispensable for the viral replication as observed in HCMV (see Non-Patent Documents 3 and 4, for example).

As a rule, use of a homologous recombination method to produce a recombinant virus or a recombinant virus vector of the herpesvirus requires destruction of one or more sites. However, the recombination sites that have been conventionally used for the preparation of HCMV recombinant viruses are not necessarily included in HHV-6 and HHV-7. Accordingly, development of a new method is needed for the preparation of a recombinant virus and a recombinant virus vector of HHV-6 and HHV-7.

As a virus vector originating in the herpesvirus, there has been proposed a foreign gene that is inserted in the genome of a herpes simplex virus under control of a promoter regulating region of the genome, and therefore serving as a vector for expressing foreign genes (see Patent Document 1, for example). There are also disclosed a DNA construct, a plasmid vector including a construct useful for the expression of foreign genes, a recombinant virus produced by such a vector, and methods concerning these. However, these publications merely describe a herpes simplex virus type 1 (HSV-1) vector and a producing method thereof, and do not disclose anything about virus vectors originating in HHV-6 or HHV-7.

Herpes simplex virus type 1 (HSV-1) and HHV-6 or HHV-7 were evolved from a common ancestor, but completely differ from each other in gene structure. Further, the homology of gene sequences is low between these viruses, and the cellular tropism, which is very important in producing a vector or performing gene therapy, is totally different. Thus, in order to produce vectors originating in HHV-6 or HHV-7, a new technique needs to be developed that is different from that used for herpes simplex virus type 1 (HSV-1).

Other publications disclose results of using the herpesvirus vector. Specifically, there has been proposed a method in which malignant cells of hematopoietic cell lines are transformed to induce expression of foreign gene substances in the cells (for example, see Patent Publication 2). However, the publication merely describes herpes simplex virus type 1, and does not disclose anything about producing methods of HHV-6 or HHV-7 vectors, or side effects of the gene therapy.

[Patent Document 1] European Patent No. 176170
[Patent Document 2] Japanese Laid-Open PCT Publication No. 11-513565
[Non-Patent Document 1] Clin. Microbiol. Rev., July, 1997, Vol. 10, No. 3, p. 521-567
[Non-Patent Document 2] J. Virol. Meth., September 2002, Vol. 105, No. 2, p. 331-341
[Non-Patent Document 3] Yuji Isegawa et al., J. Virol., October 1999, Vol. 73, No. 10, p. 8053-8063
[Non-Patent Document 4] A. George Megaw et al., Virology, 1998, Vol. 244, p. 119-132

An object of the present invention is to provide a virus vector that (i) allows for insertion of an exogenous nucleotide sequence, (ii) can easily transfect a host cell of mammals, (iii) allows a gene encoded by the exogenous nucleotide sequence to be expressed in the host cell, (iv) has a low risk of pathogenicity, and therefore (v) is suitable for gene therapy of mammals.

Another object of the present invention is to provide a virus vector producing method for easily and safely producing a virus vector that (i) allows for insertion of an exogenous nucleotide sequence, (ii) can easily transfect a host cell of mammals, (iii) allows a gene encoded by the exogenous nucleotide sequence to be expressed in the host cell, (iv) has a low risk of pathogenicity, and therefore (v) is suitable for gene therapy of mammals.

Another object of the present invention is to provide a host cell transforming method for transforming a host cell with a virus vector that (i) easily allows for transfection of a mammalian host cell with an exogenous nucleotide sequence, (ii) allows a gene encoded by the exogenous nucleotide sequence to be expressed in the host cell, (iii) has a low risk of pathogenicity, and therefore (iv) is suitable for gene therapy of mammals.

Another object of the present invention is to provide a transformed host cell that (i) is transformed by a virus vector with the insertion of an exogenous nucleotide sequence, (ii) allows a gene encoded by the exogenous nucleotide sequence to be expressed in the host cell, (iii) has a low risk of pathogenicity, and therefore (iv) can suitably be used for gene therapy and cell therapy.

Another object of the present invention is to provide a gene therapy method for mammals using a virus vector that (i) easily allows for transfection of a mammalian host cell with an exogenous nucleotide sequence, (ii) allows a gene encoded by the exogenous nucleotide sequence to be expressed in the host cell, and (iii) has a low risk of pathogenicity.

Another object of the present invention is to develop a gene therapy method, a recombinant virus, and a recombinant virus vector with the use of viruses which do not pose problems of conventionally used viruses, including poor gene introduction efficiency, instable gene expression, and a potential risk of causing cancer.

DISCLOSURE OF INVENTION

The inventors of the present invention diligently worked to solve the foregoing problems by contemplating that HHV-6 or HHV-7, which produces fairly mild symptoms and latently infects nearly 100% of healthy adult individuals may be suitably used as a virus vector for gene therapy.

Specifically, in order to make a recombinant virus, the inventors of the present invention conducted trial and error experiments in an effort to find dispensable regions that can be replaced with drug resistant genes, as will be described later in Examples.

As a result, the inventors of the present invention found a gene cluster that is non-essential and therefore dispensable for the replication and latency of human herpesvirus 6 (HHV-6) and human herpesvirus 7 (HHV-7), as will be described later in Examples.

Based on this finding, the inventors of the present invention accomplished the present invention by finding that insertion of an exogenous nucleotide sequence in a specific region of HHV-6 or HHV-7 does not impair functions of HHV-6 or HHV-7 as a virus vector, thereby enabling production of a recombinant virus and recombinant virus vector originating in HHV-6 and HHV-7, which is very difficult with conventional techniques.

Specifically, a recombinant virus vector of the present invention originates in HHV-6 and includes an exogenous nucleotide sequence in a portion corresponding to at least one region selected from the group consisting of U2, U3, U4, U5, U6, U7, U8, U24, and U25 regions of HHV-6.

It is preferable that the portion exist between nucleotide numbers 9041 and 17446, or between nucleotide numbers 36250 and 37775 of a HHV-6 DNA sequence as represented by SEQ ID NO: 1. It is also preferable that the recombinant virus vector comprises H6R28 virus or H6R24-25 virus.

A recombinant virus vector of the present invention may originate in HHV-7 and include an exogenous nucleotide sequence in a portion corresponding to at least one region selected from the group consisting of U2, U3, U4, U7, U8, U24, U24a, and U25 regions of HHV-7.

It is preferable that the portion exists between nucleotide numbers 10558 and 18483, or between nucleotide numbers 34744 and 36118 of a HHV-7 DNA sequence as represented by SEQ ID NO: 2. It is also preferable that the recombinant virus vector comprises H7R28 virus or H7R24-25 virus.

The exogenous nucleotide sequence may be a DNA sequence and/or RNA sequence.

The exogenous nucleotide sequence may encode at least one kind of substance selected from the group consisting of a bacterial artificial chromosome (BAC), cytokine gene, ribozyme, interference RNA, immunological co-stimulator molecule, signal transduction molecule, enzyme, and chemical attractant.

Further, the exogenous nucleotide sequence may be used for gene therapy of mammals. The exogenous nucleotide sequence may include a nucleotide sequence that encodes a marker gene.

A producing method of a recombinant virus of the present invention originates in HHV-6, and the method includes the step of inserting an exogenous nucleotide sequence in a portion corresponding to at least one region selected from the group consisting of U2, U3; U4, U5, U6, U7, U8, U24, and U25 regions of HHV-6.

It is preferable that, in the step of inserting an exogenous nucleotide sequence, the exogenous nucleotide sequence be inserted between nucleotide numbers 9041 and 17446, or between nucleotide numbers 36250 and 37775 of a HHV-6 DNA sequence as represented by SEQ ID NO: 1.

In the step of inserting an exogenous nucleotide sequence, homologous recombination may be carried out between a HHV-6 DNA sequence and a DNA sequence that is amplified with a primer set of a sequence represented by SEQ ID NO: 3-4 and a sequence represented by SEQ ID NO: 5-6, or a primer set of a sequence represented by SEQ ID NO: 36-37 and a sequence represented by SEQ ID NO: 38-39.

A producing method of a recombinant virus vector of the present invention may originate in HHV-7, and the method may include the step of inserting an exogenous nucleotide sequence in a portion corresponding to at least one region selected from the group consisting of U2, U3, U4, U7, U8, U24, U24a, and U25 regions of HHV-7.

In the step of inserting an exogenous nucleotide sequence, the exogenous nucleotide sequence may be inserted between nucleotide numbers 10558 and 18483, or between nucleotide numbers 34744 and 36118 of a HHV-7 DNA sequence as represented by SEQ ID NO: 2.

In the step of inserting an exogenous nucleotide sequence, homologous recombination may be carried out between a HHV-7 DNA sequence and a DNA sequence that is amplified with a primer set of a sequence represented by SEQ ID NO: 30-31 and a sequence represented by SEQ ID NO: 34-35, or a primer set of a sequence represented by SEQ ID NO: 40-41 and a sequence represented by SEQ ID NO: 42-43.

In the step of inserting an exogenous nucleotide sequence, the exogenous nucleotide sequence may be inserted inside a normal cell and/or an umbilical cord blood cell.

A transforming method of a host cell of the present invention transforms a host cell of a mammal with the recombinant virus vector of the invention, and the method includes the step of transforming, with the recombinant virus vector, a host cell of at least one kind of mammal selected from the group consisting of a human, a non-human primate, and a host that is open to HHV-6 or HHV-7 infection.

In the step of transforming a host cell, the method may transform, with the recombinant virus vector, at least one kind of host cell selected from the group consisting of a T cell, macrophage, peripheral-blood mononuclear cell, blood stem cell, liver cell, vascular endothelial cell, fibroblast, glial cell, astrocyte, CD4 positive T cell, CD8 positive T cell, dendritic cell, and natural killer cell.

A transformed host cell of the present invention is obtained by the transforming method of the invention. A transformed host cell of the present invention may be used for gene therapy of mammals.

Further, the gene therapy may be for preventing human immunodeficiency virus (HIV) infection of a compromised cell caused by HIV, and/or for immunotherapy of cancer. The host cell may be derived from a mammal of the kind subjected to the gene therapy.

A gene therapy method of the present invention is for non-human mammals, and the method includes the step of administering the transformed cell of the invention.

A gene therapy method of the present invention is for non-human mammals, and the method may include the step of transforming, with a recombinant virus vector of claim 1 or 4, a host cell of a mammal in vivo at a multiplicity of infection (MOI) of 0.01 to 20.

A gene therapy method of the present invention may include the step of expressing a gene encoded by the exogenous nucleotide sequence included in the recombinant virus vector.

Additional objects, features, and strengths of the present invention will be made clear by the description below. Further, the advantages of the present invention will be evident from the following explanation in reference to the drawings.

BRIEF DESCRIPTION OF DRAWINGS

FIG. 3(A) is a graphical view representing an increase of the cells stained with anti-HHV-6 monoclonal antibody in cells infected with H6R28; FIG. 3(B) is a graphical view representing changes in virus titer (the number of surviving cells) in the culture supernatant of the cells infected with H6R28.

FIG. 15(A) is a graphical view representing an increase in the cells stained with anti-HHV-7 monoclonal antibody in cells infected with H7R28; and FIG. 15(B) is a graphical view representing changes in virus titer (the number of surviving viruses) in the supernatant of cultured cells infected with H7R28.

FIG. 17(A) is a graphical view representing an increase in the cells stained with anti-HHV-7 monoclonal antibody in cells infected with H7R24-25; and FIG. 17(B) is a graphical view representing changes in virus titer (the number of surviving viruses) in the supernatant of cultured cells infected with H7R24-25.

BEST MODE FOR CARRYING OUT THE INVENTION

Figure 1:
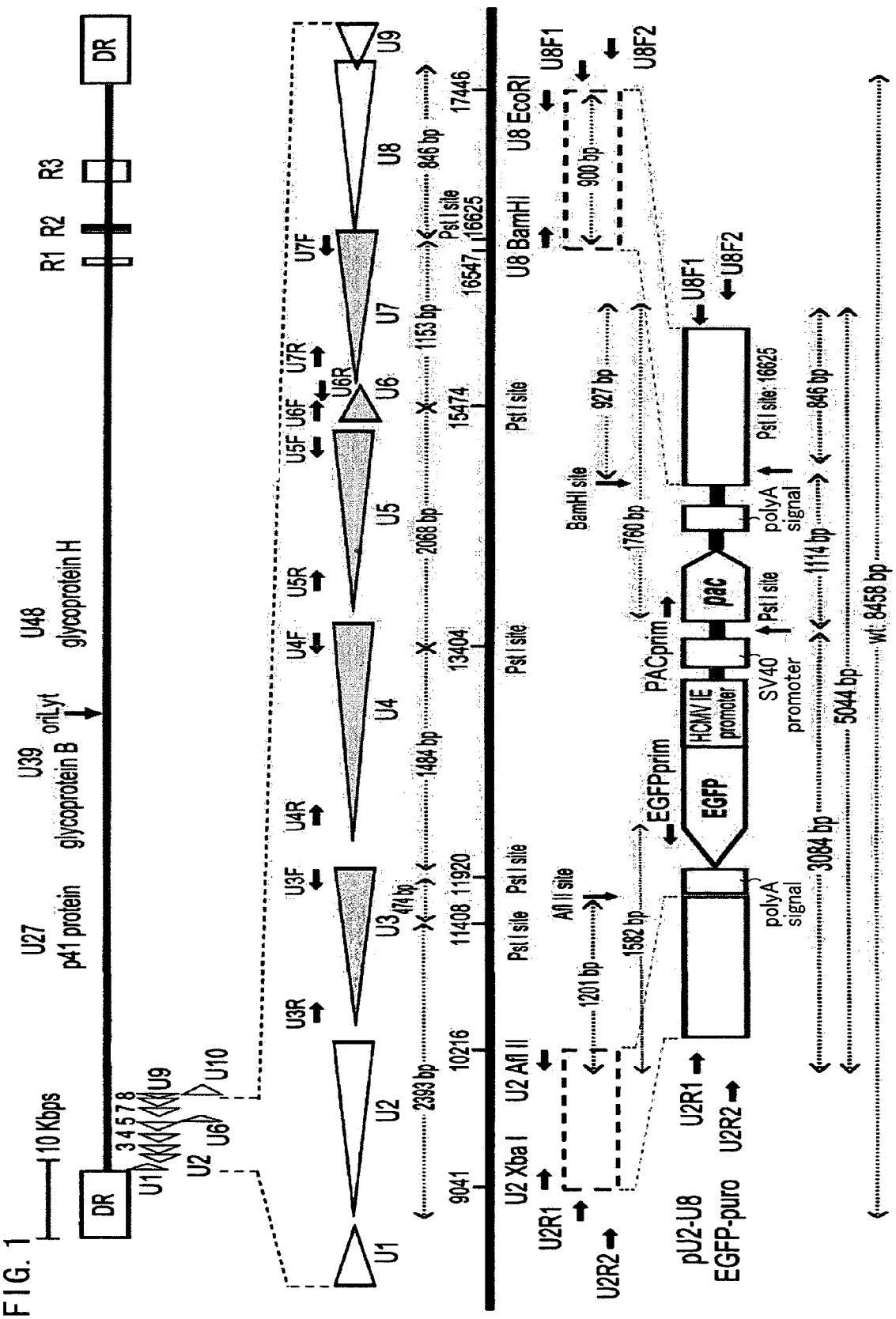
FIG. 1 is a schematic diagram representing a structure of a H6R28 genome.

The present invention is now described in detail in the embodiment below.

DEFINITIONS

As used herein, HHV-6 refers to variants A and B of human herpesvirus 6.

As used herein, HHV-7 refers to human herpesvirus 7.

As used herein, a recombinant virus and a recombinant virus vector refer to a virus or a virus vector that is prepared by incorporating foreign genes in viral genes, and that causes either one of productive infection, latent infection/reactivation, and abortive infection when used to infect a host cell.

As used herein, a dispensable region refers to a viral gene region, the lack of which does not lead to a complete loss of the proliferating ability of the virus.

As used herein, an exogenous nucleotide sequence refers to a nucleic acid sequence other than those found in naturally occurring viral genes.

As used herein, latent infection refers to a situation where production of infectious virus is suspended with the viral genes retained in the virus.

As used herein, infection refers to entry of virus into a cell, and it includes productive infection, latent infection, and abortive infection.

As used herein, abortive infection refers to a situation where a virus that has entered a cell does not actively retain viral genes while no infectious virus is produced.

As used herein, gene therapy refers to therapy in which a cell is transformed by transfecting the cell with foreign genes. In a narrow sense, it includes cell therapy in which a cell that has been transformed ex vivo by gene transfection is returned to the living organism, and virus therapy in which a cell is infected with infectious virus in vivo in order to facilitate modification of the host cell by a resulting virus.

<HHV-6-Derived Recombinant Virus and Recombinant Virus Vector>

A recombinant virus and recombinant virus vector of the present invention are derived from HHV-6 and include an exogenous nucleotide sequence in a portion corresponding to at least one region selected from the group consisting of U2, U3, U4, U5, U6, U7, U8, U24, and U25 regions of HHV-6.

The U2 region of HHV-6 is an open reading frame (ORF) encoded by nucleotide number 10768 (start) to nucleotide number 9467 (end) of HHV-6 as represented by SEQ ID NO: 1, and it shares a common motif with the US22 gene family of HCMV.

The U3 region of HHV-6 is an open reading frame (ORF) encoded by nucleotide number 12051 (start) to nucleotide number 10891 (end) of HHV-6 as represented by SEQ ID NO: 1, and it shares a common motif with the US22 gene family of HCMV.

The U4 region of HHV-6 is an open reading frame (ORF) encoded by nucleotide number 13883 (start) to nucleotide number 12276 (end) of HHV-6 as represented by SEQ ID NO: 1, and it has unknown functions.

The U5 region of HHV-6 is an open reading frame (ORF) encoded by nucleotide number 15333 (start) to nucleotide number 14002 (end) of HHV-6 as represented by SEQ ID NO: 1, and it has unknown functions.

The U6 region of HHV-6 is an open reading frame (ORF) encoded by nucleotide number 15395 (start) to nucleotide number 15652 (end) of HHV-6 as represented by SEQ ID NO: 1, and it has unknown functions.

The U7 region of HHV-6 is an open reading frame (ORF) encoded by nucleotide number 16802 (start) to nucleotide number 15678 (end) of HHV-6 as represented by SEQ ID NO: 1, and it shares a common motif with the US22 gene family of HCMV.

The U8 region of HHV-6 is an open reading frame (ORF) encoded by nucleotide number 18041 (start) to nucleotide number 16806 (end) of HHV-6 as represented by SEQ ID NO: 1, and it shares a common motif with the US22 gene family of HCMV.

The U24 region of HHV-6 is an open reading frame (ORF) encoded by nucleotide number 36616 (start) to nucleotide number 36350 (end) of HHV-6 as represented by SEQ ID NO: 1, and it has unknown functions.

The U25 region of HHV-6 is an open reading frame (ORF) encoded by nucleotide number 38770 (start) to nucleotide number 37883 (end) of HHV-6 as represented by SEQ ID NO: 1, and it shares a common motif with the US22 gene family of HCMV.

The foregoing portions of HHV-6 may exist between nucleotide number 9041 and nucleotide number 17446, or between nucleotide number 36250 and nucleotide number 37775 of the DNA sequence of HHV-6 as represented by SEQ ID NO: 1. This is because nucleotide number 9041 to nucleotide number 17446 contains U2 region to U8 region of HHV-6, which were found to be dispensable as will be described later in Examples, and because nucleotide number 36250 to nucleotide number 37775 contains U24 region to U25 region of HHV-6, which were found to be dispensable as will be described later in Examples.

The foregoing portions of HHV-6 may exist between nucleotide number 10216 and nucleotide number 16547, or between nucleotide number 36250 and nucleotide number 37775 of the DNA sequence of HHV-6 as represented by SEQ ID NO: 1. This is because nucleotide number 10216 to nucleotide number 16547 were experimentally confirmed to be dispensable as will be described later in Examples, and because nucleotide number 36250 to nucleotide number 37775 were experimentally confirmed to be usable for recombination, as will be described later in Examples.

A desirable exogenous nucleotide can easily be inserted in these portions in the manner described below. First, the HHV-6 DNA is cut at restriction enzyme cutting sites in these portions under appropriate conditions, using commercially available restriction enzymes. Then, the HHV-6 DNA is ligated under appropriate conditions to an exogenous nucleotide having complementary ends, using a commercially available ligase.

As to functions of US22 family genes, some information is available for human cytomegalovirus or mouse cytomegalovirus that belongs to β-herpes virus as does HHV-6 or HHV-7. However, no information is available for HHV-6 and HHV-7. The present invention, for the first time, analyzed functions of US22 family genes of HHV-6 and HHV-7 concerning their proliferation and latency.

The US22 family genes of HHV-6 and HHV-7 are merely classified according to a virtual motif on amino acid sequences whose functions are yet to be determined. As such, the fact that the genes belong to this family does not necessarily mean that their functions can be predicted. Further, there is no strong amino acid homology between homologous proteins of the HHV-6, HHV-7, and cytomegalovirus.

<HHV-7-Derived Recombinant Virus and Recombinant Virus Vector>

A recombinant virus and recombinant virus vector of the present invention may be derived from HHV-7 and may include an exogenous nucleotide sequence in a portion corresponding to at least one region selected from the group consisting of U2, U3, U4, U7, U8, U24, U24a, and U25 regions of HHV-7.

The U2 region of HHV-7 is an open reading frame (ORF) encoded by nucleotide number 11637 (start) to nucleotide number 10558 (end) of HHV-7 as represented by SEQ ID NO: 2, and it shares a common motif with the US22 gene family of HCMV.

The U3 region of HHV-7 is an open reading frame (ORF) encoded by nucleotide number 12953 (start) to nucleotide number 11799 (end) of HHV-7 as represented by SEQ ID NO: 2, and it shares a common motif with the US22 gene family of HCMV.

The U4 region of HHV-6 is an open reading frame (ORF) encoded by nucleotide number 14603 (start) to nucleotide number 12975 (end) of HHV-7 as represented by SEQ ID NO: 2, and it is associated with exon 2 of U7.

Exon 1 (also known as U5) in the U7 region of HHV-7 is an open reading frame (ORF) encoded by nucleotide number 17324 (start) to nucleotide number 16348 (end) of HHV-7 as represented by SEQ ID NO: 2, and it shares a common motif with the US22 gene family of HCMV.

Exon 2 (also known as U7) in the U7 region of HHV-7 is an open reading frame (ORF) encoded by nucleotide 16266 (start) to nucleotide number 14628 (end) of HHV-7 as represented by SEQ ID NO: 2, and it is associated with the U4 region.

The U24 region of HHV-7 is an open reading frame (ORF) encoded by nucleotide number 34992 (start) to nucleotide number 34744 (end) of HHV-7 as represented by SEQ ID NO: 2, and it has unknown functions.

The U24a region of HHV-7 is an open reading frame (ORF) encoded by nucleotide number 35166 (start) to nucleotide number 34996 (end) of HHV-7 as represented by SEQ ID NO: 2, and it has unknown functions.

The U25 region of HHV-6 is an open reading frame (ORF) encoded by nucleotide number 36118 (start) to nucleotide number 35156 (end) as represented by SEQ ID NO: 2, and it shares a common motif with the US22 gene family of HCMV.

The foregoing portions of HHV-7 may exist between nucleotide number 10558 and nucleotide number 18483, or between nucleotide number 34744 and nucleotide number 36118 of the DNA sequence of HHV-7 as represented by SEQ ID NO: 2. This is because nucleotide number 10558 to nucleotide number 18483 contains U2, U3, U4, U7, and U8 regions of HHV-7, which were found to be dispensable as will be described later in Examples, and because nucleotide number 34744 to nucleotide number 36118 contains U24, U24a, and U25 regions of HHV-7, which were found to be dispensable as will be described later in Examples.

The foregoing portions of HHV-7 may exist between nucleotide number 11631 and nucleotide number 17221, or between nucleotide number 34744 and nucleotide number 36118 of the DNA sequence of HHV-7 as represented by SEQ ID NO: 2. This is because nucleotide number 11631 to nucleotide number 17221 were experimentally confirmed to be dispensable as will be described later in Examples, and because nucleotide number 34744 to nucleotide number 36118 were experimentally confirmed to be usable for recombination, as will be described later in Examples.

A desirable exogenous nucleotide can easily be inserted in these portions in the manner described below. First, the HHV-7 DNA is cut at restriction enzyme cutting sites in these portions under appropriate conditions, using commercially available restriction enzymes. Then, the HHV-7 DNA is ligated under appropriate conditions to an exogenous nucleotide having complementary ends, using a commercially available ligase.

<Exogenous Nucleotide Sequence>

The exogenous nucleotide sequence may be a DNA sequence and/or an RNA sequence. The DNA sequence may be a genomic DNA sequence or cDNA sequence.

Further, the exogenous nucleotide sequence may be a nucleotide sequence that encodes one or more substances selected from the group consisting of bacterial artificial chromosome (BAC), a cytokine gene, a ribozyme, interference RNA, immunological co-stimulator molecule, and a chemical attractant.

Further, the exogenous nucleotide sequence may be a sequence used for gene therapy of mammals. Further, the exogenous nucleotide sequence may be a nucleotide sequence that encodes an immunoregulatory protein useful for a tumor treatment and/or immune treatment of mammals.

Further, the exogenous nucleotide sequence may include a nucleotide sequence that encodes a maker gene. The marker gene may be an antibiotic-resistant gene.

<Producing Method of Recombinant Virus and Recombinant Virus Vector>

A producing method of a recombinant virus and recombinant virus vector of the present invention is for producing a recombinant virus and recombinant virus vector derived from HHV-6, the method including the step of inserting an exogenous nucleotide sequence in a portion corresponding to at least one region selected from the group consisting of U2, U3, U5, U6, U7, U8, U24, and U25 regions of HHV-6.

The step of inserting an exogenous nucleotide sequence preferably includes the step of cutting the HHV-6 DNA under appropriate conditions at restriction enzyme cutting sites in the foregoing portion, using a commercially available restriction enzyme, and the step of ligating the HHV-6 DNA under appropriate conditions with an exogenous nucleotide having complementary ends, using a commercially available ligase. In this manner, with the commercially available restriction enzyme and ligase, a desirable exogenous nucleotide can easily be inserted in the foregoing portions.

The step of inserting an exogenous nucleotide sequence may include the step of inserting an exogenous nucleotide sequence between nucleotide number 9041 and nucleotide number 17446 or between nucleotide number 36250 and nucleotide number 37775 of the DNA sequence of HHV-6 as represented by SEQ ID NO: 1. This is because nucleotide number 9041 to nucleotide number 17446 contains U2 region to U8 region of HHV-6, which were found to be dispensable as will be described later in Examples, and because nucleotide number 36250 to nucleotide number 37775 contains U24 region to U25 region of HHV-6, which were found to be dispensable as will be described later in Examples.

Further, the step of inserting an exogenous nucleotide sequence may include the step of inserting an exogenous nucleotide sequence between nucleotide number 10216 and nucleotide number 16547 or between nucleotide number 36250 and nucleotide number 37775 of the DNA sequence of HHV-6 as represented by SEQ ID NO: 1. This is because nucleotide number 10216 to nucleotide number 16547 were experimentally confirmed to be dispensable as will be described later in Examples, and because nucleotide number 36250 to nucleotide number 37775 were experimentally confirmed to be usable for recombination, as will be described later in Examples.

Further, the step of inserting an exogenous nucleotide sequence may include the step of performing homologous recombination between a DNA sequence of HHV-6 and a DNA sequence amplified with a combination of primers having the sequences of SEQ ID NOs: 3 and 4 and primers having the sequences of SEQ ID NOs: 5 and 6, or a combination of primers having the sequences of SEQ ID NOs: 36 and 37 and primers having the sequences of SEQ ID NOs: 38 and 39.

TABLE 1

(SEQ ID NOS 3-27 and 36-39, respectively, in order of appearance)

| PRIMER | SEQ ID NO: | PRIMER SEQUENCE |
|---|---|---|
| U2 Xba I | 3 | 5'- GCTCTAGACTGCCACGTGAGCGAAAGCATACAC -3' |
| U2 Afl II | 4 | 5'- TTACTTAAGTCATCGGGGTCACTATCTTCGCAG -3' |
| U8 Bam HI | 5 | 5'- CCGGATCCGAGTTAATGCATACATGGGAGGCCAGG -3' |
| U8 Eco RI | 6 | 5'- CGGAATTCCTGTGTACCGTCATGGCTTGT -3' |
| U2R1 | 7 | 5'- GACATGCCTACGCGGCCTCACCGAG -3' |
| U2R2 | 8 | 5'- GGACGCGTGTAGAAACGGCCAACG -3' |
| U8F1 | 9 | 5'- GTACTAACATCATCACATGCGCGGAG -3' |
| U8F2 | 10 | 5'- GGGACTATTCAGATTCCTTACAGAG -3' |
| EGFPprim | 11 | 5'- GACTCAGATCTCGAGCTCAAGCTTCG -3' |
| PACprim | 12 | 5'- CCTTCTACGAGCGGCTCGGCTTCAC -3' |
| U3F | 13 | 5'- ATGGAAACGACAAACAGCCGGCGTG -3' |
| U3R | 14 | 5'- CTATCGAACTACGTCGTGCACGGC -3' |
| U4F | 15 | 5'- CGGCACGTTGACCGCAGAGGATCTG -3' |
| U4R | 16 | 5'- CTCCGGTGCTCCTGCAACCTGATGTC -3' |
| U5F | 17 | 5'- GAAGTGGCAGTGCATCACTAAACTGGC -3' |
| U5R | 18 | 5'- CCATTCAGTTCGCCGGCACAGTCC -3' |
| U6F | 19 | 5'- GCCAAATCTAGCTGCTGAGGTTCCC -3' |
| U6R | 20 | 5'- CTGTTTGCGGTGCGTCTGGACGAAG -3' |
| U7F | 21 | 5'- GAGGGCGGAAAGCGAGTCTTGTGTG -3' |
| U7R | 22 | 5'- CATCCTCGAAGAATTGTCTTTTCGGG -3' |
| EGFP R1 | 23 | 5'- CGTAGCCTTCGGGCATGGCGGACTTG -3' |
| EGFP R2 | 24 | 5'- CCTTCAGCTCGATGCGGTTCACCAGG -3' |
| RL-1 | 25 | 5'- CTTATGAGTATTTCTTCCAGGGTACTCGAGGCTGGGTAGTCCCCACCTTTCTAGATTTTTTTTTTTTTTTTT -3' |
| N1 | 26 | 5'- GCTGGGTAGTCCCCACCTTTCTAGA -3' |
| N2 | 27 | 5'- CTTATGAGTATTTCTTCCAGGGTACTCGAG -3' |
| U24 Spe I | 36 | 5'- GGACTAGTCAGATTTGTCATGTTAGTTTAATAGTCG -3' |
| U25 Eco RI | 37 | 5'- GGAATTCCGCAAGATACGGACTATATTAAGCAGG -3' |
| U25 Mlu I | 38 | 5'- CGACGCGTCCATTGCGTATGCAACCGACGATTCTC -3' |
| U25 Kpn I | 39 | 5'- GGGGTACCCTGAGCCGGGCAGTTCATCGTTATGG -3' |

A producing method of a recombinant virus and recombinant virus vector of the present invention is for producing a recombinant virus and recombinant virus vector derived from HHV-7, the method including the step of inserting an exogenous nucleotide sequence in a portion corresponding to at least one region selected from the group consisting of U2, U3, U4, U7, U8, U24, U24a, and U25 regions of HHV-7.

The step of inserting an exogenous nucleotide sequence preferably includes the step of cutting the HHV-7 DNA under appropriate conditions at restriction enzyme cutting sites in the foregoing portion, using a commercially available restriction enzyme, and the step of ligating the HHV-7 DNA under appropriate conditions with an exogenous nucleotide having complementary ends, using a commercially available ligase. In this manner, with the commercially available restriction enzyme and ligase, a desirable exogenous nucleotide can easily be inserted in the foregoing portions.

The step of inserting an exogenous nucleotide sequence may include the step of inserting an exogenous nucleotide sequence between nucleotide number 10558 and nucleotide number 18483 or between nucleotide number 34744 and nucleotide number 36118 of the DNA sequence of HHV-7 as represented by SEQ ID NO: 2. This is because nucleotide number 10558 to nucleotide number 18483 contains U2, U3, U4, U7, and U8 regions of HHV-7, which were found to be dispensable as will be described later in Examples, and because nucleotide number 34744 to nucleotide number 36118 contains U24, U24a, and U25 regions of HHV-7, which were found to be dispensable as will be described later in Examples.

Further, the step of inserting an exogenous nucleotide sequence may include the step of inserting an exogenous nucleotide sequence between nucleotide number 1163 and nucleotide number 17221 or between nucleotide number 34744 and nucleotide number 36118 of the DNA sequence of HHV-7 as represented by SEQ ID NO: 2. This is because nucleotide number 1163 to nucleotide number 17221 were experimentally confirmed to be dispensable as will be described later in Examples, and because nucleotide number 34744 to nucleotide number 36118 were experimentally confirmed to be usable for recombination, as will be described later in Examples.

Note that, the step of inserting an exogenous nucleotide may include the step of inserting an exogenous nucleotide sequence inside a normal cell and/or a normal umbilical cord blood cell. A drawback of the adenovirus conventionally used to construct a recombinant virus vector is that construction of recombinant virus is difficult unless it is performed inside HEK293 cell lines derived from kidney cancer cells. An advantage of a recombinant virus vector of the present invention, on the other hand, is that it can be constructed inside a normal cell, or more preferably inside a normal umbilical cord blood cell.

<Transformation Method of Host Cell>

A method for transforming a host cell of the present invention is for transforming a host cell of mammals with use of the recombinant virus and recombinant virus vector, and the method includes the step of transforming a host cell with the recombinant virus and recombinant virus vector at a multiplicity of infection (MOI) of 0.01 to 20.

The transformation step may include the step of transforming, with the recombinant virus and recombinant virus vector, a host cell derived from one or more kinds of mammals selected from the group consisting of a human, a non-human primate, and a host that is open to HHV-6 or HHV-7 infection.

Further, the transformation step may include the step of transforming, with the recombinant virus and recombinant virus vector, at least one kind of a host cell selected from the group consisting of a T cell, macrophage, peripheral-blood mononuclear cell, blood stem cell, liver cell, vascular endothelial cell, fibroblast, glial cell, astrocyte, CD4 positive T cell, CD8 positive T cell, dendritic cell, and natural killer cell.

Conventionally, these cells had the problem of transfection efficiency and expression when used with conventional vectors. With a recombinant virus vector of the present invention, foreign genes can be introduced into these cells and expressed therein.

The transformation step may be performed either ex vivo or in vivo.

<Transformed Host Cells>

A transformed host cell of the present invention is obtained by the foregoing method of transforming a host cell.

A transformed host cell of the present invention may be used in gene therapy methods of mammals. The gene therapy for which a transformed host cell of the present invention is used may be gene therapy (i) for preventing human immunodeficiency virus (HIV) infection in a compromised cell caused by HIV, and/or (ii) for immunotherapy of cancer.

Further, the host cell may be derived from a mammal of the kind subjected to the gene therapy.

<Gene Therapy Method>

A gene therapy method of the present invention is for non-human mammals, and it includes the step of administering the transformed cell into such mammals.

A gene therapy method of the present invention may be used not only for gene therapy but also for virus therapy and cell therapy as well. The cell therapy refers to a method in which a cell that has been transformed by gene transfection is administered to a patient. The virus therapy refers to a method in which a patient is administered with a virus that is infectious and is intended to multiply inside the human body.

A gene therapy method of the present invention is for non-human mammals, and includes the step of transforming, with use of the recombinant virus and recombinant virus vector, a host cell inside the body of the mammal at a multiplicity of infection (MOI) of 0.01 to 20.

A gene therapy method of the present invention may include the step of expressing a gene encoded by an exogenous nucleotide sequence included in the recombinant virus and recombinant virus vector.

The following will describe the present invention in more detail based on Examples. It should be noted however that the present invention is not limited in any way by the following description.

The following Examples were carried out with samples obtained with the informed consent of the blood donors who participated in the study.

<Construction of HHV-6 Recombinant Virus Vector H6R28>

In order to construct recombinant virus H628R, a U3-U7 gene cluster of human herpesvirus 6 (HHV-6) was replaced with EGFP-puro, a gene cassette containing the gene for enhanced green fluorescent protein (EGFP) under control of the human cytomegalovirus major immediate-early enhancer-promoter (MIEP) and the puromycin resistance gene under control of the simian virus 40 (SV40) early promoter. To insert the EGFP-puro cassette into the HHV-6 genome by homologous recombination, 1-kb segments of viral genome were inserted into each end of the cassette (FIG. 1).

The following gene clusters were examined: the DR2-DR7 genes, which are duplicated in the viral genome; U95, the positional homologue of the murine cytomegalovirus (MCMV) immediate-early (IE) 2 gene, which is known to be dispensable for viral replication; and the U3-U7 genes. Of these, it was found that replacement of the U3-U7 genes with EGFP-puro resulted in a successfully replicating virus.

The following specifically describes the construct procedure.

FIG. 1 schematizes a structure of the recombinant virus H6R28.

At the top is a map of the HHV-6B HST genome, with the region U1 to U9 expanded below (in the middle).

In the recombinant virus vector H6R28, shaded arrows in the middle show the U3-U7 open reading frames replaced by the EGFP-puro cassette.

The bottom diagram represents pU2-U8 EGFP-puro, a plasmid for homologous recombination in which U2 DNA fragments and U8 DNA fragments used for homologous recombination are inserted at the both ends of the EGFP-puro cassette.

The annealing sites of the primers used are depicted by small arrows pointing left or right. The recognition sites of the restriction enzymes used are depicted by small arrows pointing upward or downward. The sizes of the amplified or digested fragments are indicated by dotted arrows.

The EGFP gene and HCMV MIEP of the EGFP-puro cassette were derived from pEGFP-C1 (nucleotide numbers 8 to 1640) (Clontech). Multiple cloning sites of pEGFP-C1 including PstI were deleted.

The puromycin-N-acetyl-transferase gene (pac) and SV40 early promoter gene of the EGFP-puro cassette were derived from pPUR (nucleotide numbers 408 to 1392) (Clontech).

For the construct, the U2 gene was amplified by PCR with primers U2 XbaI and U2 MlI, and the U8 gene was amplified with U8 BamHI and U8 EcoRI. After a restriction enzyme digestion, the digested products were inserted into each end of pEGFP-puro to obtain pU2-U8 EGFP-puro.

The cloned plasmid pU2-U8 EGFP-puro was introduced into phytohemagglutinin (PHA)-stimulated peripheral blood mononuclear cells by using a Nucleofector™ electroporator (Amaxa Biosystems, Germany) according to the manufacturer's recommended protocol.

Briefly, $5 \times 10^6$ cells were mixed with 5 μg of the plasmid and 100 μl of Nucleofector™ solution for T cells, and electroporation was performed with the Nucleofector™ using the program U-14.

Alternatively, a conventional electroporation method was used. In this case, $1 \times 10^7$ cells were mixed with 50 μg of the plasmid suspended in 500 μl of K-phosphate-buffered saline (30.8 mM NaCl, 120.7 mM KCl, 8.1 mM $Na_2HPO_4$, 1.46 mM $KH_2PO_4$, and 25 mM $MgCl_2$), and the mixture was placed in an electroporation cuvette (Gene Pulser cuvette, 0.4-cm diameter; Bio-Rad).

Electroporation was performed with a Gene Pulser II electroporation system (Bio-Rad) with resistance at infinity, voltage at 300 V, and capacitance at 960 μF. After 6 hours, the cells were infected with HHV-6 variant B of the HST strain at a multiplicity of infection (MOI) of 0.5 using the centrifuge method.

Cells were cultured for 3 days in RPMI 1640 supplemented with 10% fetal bovine serum and frozen as a virus stock. To enrich for the recombinant virus, PHA-stimulated umbilical cord blood mononuclear cells (CBMCs) were infected with the virus stock and cultured for 1 day, treated with 7.5 μg of puromycin/ml for 1 day, washed with the medium, and cultured with CBMCs for 3 days. The infected cells were then frozen as a new virus stock.

This selection procedure was repeated five times, and the recombinant virus (H6R28) was subsequently cloned by limiting dilution using CBMCs cultured in 96-well plates.

<Construction Confirmation of HHV-6 Recombinant Virus Vector H6R28>

To confirm the insertion of the EGFP-puro cassette into the expected region, viral DNA was amplified by double-nested PCR with KOD Plus DNA polymerase (TOYOBO, Otsu, Japan) using primers against regions outside the homologous hinge regions (outer primer set U2R2-U8F2 and inner primer set U2R1-U8F1) (FIG. 1).

Figure 2A:
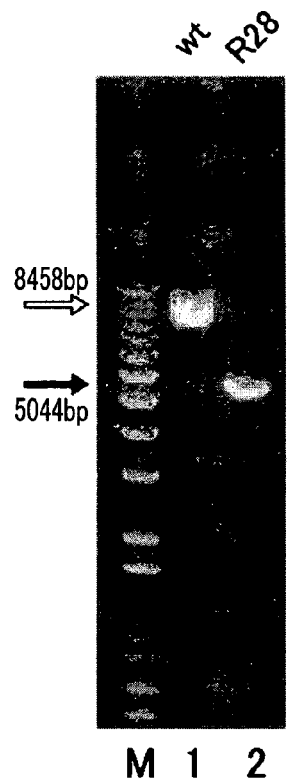
FIG. 2(A) is an electrophoretogram view representing results of PCR amplification between regions U2 and U8 of wild-type (wt) virus DNA and H6R28 virus DNA.

The amplified products were subjected to electrophoresis. As the gel, 0.6% agarose gel was used. The results are shown in FIG. 2(A). An amplified product of approximately 8.5 kb was observed in the wild-type (wt) virus (lane 1), conforming to the expected value (open arrow in FIG. 2(A)). An amplified product of approximately 5.0 kb was observed in H6R28 (lane 2), conforming to the expected value (solid arrow in FIG. 2(A)). Note that, the 5.0-kb bands were observed in three clones of H6R28.

The amplified products were confirmed by partial sequencing (data not shown). The 8.5-kb product was not observed in the recombinants, which indicated that they were not contaminated with the wt virus.

Figure 2B:
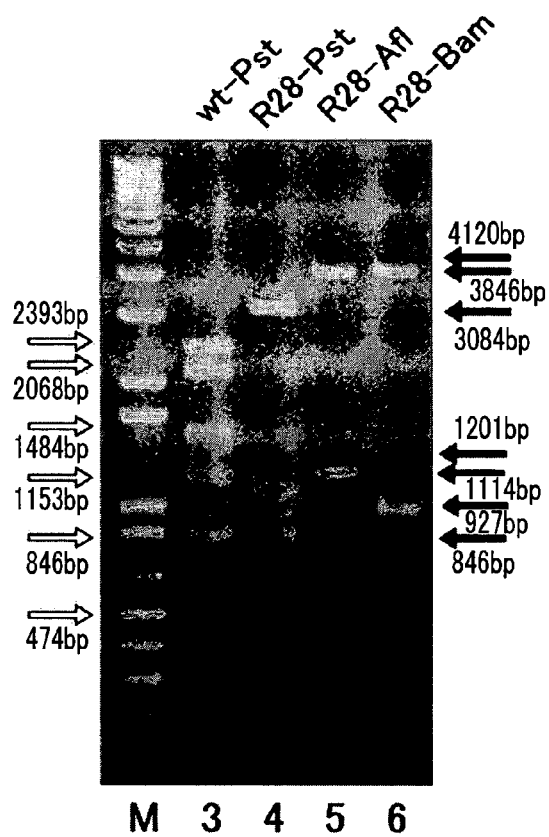
FIG. 2(B) is an electrophoretogram view of fragments obtained by digesting the PCR products of FIG. 2(A) with restriction enzymes.

The amplified products were digested with the restriction enzymes (PstI, AflII, and BamHI) (FIG. 1), and were subjected to 1.0% agarose gel electrophoresis. The results are shown in FIG. 2(B). In FIG. 2(B), open arrows on the left-hand side depict the expected sizes of the digested fragments in the wt virus, and solid arrows in the right-hand side depict the expected sizes of the digested fragments in H6R28. As FIG. 2(B) clearly shows, the treatment of the amplified products with the restriction enzymes gave rise to the expected bands in both wt virus (lane 1) and H6R28 (lanes 4-6).

The inserted position of EGFP-puro was also examined. Specifically, PCR was run with a primer U2R1-EGFPprim and a primer U8F1-PACprim, using DNA of H6R28 as a template. The amplified products were subjected to 1.0% agarose gel electrophoresis.

Figure 2C:
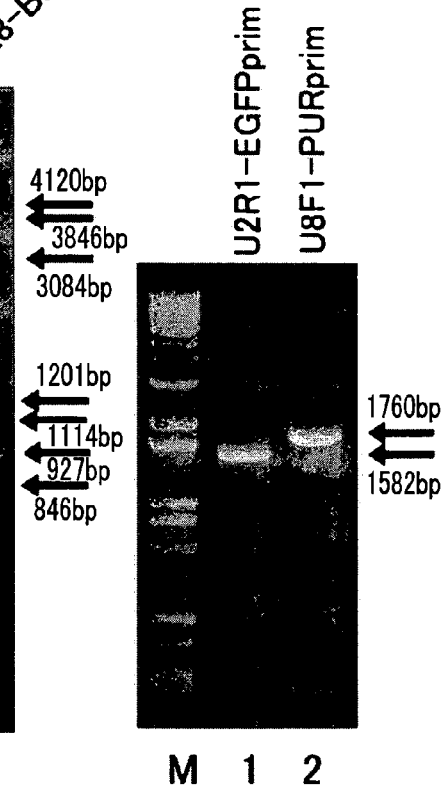
FIG. 2(C) is an electrophoretogram view representing results of PCR amplification that was performed to confirm an insertion position of an EGFP-puro cassette in H6R28 virus DNA.

The results are shown in FIG. 2(C). Solid arrows on the right-hand side depict the expected size (1582 bp) of the fragment amplified by the primer U2R1-EGFPprim, and the expected size (1760 bp) of the fragment amplified by the primer U8F1-PACprim. As FIG. 2(C) clearly shows, bands of the expected sizes were obtained in both the fragment amplified with the primer U2R1-EGFPprim (lane 1), and the fragment amplified with the primer U8F1-PACprim (lane 2).

The possibility of the ectopic expression of U3-U7 genes was addressed. Specifically, an attempt was made to amplify the respective open reading frames of the U3 to U7 genes in which EGFP-puro has supposedly replaced the ORF. PCR was run using the wt viral DNA or H6R28 DNA as a template. For the amplification of U3, U4, U5, U6, and U7, the primer pairs U3F1-U3R1, U4F1-U4R1, U5F1-U5R1, U6F1-U6R1, and U7F1-U7R1 were used, respectively. The PCR products were subjected to 1.0% agarose gel electrophoresis.

Figure 2D:
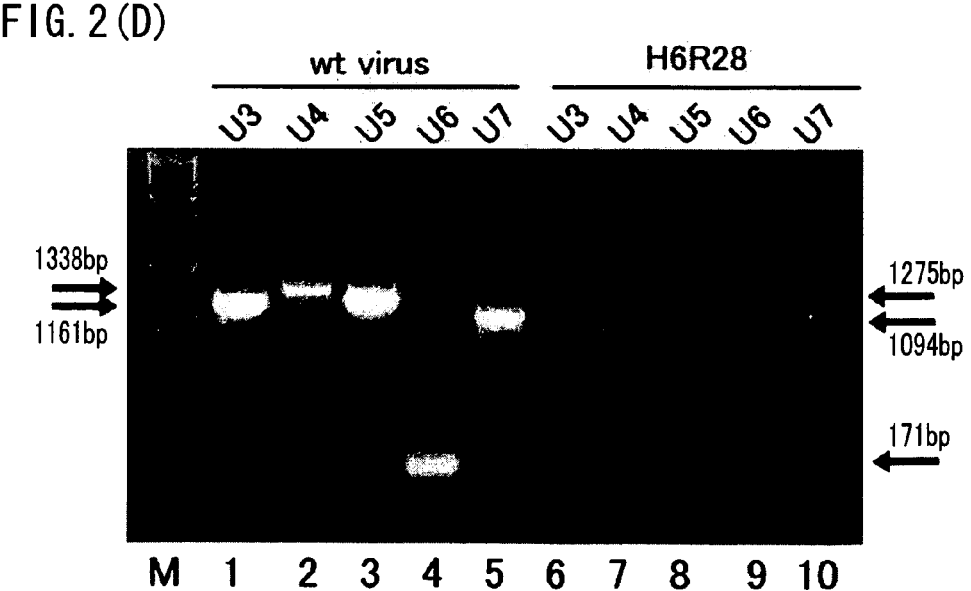
FIG. 2(D) is an electrophoretogram view representing results of PCR amplification that was performed to amplify region U3 to U7 of wild-type (wt) virus DNA and H6R28 virus DNA.

The results are shown in FIG. 2(D). Solid arrows on the left-hand side and right-hand side depict the expected sizes of the fragments amplified by the primer pairs. The sizes of U3F-U3R, U4F-U4R, U5F-U5R, U6F-U6R, and U7F-U7R were 1161 bp, 1338 bp, 1275 bp, 171 bp, and 1094 bp, respectively.

As FIG. 2(D) clearly shows, the wt virus (lanes 1-5) gave rise to fragments of sizes as expected from the respective primer pairs. In H6R28 (lanes 6-10), no amplified fragments were detected.

<Productive Infection of HHV-6 Recombinant Virus Vector H6R28>

The inventors of the present invention produced three independent isolates of H6R28 by three individual electroporations and examined the replication kinetics in CBMCs. Virus titration was performed using CBMCs according to the method of Asada et al. (H. Asada, et. al, J. Clin. Microbiol. 27:2204-2207, 1989) as described above. CBMCs were infected at a MOI of 0.05, and the three H6R28 clones and the wt virus showed similar levels of viral spreading (FIG. 3(A)) and virus production (FIG. 3(B)) over time.

FIG. 3 a graph representing productive infection of H6R28.

FIG. 3(A) represents kinetics of the increase in cells infected with wt virus and H6R28. CBMCs were infected with wt virus and three independent clones of H6R28 at an MOI of 0.05 (50% tissue culture infectious doses (TCID50)/cell), and the percentages of cells reacting with a mixture of monoclonal antibodies to glycoprotein B and glycoprotein H were determined by IFA staining using monoclonal antibodies. The percentages of cells infected with wt virus (open circle), H6R28 clone 1 (solid triangle), clone 2 (solid circle), and clone 3 (solid square) are shown. Data shown are mean values of results for three replicate cultures.

FIG. 3(B) represents growth curves for wt virus and H6R28.

CBMCs were infected as described above, and infected cells were harvested at the indicated times and frozen at −80° C. Progeny viruses were titrated on CBMCs using IFA staining. Virus titer was indicated as 50% TCID per milliliter. Titers from cells infected with wt virus (open square), H6R28 clone 1 (solid triangle), clone 2 (solid circle), and clone 3 (solid square) are shown. Values on day 0 represent the titers of the input viruses. Data shown are mean values of results for three replicate cultures.

It was found from the results shown in FIG. 3(A) and FIG. 3(B) that H6R28 had the same level of proliferation as the wt virus. In other words, it was found that the insertion of foreign genes at the U2 to U8 sites had no effect on virus proliferation.

<Construction of HHV-6 Recombinant Vector H6R24-25>

Recombinant virus vector H6R24-25 was constructed that used the U24 and U25 regions of HHV-6 as recombinant sites.

Figure 4:
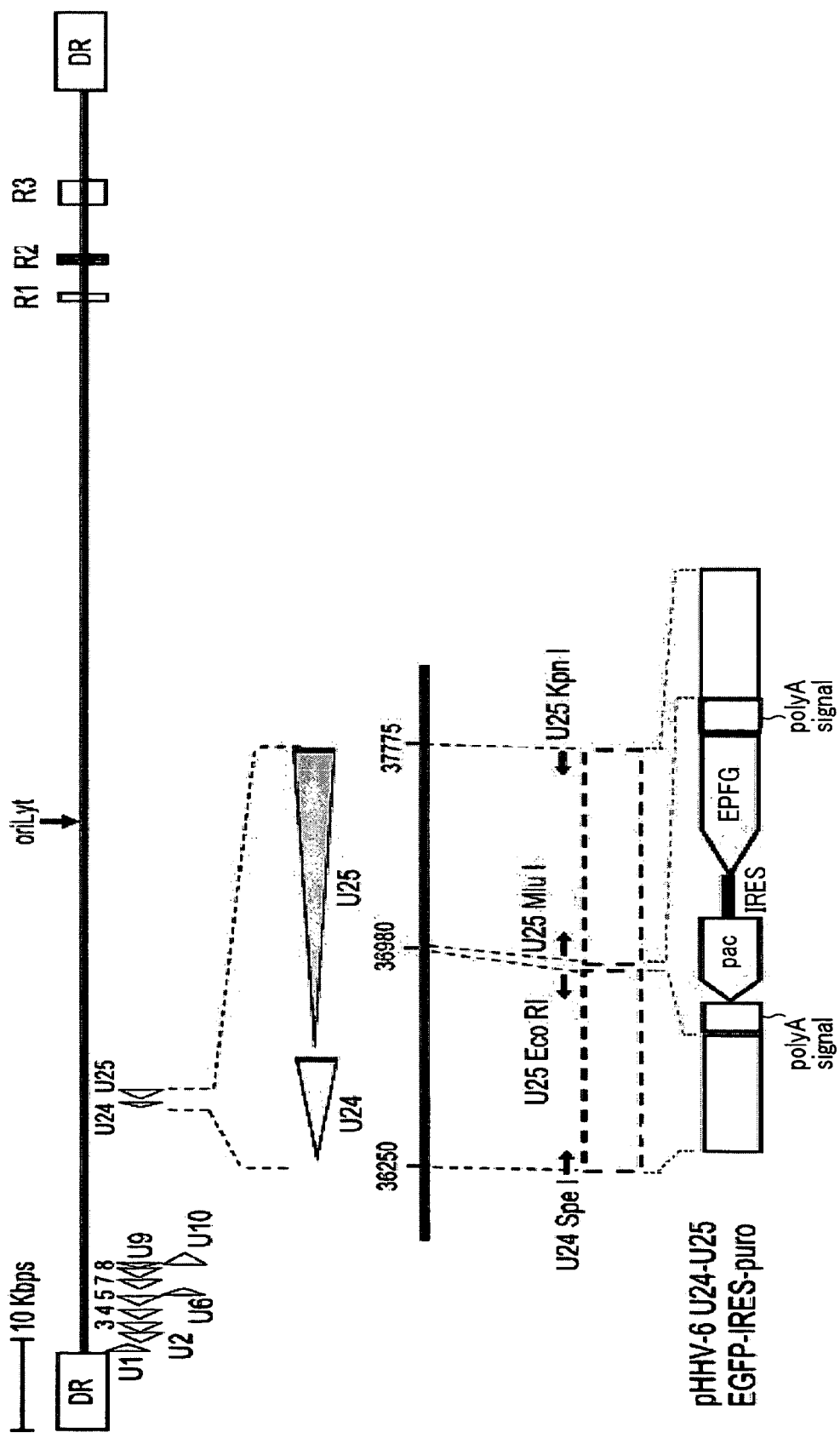
FIG. 4 is a schematic diagram representing a structure of H6R24-25 genome.

FIG. 4 schematizes a structure of the recombinant virus H6R24-25.

At the top is a map of the HHV-6B HST genome, with the regions U24 and U25 expanded below (in the middle).

The bottom diagram represents pHHV-6 U24-U25 EGFP-IRES-puro, a plasmid for homologous recombination in which U24 DNA fragments and U25 DNA fragments used for homologous recombination are inserted at the both ends of the EGFP-puro cassette.

The annealing sites of the primers used are depicted by small arrows pointing left or right.

The numbers 36250, 36980, and 37775 are the base numbers of the HHV-6HST strain.

In order to allow genes to be inserted in shorter recombinant sites than those of the recombinant virus H6R28, the size of genes was reduced using internal ribosomal entry site (IRES).

The construct procedure was the same as for H6R28 except that primers U24 SpeI and U25 EcoRI and primers U25 MluI and U25 KpnI were used for the amplification of U24 and U25 genes used for homologous recombination.

Confirmation of the H6R24-25 construct was made in the manner described in conjunction with the H6R28 construct. The same results were obtained. To avoid redundancy, no further explanation will be made.

As with the H6R28, H6R24-25 was examined in regard to the efficiency of viral spreading among cells and the efficiency of virus production in the infected cells. The experiment method was the same as that for H6R28.

Figure 5:
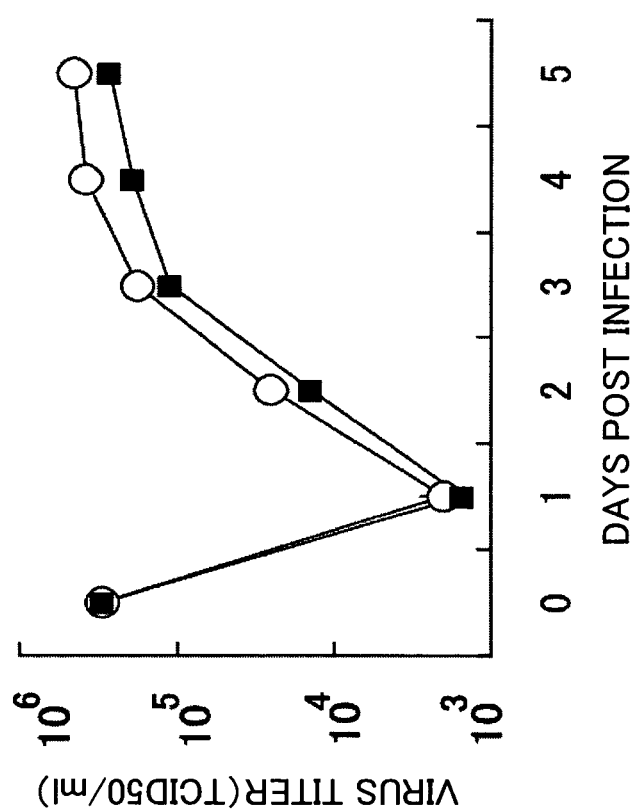
FIG. 5(A) is a graphical view representing an increase of anti-HHV-6 monoclonal antibody positive cells in cells infected with H6R24-25.
FIG. 5(B) is a graphical view representing changes in virus titer (the number of surviving cells) in the culture supernatant of cells infected with H6R24-25.
Figure 5:
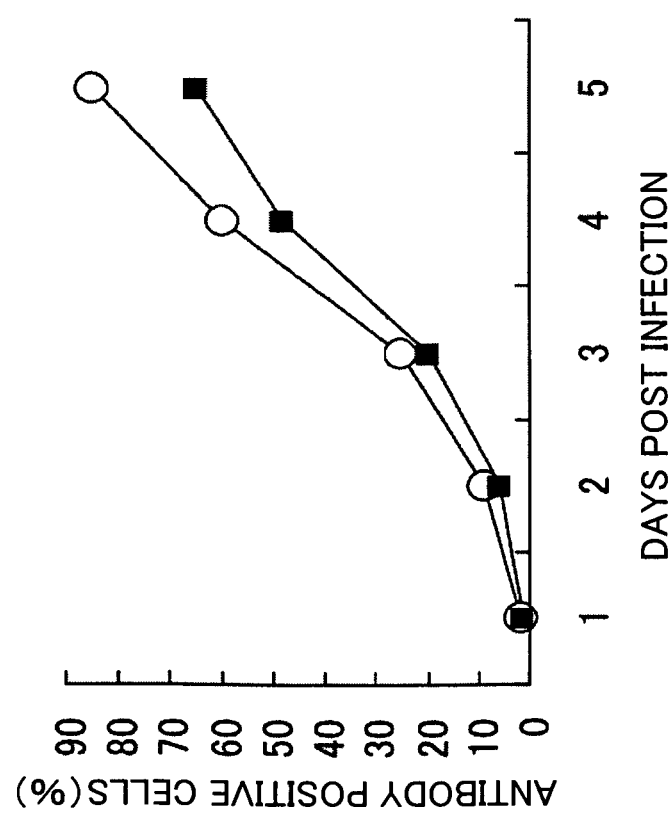

FIG. 5(A) represents an increase in virus antigen positive cells. FIG. 5(B) represents a growth curve of the virus. In FIGS. 5(A) and 5(B), open circle denotes the wt virus, and solid square represents H6H24-25.

It was found from the results shown in FIG. 5(A) and FIG. 5(B) that H6R24-25 had the same level of proliferation as the wt virus. In other words, it was found that the insertion of foreign genes at the U24 and U25 sites had no effect on virus proliferation.

It was found from the data of H6R28 and H6R24-25 that, in HHV-6, the U3, U4, U5, U6, U7, U8, U24, and U25 regions were usable as the insertion sites of foreign genes.

<Latent Infection Ability and Reactivation Efficiency of HHV-6 Recombinant Virus Vector>

The inventors of the present invention investigated H6R28 for its ability to establish latency and its efficiency of reactivation.

To evaluate the establishment of latency, peripheral blood macrophages were infected with wt virus and H6R28 and the percentage of HHV-6 DNA-positive cells was monitored according to method described in Kondo et al. (J. Gen. Virol. 72: 1401-1408, 1991, J. Virol. 77: 2258-2264, 2003, J. Virol. 76: 4145-4151, 2002).

Briefly, peripheral blood macrophages were cultured in RPMI 1640 supplemented with 25% horse serum on plastic plates coated with collagen (Sumitomo Bakelite Co., Ltd. Japan).

The macrophages were infected with HHV-6 on day 7 and cultured for 4 to 6 weeks. The infected macrophages were detached from the plates, and the absence of viral replication was confirmed by immunofluorescent antibody (IFA) staining using monoclonal antibodies against glycoproteins B and H.

The cells were serially diluted ($10^4$ to 1 cell per tube) into sample tubes using four tubes for each dilution, and the DNA was isolated from each sample tube. Viral DNA was detected by double-nested PCR (K Kondo, et. al, J. Infect. Dis. 167: 1197-1200, 1993), and the numbers of HHV-6 DNA positive cells were calculated by the Reed-Muench method (Reed, L. J., and H. Muench, Am. J. Hyg. 27:493, 1938).

To study the reactivation efficiency, viral reactivation was induced by tetradecanoyl phorbol acetate (TPA) treatment according to the method described in Kondo et al. (J. Gen. Virol. 72: 1401-1408, 1991, J. Virol. 76: 4145-4151, 2002). Briefly, latently infected cells were detached from the culture dish, serially diluted, and cocultivated with an uninfected macrophage feeder layer. Subsequently, the cells were treated with TPA (20 ng/ml) for 7 days and cocultivated with CBMCs for 7 days. The efficiency of the viral reactivation was calculated by the Reed-Muench method (Reed, L. J., and H. Muench, Am. J. Hyg. 27: 493, 1938).

Figure 6A:
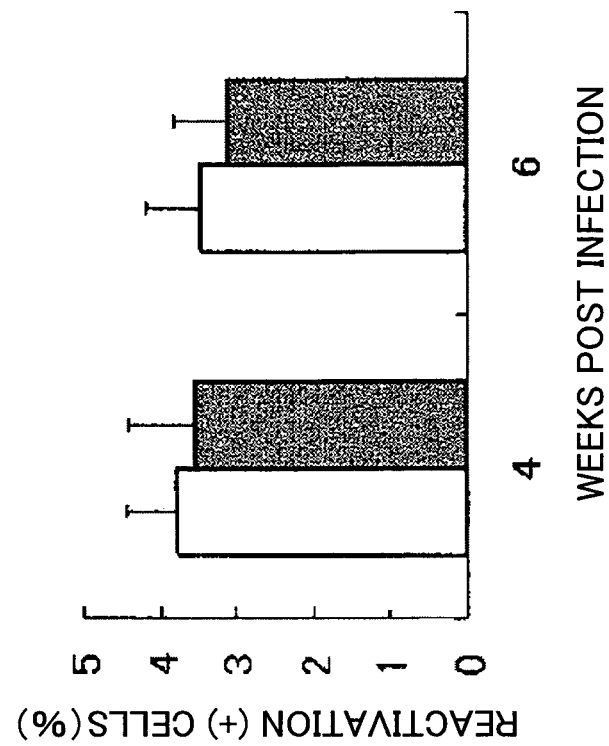
FIG. 6(A) is a graphical view representing percentages of HHV-6 DNA positive cells in cells latently infected with H6R28.
Figure 6B:
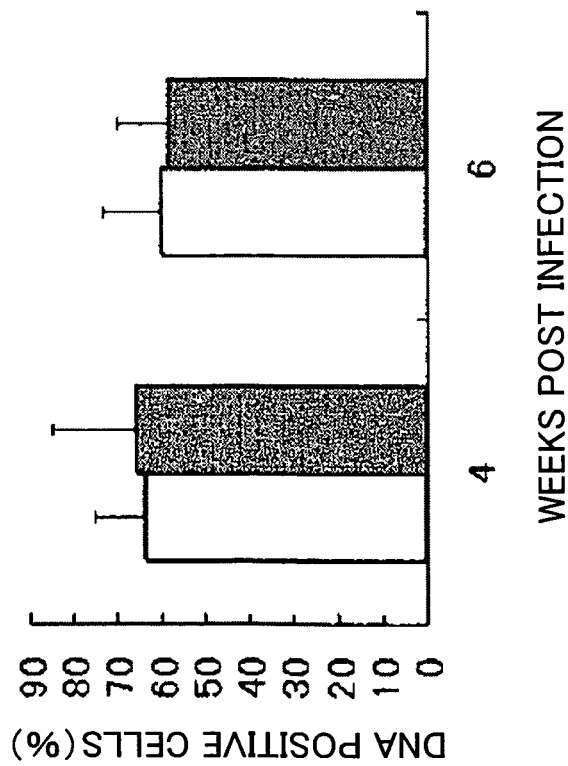
FIG. 6(B) is a graphical view representing percentages of reactivated cells in cells latently infected with H6R28.

The results are shown in FIGS. 6(A) and 6(B).

FIG. 6(A) represents percentages of HHV-6 DNA-positive cells. The percentages of HHV-6 DNA positive cells were examined 4 and 6 weeks postinfection. The data shown are mean values and standard deviations of results for three replicate cultures of wt virus and three clones of H6R28. Open column indicates wt virus. Shaded column indicates H6R28.

FIG. 6(B) represents percentages of reactivation positive cells. Viral reactivation was induced, and the percentages of reactivation-positive cells were calculated. The data shown are mean values and standard deviations of results for three replicate cultures of wt virus and three clones of H6R28. Open column indicates wt virus. Shaded column indicates H6R28.

As is clear from FIG. 6(A) and FIG. 6(B), the percentages of HHV-6 DNA positive cells and reactivation positive cells were found to be similar for the wt virus and H6R28. From these data, it was concluded that the establishment of latency and the reactivation process were not impaired by the deletion of the U3-U7 genes.

<Transfection of Various Cells with HHV-6 Recombinant Virus Vector>

(1) Macrophage, CBMCs, Molt-3, HeLa

Figure 7A:
FIG. 7(A) is a fluorescent micrograph view of macrophage latently infected with H6R28.

Interestingly, during HHV-6 latency, the inventors of the present invention failed to detect the expression of EGFP that was driven by the HCMV major immediate-early enhancer-promoter (MIEP) (FIG. 7(A)). On the other hand, EGFP expression was observed in the latently infected macrophage (FIG. 7(B)) transfected with the plasmid pU2-U8 EGFP-puro illustrated in FIG. 1, reactivation-induced macrophages (FIG. 7(C)), productively infected CBMCs and Molt-3 cells (FIGS. 7(D) and 7(E)), and abortively infected HeLa cells (FIG. 7(D)).

FIG. 7 represents fluorescence micrographs showing EGFP expression in various types of cells. In FIG. 7, cultured live cells were observed under fluorescent illumination.

Figure 7B:
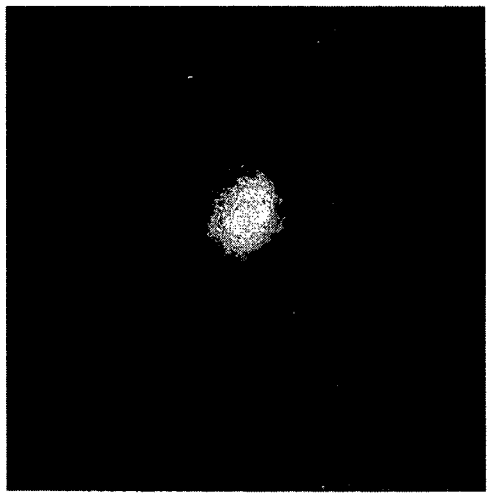
FIG. 7(B) is a fluorescent micrograph view of latently infected macrophage transfected with plasmid pU2-U8EGFP-puro.
Figure 7C:
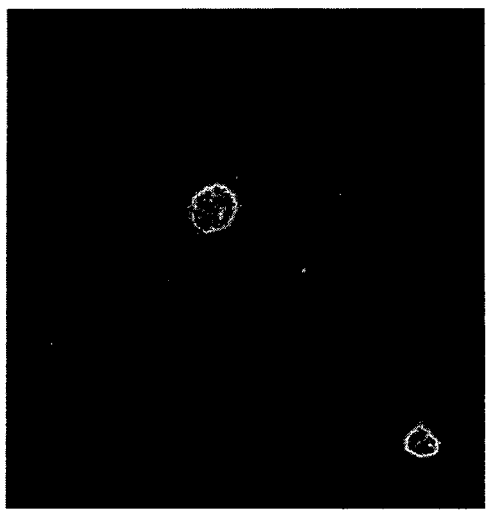
FIG. 7(C) is a fluorescent micrograph view of reactivation-induced macrophage.

FIG. 7(A) shows macrophages that were latently infected with H6R28. FIG. 7(B) shows latently infected macrophages that were transfected with the plasmid pU2-U8 EGFP-puro shown in FIG. 1 (transfection was performed according to the method described in Kondo et al. (J. Virol. 77: 2258-2264, 2003)). FIG. 7(C) shows reactivation-induced macrophages that were treated with 20 ng of TPA/ml for 7 days.

Figure 7D:
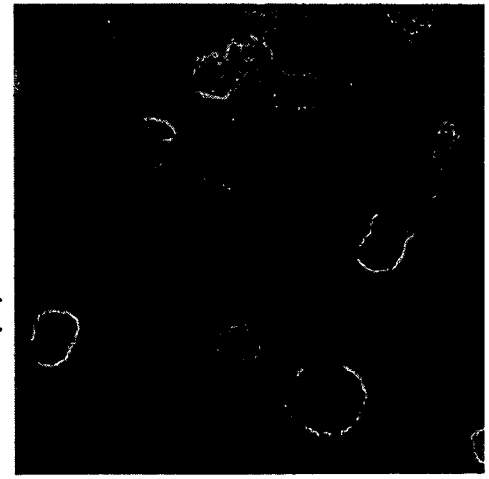
FIG. 7(D) is a fluorescent micrograph view of CBMCs infected with H6R28.
Figure 7E:
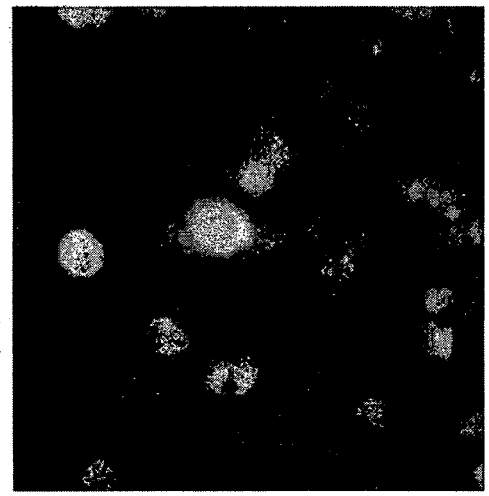
FIG. 7(E) is a fluorescent micrograph view of Molt-3 cells infected with H6R28.
Figure 7F:
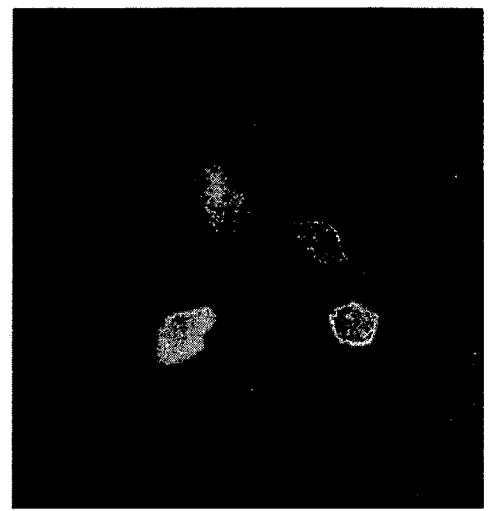
FIG. 7(F) is a fluorescent micrograph view of HeLa cells infected with H6R28.

FIG. 7(D) shows CBMCs infected with H6R28. FIG. 7(E) shows Molt-3 cells infected with H6R28. FIG. 7(F) shows HeLa cells infected with H6R28.

The cells were observed 4 weeks (A to C) or 2 days (E to F) postinfection. The transfected cells were observed 1 day post transfection (B).

(2) Natural Killer (NK) Cells

Adult peripheral blood mononuclear cells cultured in the presence of interleukin-2 (IL-2) were infected with the free virus of H6R28 at a multiplicity of infection (MOI) 1. Gene transfection in the CD56 positive cells (NK cells) was confirmed through EGFP expression, using FACS on day 3 postinfection.

Figure 8A:
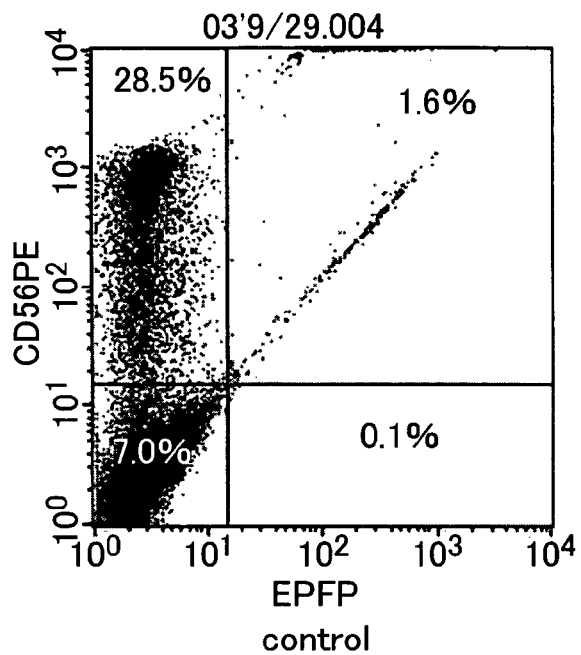
FIG. 8(A) is a view showing the result of FACS on EGFP expression of natural killer cells uninfected with H6R28.
Figure 8B:
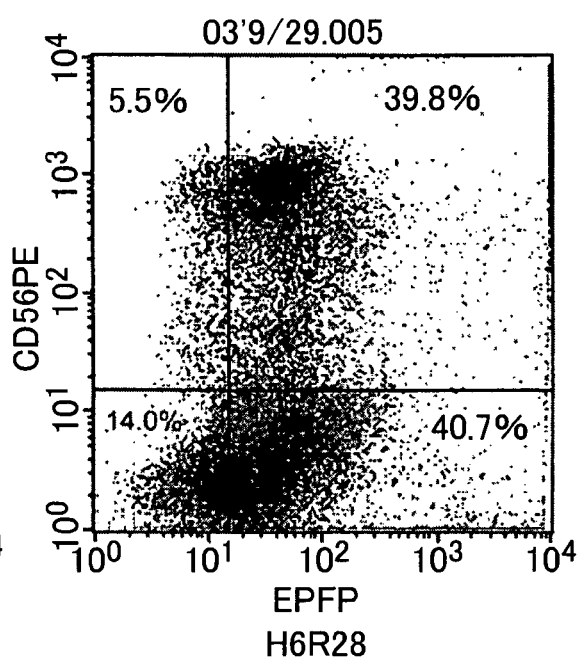
FIG. 8(B) is a view showing the result of FACS on EGFP expression of natural killer cells infected with H6R28.
Figure 8C:
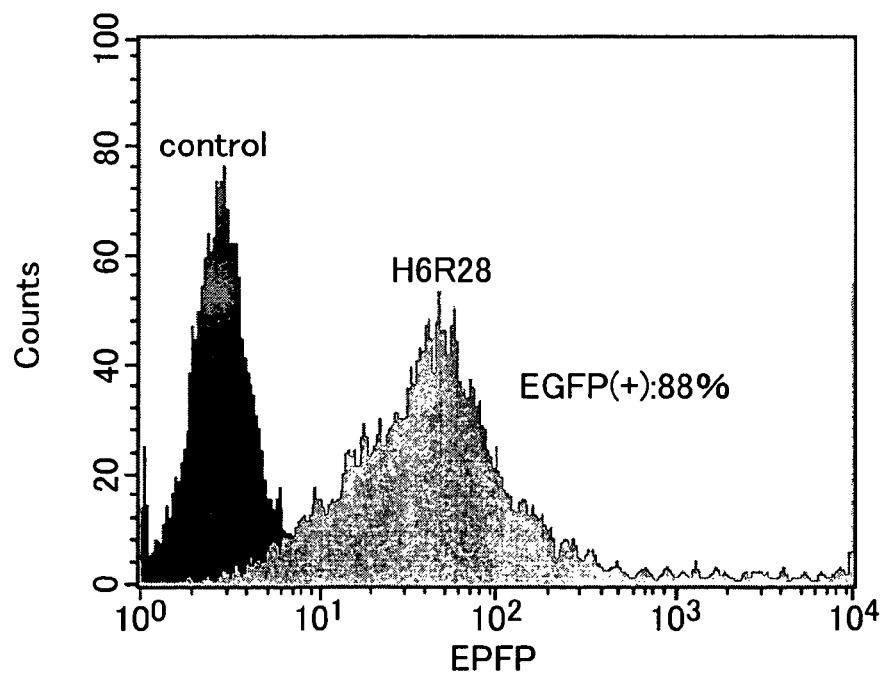
FIG. 8(C) is a view summering the results shown in FIGS. 8(A) and 8(B).

The results are shown in FIG. 8(A) through FIG. 8(C). FIG. 8(A) shows the result for cells uninfected with H6R28. FIG. 8(B) shows the result for cells infected with H6R28. FIG. 8(C) is a graph summarizing the results shown in FIGS. 8(A) and 8(B).

As is clear from FIGS. 8(A) through 8(C), HHV-6 allowed for efficient transfection of the NK cells with foreign gene EGFP. The transfection rate was 88% [39.8%/(5.5%+39.8%)].

(3) Astrocytes

The primary culture of human astrocytes cultured in the presence of a basic fibroblast growth factor (bFGF) was infected with the free virus of H6R28 at a multiplicity of infection (MOI) 1. Gene transfection was confirmed through EGFP expression on day 2 postinfection, using a fluorescent microscope.

Figure 9:
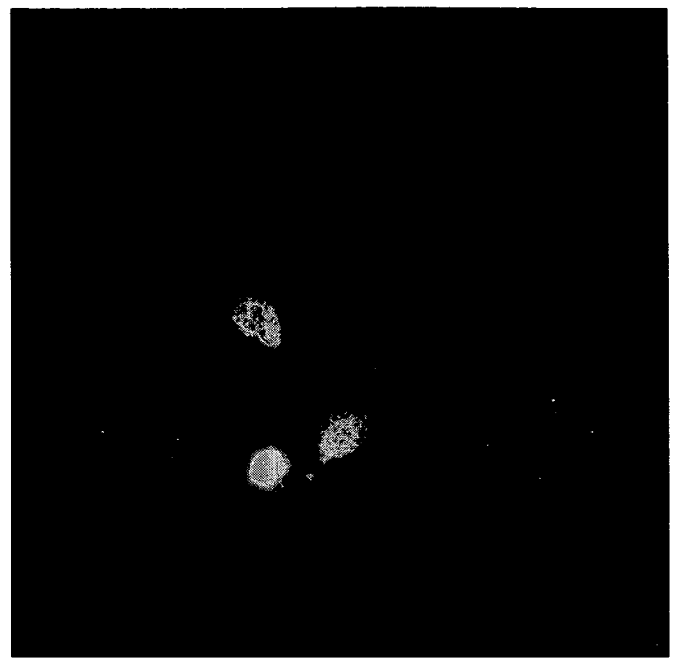
FIG. 9 is a fluorescent micrograph view showing the EGFP expression of astrocytes infected with H6R28.

FIG. 9 represents the fluorescence micrograph. HHV-6 allowed about 40% of the primary culture of human astrocytes to be transfected with foreign gene EGFP.

(4) CD4 Positive T Cells

Adult peripheral blood mononuclear cells cultured in the presence of phytohemagglutinin (PHA) was infected with the free virus of H6R28 at a multiplicity of infection (MOI) 1. Gene transfection was confirmed through EGFP expression on day 1 postinfection, using FACS.

Figure 10:
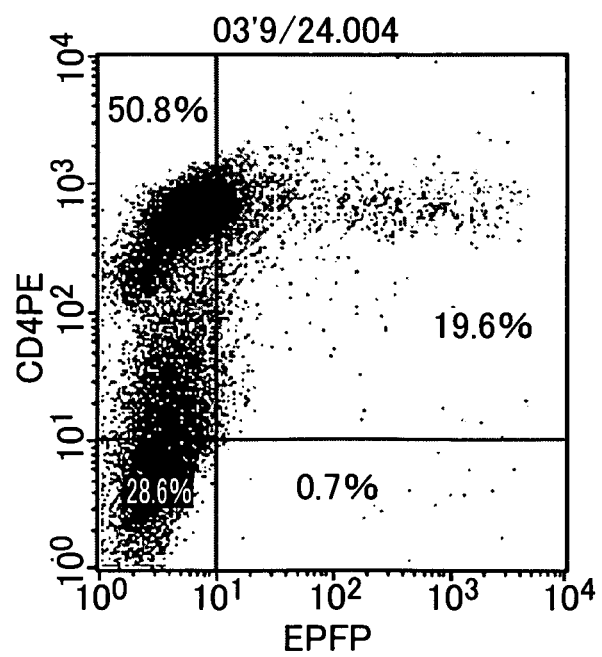
FIG. 10 is a view showing the result of FACS on EGFP expression of CD4 positive T cells infected with H6R28.

FIG. 10 shows the result. HHV-6 allowed for transfection of about 30% [19.6%/(50.8%+19.6%)] of the CD4 positive T cells with foreign gene EGFP.

(5) CD8 Positive T Cells

Adult peripheral blood mononuclear cells cultured in the presence of phytohemagglutinin (PHA) was infected with the free virus of H6R28 at a multiplicity of infection (MOI) 1. Gene transfection was confirmed through EGFP expression on day 3 postinfection, using FACS.

Figure 11:
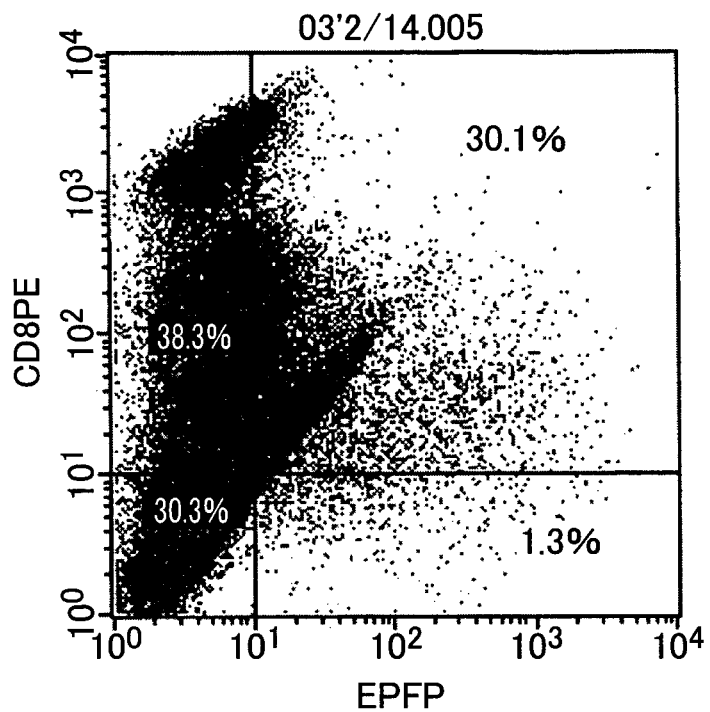
FIG. 11 is a view showing the result of FACS on EGFP expression of CD8 positive T cells infected with H6R28.

FIG. 11 shows the result. HHV-6 allowed for transfection of about 40% [30.1%/(38.3%+30.1%)] of the CD8 positive T cells with foreign gene EGFP.

(6) Dendritic Cells

Adult peripheral blood mononuclear cells cultured in the presence of interleukin-4 (IL-4) and granulocyte-macrophage colony-stimulating factor (GM-CSF) was infected with the free virus of H6R28 at a multiplicity of infection (MOI) 1. Gene transfection of the CD83 positive cells (dendritic cells) was confirmed through EGFP expression on day 3 postinfection, using FACS.

Figure 12:
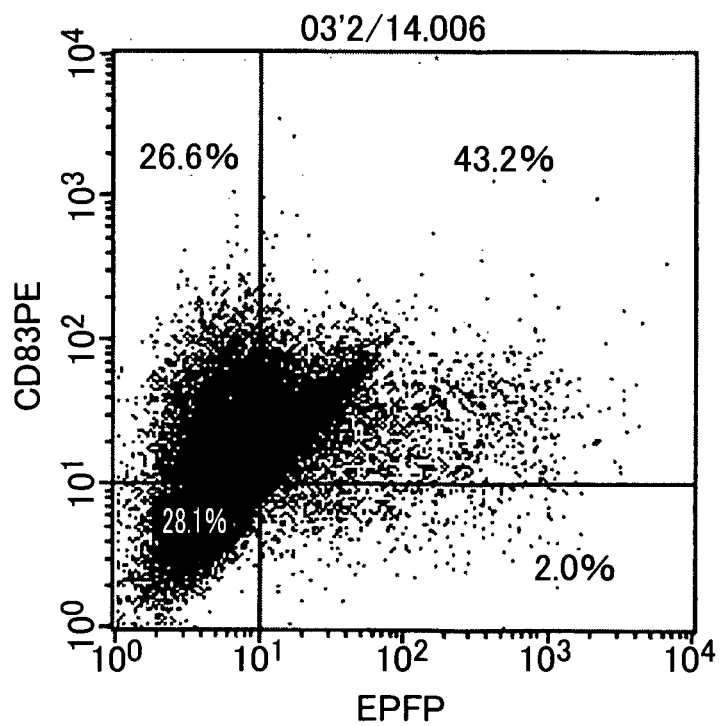
FIG. 12 is a view showing the result of FACS on EGFP expression of dendritic cells infected with H6R28.

FIG. 12 shows the result. HHV-6 allowed for transfection of about 60% [43.2%/(26.6%+43.2%)] of the CD83 positive dendritic cells with foreign gene EGFP.

Note that, though no Examples are given, there have been reports that the wt HHV-6 also infects blood stem cells, liver cells, vascular endothelial cells, and fibroblasts (see Reference Documents 1-5), suggesting that the H6R28 free virus can also infect these types of cells.

(Reference Document 1)

Luppi M, Barozzi P, et. al, J. Virol., January, 1999, Vol. 73, No. 1, P. 754-9. "Human herpesvirus 6 latently infects early bone marrow progenitors in vivo"

(Reference Document 2)

Tajiri H, Tanaka-Taya K, et. al, Pediatr., September 1997, Vol. 131, No. 3, p. 473-5. "Chronic hepatitis in an infant, in association with human herpesvirus-6 infection"

(Reference Document 3)

Wu C A, Shanley J D., March 1998, Vol. 79, No. 5, p. 1247-56. "Chronic infection of human umbilical vein endothelial cells by human herpesvirus-6"

(Reference Document 4)

Rotola A, Di Luca D, et. al, J Clin Microbiol., August 2000, Vol. 38, No. 8, p. 3135-6. "Human herpesvirus 6 infects and replicates in aortic endothelium"

(Reference Document 5)

Luka J, Okano M, Thiele G., J Clin Lab Anal., April 1990, Vol. 4, No. 6, p. 483-6. "Isolation of human herpesvirus-6 from clinical specimens using human fibroblast cultures"

<Function of HCMV Promoter in Latently Infected HHV-6>

To investigate the gene expression from the IE1/IE2 promoter, 5' RACE was performed (J. Virol. 77: 2258-2264, 2003, J. Virol. 76:4145-4151, 2002, Proc. Natl. Acad. Sci. USA, 93: 11137-11142, 1996).

Briefly, the 5' end of the cDNA was dA tailed and annealed with an anchor primer, RL-1. The initial 10 cycles of PCR were performed with Taq polymerase (Roche Diagnostics) using the following conditions: denaturation for 1 min at 94° C., annealing for 1 min at 55° C., and extension for 1 min at 72° C.

PCR amplification was performed with PCR with KOD Plus DNA polymerase (TOYOBO, Otsu, Japan) using primers N1 and EGFP-R1 followed by primers N2 and EGFP-R2 (FIG. 13(A)) under the following conditions: denaturation for 1 min at 94° C., annealing for 30 sec. at 65° C., and extension for 1 min at 68° C. (15 cycles per amplification). The amplified products were sequenced.

In the latent cells, transcription of the mRNA from the usual transcription start position (productive infection transcription start site [PSS]) was not detected (FIG. 13(B)); however, small amounts of mRNA were transcribed from the latent infection transcription start sites (LSSs) 1 and 2 of HCMV, which are used to express the latency-associated transcripts of HCMV.

In contrast, the PSS was used in the latently infected macrophage transfected with the plasmid pU2-U8 EGFP-puro, reactivation-induced macrophages, and the productively infected Molt-3 cells and the abortively infected HeLa cells (FIG. 13(B)). Since HCMV MIEP showed the latency-associated performance in the context of HHV-6 latency, it is suggested that the transcriptional control of HHV-6 latency may share some common mechanism with HCMV latency. These findings may be related to the fact that HCMV shows some similarity with HHV-6, such as the site of latency.

Figure 13:
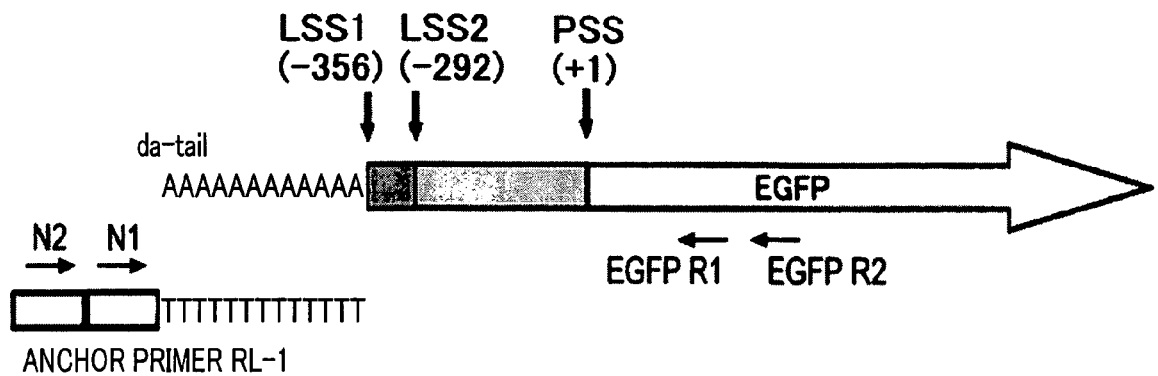
FIG. 13(A) is a schematic diagram representing the 5' RACE method used to examine functions of HCMV promoter during H6R28 latency ('AAAAAAAAAAAA' disclosed as SEQ ID NO: 44 and 'TTTTTTTTTTTT' disclosed as SEQ ID NO: 45)
FIG. 13(B) is an electrophoretogram view showing fragments amplified by 5' RACE.
Figure 13:
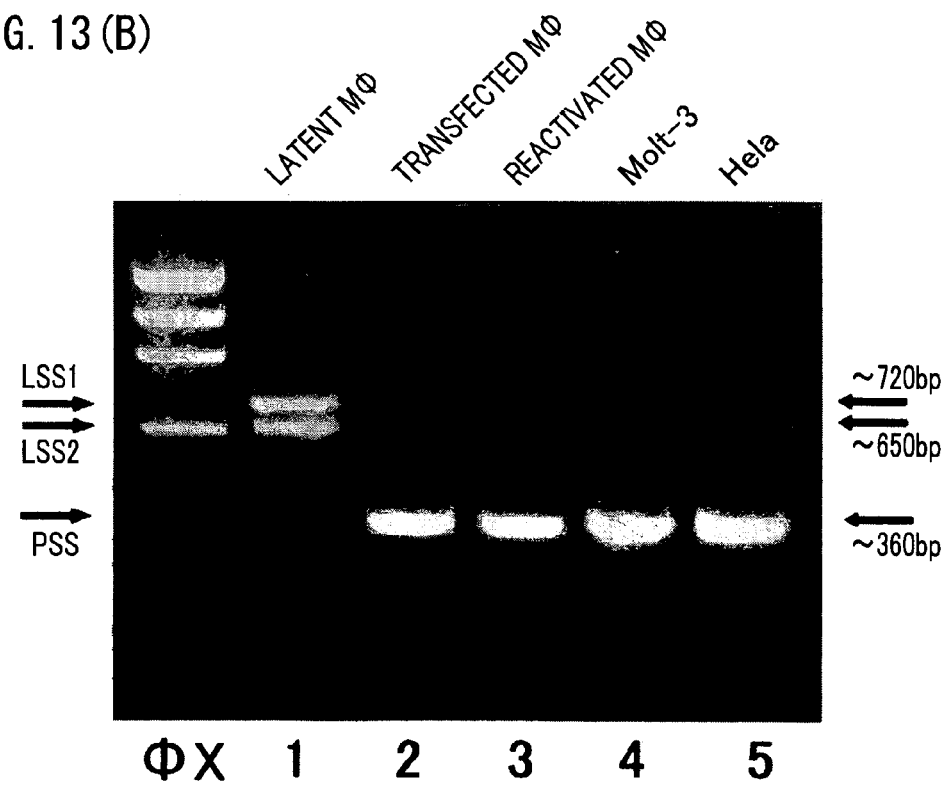

FIG. 13 is a schematic diagram and an electrophoretogram showing functions of the HCMV promoter in the latently infected HHV-6.

FIG. 13(A) shows HCMV IE1/IE2 promoter and PCR primers. The EGFP gene and transcription start sites are drawn to scale. The PSS of IE1/IE2 mRNA (indicated as +1) and two LSSs (LSS1 and LSS2) are shown. The locations of the PCR primers are depicted, and a schematic drawing shows the usage of the anchor primer RL-1. Primer sequences are shown in Table 1.

FIG. 13(B) represents 5' RACE amplification of the EGFP transcripts.

Lane 1 shows RNA from $1 \times 10^5$ latently infected macrophages (Mf). Lane 2 shows $1 \times 10^5$ latently infected macrophages that were transfected with the plasmid pU2-U8 EGFP-puro shown in FIG. 1. Lane 3 shows $1 \times 10^5$ reactivation-induced macrophages. Lane 4 shows $1 \times 10^2$ productively infected Molt-3 cells. Lane 5 shows $1 \times 10^3$ abortively infected HeLa cells.

These cells were analyzed by the 5' RACE method. The RACE method used was the same as that commonly used. The 5' end of the transcript was dA tailed and annealed with the anchor primer RL-1 (FIG. 13A) and amplified first with primers N2-EGFP R2 and then with primers N1-EGFP R1. The 5' ends of the transcript initiating at PSS (up to 360 bp), LSS1 (up to 720 bp), and/or LSS2 (up to 650 bp) were detected. HaeIII-digested ΦX174 DNA fragments were used as size markers (ΦX).

<Construction of HHV-7 Recombinant Virus Vector H7R28>

In order to construct recombinant virus H7R28, a U2-U8 gene cluster of human herpesvirus 7 (HHV-7) was replaced with EGFP-puro, a gene cassette containing the gene for enhanced green fluorescent protein (EGFP) under control of the human cytomegalovirus major immediate-early enhancer-promoter (MIEP) and the puromycin resistance gene under control of the SV40 early promoter. To insert the EGFP-puro cassette into the HHV-7 genome by homologous recombination, 1-kb segments of viral genome were inserted into each end of the cassette (FIG. 14).

The U2-U8 gene clusters were examined. It was found that replacement of the U2-U8 genes with EGFP-puro resulted in a successfully replicating virus.

The following specifically describes the construct procedure.

Figure 14:
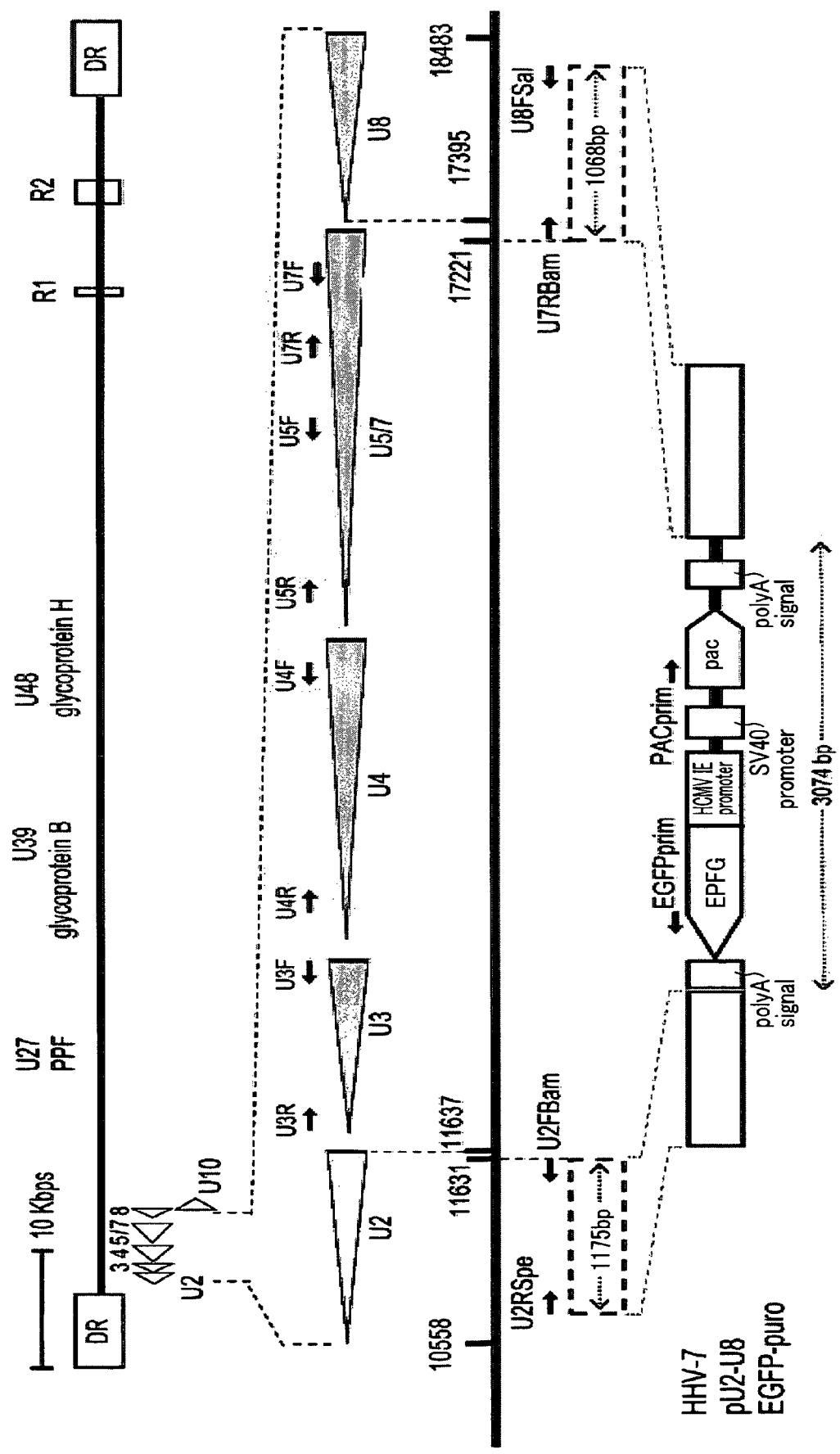
FIG. 14 is a schematic diagram showing a structure of the H7R28 genome.

FIG. 14 schematizes a structure of the recombinant virus H7R28.

At the top is a map of the HHV-7 RK genome, with the region U2 to U8 expanded below (in the middle).

The bottom diagram represents HHV-7 pU2-U8 EGFP-puro, a plasmid for homologous recombination in which DNA fragments used for homologous recombination are inserted at the both ends of the EGFP-puro cassette.

The annealing sites of the primers used are depicted by small arrows pointing left or right.

The numbers 10558, 11637, and 18483 are the base numbers of the HHV-7RK strain.

Primer sequences are shown in Table 2 below.

TABLE 2

(SEQ ID NOS 28-35, 46 and 41-43, respectively, in order of appearance)

| PRIMER | SEQ ID NO: | PRIMER SEQUENCE |
|---|---|---|
| 7U2F1 | 28 | 5'- CAGCGTTTCCTGATGTTGGAACCCAG -3' |
| 7U2R1 | 29 | 5'- GCATCTTACCAATGATGATCGCAAGC -3' |
| 7U2FBam | 30 | 5'- TTGGATCCTGATCATTTGCATGTTGCTAG TATGTCAG -3' |
| 7U2RSpe | 31 | 5'- GACTAGTCTCCGAATCGAAGCTAATCTGA GAGC -3' |
| 7U8F1 | 32 | 5'- CCGATTCCTACTTTCGACAAGAGG -3' |
| 7U8R1 | 33 | 5'- CTCCGTACCACAGTCTGTCTAGCTC -3' |
| 7U8FSal | 34 | 5'- GCGTCGACAGCCAGTTGACGTTGCTGGTT ACTCAG -3' |
| 7U7RBam | 35 | 5'- TTGGATCCATGCCTTCTCCATATGAAGAC AGCAGC -3' |
| 7U24 Spe I | 40 | 5'- GGACTAGTCACTGCGCAATTAGAAGAAGC CTAG -3' |
| 7U25 Eco RI | 41 | 5'- GGAATTCGATGATGAACAAATCATTTTTC TCGCAC -3' |
| 7U25 Mlu I | 42 | 5'- CGACGCGTCACCAAAAATTTTCCCATTCA CATCG -3' |
| 7U25 Kpn I | 43 | 5'- GGGGTACCGCATGGATTTCTTAGCGAATT TGTGCTG -3' |

For the construct, the U2 gene was amplified by PCR with primers 7U2FBam and 7U2RSpe, and the U7-U8 genes were amplified with primers 7U8FSal and 7U7RBam.

The amplified U2 gene product was digested with SpeI-BamHI. The amplified U7U8 gene product was digested with SalI-BamHI. The digested products were then inserted into each end of pEGFP-puro (HHV-7 pU2-U8 EGFP-puro in FIG. 14).

The cloned plasmid HHV-7 pU2-U8 EGFP-puro was transfected into phytohemagglutinin (PHA)-stimulated peripheral blood mononuclear cells (PBMCs) by using a Nucleofector™ electroporator (Amaxa Biosystems, Germany) according to the manufacturer's recommended protocol.

Briefly, $5 \times 10^6$ cells were mixed with 5 µg of the plasmid and 100 µl of Nucleofector™ solution for T cells, and electroporation was performed with the Nucleofector™ using the program U-14.

Alternatively, a conventional electroporation method was used. In this case, $1 \times 10^7$ cells were mixed with 50 µg of the plasmid suspended in 500 µl of K-phosphate-buffered saline (30.8 mM NaCl, 120.7 mM KCl, 8.1 mM $Na_2HPO_4$, 1.46 mM $KH_2PO_4$, and 25 mM $MgCl_2$), and the mixture was placed in an electroporation cuvette (Gene Pulser cuvette, 0.4-cm diameter; Bio-Rad).

Electroporation was performed with a Gene Pulser II electroporation system (Bio-Rad) with resistance at infinity, voltage at 300 V, and capacitance at 960 µF. After 6 hours, the cells were infected with HHV-7 KHR strain at a multiplicity of infection (MOI) of 0.5 using the centrifuge method.

Cells were cultured for 3 days in RPMI 1640 supplemented with 10% fetal bovine serum and frozen as a virus stock. To enrich for the recombinant virus, PHA-stimulated umbilical cord blood mononuclear cells (CBMCs) were infected with the virus stock and cultured for 1 day, treated with 7.5 μg of puromycin/ml for 1 day, washed with the medium, and cultured with CBMCs for 3 days. The infected cells were then frozen as a new virus stock.

This selection procedure was repeated five times, and the recombinant virus (H7R28) was subsequently cloned by limiting dilution using CBMCs cultured in 96-well plates.

<Construction Confirmation of HHV-7 Recombinant Virus Vector H7R28>

Construction of the HHV-7 recombinant virus vector was confirmed by the method used to confirm construction of the HHV-6 recombinant virus vector H6R28. The results were the same. To avoid redundancy, no further explanation will be made.

<Productive Infection of HHV-7 Recombinant Virus Vector H7R28>

H7R28 was examined in regard to the efficiency of viral spreading among cells and the efficiency of virus production in the infected cells. The experiment method was the same as that for H6R28, except that the anti-HHV-7 monoclonal antibody (KR4) was used instead of the anti-HHV-6 monoclonal-antibody.

FIG. 15(A) represents an increase in virus antigen positive cells. FIG. 15(B) represents a growth curve of the virus. In FIGS. 15(A) and 15(B), open circle denotes the wt virus, and solid square represents H7R28.

It was found from the results shown in FIG. 15(A) and FIG. 15(B) that H7R28 had the same level of proliferation as the wt virus. In other words, it was found that the insertion of foreign genes at the U2, U3, U4, U5, U7, and U8 sites had no effect on virus proliferation.

<Construction of HHV-7 Recombinant Vector H7R24-25>

Recombinant virus vector H7R24-25 was constructed that used the U24 and U25 regions of HHV-7 as recombinant sites.

Figure 16:
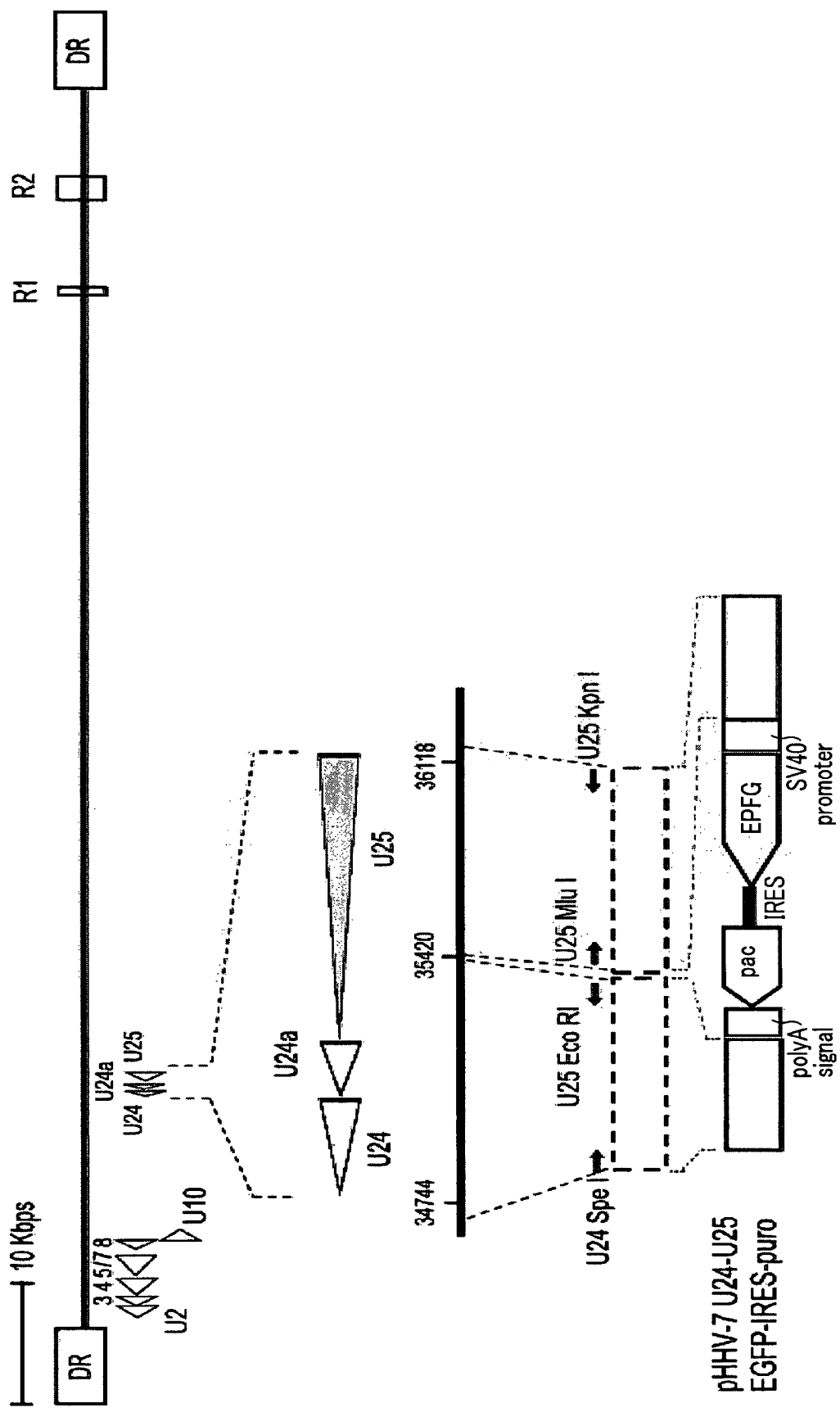
FIG. 16 is a schematic diagram showing a structure of the H7R24-25 genome.

FIG. 16 schematizes a structure of the recombinant virus H7R24-25.

At the top is a map of the HHV-7 RK genome, with the regions U24 and U25 expanded below (in the middle).

The bottom diagram represents pHHV-7 U24-U25 EGFP-IRES-puro, a plasmid for homologous recombination in which DNA fragments used for homologous recombination are inserted at the both ends of the EGFP-puro cassette.

The annealing sites of the primers used are depicted by small arrows pointing left or right.

The numbers 34744, 35420, and 36118 are the base numbers of the HHV-7RK strain.

In order to allow genes to be inserted in shorter recombinant sites than those of the recombinant virus H7R28, the size of genes was reduced using internal ribosomal entry site (IRES).

The construct procedure was the same as for H7R28 except that primers U24 SpeI and U25 EcoRI and primers U25 MluI and U25 KpnI were used for the amplification of U24 and U25 genes used for homologous recombination.

Confirmation of the H6R24-25 construct was made in the manner described in conjunction with the H6R28 construct. The same results were obtained. To avoid redundancy, no further explanation will be made.

As with the H6R28, H7R24-25 was examined in regard to the efficiency of viral spreading among cells and the efficiency of virus production in the infected cells. The experiment method was the same as that for H6R28, except that the anti-HHV-7 monoclonal antibody (KR4) was used instead of the anti-HHV-6 monoclonal antibody.

FIG. 17(A) represents an increase in virus antigen positive cells. FIG. 17(B) represents a growth curve of the virus. In FIGS. 17(A) and 17(B), open circle denotes the wt virus, and solid square represents H7H24-25.

It was found from the results shown in FIG. 17(A) and FIG. 17(B) that H7R24-25 had the same level of proliferation as the wt virus. In other words, it was found that the insertion of foreign genes at the U24 and U25 sites had no effect on virus proliferation.

It was found from the data of H7R28 and H7R24-25 that, in HHV-7, the U3, U4, U5, U7, U8, U24, U24a, and U25 regions were usable as the insertion sites of foreign genes.

<Latent Infection Ability and Reactivation Efficiency of HHV-7 Recombinant Virus Vector>

As with HHV-6 recombinant virus vector, HHV-7 recombinant virus vector was investigated for its ability to establish latency and its efficiency of reactivation. The method used for the HHV-6 recombinant virus vector was used, and the same results were obtained. To avoid redundancy, no further explanation will be made.

<Transfection of Various Cells with HHV-7 Recombinant Virus Vector>

(1) Macrophage

Adult peripheral blood mononuclear cells cultured in the collagen coat dish were infected with the free virus of H7R28 at a multiplicity of infection (MOI) 1. Gene transfection in the adhesive cell, i.e., CD11c positive cells (macrophage), was confirmed through EGFP expression, using FACS on day 3 postinfection.

Figure 18:
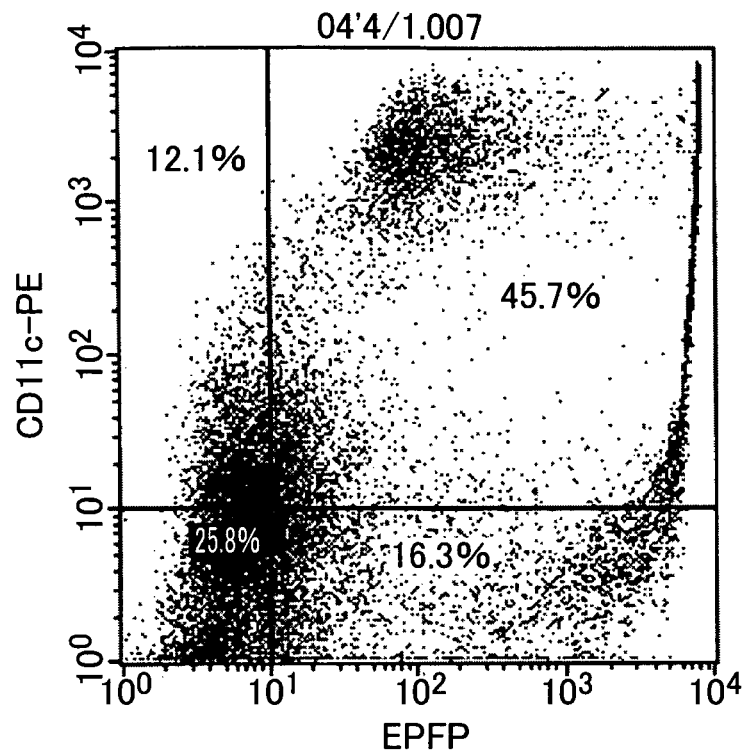
FIG. 18 is a view showing the result of FACS on EGFP expression of macrophages infected with H7R28.

The results are shown in FIG. 18. HHV-7 allowed about 80% [45.7%/(12.1%+45.7%)] of the macrophage to be transfected with foreign gene EGFP.

(2) CD4 Positive T Cells

Adult peripheral blood mononuclear cells cultured in the presence of phytohemagglutinin (PHA) was infected with the free virus of H7R28 at a multiplicity of infection (MOI) 1. Gene transfection in the CD4 positive T cells was confirmed through EGFP expression on day 3 postinfection, using FACS.

Figure 19:
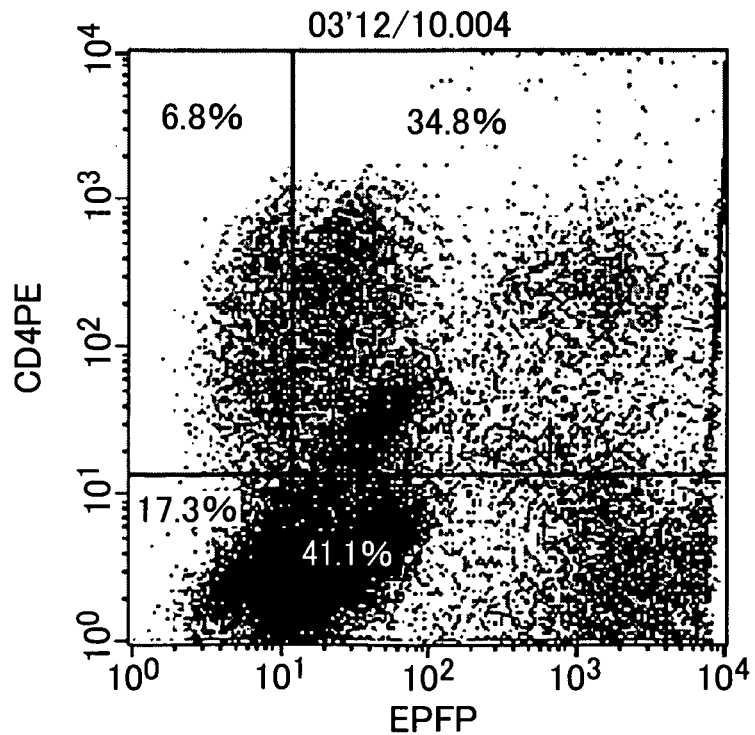
FIG. 19 is a view showing the result of FACS on EGFP expression of CD4 positive T cells infected with H7R28.

FIG. 19 shows the result. HHV-7 allowed for transfection of about 48% [34.8%/(6.8%+34.8%)] of the CD4 positive T cells with foreign gene EGFP.

(3) Dendritic Cells

Adult peripheral blood mononuclear cells cultured in the presence of interleukin-4 (IL-4) and granulocyte-macrophage colony-stimulating factor (GM-CSF) was infected with the free virus of H7R28 at a multiplicity of infection (MOI) 1. Gene transfection of the CD83 positive cells (dendritic cells) was confirmed through EGFP expression on day 3 postinfection, using FACS.

Figure 20:
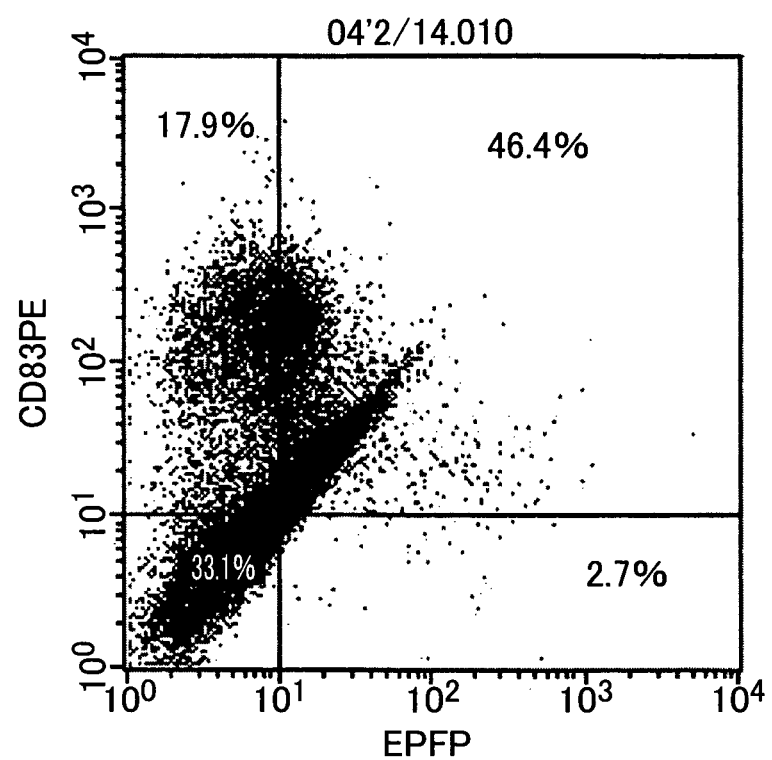
FIG. 20 is a view showing the result of FACS on EGFP expression of dendritic cells infected with H7R28.

FIG. 20 shows the result. HHV-6 allowed for transfection of about 70% [46.4%/(17.9%+46.4%)] of the CD83 positive dendritic cells with foreign gene EGFP.

<Insertion of Replication Origins of BAC (Bacterial Artificial Chromosome) in HHV-6 and HHV-7>

The U2-U8 regions of HHV-6 and HHV-7 provide large insertion sites for foreign genes, and therefore allow relatively large genes to be transfected. Specifically, if the replication origins of bacterial artificial chromosome (BAC) could be inserted, then it would be possible to produce vectors according to a so-called BAC system. Production of recombinant virus by the BAC system has been established in many types of viruses, including other types of herpes viruses. However, there has been no established method in HHV-6 and HHV-7.

(1) Production of Recombinant HHV-6 with the Insertion of BAC Replication Origins (H6R28 BAC)

Figure 21:
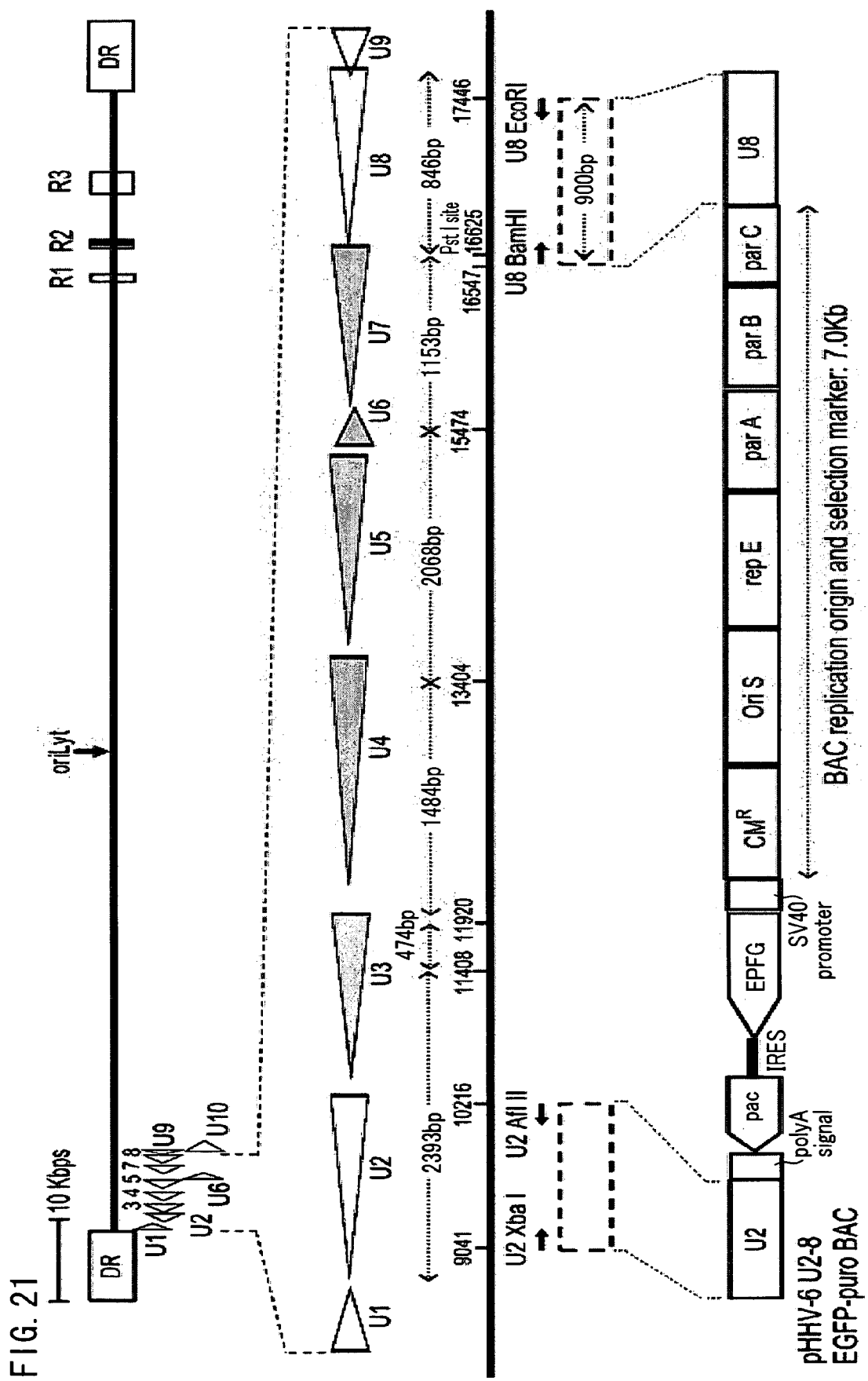
FIG. 21 is a schematic diagram showing a structure of the H6R28 BAC genome.

FIG. 21 is a schematic diagram representing a structure of H6R28 BAC.

As in H6R28, the U2 and U8 sequences were used for homologous recombination. Plasmid pHHV-6 U2-8 EGFP-puro BAC was prepared in which BAC replication origins [chloramphenicol resistant gene (CMR), BAC replication origins (Ori S, rep E, par A, par B, par C)] were placed inside the homologous recombination sites. As the selection marker, EGFP and puromycin resistant gene (pac) ligated to each other with internal ribosomal entry site (IRES) were used.

The method of producing the virus by homologous recombination is the same as that described in conjunction with the construction of H6R28. To avoid redundancy, no further explanation will be made.

The homologous recombination was followed by selection, which was carried out 6 times with puromycin. As a result, a recombinant virus with the BAC replication origins was produced.

Figure 22:
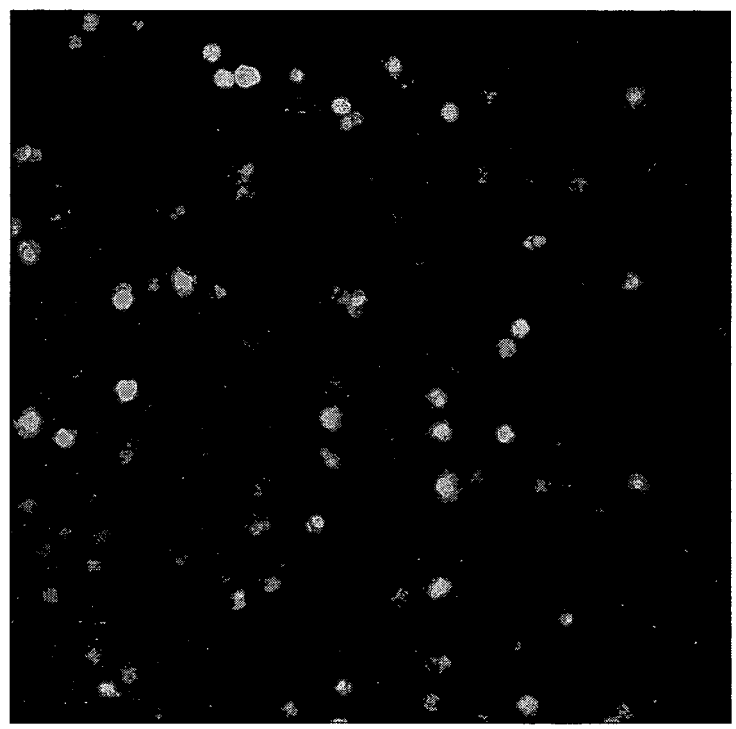
FIG. 22 is a fluorescent micrograph view of Molt-3 cells infected with H6R28 BAC.

The recombinant virus showed stable growth, and reached about 90% of the population after 6 rounds of puromycin selection. FIG. 22 is a fluorescent micrograph showing Molt-3 cells infected with H6R28 BAC. The result shows that HHV-6 with the BAC replication origins was successfully produced by the foregoing method.

(2) Production of Recombinant HHV-7 with the Insertion of BAC Replication Origins (H7R28 BAC)

Figure 23:
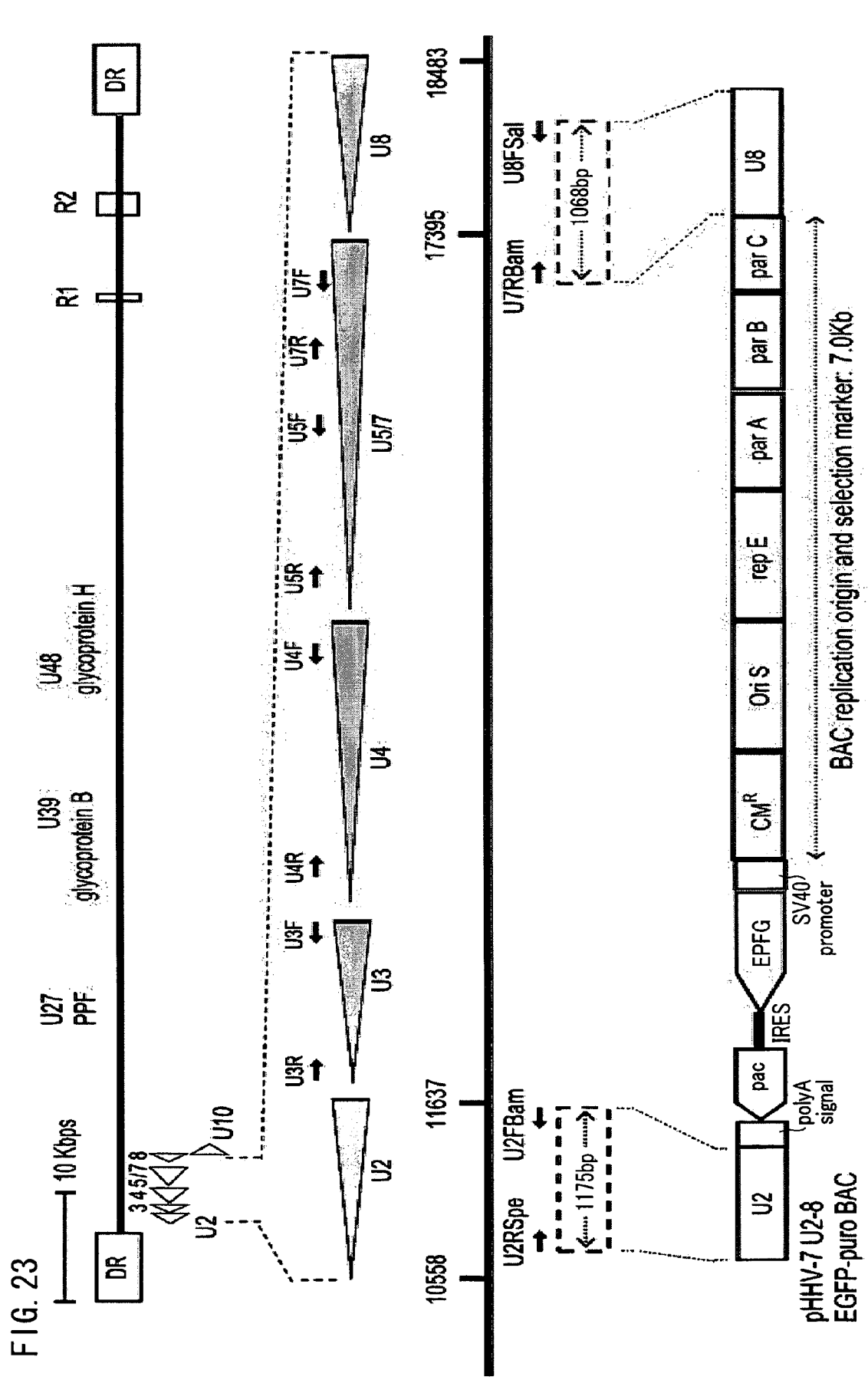
FIG. 23 is a schematic diagram showing a structure of the H7R28 BAC genome.

FIG. 23 is a schematic diagram representing a structure of H7R28 BAC.

As in H7R28, the U2 and U8 sequences were used for homologous recombination. Plasmid pHHV-7 U2-8 EGFP-puro BAC was prepared in which BAC replication origins [chloramphenicol resistant gene (CMR), BAC replication origins (Ori S, rep E, par A, par B, par C)] were placed inside the homologous recombination sites. As the selection marker, EGFP and puromycin resistant gene (pac) ligated to each other with internal ribosomal entry site (IRES) were used.

The method of producing the virus by homologous recombination is the same as that described in conjunction with the construction of H7R28. To avoid redundancy, no further explanation will be made.

The homologous recombination was followed by selection, which was carried out 6 times with puromycin. As a result, a recombinant virus with the BAC replication origins was produced.

Figure 24:
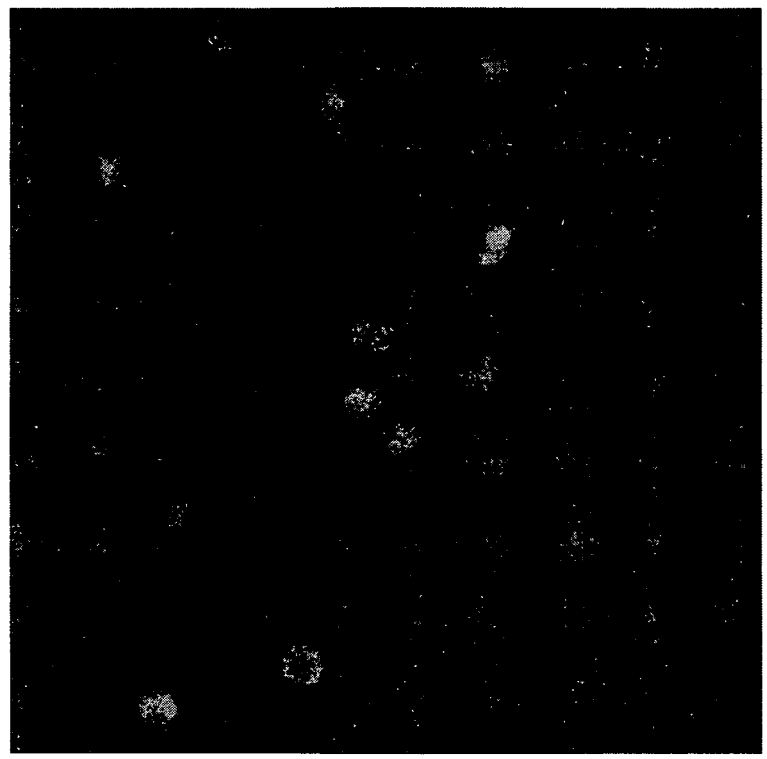
FIG. 24 is a fluorescent micrograph view of SupT1 cells infected with H7R28 BAC.

The recombinant virus showed stable growth, and reached about 90% of the population after 6 rounds of puromycin selection. FIG. 24 is a fluorescent micrograph showing SupT1 cells infected with H7R28 BAC. The result shows that HHV-7 with the BAC replication origins was successfully produced by the foregoing method.

<Summary of Evaluation Results>

Overall, the recombinant virus H6R28 revealed that the fairly large gene cluster U3-U7 was dispensable for viral replication, latency, and reactivation. Of the deleted genes, the characteristics of U4 and U6 have not been reported.

Similarly, the H7R28 revealed that the fairly large gene cluster U3-U7 was dispensable for viral replication, latency, and reactivation.

Genes U3, U5, U7, and U25 of HHV-6, and genes U3, U7, and U25 of HHV-7 belong to the US22 gene family, whose members are related to the HCMV US22 gene having the common motifs of unknown functions. Every betaherpesvirus encodes several US22 family genes that encode at least one of four conserved motifs. Although the functions of most of the US22 family genes are unknown, some of them, such as the murine cytomegalovirus (MCMV) immediate-early 2 (IE2) gene and the HCMV UL36-38 genes, encode proteins with transactivating functions.

However, MCMV IE2 is known to be dispensable for viral replication and latency and reactivation. Deletion of the US22 family genes of H6R28 showed them to have similar properties; HHV-6 U3 encodes a protein with a weak transactivating function, and the inventors of the present invention failed to find any difference in the viral replication or latency and reactivation between the wt and recombinant virus.

The US22 family genes UL36 and UL37 of HCMV have an antiapoptotic function. However, the inventors of the present invention did not observe increased apoptosis in H6R28- or H7R28-infected cells in the present study.

Other US22 family genes, such as the MCMV M140 and M141 genes, confer altered cell and tissue tropism. Since the in vivo host tissue range of HHV-6 is broad and since the virus infects various types of cells, it is possible that the HHV-6 US22 family genes contribute to the broad organ tropism of this virus.

H6R28 appears to be a useful tool for the study of HHV-6 latency and reactivation. H7R28 appears to be a useful tool for the study of HHV-7 latency and reactivation. Moreover, in HHV-6 and HHV-7, this large dispensable locus can be a useful site for inserting a large gene, such as a bacterial artificial chromosome (BAC) vector. In fact, the inventors of the present invention have shown that the BAC gene can actually be stably inserted in HHV-6 and HHV-7.

It is believed that this is the first report of a successful recombinant HHV-6 virus vector and recombinant HHV-7 virus vector, and the invention can provide HHV-6 and HHV-7 investigators with a detailed protocol for making it.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

A virus vector of the present invention (i) allows for insertion of an exogenous nucleotide sequence, (ii) can easily transfect a host cell of mammals, (iii) allows a gene encoded by the exogenous nucleotide sequence to be expressed in the host cell, (iv) has a low risk of pathogenicity, and therefore (v) is suitable for gene therapy of mammals.

A producing method of a virus vector of the present invention is for easily producing a virus vector that (i) allows for insertion of an exogenous nucleotide sequence, (ii) can easily transfect a host cell of mammals, (iii) allows a gene encoded by the exogenous nucleotide sequence to be expressed in the host cell, (iv) has a low risk of pathogenicity, and therefore (v) is suitable for gene therapy of mammals.

A method for making recombinant viruses, used in a producing method of a virus vector of the present invention is indispensable when other vector developing techniques such as the BAC system or amplicon system were to be applied to HHV-6 and HHV-7.

A transforming method of a host cell of the present invention is a method for transforming a host cell with a virus vector that (i) easily allows for transfection of a mammalian host cell with an exogenous nucleotide sequence, (ii) allows a gene encoded by the exogenous nucleotide sequence to be expressed in the host cell, (iii) has a low risk of pathogenicity, and (v) therefore is suitable for gene therapy of mammals.

A transformed host cell of the present invention (i) is transformed with a virus vector with the insertion of an exogenous nucleotide sequence, (ii) allows a gene encoded by the exogenous nucleotide sequence to be expressed in the host cell, (iii) has a low risk of pathogenicity, and therefore (iv) can suitably be used for gene therapy.

A gene therapy method of the present invention is a gene therapy method for mammals using a virus vector that (i) easily allows for transfection of a mammalian host cell with an exogenous nucleotide sequence, (ii) allows a gene encoded by the exogenous nucleotide sequence to be expressed in the host cell, and (iii) has a low risk of pathogenicity.

Virus vectors of the present invention can be used for AIDS treatment by taking advantage of the fact that both HHV-6 and HHV-7 infect the CD4 positive T cells as does HIV. In this case, it is preferable that virus vectors of the present invention include anti-HIV genes such as ribozyme and interference RNA.

Further, virus vectors of the present invention can be used for AIDS treatment by taking advantage of the fact that HHV-6 can latently infect macrophage as does HIV. In this case, it is also preferable that virus vectors of the present invention include anti-HIV genes such as ribozyme and interference RNA.

Further, virus vectors of the present invention can be used to introduce cytokine to the CD4 positive T cells, macrophage, natural killer cells, lymphokine activated killer (LAK) cells, and the like by taking advantage of the fact that both HHV-6 and HHV-7 infect the immunocompetent cells of these cells. Thus, virus vectors of the present invention can be used for the immunotherapy of cancer.

Further, virus vectors of the present invention are also applicable to anti-tumor treatment. In this case, pancreatic cancer cells are infected with HHV-6 to kill cancer cells, by taking advantage of the fact that HHV-6 can enter the cells by binding to CD46 molecules serving as receptors, which are abundantly expressed in pancreatic cancer cells or other refractory digestive system tumors.

The invention claimed is:

1. A recombinant HHV-viral vector that comprises the full-length sequence of an HHV-6 Variant B and an exogenous nucleotide sequence wherein (i) the full length U2 through U8 regions of the HHV-6 has have been replaced with said exogenous nucleotide sequence or (ii) the full length U24 and U25 regions of the HHV-6 has been replaced with said exogenous nucleotide sequence.

2. The recombinant HHV-viral vector as set forth in claim 1 wherein:

the full length U2 through U8 regions of the HHV-6 are between nucleotide numbers 9041 and 17446 of the HHV-6 DNA sequence presented in SEQ ID NO: 1, and the full length U24 and U25 regions of the HHV 6 are between nucleotide numbers 36250 and 37775 of the HHV-6 DNA sequence presented in SEQ ID NO: 1.

3. The recombinant HHV-viral vector as set forth in claim 1, wherein the exogenous nucleotide sequence is a DNA sequence.

4. The recombinant vector as set forth in claim 3, wherein the DNA sequence encodes a biomolecule selected from the group consisting of a bacterial artificial chromosome (BAC), a cytokine gene, a ribozyme, an interference RNA, an immunological co-stimulator molecule, a signal transduction molecule, an enzyme, and a chemical attractant.

5. The recombinant HHV-viral vector as set forth in claim 3, wherein the DNA sequence encodes a mammalian therapeutic gene for gene therapy.

6. A method of producing a recombinant HHV-viral vector, said method comprising the step of inserting an exogenous nucleotide sequence into a full-length sequence of an HHV-6 Variant B such that (i) the full length U2 through U8 regions of the HHV-6 is replaced by the exogenous nucleotide sequence or (ii) the full length U24 and U25 regions of the HHV-6 is replaced by the exogenous nucleotide sequence.

7. The method of producing a recombinant virus vector as set forth in claim 6, wherein:
in the step of inserting an exogenous nucleotide sequence in the regions corresponding to the full length U2 through U8 regions of the HHV-6, the exogenous nucleotide sequence is inserted between nucleotide numbers 9041 and 17446 of the HHV-6 DNA sequence presented in SEQ ID NO: 1, and
in the step of inserting an exogenous nucleotide sequence in the regions corresponding to the full length U24 and U25 regions of the HHV-6, the exogenous nucleotide sequence is inserted between nucleotide numbers 36250 and 37775 of the HHV-6 DNA sequence presented in SEQ ID NO: 1.

8. The method of producing the recombinant HHV-viral vector as set forth in claim 6, wherein the step of inserting is performed inside a host cell selected from a somatic cell or an umbilical cord blood cell.

* * * * *

UNITED STATES PATENT AND TRADEMARK OFFICE
CERTIFICATE OF CORRECTION

| | | |
|---|---|---|
| PATENT NO. | : 8,642,045 B2 | Page 1 of 1 |
| APPLICATION NO. | : 10/570589 | |
| DATED | : February 4, 2014 | |
| INVENTOR(S) | : Kondo | |

It is certified that error appears in the above-identified patent and that said Letters Patent is hereby corrected as shown below:

On the title page

Item [75], delete "Kazuhiro Konda" and insert -- Kazuhiro Kondo --.

Signed and Sealed this
Twenty-second Day of July, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,642,045 B2 | Page 1 of 1 |
| APPLICATION NO. | : 10/570589 | |
| DATED | : February 4, 2014 | |
| INVENTOR(S) | : Kondo | |

It is certified that error appears in the above-identified patent and that said Letters Patent is hereby corrected as shown below:

On the title page

Item [12], delete "Konda" and insert --Kondo--.

Item [75], delete "Kazuhiro Konda" and insert --Kazuhiro Kond<u>o</u>--.

This certificate supersedes the Certificate of Correction issued July 22, 2014.

Signed and Sealed this
Twelfth Day of August, 2014

Michelle K. Lee
*Deputy Director of the United States Patent and Trademark Office*